US011879137B2

(12) United States Patent
Fiorina et al.

(10) Patent No.: US 11,879,137 B2
(45) Date of Patent: Jan. 23, 2024

(54) TREATMENT OF TYPE 1 DIABETES AND AUTOIMMUNE DISEASES OR DISORDERS

(71) Applicant: THE CHILDREN'S MEDICAL CENTER CORPORATION, Boston, MA (US)

(72) Inventors: Paolo Fiorina, Boston, MA (US); Moufida Ben-Nasr, Boston, MA (US)

(73) Assignee: THE CHILDREN'S MEDICAL CENTER CORPORATION, Boston, MA (US)

( * ) Notice: Subject to any disclaimer, the term of this patent is extended or adjusted under 35 U.S.C. 154(b) by 603 days.

(21) Appl. No.: 16/648,469

(22) PCT Filed: Sep. 21, 2018

(86) PCT No.: PCT/US2018/052198
§ 371 (c)(1),
(2) Date: Mar. 18, 2020

(87) PCT Pub. No.: WO2019/060708
PCT Pub. Date: Mar. 28, 2019

(65) Prior Publication Data
US 2020/0332258 A1 Oct. 22, 2020

Related U.S. Application Data

(60) Provisional application No. 62/663,367, filed on Apr. 27, 2018, provisional application No. 62/562,111, filed on Sep. 22, 2017.

(51) Int. Cl.
| | |
|---|---|
| *C12N 5/0789* | (2010.01) |
| *A61K 35/12* | (2015.01) |
| *A61K 35/28* | (2015.01) |
| *A61P 3/10* | (2006.01) |

(52) U.S. Cl.
CPC ............ *C12N 5/0647* (2013.01); *A61K 35/12* (2013.01); *A61K 35/28* (2013.01); *A61P 3/10* (2018.01); *C12N 2501/65* (2013.01)

(58) Field of Classification Search
CPC .. C12N 5/0647; C12N 2501/65; A61K 35/12; A61K 35/28
See application file for complete search history.

(56) References Cited

U.S. PATENT DOCUMENTS

| | | | |
|---|---|---|---|
| 5,460,964 A | 10/1995 | McGlave et al. |
| 5,635,387 A | 6/1997 | Fei et al. |
| 5,677,136 A | 10/1997 | Simmons et al. |
| 5,716,827 A | 2/1998 | Tsukamoto et al. |
| 5,750,397 A | 5/1998 | Tsukamoto et al. |
| 5,759,793 A | 6/1998 | Schwartz et al. |
| 5,854,033 A | 12/1998 | Lizardi et al. |
| 6,610,719 B2 | 8/2003 | Paralkar et al. |
| 6,747,037 B1 | 6/2004 | Old et al. |
| 7,592,177 B2 | 9/2009 | Chen et al. |
| 7,951,592 B2 | 5/2011 | Chen et al. |
| 8,071,369 B2 | 12/2011 | Jaenisch et al. |
| 8,168,428 B2 | 5/2012 | Zon et al. |
| 8,309,555 B2 | 11/2012 | Chen et al. |
| 8,481,022 B2 | 7/2013 | Lodie et al. |
| 8,906,677 B2 | 12/2014 | Li et al. |
| 8,932,856 B2 | 1/2015 | Jaenisch et al. |
| 9,028,811 B2 | 5/2015 | Zon et al. |
| 9,056,085 B2 | 6/2015 | Zon et al. |
| 9,402,852 B2 | 8/2016 | Zon et al. |
| 10,023,879 B2 | 7/2018 | Flynn et al. |
| 10,201,557 B2 | 2/2019 | Bishopric et al. |
| 2003/0194803 A1 | 10/2003 | Mellor et al. |
| 2004/0053307 A1 | 3/2004 | Wood et al. |
| 2006/0003452 A1 | 1/2006 | Humeau et al. |
| 2006/0154853 A1 | 7/2006 | Steptoe et al. |
| 2006/0247214 A1 | 11/2006 | Delong et al. |
| 2007/0116691 A1 | 5/2007 | Cambier et al. |
| 2007/0122377 A1 | 5/2007 | Best et al. |
| 2007/0254884 A1 | 11/2007 | Chen et al. |
| 2008/0175825 A1 | 7/2008 | Hampson et al. |
| 2009/0209621 A1 | 8/2009 | Mendell et al. |
| 2010/0203056 A1 | 8/2010 | Irving et al. |
| 2010/0233804 A1 | 9/2010 | Zhou et al. |
| 2010/0310525 A1 | 12/2010 | Chevalier et al. |

(Continued)

FOREIGN PATENT DOCUMENTS

| | | |
|---|---|---|
| CA | 3013683 A1 | 9/2017 |
| CA | 3040048 A1 | 4/2018 |

(Continued)

OTHER PUBLICATIONS

Chen et al. Regulation of PD-L1: a novel role of pro-survival signalling in cancer. Annals of Oncology 27: 409-416 (Year: 2016).*
He et al., "Programmed death-1 ligands-transfected dendritic cells loaded with glutamic acid decarboxylase 65 (GAD65) inhibit both the alloresponse and the GAD65-reactive lymphocyte response." Clinical & Experimental Immunology 151(1):86-93 (2008).
Heneghan et al. "Autoimmune Hepatitis" Lancet 382(9902): 1433-1444 (2013).
Herrler et al., "Prostaglandin E positively modulates endothelial progenitor cell homeostasis: an advanced treatment modality for autologous cell therapy." Journal of Vascular Research 46(4):333-346 (2009).
Hoggatt et al., "Prostaglandin E2 enhances hematopoietic stem cell homing, survival, and proliferation." Blood 113(22):5444-5455 (2009).
Kamat et al. "MicroRNA screen of human embryonic stem cell differentiation reveals miR-105 as an enhancer of megakaryopoiesis from adult CD34+ cells." Stem Cells 32(5): 1337-1346 (2014).

(Continued)

*Primary Examiner* — Taeyoon Kim
(74) *Attorney, Agent, or Firm* — NIXON PEABODY LLP; David S. Resnick; Jeanne Jodoin

(57) ABSTRACT

Described herein are methods and compositions for producing modified, PD-L1 expressing hematopoietic stem cells, and uses thereof. Aspects of the invention relate to modulating the expression of micro RNA that controls the expression of PD-L1 in the hematopoietic stem cell. Methods for modulating the expression of micro RNA include, e.g., introducing to the cell a nucleic acid encoding a given micro RNA, or an agent that inhibits a given micro RNA.

16 Claims, 84 Drawing Sheets

Specification includes a Sequence Listing.

(56) References Cited

U.S. PATENT DOCUMENTS

| | | |
|---|---|---|
| 2011/0076678 A1 | 3/2011 | Jaenisch et al. |
| 2011/0110899 A1 | 5/2011 | Shi et al. |
| 2012/0003189 A1 | 1/2012 | Pelus et al. |
| 2012/0028351 A1 | 2/2012 | Li et al. |
| 2012/0202288 A1 | 8/2012 | Mendlein et al. |
| 2012/0251514 A1 | 10/2012 | Fowler et al. |
| 2012/0263692 A1 | 10/2012 | Bertone |
| 2012/0264218 A1 | 10/2012 | Lin et al. |
| 2012/0277652 A1 | 11/2012 | Zhao et al. |
| 2013/0102074 A1 | 4/2013 | Jaenisch et al. |
| 2013/0323832 A1 | 12/2013 | Munn et al. |
| 2014/0030232 A1 | 1/2014 | Shoemaker et al. |
| 2014/0234373 A1 | 8/2014 | Mellor et al. |
| 2014/0341933 A1 | 11/2014 | Riley et al. |
| 2014/0369972 A1 | 12/2014 | Shoemaker et al. |
| 2015/0139994 A1 | 5/2015 | Xu |
| 2015/0366914 A1 | 12/2015 | Yu et al. |
| 2017/0211042 A1 | 7/2017 | Riley et al. |
| 2017/0246279 A1 | 8/2017 | Berger et al. |
| 2018/0112180 A1 | 4/2018 | Robbins et al. |

FOREIGN PATENT DOCUMENTS

| | | |
|---|---|---|
| CN | 101072880 A | 11/2007 |
| CN | 102188446 A | 9/2011 |
| RU | 2425876 C2 | 8/2011 |
| WO | 2000038663 A2 | 7/2000 |
| WO | 2001012596 A1 | 2/2001 |
| WO | 2005040391 A1 | 5/2005 |
| WO | 2006072016 A2 | 7/2006 |
| WO | 2007071456 A1 | 6/2007 |
| WO | 2007112084 A2 | 10/2007 |
| WO | 2008070310 A2 | 6/2008 |
| WO | 2008073748 A1 | 6/2008 |
| WO | 2009023566 A2 | 2/2009 |
| WO | 2009086425 A1 | 7/2009 |
| WO | 2009155041 A2 | 12/2009 |
| WO | 2010096264 A2 | 8/2010 |
| WO | 2010108028 A2 | 9/2010 |
| WO | 2010108126 A2 | 9/2010 |
| WO | 2011031875 A2 | 3/2011 |
| WO | 2011060381 A1 | 5/2011 |
| WO | 2011127180 A1 | 10/2011 |
| WO | 2012021845 A2 | 2/2012 |
| WO | 2013040552 A2 | 3/2013 |
| WO | 2013082241 A2 | 6/2013 |
| WO | 2013082243 A1 | 6/2013 |
| WO | 2014152603 A1 | 9/2014 |
| WO | 2015134652 A1 | 9/2015 |
| WO | 2016077574 A1 | 5/2016 |
| WO | 2016123100 A1 | 8/2016 |
| WO | 2016123117 A1 | 8/2016 |
| WO | 2016142532 A1 | 9/2016 |
| WO | 2016161196 A1 | 10/2016 |
| WO | 2017015320 A1 | 1/2017 |
| WO | 2017040078 A1 | 3/2017 |
| WO | 2017069958 A2 | 4/2017 |
| WO | 2017078807 A1 | 5/2017 |
| WO | 2017100587 A1 | 6/2017 |

OTHER PUBLICATIONS

Keir et al., "Tissue expression of PD-L1 mediates peripheral T cell tolerance." Journal of Experimental Medicine 203(4):883-895 (2006).
Khoury et al. "The roles of the new negative T cell costimulatory pathways in regulating autoimmunity." Immunity 20(5): 529-538 (2004).
Kao et al. "Tumor suppressor microRNAs contribute to the regulation of PD-L1 expression in malignant pleural mesothelioma." Journal of Thoracic Oncology 12(9): 1421-1433 (2017).
Kwoh et al. "Transcription-based amplification system and detection of amplified human immunodeficiency virus type 1 with a bead-based sandwich hybridization format." Proc. Natl. Acad. Sci USA 86(4): 1173-1177 (1989).
Lanzinger et al., "Ambivalent effects of dendritic cells displaying prostaglandin E 2-induced indoleamine 2, 3-dioxygenase." European Journal of Immunology 42(5):1117-1128 (2012).
Lemoli et al. "Hematopoietic stem cell mobilization." Haematologica 93(3): 321-324 (2008).
Liu et al. "Ex vivo expansion of hematopoietic stem cells derived from umbilical cord blood in rotating wall vessel" J. Biotechnol. 124(3): 592-601 (2006).
Lizardi et al. "Exponential amplification of recombinant-RNA hybrization probes." Bio/Technology 6(10): 1197-1202 (1988).
Munn et al. "Indoleamine 2,3 dioxygenase and metabolic control of immune responses." Trends Immunol. 34(3): 137-143 (2013).
Nasr et al., "Co-transplantation of autologous MSCs delays islet allograft rejection and generates a local Immunoprivileged site." Acta Diabetologica 52(5):917-927 (2015).
Nasr et al., "PD-L1+ HSCs Are Immunoregulatory and Revert Experimental Autoimmune Diabetes." Diabetes 64(1) 75th Scientific Sessions of the American-Diabetes-Association, Boston, MA (2015).
Nasr et al., "The rise, fall, and resurgence of immunotherapy in type 1 diabetes", Pharmacol Res. 98: 31-8 (2015).
Nosov et al., "Role of lentivirus-mediated overexpression of programmed death-ligand 1 on corneal allograft survival" Am J Transplant 12(5):1313-1322 (2012).
O'Connell et al. "MicroRNAs enriched in hematopoietic stem cells differentially regulate long-term hematopoietic output." Proceedings of the National Academy of Sciences 107(32): 14235-14240 (2010).
Okita et al. "Generation of mouse induced pluripotent stem cells without viral vectors." Science 322(5903): 949-953 (2008).
Ooi et al. "MicroRNA-125b expands hematopoietic stem cells and enriches for the lymphoid-balanced and lymphoid-biased subsets." Proceedings of the National Academy of Sciences 107(50): 21505-21510 (2010).
Ozkaynak et al. "Programmed death-I targeting can promote allograft survival." J Immunol. 69(11): 6546-6553 (2002).
Paladini et al. "Targeting microRNAs as key modulators of tumor immune response." Journal of Experimental & Clinical Cancer Research 35(1): 103 pp. 1-19 (2016).
Pallotta et al., "Forced IDO 1 expression in dendritic cells restores immunoregulatory signalling in autoimmune diabetes." Journal of Cellular and Molecular Medicine 18(10):2082-2091 (2014).
Pelus. "Peripheral blood stem cell mobilization: new regimens, new cells, where do we stand." Curr. Opin. Hematol. 15(4): 285-292 (2008).
Pen et al., "Interference with PD-L1/PD-1 co-stimulation during antigen presentation enhances the multifunctionality of antigen-specific T cells" Gene Therapy 21:262-271 (2014).
Petrelli et al., "IL-21 is an antitolerogenic cytokine of the late-phase alloimmune response." Diabetes 60:3223-3234 (2011).
Pittenger et al. "Multilineage potential of adult human mesenchymal stem cells." Science 284(5411): 143-147 (1999).
Prockop. "Marrow stromal cells as stem cells for nonhematopoietic tissues." Science 276(5309): 71-74 (1997).
Rachamim et al., "Tolerance induction by 'megadose' hematopoietic transplants: donor-type human CD34 stem cells induce potent specific reduction of host anti-donor cytotoxic T lymphocyte precursors in mixed lymphocyte culture" Transplantation, 65(10):1386-93 (1998).
Riella et al. "Role of the PD -1 pathway in the immune response." Am. J Transplant. 12(10): 2575-2587 (2012).
Roden et al. "MicroRNAs in control of stem cells in normal and malignant hematopoiesis." Current Stem Cell Reports 2(3): 183-196 (2016).
Steidl et al. "Gene expression profiling identifies significant differences between the molecular phenotypes of bone marrow-derived and circulating human CD34+ hematopoietic stem cells." Blood 99(6): 2037-2044 (2002).

(56) References Cited

OTHER PUBLICATIONS

Steptoe et al., "Autoimmune diabetes is suppressed by transfer of proinsulin-encoding Gr-1+ myeloid progenitor cells that differentiate in vivo into resting dendritic cells" Diabetes 54(2):434-42 (2005).
Takahashi et al. "Induction of pluripotent stem cells from mouse embryonic and adult fibroblast cultures by defined factors." Cell 126(4): 663-676 (2006).
Tian et al., "Induction of robust diabetes resistance and prevention of recurrent type 1 diabetes following islet transplantation by gene therapy." The Journal of Immunology 179(10) 6762-6769 (2007).
Varghese et al. "Engineering Musculoskeletal Tissues with Human Embryonic Germ Cell Derivatives." Stem Cells 28(4): 765-774 (2010).
Vergani et al., "A novel clinically relevant strategy to abrogate autoimmunity and regulate alloimmunity in NOD mice." Diabetes 59(9):2253-2264 (2010).
Voltarelli et al. "Autologous nonmyeloablative hematopoietic stem cell transplantation in newly diagnosed type 1 diabetes mellitus" JAMA 297(14): 1568-76 (2007).
Wang et al., "Protective role of programmed death 1 ligand 1 in nonobese diabetic mice: the paradox in transgenic models." Diabetes 57(7):1861-1869 (2008).
Wang et al. "The roles of microRNAs in regulating the expression of PD-1/PD-L1 immune checkpoint." International Journal of Molecular Sciences 18(12): 2540 pp. 1-11 (2017).
Wernig et al. "In vitro reprogramming of fibroblasts into a pluripotent ES-cell-like state." Nature 448(7151): 318-324 (2007).
White et al. "Acute myocardial infarction." The Lancet 372(9638): 570-584 (2008).
Woltjen et al. "piggyBac ransposition reprograms fibroblasts to induced pluripotent stem cells." Nature 458(7239): 766-770 (2009).
Xu et al. "miR-424 (322) reverses chemoresistance via T-cell immune response activation by blocking the PD-L1 Immune checkpoint." Nature Communications 7(1): 1-13 (2016).
Yalcin et al. "Microrna mediated regulation of hematopoietic stem cell aging." Blood 124(21): 602 (2014).
Yokosuka et al., "Programmed cell death 1 forms negative costimulatory microclusters that directly inhibit T cell receptor signaling by recruiting phosphatase SHP2" J. Exp. Med. 209:1201-17 (2012).
Zheng et al., "Ex Vivo Expanded Hematopoietic Stem Cells Overcome the MHC Barrier in Allogeneic Transplantation", Cell Stem Cell 9(2):119-130 (2011).
Zhou et al. "Generation of induced pluripotent stem cells using recombinant proteins." Cell Stem Cell. 4(5): 381-384 (2009).
Bachar-Lustig et al., "Megadose of T cell-depleted bone marrow overcomes MHC barriers in sublethally irradiated mice" Natural Medicine 1(12):1268-1273 (1995).
Barany. "Genetic disease detection and DNA amplification using cloned thermostable ligase." Proc. Natl. Acad. Sci. USA 88(1): 189-193 (1991).
Beilhack et al. "Purified Allogeneic Hematopoietic Stem Cell Transplantation Blocks Diabetes Pathogenesis in NOD Mice." Diabetes. 52(1): 59-68 (2003).
Bluestone et al., "Genetics, pathogenesis and clinical interventions in type 1 diabetes." Nature 464 (7293):1293-1300 (2010).
Carvello et al., "Inotuzumab Ozogamicin Murine Analog-Mediated B-Cell Depletion Reduces Anti-islet Allo-and Autoimmune Responses." Diabetes 61(1):155-165 (2012).
Couri et al., "C-peptide levels and insulin independence following autologous nonmyeloablative hematopoietic stem cell transplantation in newly diagnosed type 1 diabetes mellitus." Jama 301(15):1573-1579 (2009).

Cutler et al., "Prostaglandin-modulated umbilical cord blood hematopoietic stem cell transplantation" Blood 122 (17):3074-3081 (2013).
D'Addio et al., "Autologous nonmyeloablative hematopoietic stem cell transplantation in new-onset type 1 diabetes: a multicenter analysis." Diabetes 63(9):3041-3046 (2014).
D'Addio et al., "The link between the PDL1 costimulatory pathway and Th17 in fetomaternal tolerance" J. Immunol. 187(9):4530-41 (2011).
Daneman. "Type 1 diabetes." Lancet 367(9513): 847-858 (2006).
DCCT Group (Diabetes Control and Complications Trial Research Group) "Effect of intensive therapy on residual beta-cell function in patients with type 1 diabetes in the diabetes control and complications trial. A randomized, controlled trial." Ann Intern Med. 128:517-523 (1998).
Fife et al., "Insulin-induced remission in new-onset NOD mice is maintained by the PD-1-PD-L1 pathway." Journal of Experimental Medicine 203(12):2737-2747 (2006).
Fife et al., "Interactions between programmed death-1 and programmed death ligand-1 promote tolerance by blocking the T cell receptor-induced stop signal." Nature Immunology 10(11):1185-1192 (2009).
Filippi et al., "Immunoregulatory mechanisms triggered by viral infections protect from type 1 diabetes in mice." The Journal of Clinical Investigation 119(6):1515-1523 (2009).
Fiorina et al. "Immunological Applications of Stem Cells in Type 1 Diabetes." Endocrine Reviews 32(6): 725-754 (2011).
Fiorina et al., "Immunomodulatory function of bone marrow-derived mesenchymal stem cells in experimental autoimmune type 1 diabetes." The Journal of Immunology 183(2):993-1004 (2009).
Fiorina et al., "Targeting CD22 reprograms B-cells and reverses autoimmune diabetes" Diabetes 57(11):3013-3024 (2008).
Fiorina et al., "Targeting the CXCR4-CXCL12 Axis Mobilizes Autologous Hematopoietic Stem Cells and Prolongs Islet Allograft Survival via Programmed Death Ligand 1" J Immunol., 186(1):121-131 (2011).
Fowler et al., "Transplant and Autoimmune Therapy Using T-Cells" National Cancer Institute, Federal Register 75(185):58401-58402 (2010).
Guatelli et al. "Isothermal, in vitro amplification of nucleic acids by a multienzyme reaction modeled after retroviral replication." Proc. Natl. Acad. Sci USA 87(5): 1874-1878 (1990).
Guleria et al. "Mechanisms of PDLI-mediated regulation of autoimmune diabetes." Clin. Immunol. 125(1): 16-25 (2007).
Gur et al., "Immune regulatory activity of CD34+ progenitor cells: evidence for a deletion-based mechanism mediated by TNF-alpha" Blood 105(6):2585-93 (2005).
Hartshorn et al. "Ex vivo expansion of hematopoietic stem cells using defined culture media." Cell Technology for Cell Products, R. Smith (ed.), Springer Netherlands, pp. 221-224 (2007).
Haynesworth et al. "Cell surface antigens on human marrow-derived mesenchymal cells are detected by monoclonal antibodies." Bone 13(1): 69-80 (1992).
Ansari et al. "The programmed death-1 (PD-1) pathway regulates autoimmune diabetes in nonobese diabetic (NOD) mice." The Journal of Experimental Medicine 198(1): 63-69 (2003).
Ben Nasr et al. "PD-L1 genetic overexpression or pharmacological restoration in hematopoietic stem and progenitor cells reverses autoimmune diabetes." Science Translational Medicine 9(416): 1-14 (2017).
Cortez et al. "PDL1 Regulation by p53 via miR-34." JNCI: Journal of the National Cancer Institute 108(1): 1-9 (2016).
Grenda et al. "New Dancing Couple: PD-L1 and Micro RNA." Scandinavian Journal of Immunology 86(3): 130-134 (2017).

* cited by examiner

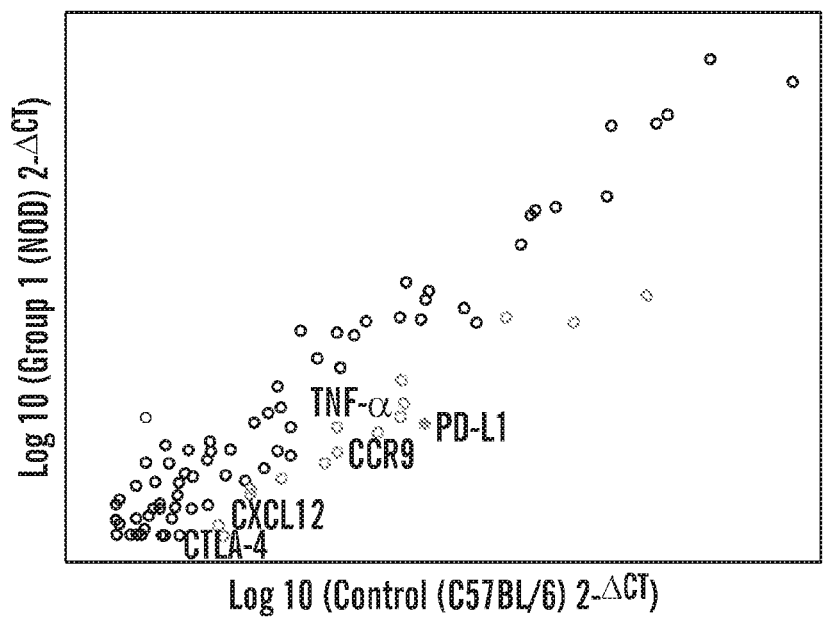
FIG. 1A
| Gene Symbol | P-value | Fold change |
|---|---|---|
| CD274 (PD-L1) | 0.003313 | -14.4402 |
| CCR9 | 0.005054 | -8.6234 |
| CTLA-4 | 0.072520 | -7.2386 |
| CXCL12 | 0.019921 | -5.3904 |
| TNF-α | 0.056009 | -2.5213 |
FIG. 1B
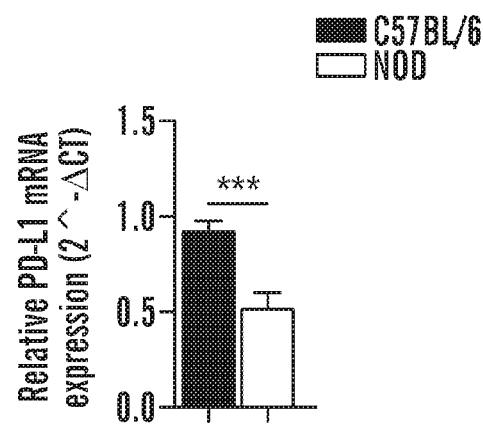
FIG. 1C

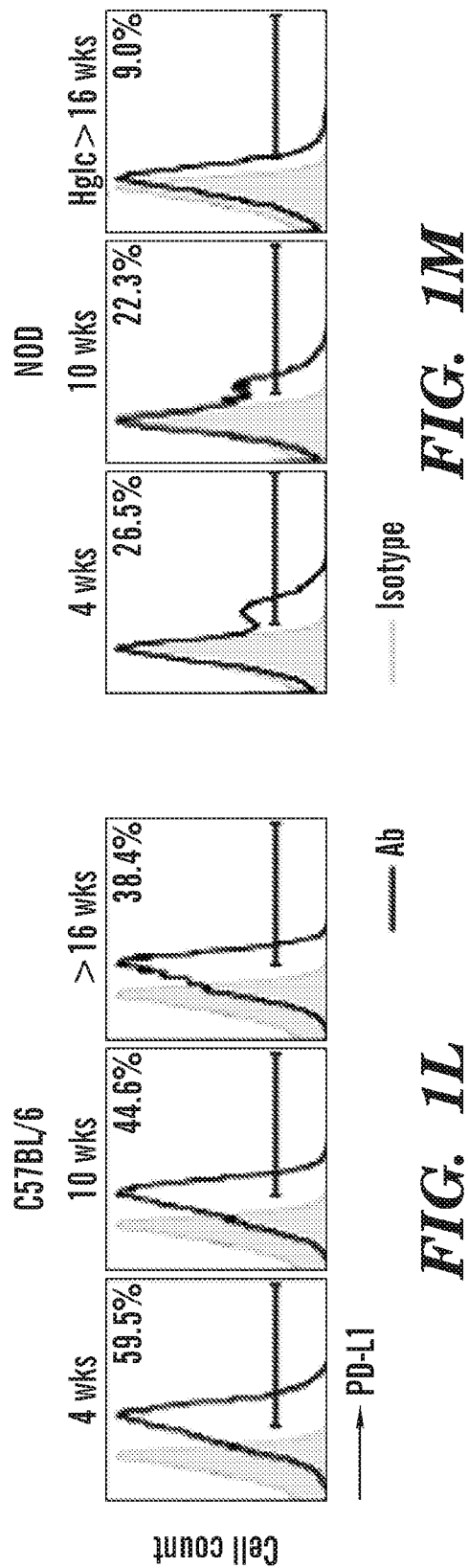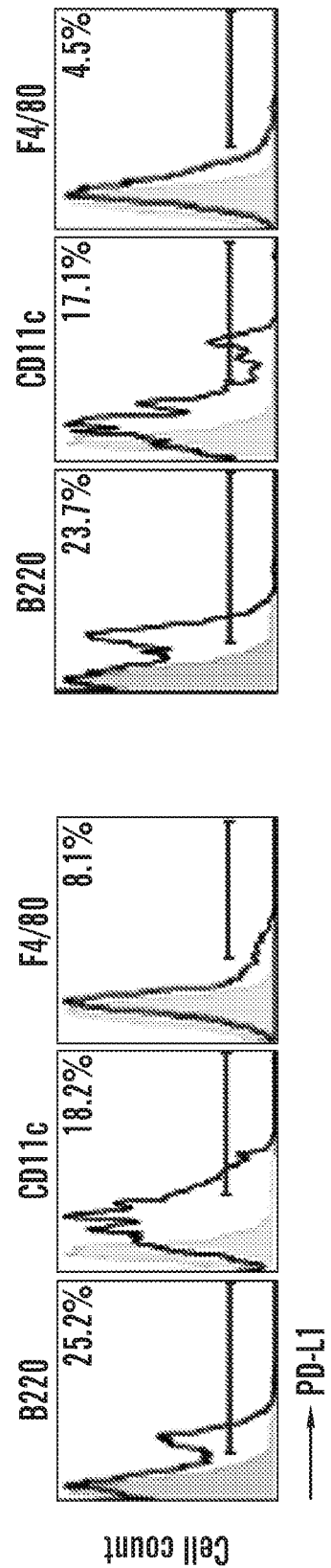

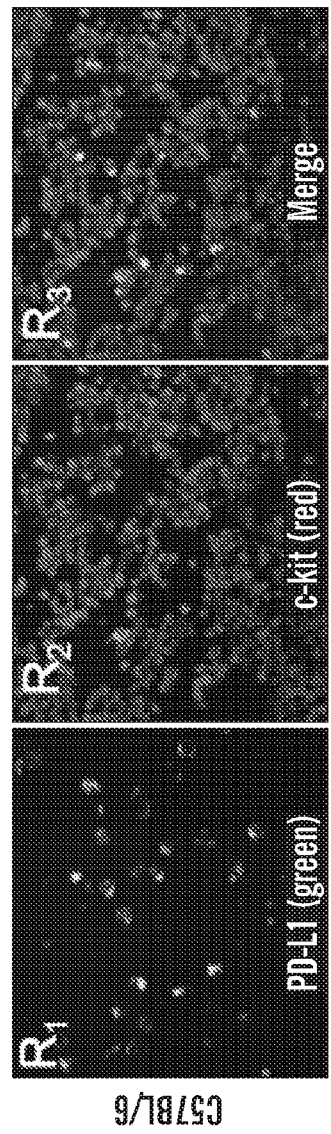
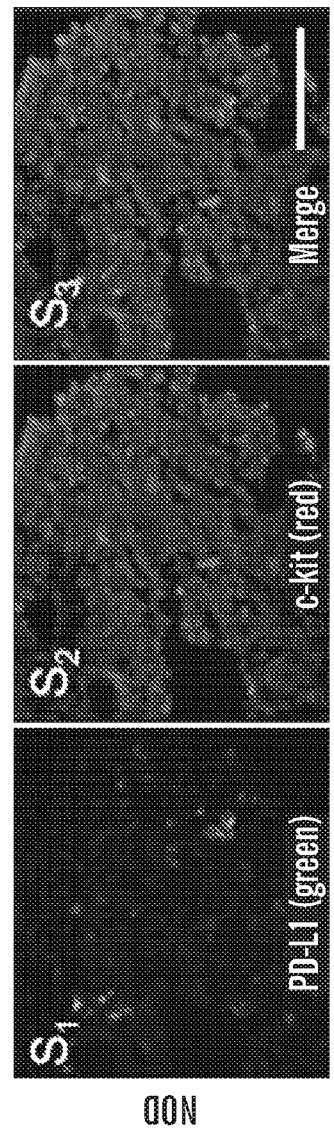
FIG. 1R1  FIG. 1R2  FIG. 1R3
FIG. 1S1  FIG. 1S2  FIG. 1S3

| Gene Symbol | Fold Change in KLS (linear) (NOD vs. C57BL/6) | ANOVA p-value |
|---|---|---|
| Mir5103 | 1.15 | 0.000783 |
| Mir6980 | 1.32 | 0.001285 |
| Mir6403 | 1.22 | 0.002286 |
| Mir1a-1 | 1.21 | 0.004198 |
| Mir7003 | 1.20 | 0.007257 |
| Mir744 | 1.15 | 0.009597 |
| Mir3085 | 1.59 | 0.009612 |
| Mir374c | 1.20 | 0.009665 |
| Mir1905 | 1.15 | 0.010847 |
| Mir7069 | 1.20 | 0.015308 |
| Mir6396 | 1.18 | 0.017188 |
| Mirlet7j | 1.19 | 0.017254 |
| Mir99a | 1.22 | 0.021452 |
| Mir125b-1 | 1.11 | 0.024741 |
| Mir3090 | 1.29 | 0.030353 |
| Mir6991 | 1.43 | 0.034347 |
| Mir7652 | 1.19 | 0.035569 |
| Mir1934 | 1.43 | 0.037478 |
| Mir697 | 1.20 | 0.038232 |
| Mir7680 | 1.13 | 0.038836 |
| Mir883a | 1.31 | 0.042102 |
| Mir6420 | 1.36 | 0.047160 |
| Mir6947 | 1.25 | 0.049832 |

*FIG. 2E*

| Gene Symbol | Fold Change in KLS (linear) (NOD vs. C57BL/6) | ANOVA p-value |
| --- | --- | --- |
| Mir3970 | -1.07 | 0.004263 |
| Mir143hg | -1.08 | 0.005565 |
| Mir3105 | -1.21 | 0.006781 |
| Mir297b | -1.64 | 0.012577 |
| Mir26b | -1.17 | 0.013327 |
| Mir6351 | -1.04 | 0.017714 |
| Mir105 | -1.12 | 0.018491 |
| Mir599 | -1.19 | 0.019421 |
| Mir487b | -1.12 | 0.019875 |
| Mir206 | -1.04 | 0.019993 |
| Mir6374 | -1.29 | 0.022005 |
| Mir7078 | -1.22 | 0.023855 |
| Mir1935 | -1.05 | 0.024732 |
| Mir467c | -1.34 | 0.026936 |
| Mir467e | -1.49 | 0.030203 |
| Mir182 | -1.09 | 0.032037 |
| Mir6372 | -1.07 | 0.034827 |
| Mir6931 | -1.73 | 0.036027 |
| Mir7660 | -1.43 | 0.042443 |
| Mir344d-1 | -1.06 | 0.042523 |
| Mirlet7c-2 | -1.04 | 0.043381 |
| Mir1928 | -1.12 | 0.045996 |
| Mir1190 | -2.10 | 0.046372 |
| Mir466b-3 | -1.14 | 0.049132 |
| Mir7015 | -1.33 | 0.049148 |

*FIG. 2F*

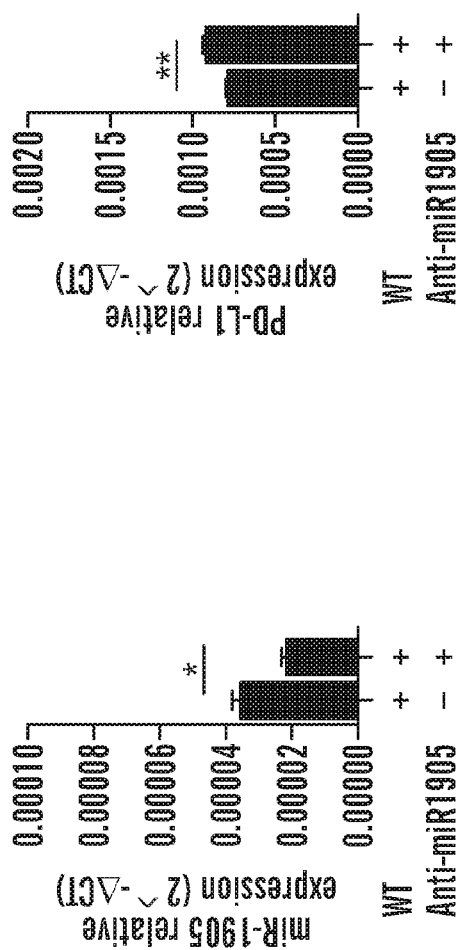
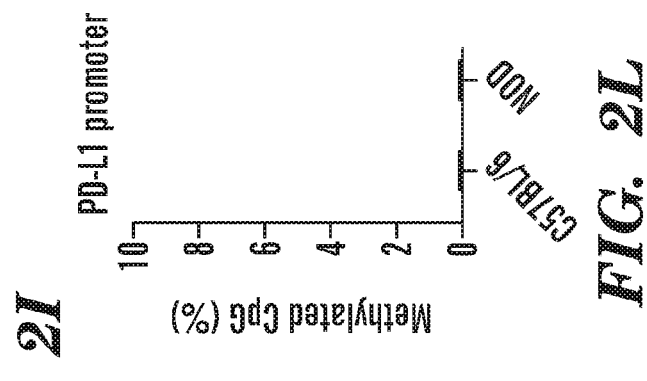
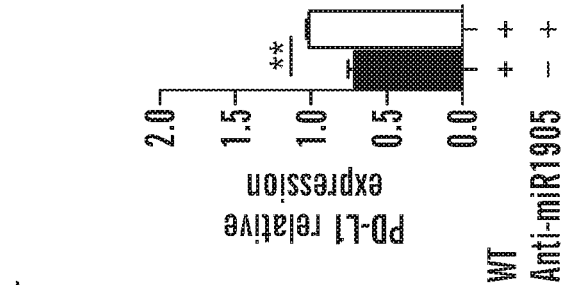
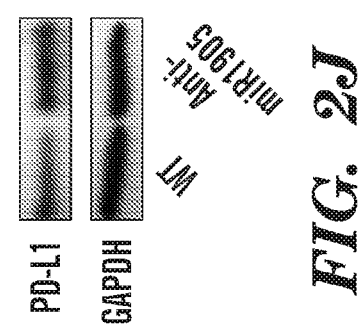
FIG. 2H
FIG. 2I
FIG. 2J
FIG. 2K
FIG. 2L

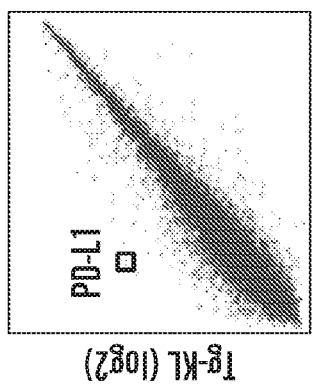
*FIG. 3F*
| Gene Symbol | Tg | Mock | Fold Change |
|---|---|---|---|
| CD274 (PD-L1) | 14.12 | 5.77 | 327.59 |
*FIG. 3G*
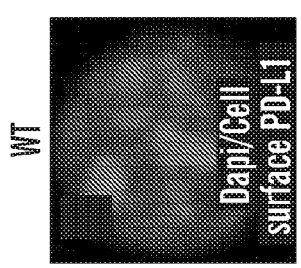
*FIG. 3D*
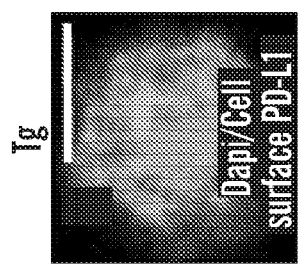
*FIG. 3E*

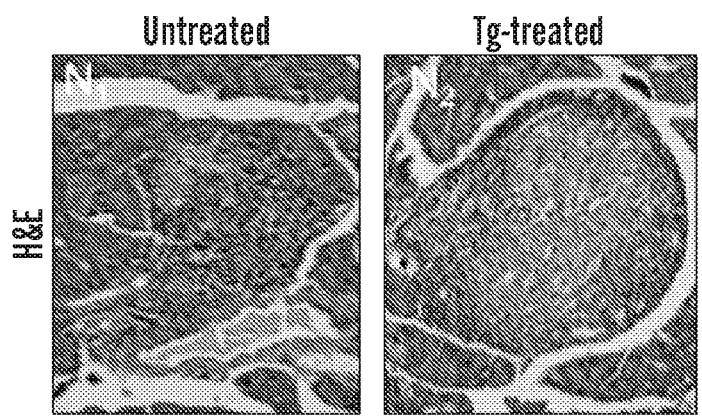
FIG. 3N1  FIG. 3N2
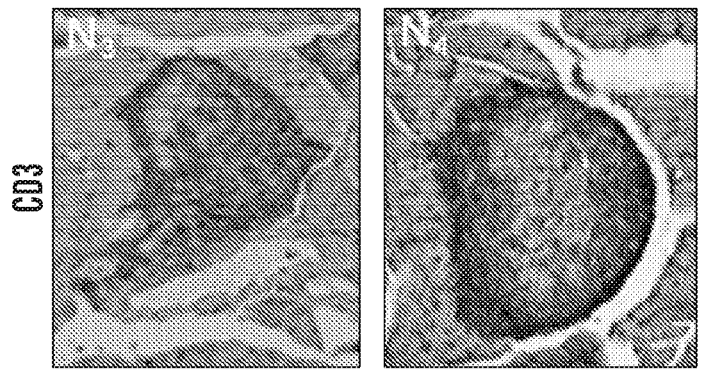
FIG. 3N3  FIG. 3N4
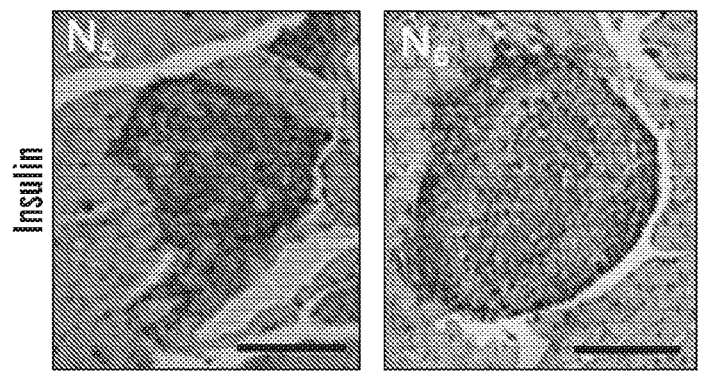
FIG. 3N5  FIG. 3N6

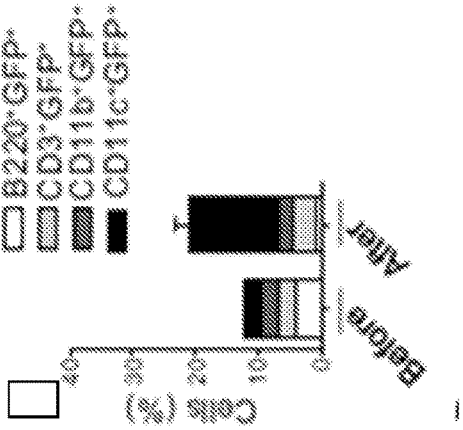
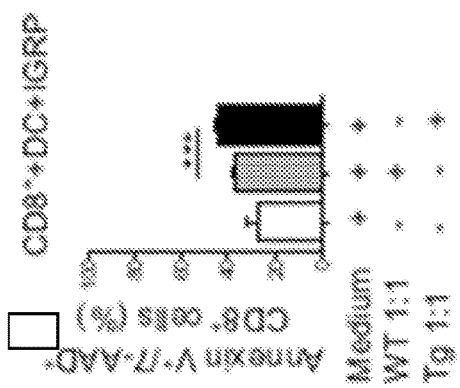
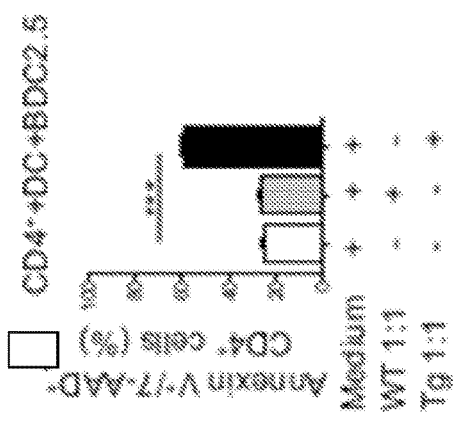
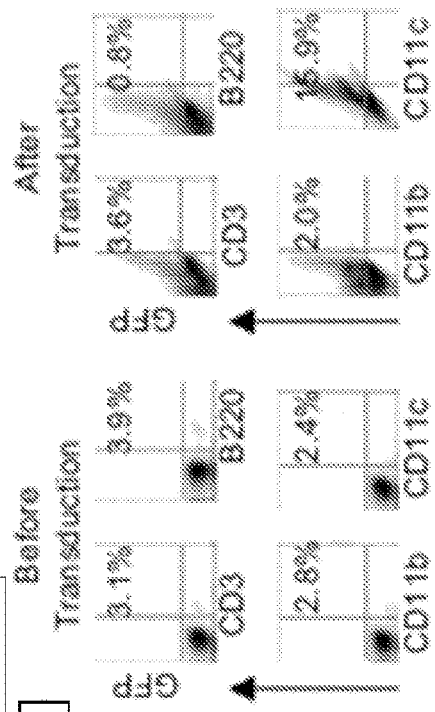

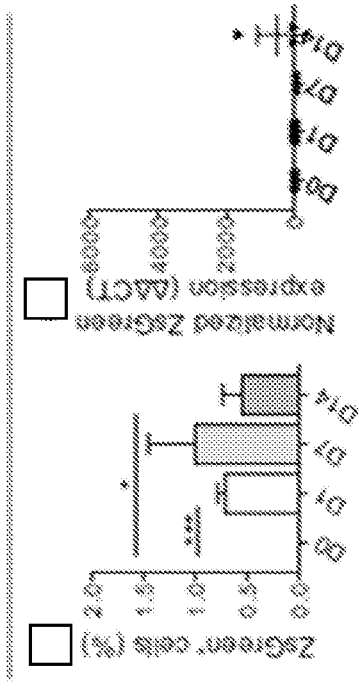
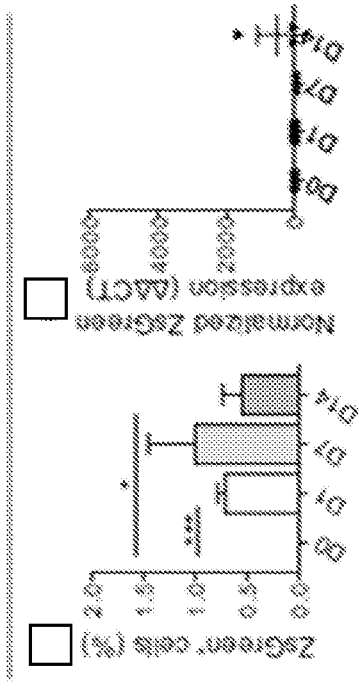
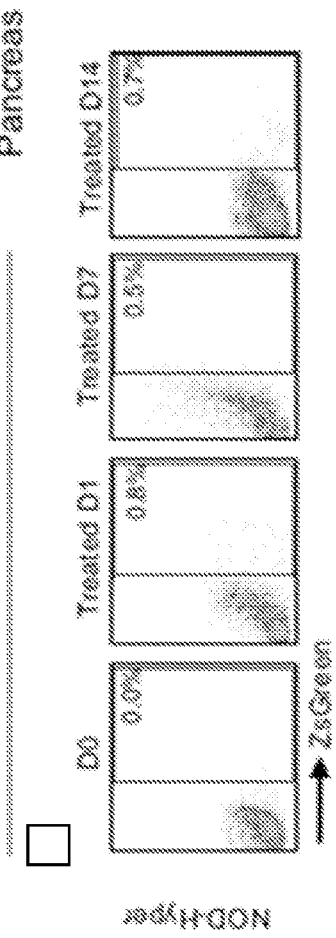
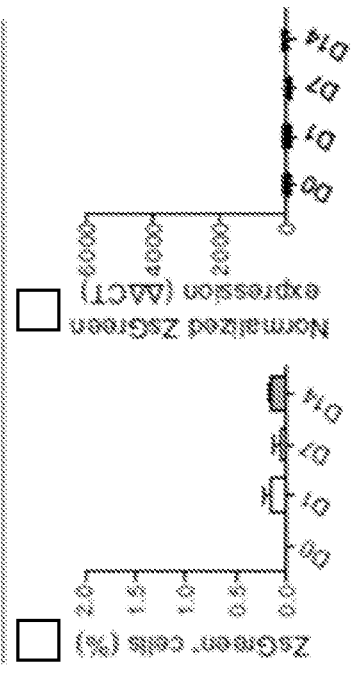
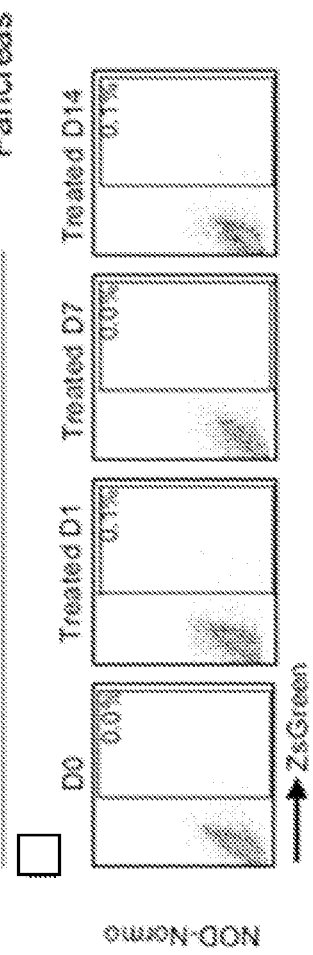

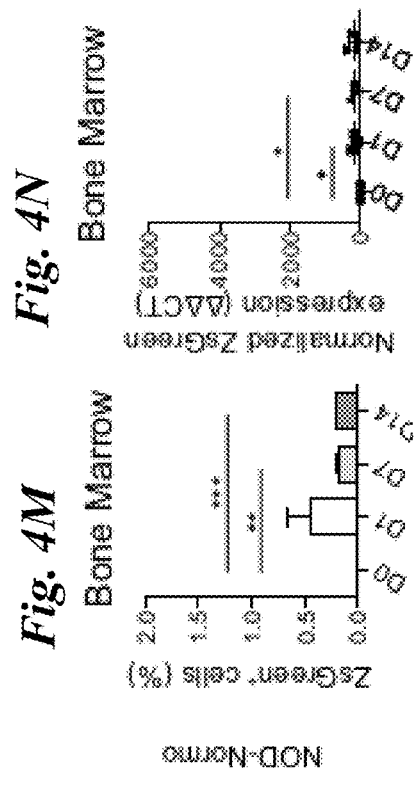
*Fig. 4K* *Fig. 4L* *Fig. 4M* *Fig. 4N*
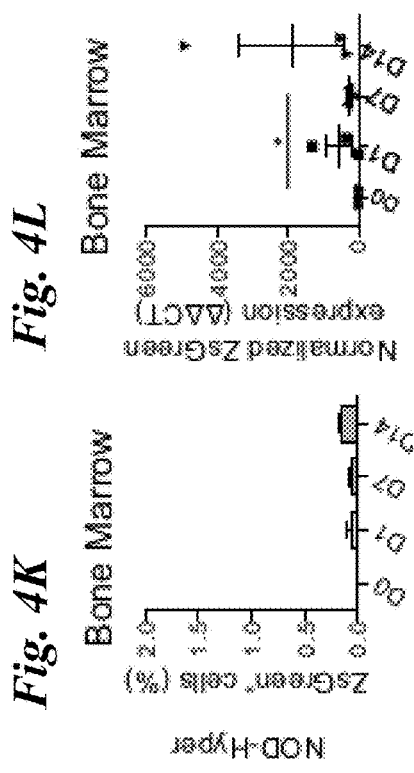
*Fig. 4O* *Fig. 4P* *Fig. 4Q* *Fig. 4R*
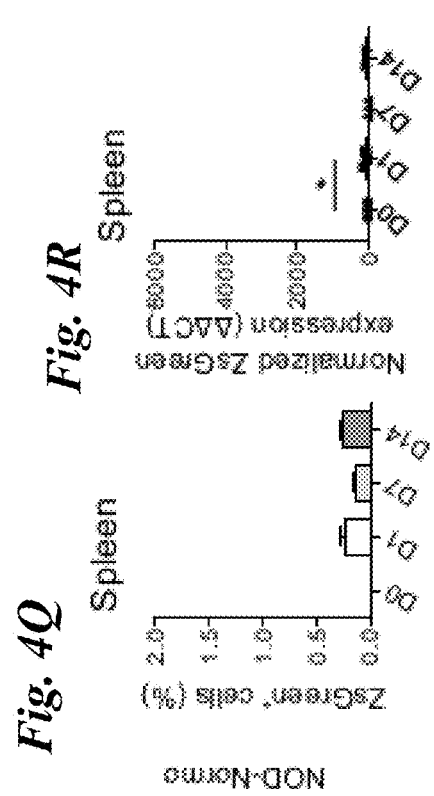
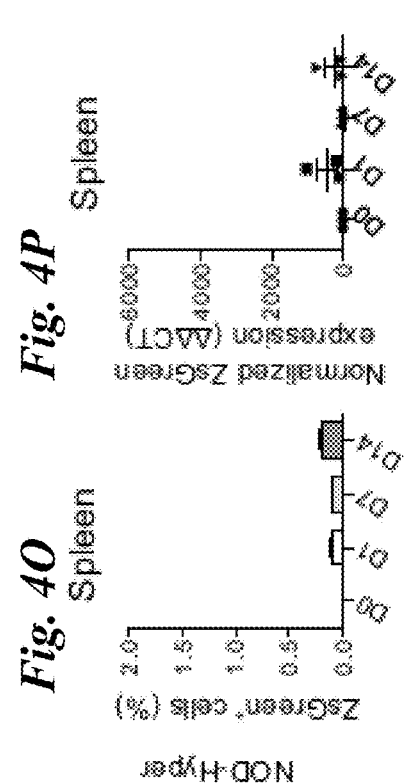

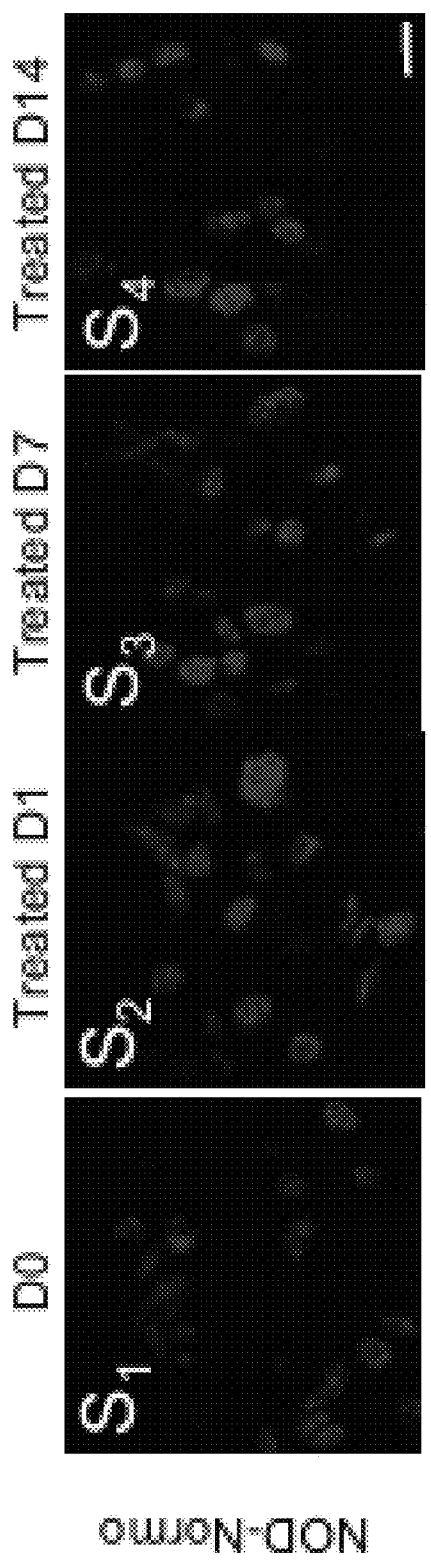
Fig. 4S1-4S4
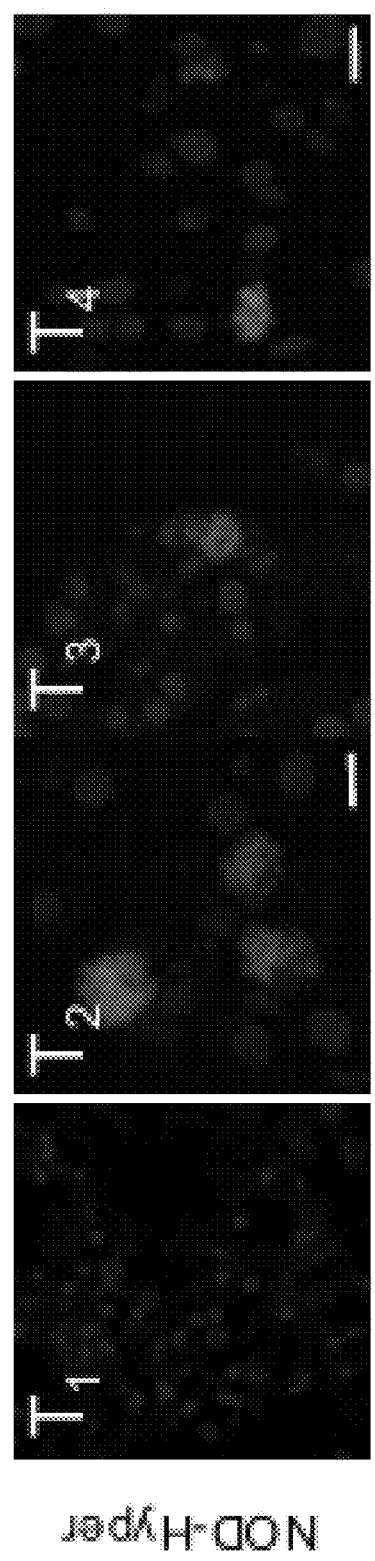
Fig. 4T1-4T4

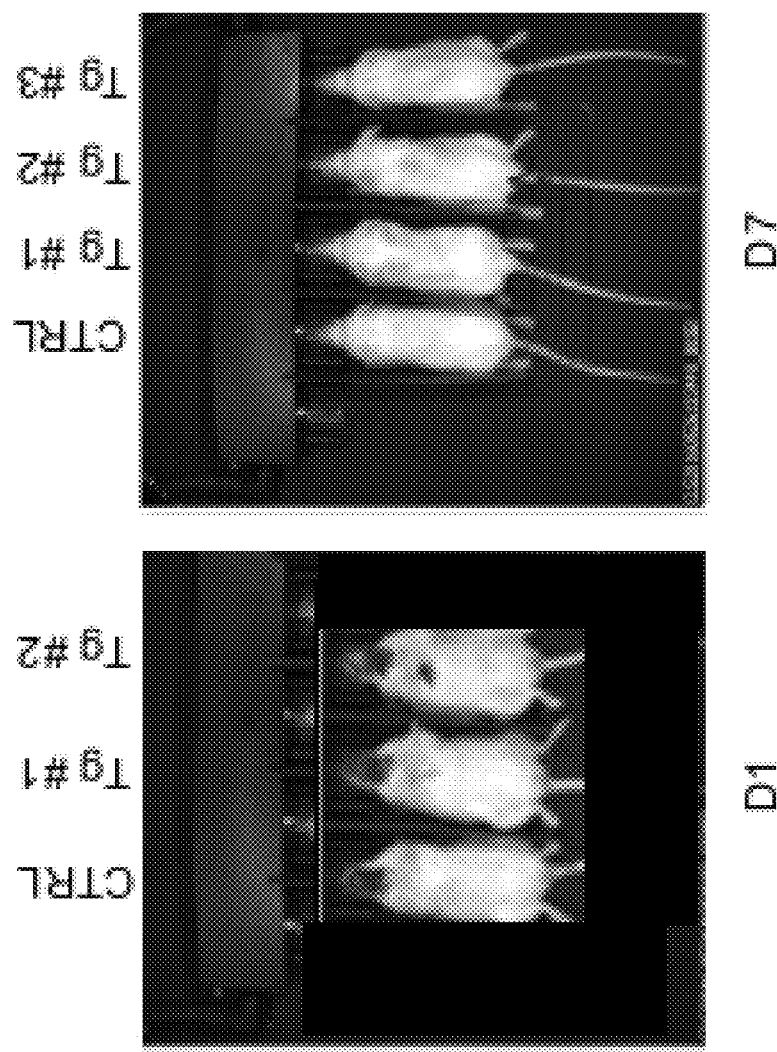

| Receptor | TLR26 | TLR1/2 | TLR2 | TLR9 |
|---|---|---|---|---|
| Ligand | FSL1 | Pam3 | HKLM | PamFC |
| Conc | ng/ml | ng/ml | cells/ml | ng/ml |
| A | 1 | 2 | 3 | 4 |
| B | 100 | 100 | $10^8$ | $10^4$ |
| C | 10 | 10 | $10^7$ | $10^3$ |
| D | 0.1 | 0.1 | $10^6$ | $10^2$ |
| E | 0.01 | 0.01 | $10^5$ | 10 |
| F | 0.001 | 0.001 | $10^4$ | 1 |
| G | 0.0001 | 0.0001 | $10^3$ | 0.1 |
| H | 0 | 0 | $10^2$ | 0.01 |
|   |   |   | 0 | 0 |

| TLR4 LPS-EB Ultrapure | TLR5 FLAST | TLR7 IMIQ | TLR7/8 R848 | TLR9 ODN 2006 | TLR9 ODN 2216 | NOD1 C12-iE-DAP | NOD2 MDP |
|---|---|---|---|---|---|---|---|
| ng/ml | ng/ml | ng/ml | ng/ml | ng/ml | ng/ml | ng/ml | ng/ml |
| 5 | 6 | 7 | 8 | 9 | 10 | 11 | 12 |
| $10^3$ | 100 | $10^4$ | $10^4$ | $10^4$ | $10^4$ | $10^4$ | $10^4$ |
| $10^2$ | 10 | $10^3$ | $10^3$ | $10^3$ | $10^3$ | $10^3$ | $10^3$ |
| 10 | 0 | $10^2$ | $10^2$ | $10^2$ | $10^2$ | $10^2$ | $10^2$ |
| 1 | 0.1 | 10 | 10 | 10 | 10 | 10 | 10 |
| 0.1 | 0.001 | 1 | 1 | 1 | 1 | 1 | 1 |
| 0.01 | 0.0001 | 0.1 | 0.1 | 0.1 | 0.1 | 0.1 | 0.1 |
| 0.001 | 0.00001 | 0.01 | 0.01 | 0.01 | 0.01 | 0.01 | 0.01 |
| 0 | 0 | 0 | 0 | 0 | 0 | 0 | 0 |

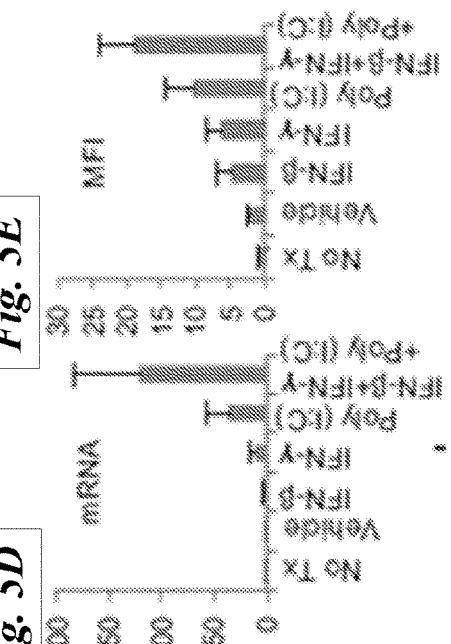

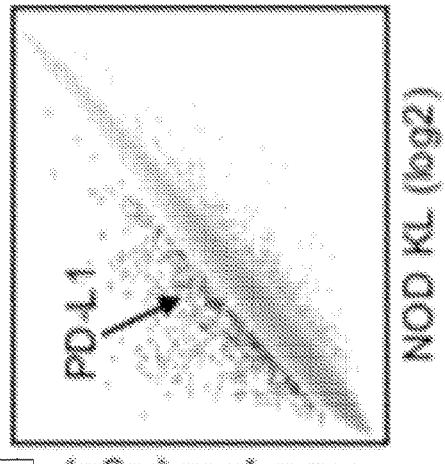
*Fig. 5K*
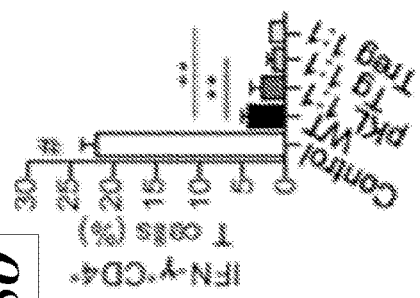
*Fig. 5L*
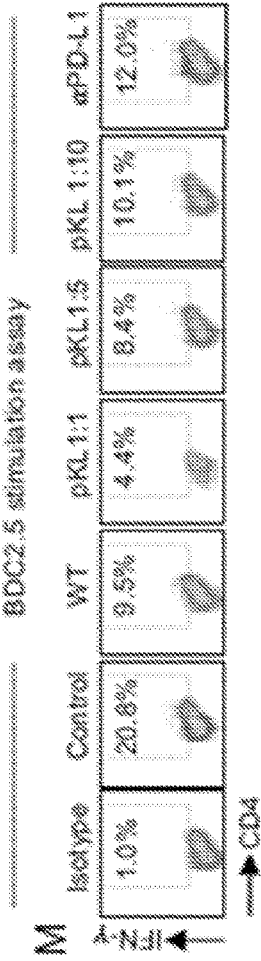
*Fig. 5O*
*Fig. 5N*
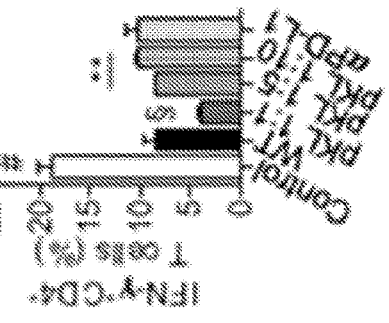
*Fig. 5M*

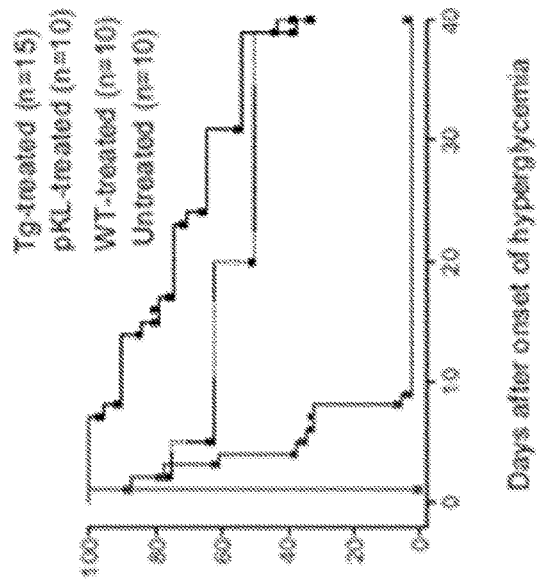
Fig. 6B
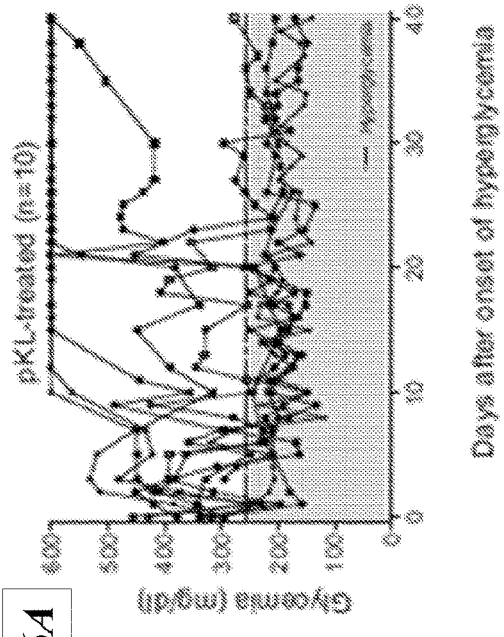
Fig. 6A
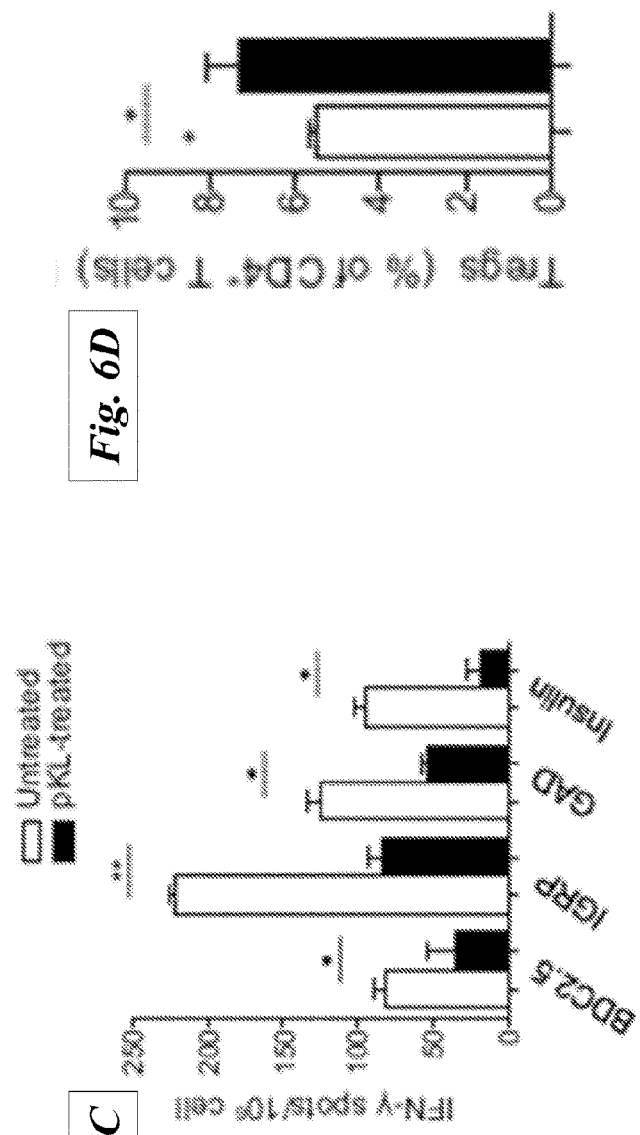
Fig. 6D
Fig. 6C

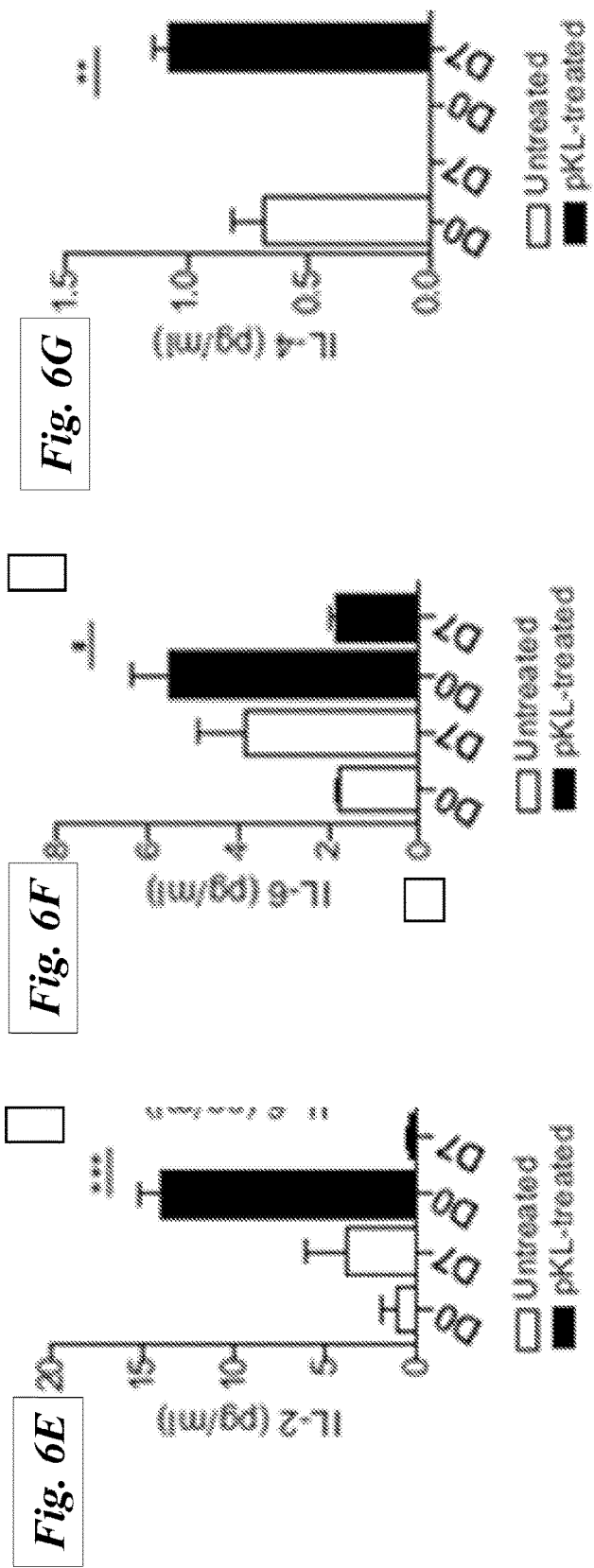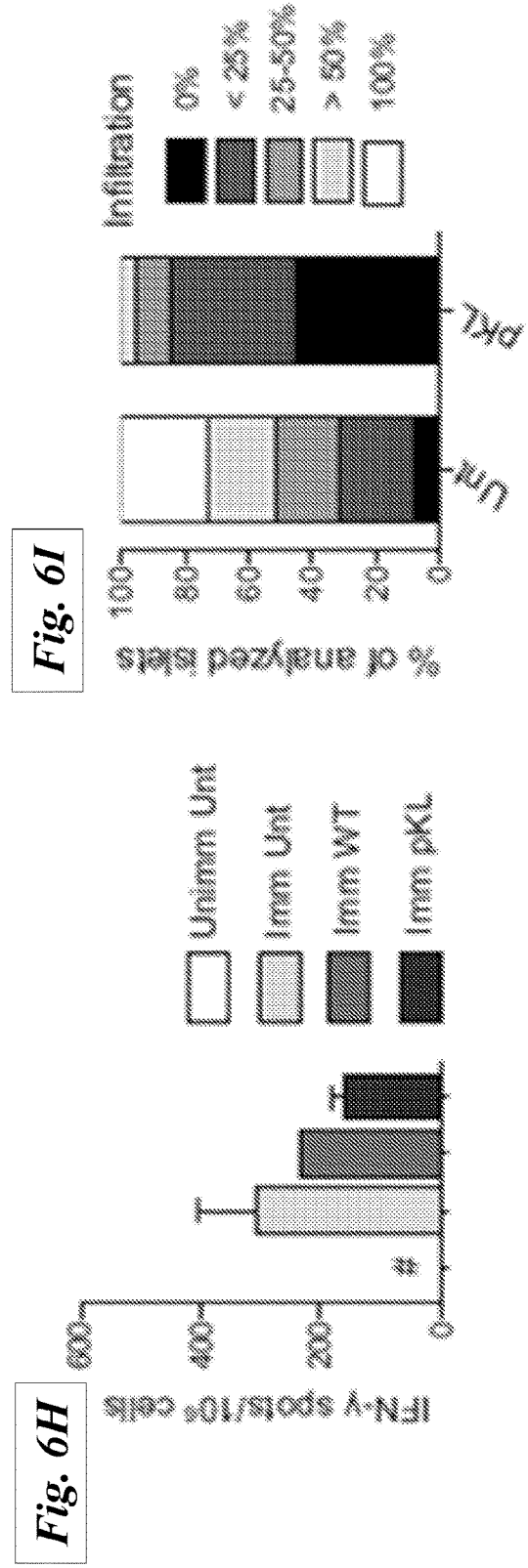

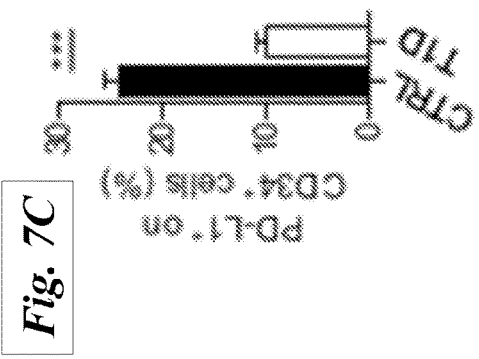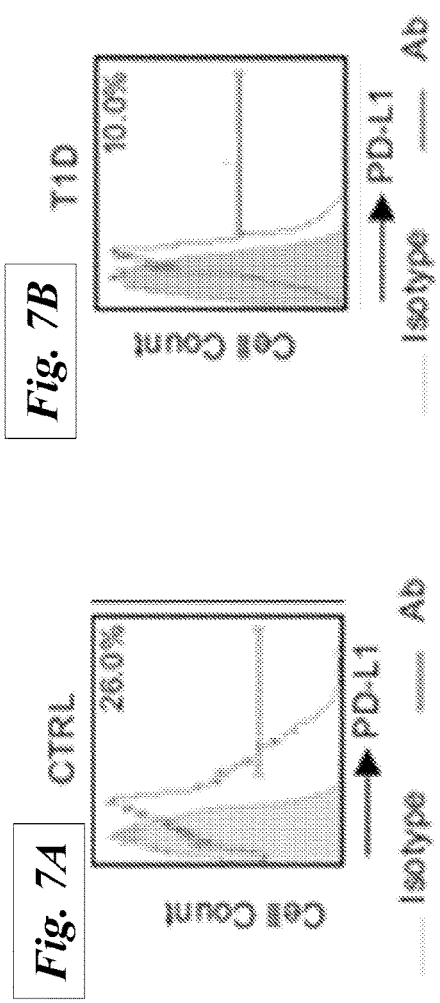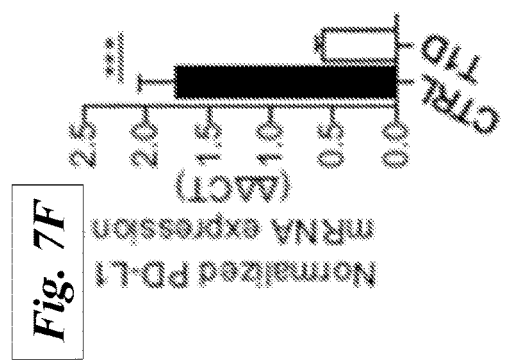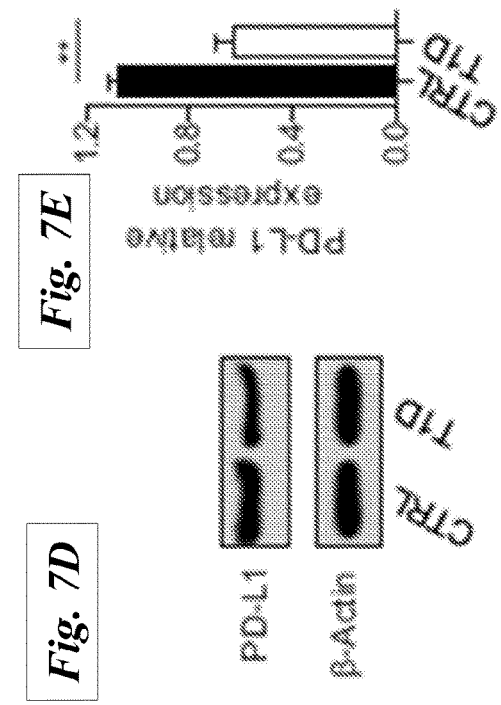

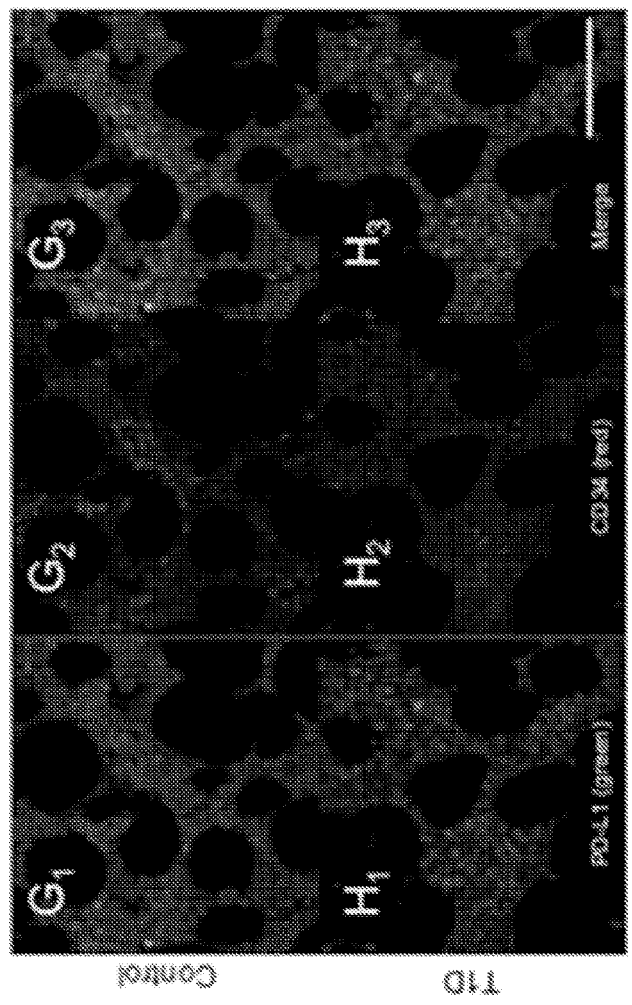
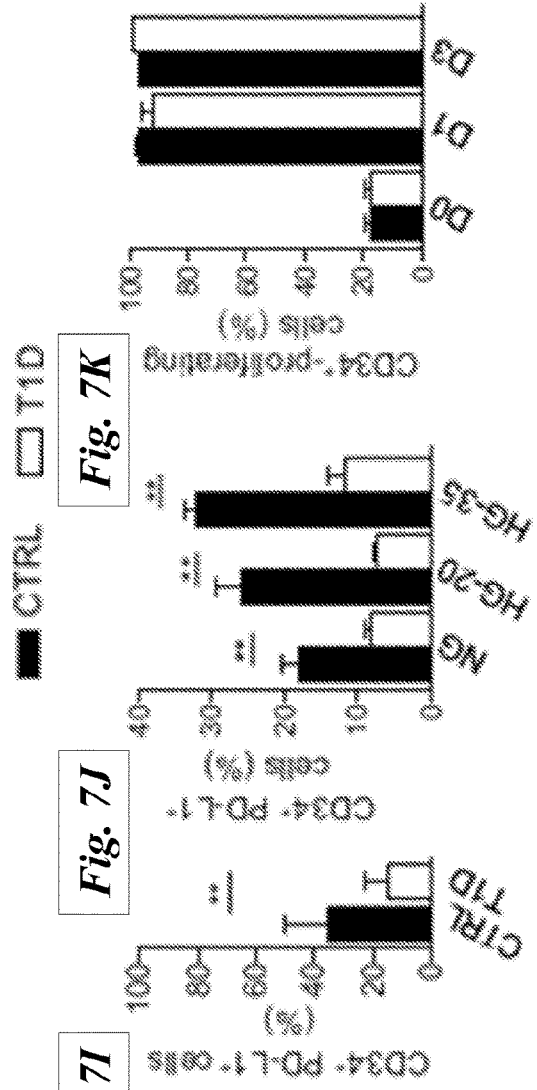
Fig. 7G
Fig. 7H
Fig. 7I
Fig. 7J
Fig. 7K

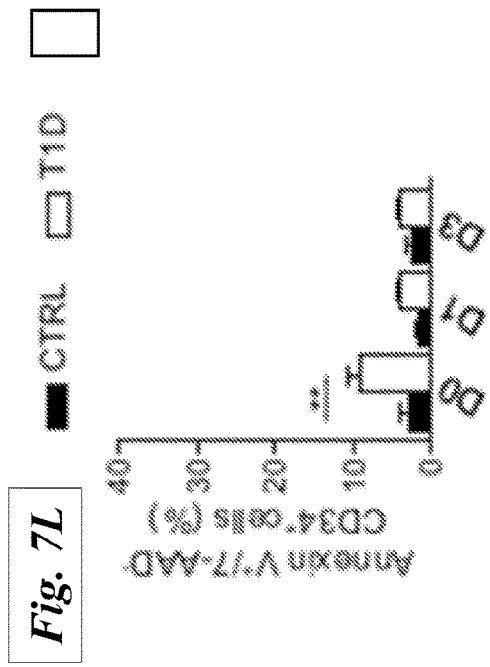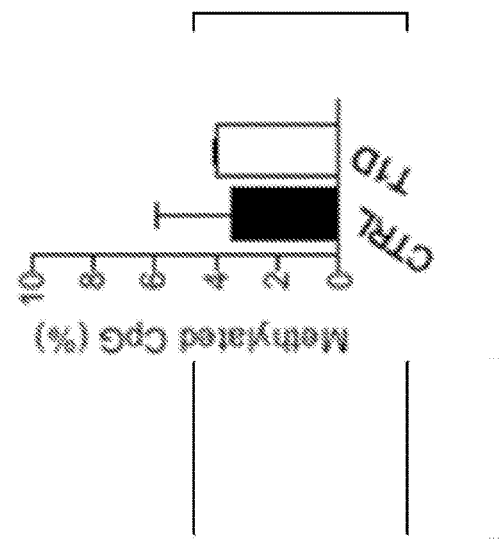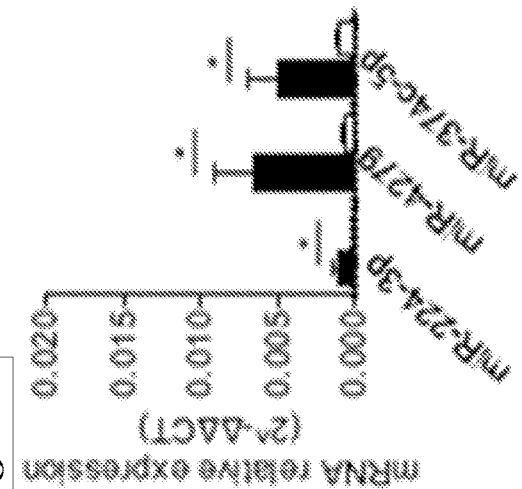
Fig. 7M
Fig. 7L
Fig. 7N
Fig. 7O

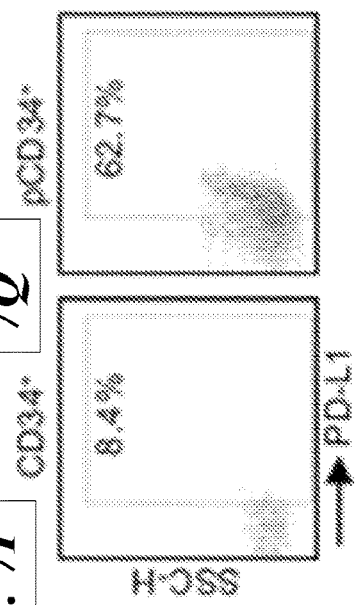
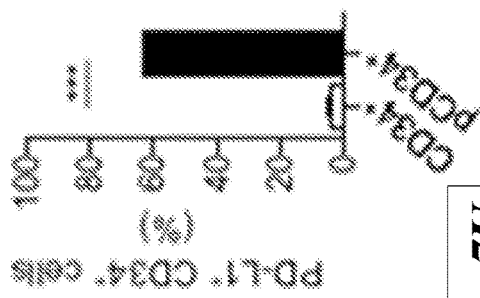
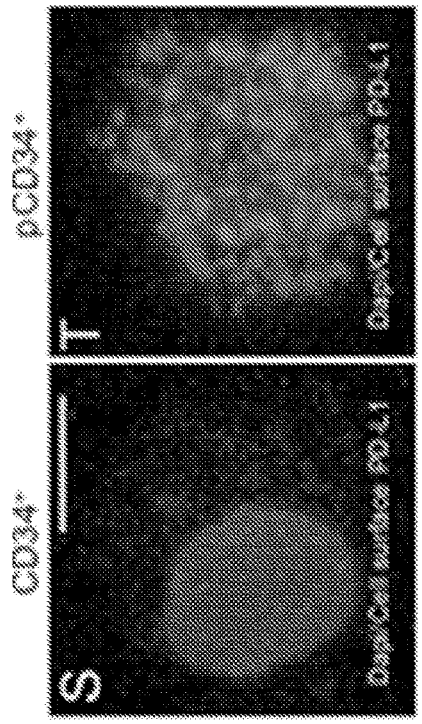
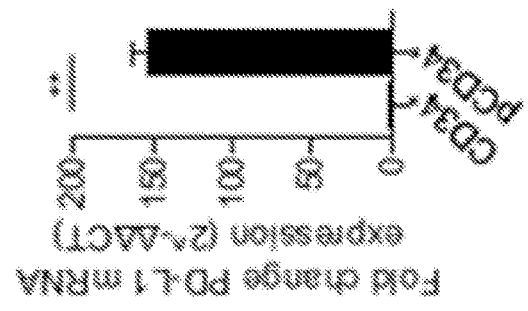

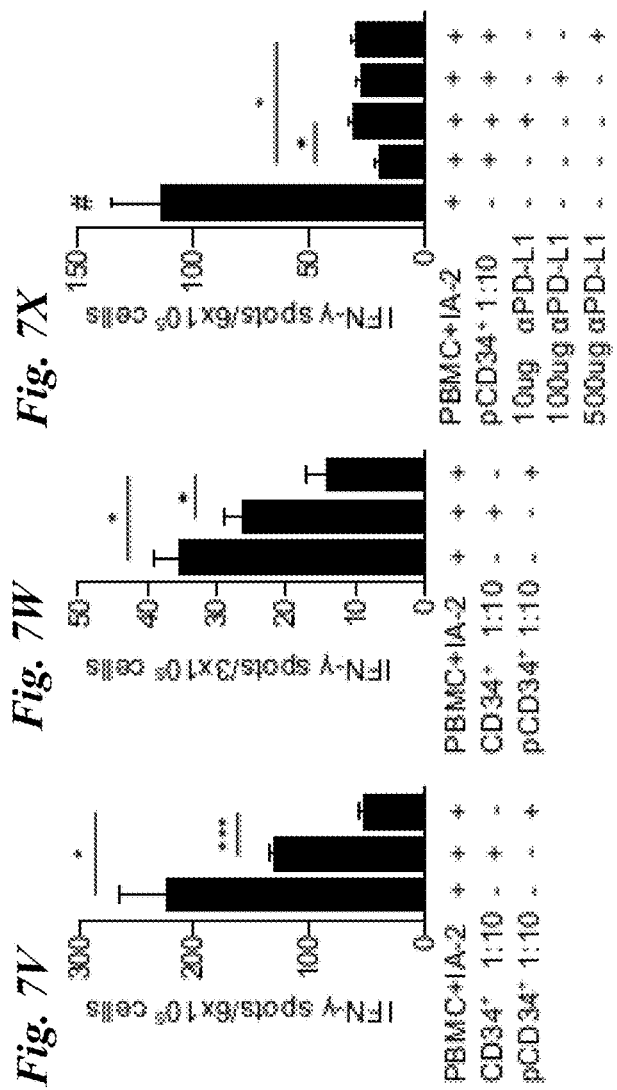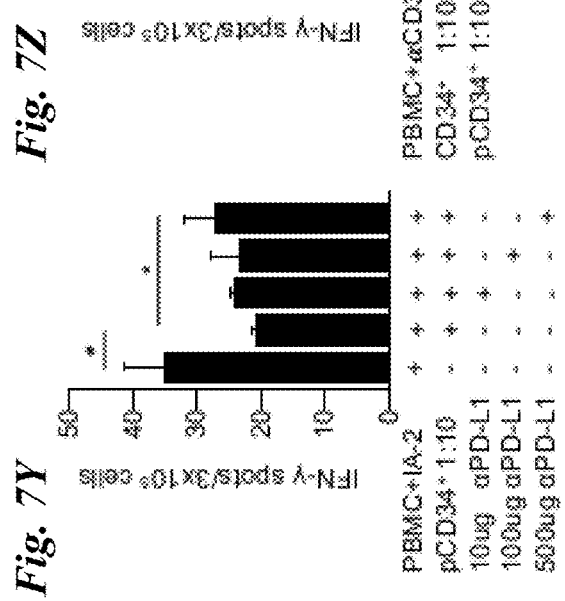

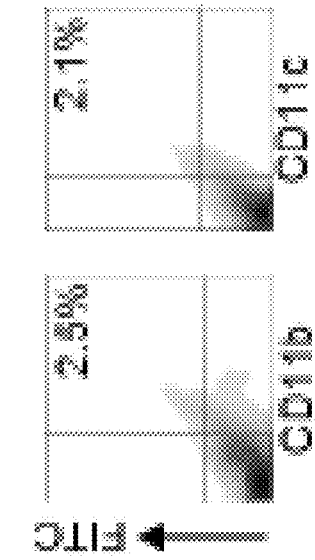
Fig. 9F Pancreas
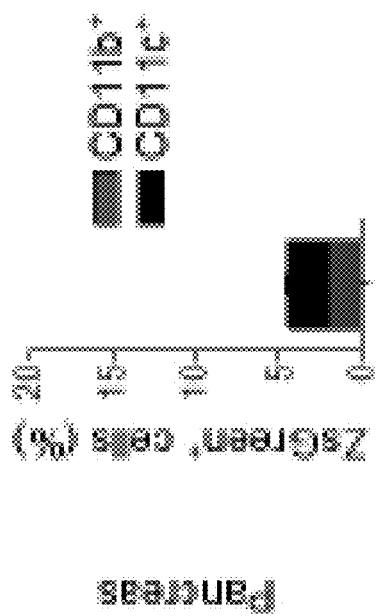
Fig. 9G
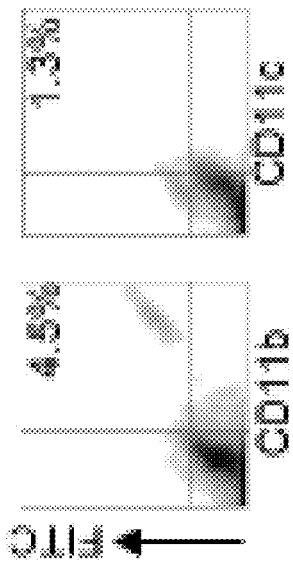
Fig. 9H PLN
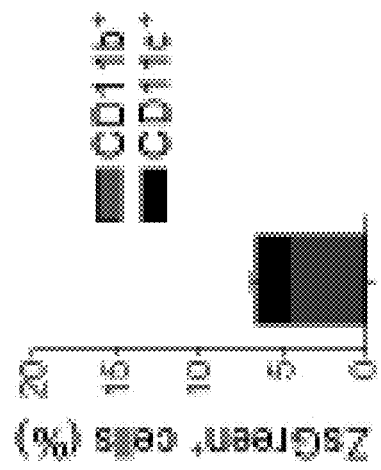
Fig. 9I

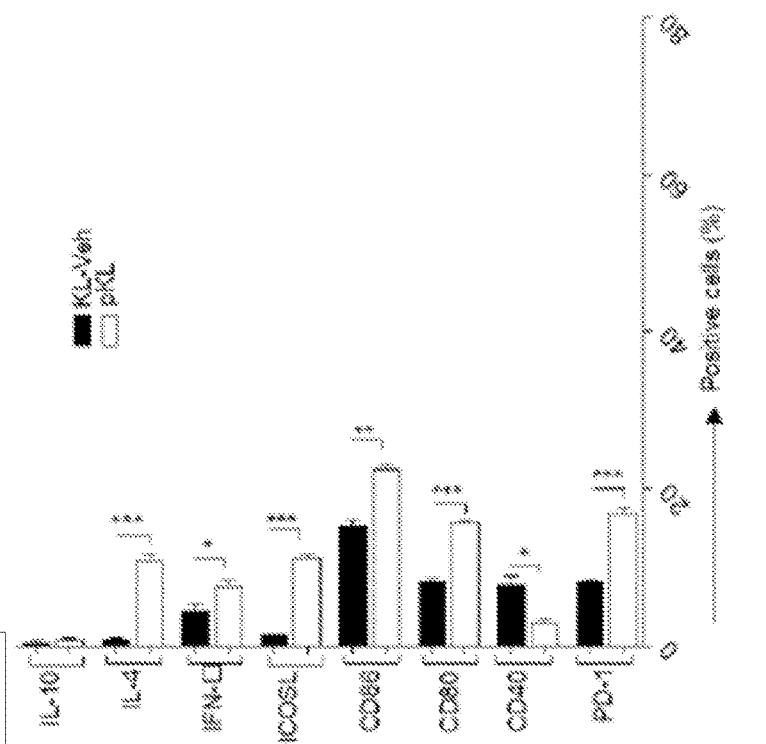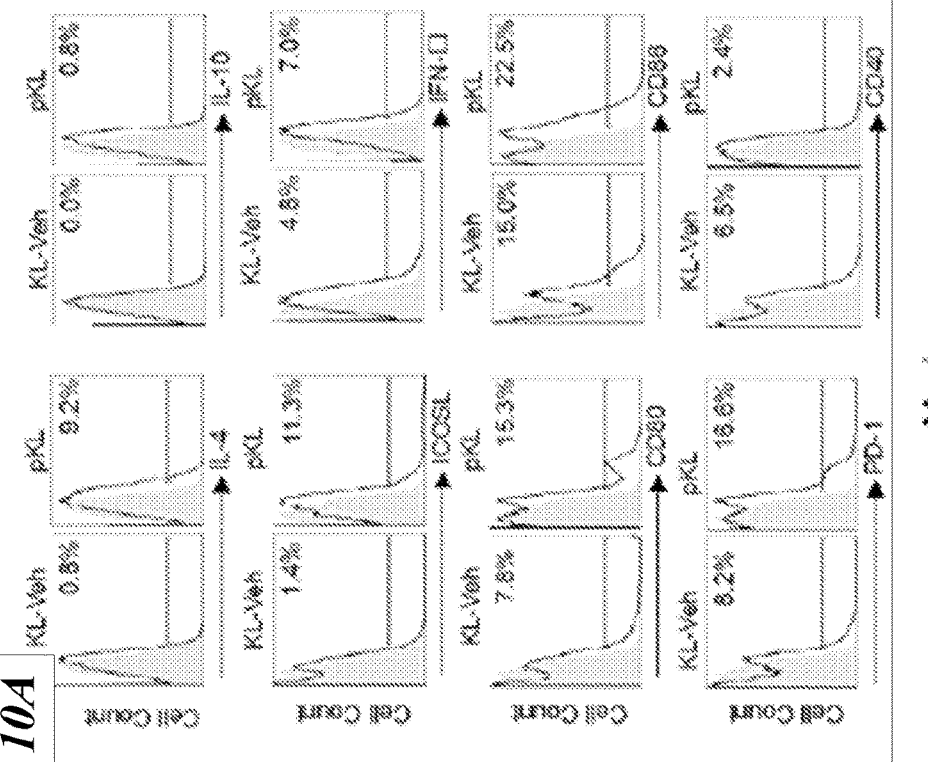

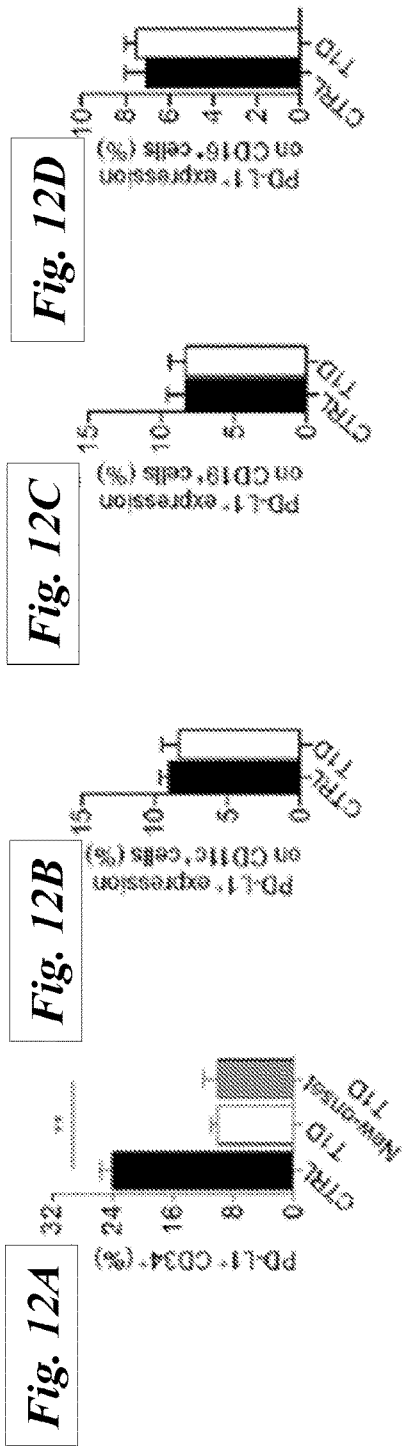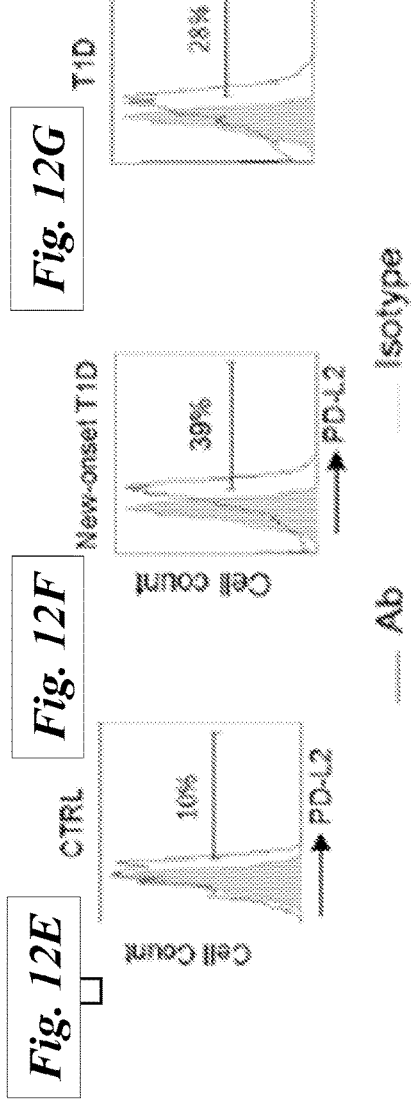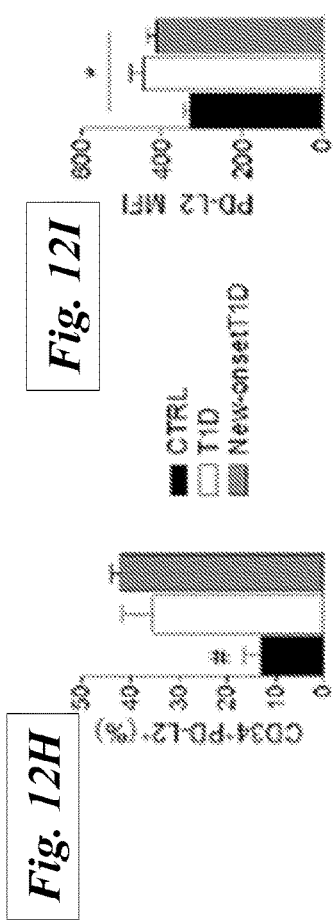

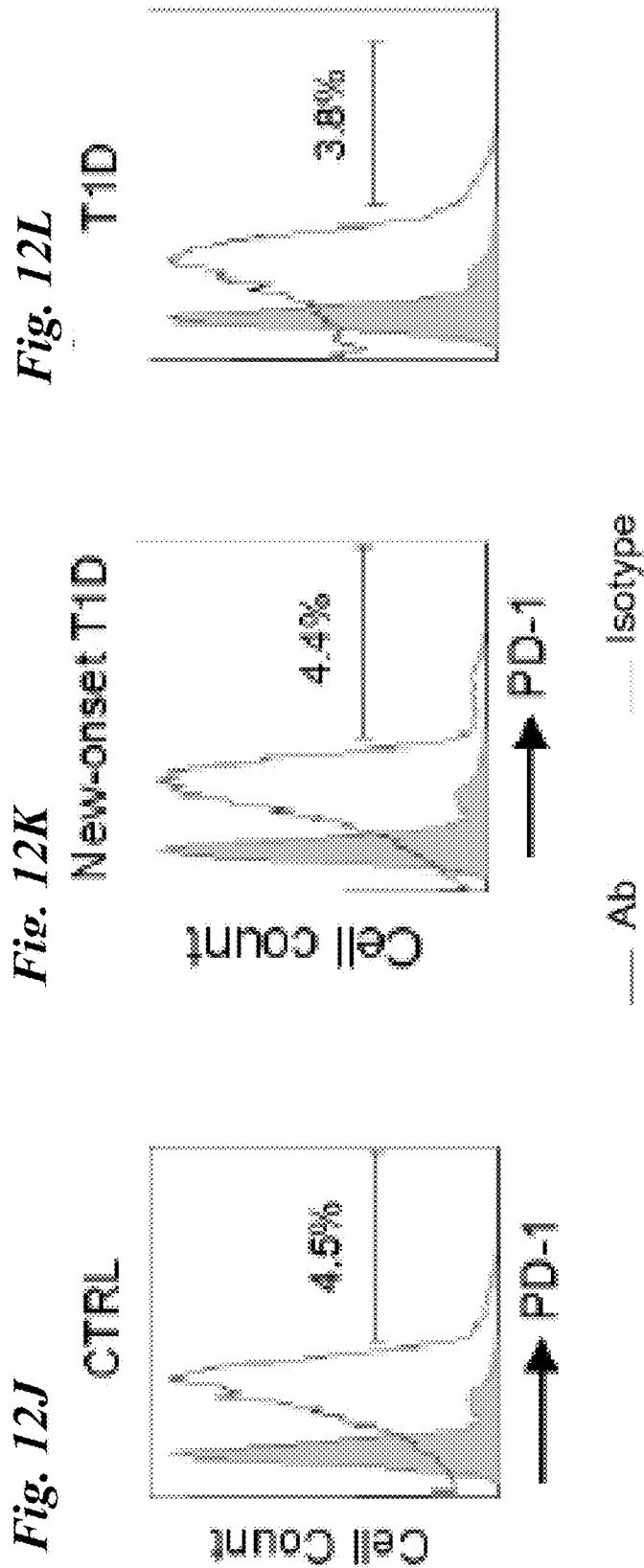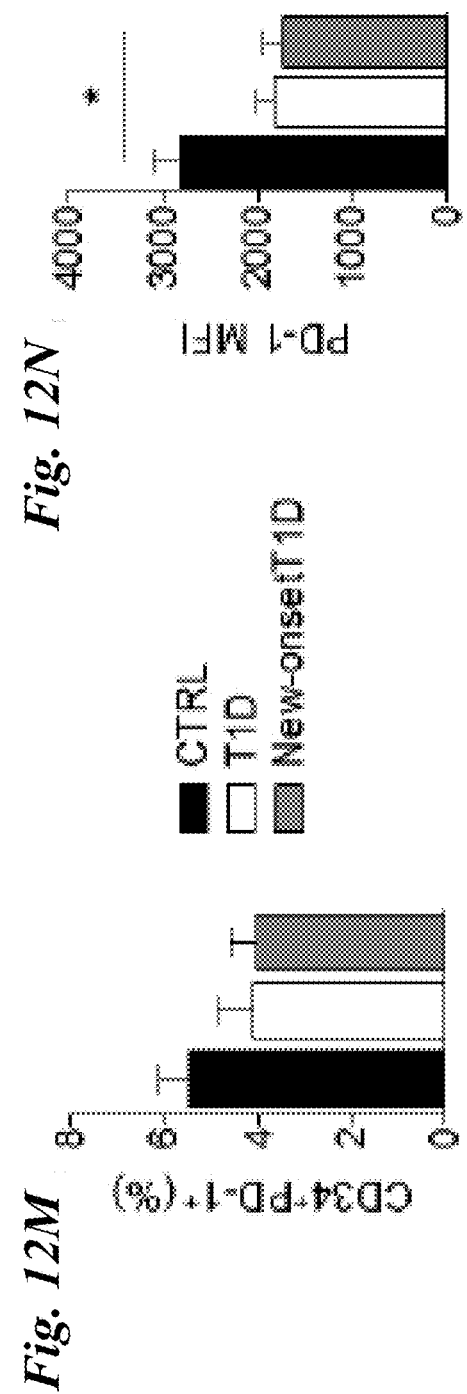

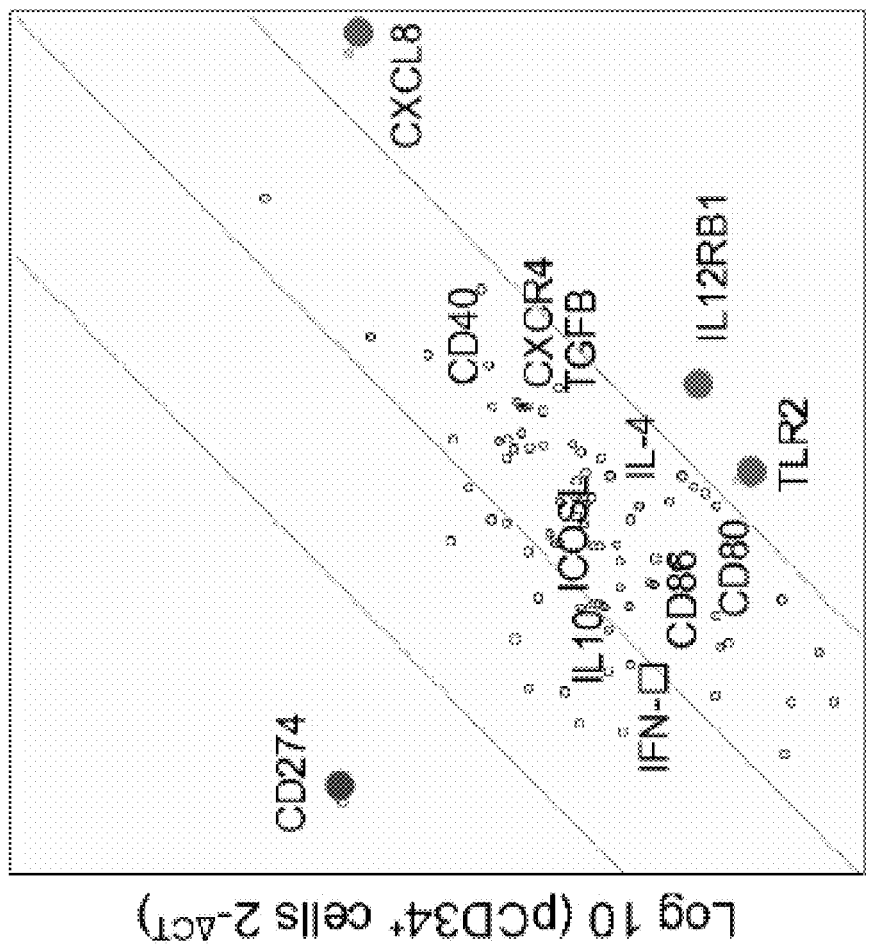

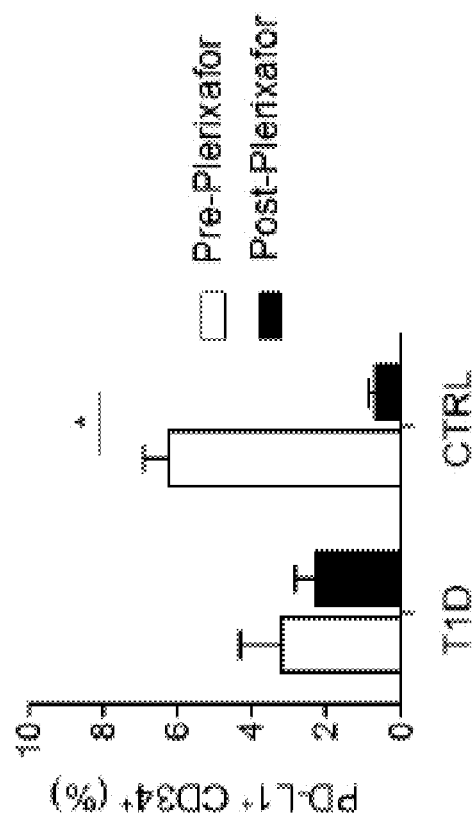
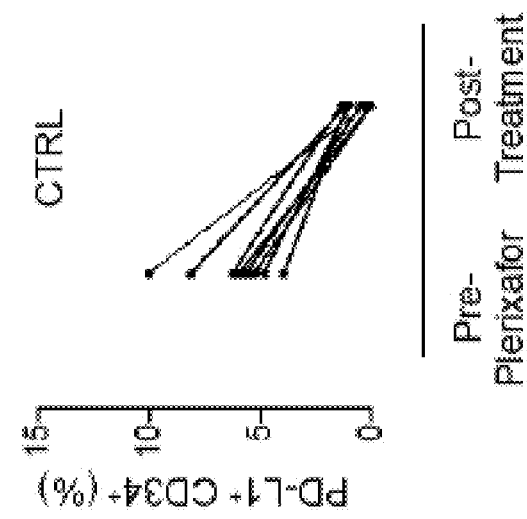
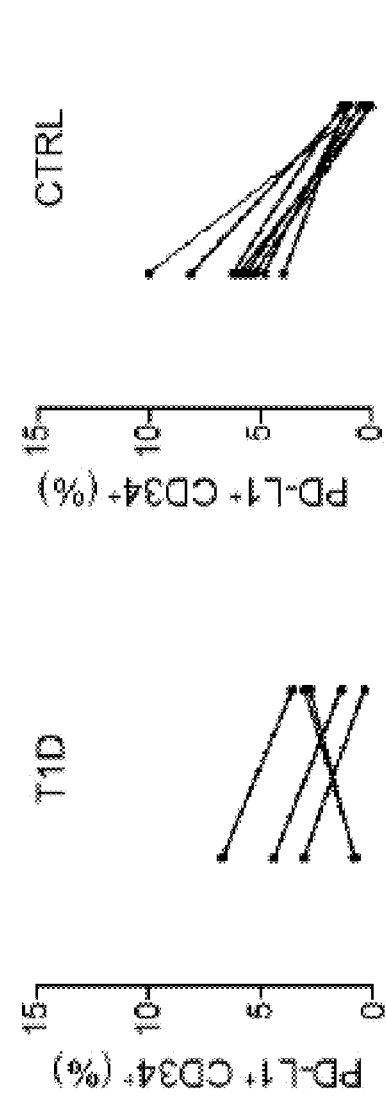
Fig. 15A
Fig. 15B
Fig. 15C

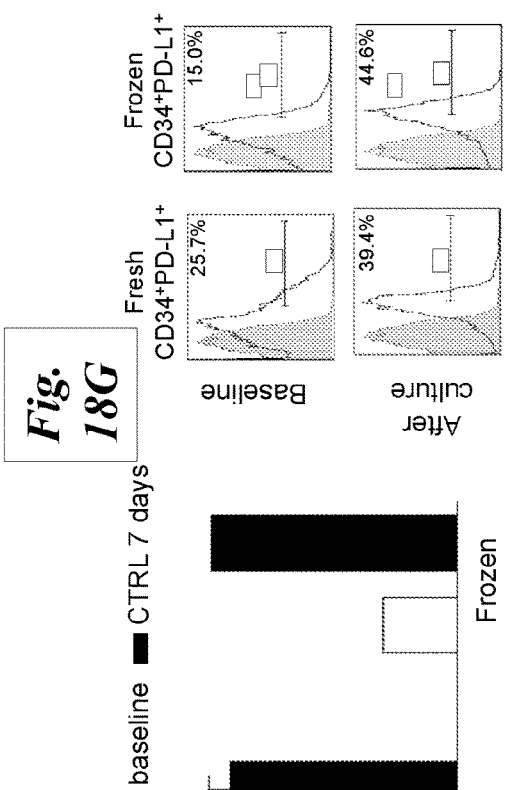
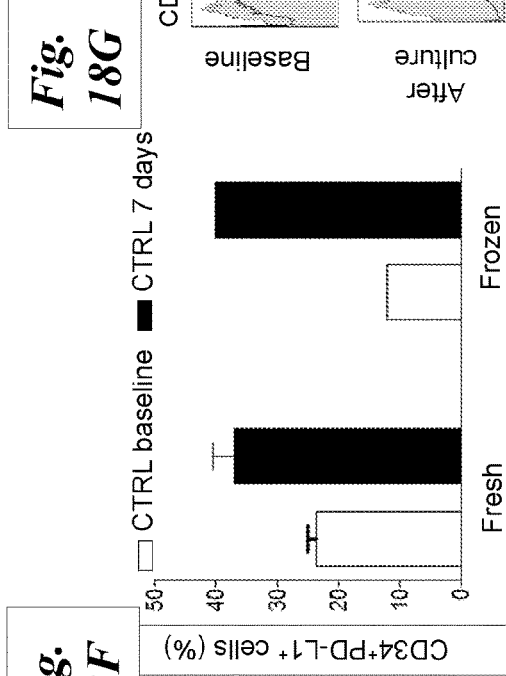
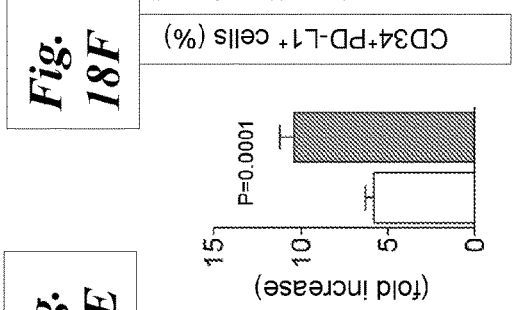
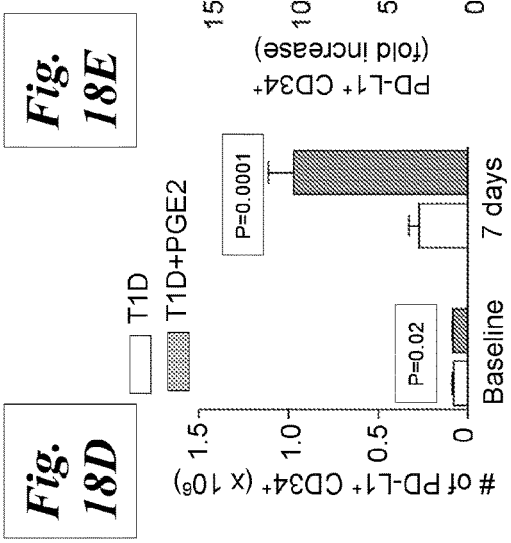
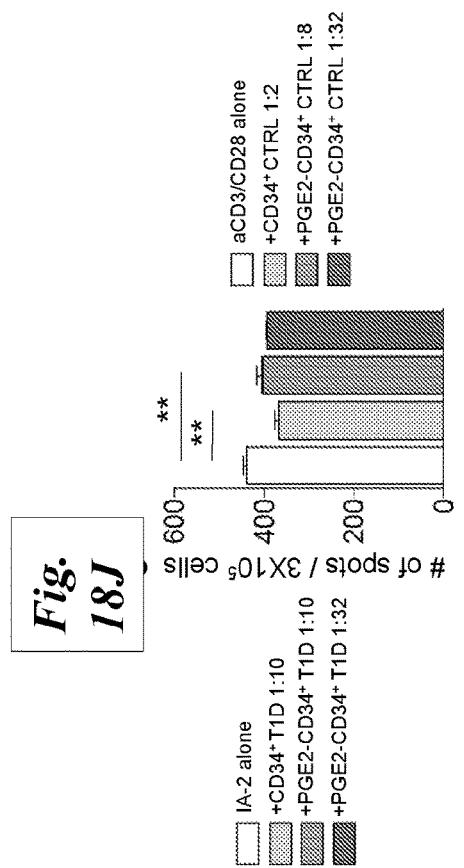

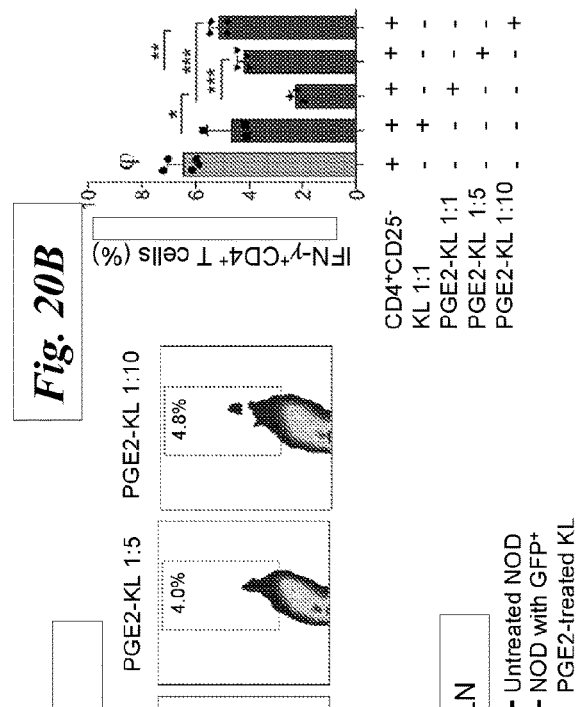
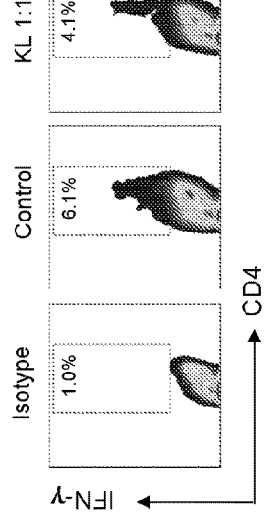
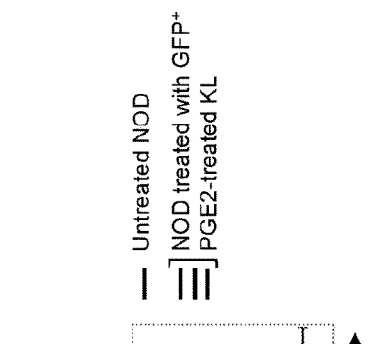
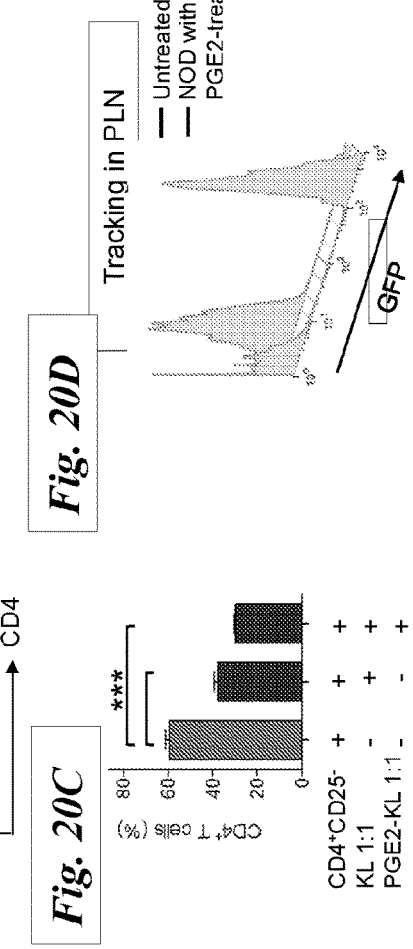
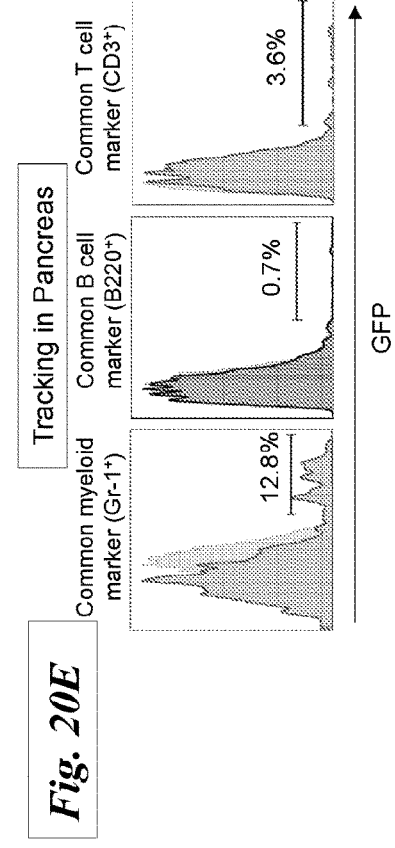

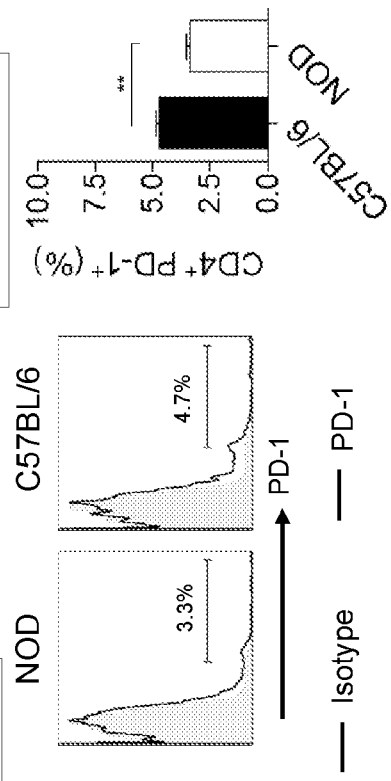
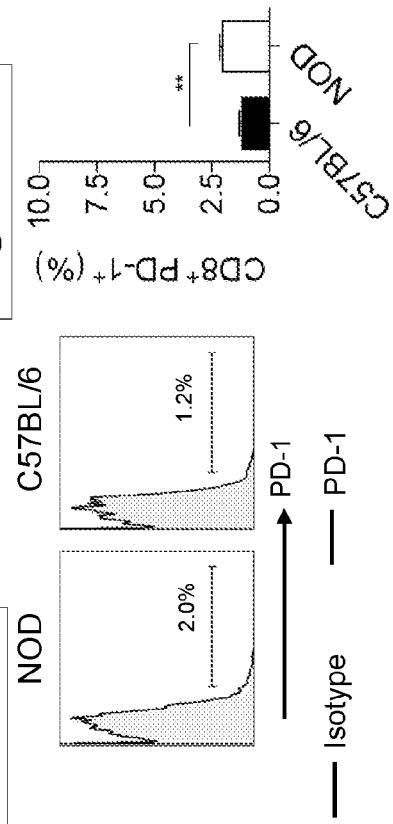
Fig. 21A  Fig. 21B  Fig. 21C  Fig. 21D

TREATMENT OF TYPE 1 DIABETES AND AUTOIMMUNE DISEASES OR DISORDERS

CROSS-REFERENCE TO RELATED APPLICATION

This application is a 35 U.S.C. § 371 National Phase Entry Application of International Application No. PCT/US2018/052198 filed Sep. 21, 2018, which designates the U.S. and claims benefit under 35 U.S.C. § 119(e) of the U.S. Provisional Application No. 62/562,111 filed Sep. 22, 2017; and U.S. Provisional Application No. 62/663,367 filed Apr. 27, 2018, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Nov. 29, 2018, is named 701039-090260WOPT_SL.txt and is 6,085 bytes in size.

FIELD OF THE DISCLOSURE

This invention relates to treatment or autoimmune diseases or disorders.

BACKGROUND

Since the search for feasible and safe immunological approaches to re-establish tolerance toward islet auto-antigens and preserve β-cell function in type 1 diabetes (T1D) began, very little progress has been made (1). However, most immunotherapies tested thus far are simply broadly immunosuppressive and are not clearly linked to any immunological abnormalities detected in T1D (2). Thus, the development of an effective treatment that is specific for an autoimmune diseases and disorder, e.g., T1D, is essential.

SUMMARY

Immunologically-based clinical trials performed thus far have failed to cure type 1 diabetes (T1D), in part because these approaches were nonspecific. Transplantation of hematopoietic stem and progenitor cells (HSPCs) has been recently offered as a therapy for T1D. Interestingly, transcriptomic profiling of HSPCs revealed that these cells are deficient in PD-L1 in the T1D NOD mouse model. It was therefore sought to determine whether genetic/pharmacological restoration of this defect would cure T1D.

Genetically engineered (or pharmacologically modulated) HSPCs overexpressing PD-L1 (PD-L1 Tg HSPCs) inhibited the autoimmune response in vitro, reverted diabetes in newly hyperglycemic NOD mice in vivo, and homed to the pancreas of hyperglycemic NOD mice. The PD-L1 expression defect was confirmed in human HSPCs in T1D patients as well, and pharmacologically modulated human HSPCs also inhibited the autoimmune response in vitro. Targeting a specific immune checkpoint defect in HSPCs thus contributes to establishing a therapeutic for T1D.

One aspect of the invention described herein provides an ex vivo method of producing a population of modified, PD-L1+ expressing hematopoietic stem cells (HSCs) comprising modulating the expression of miRNAs controlling the expression of PD-L1 in the HSCs.

In one embodiment of any aspect, the modulation of the expression of miRNAs is increasing the expression of miRNA or decreasing the expression of miRNA.

In one embodiment of any aspect, the miRNA expression is increased by introducing an exogenous copy of a nucleic acid encoding the miRNA for the expression of the miRNA in the cell.

In one embodiment of any aspect, the miRNA expression is decreased by an agent that inhibits the expression of the miRNA. Exemplary agents include, but are not limited to an antagomir of the miRNA, an anti-miRNA oligonucleotide to the miRNA, an antisense oligonucleotide to the miRNA or a locked nucleic acid that anneals to miRNA.

In one embodiment of any aspect, the exogenous copy is introduced by a vector, such as a viral vector.

In one embodiment of any aspect, the agent is introduced into the HSC by a vector, such as a viral vector.

In one embodiment of any aspect, the miRNA is selected from the group consisting of miR-4282, miR-7853, miR-7853-5p, miR-105, miR-105-5p, miR-224, miR-224-3p, miR-4279, miR-522, miR-522-3p, miR-374c, and miR-374c-5p.

In one embodiment of any aspect, the modified, PD-L1+ expressing HSCs carries an exogenous copy of a nucleic acid encoding a miRNA selected from the group consisting of miR-4282, miR-7853, miR-7853-5p, miR-105, miR-105-5p, miR-224, miR-224-3p, miR-4279, miR-522, miR-522-3p, miR-374c, and miR-374c-5p.

Another aspect of the invention described herein provides a population of modified hematopoietic stem cells (HSCs) in which the modified cells have increased PD-L1 expression compared to control, non-modified cells, wherein the cells carry an exogenous copy of a nucleic acid encoding a miRNAs that controls the expression of programmed cell death-1 receptor ligand (PD-L1) or an agent that inhibits the expression of the miRNA, for example, an antagomir of the miRNA, an anti-miRNA oligonucleotide to the miRNA, an antisense oligonucleotide to the miRNA or a locked nucleic acid that anneals to miRNA.

In one embodiment of any aspect, the HSC cells are mammalian HSC cells. In one embodiment of any aspect, the mammalian HSC cells are human HSC cells.

In one embodiment of any aspect, prior to the modification, the HSCs are obtained from the bone marrow, umbilical cord, amniotic fluid, chorionic villi, cord blood, placental blood or peripheral blood. In one embodiment of any aspect, the HSCs are obtained from mobilized peripheral blood.

In one embodiment of any aspect, the HSCs are obtained from a healthy individual.

In one embodiment of any aspect, the HSCs are obtained from an individual with a diagnosed disease or disorder. In one embodiment of any aspect, the diagnosed disease or disorder is an autoimmune disease or disorder. In one embodiment of any aspect, the autoimmune disease or disorder is Type 1 diabetes (TID).

In one embodiment of any aspect, the HSC cells are ex vivo cultured before or after or both before and after the modification of the PD-L1 expression.

In one embodiment of any aspect, the HSC cells are cryopreserved prior to or after or both prior to and after the modification of the PD-L1 expression. In one embodiment of any aspect, the modified HSC cells are cryopreserved prior to use.

In one embodiment of any aspect, the HSC cells are produced by a method comprising: (a) contacting a sample of HSCs with a vector carrying an exogenous copy of a nucleic acid encoding miRNAs that controls the expression of programmed cell death-1 receptor ligand (PD-L1) or an agent that inhibits the expression of the miRNA such as an antagomir of the miRNA, an anti-miRNA oligonucleotide to the miRNA, an antisense oligonucleotide to the miRNA, or a locked nucleic acid that anneals to miRNA; (b) ex vivo culturing the resultant modified cells from the contacting; and (c) establishing the expression of PD-L1 on the modified HSCs, thereby producing a population of modified HSCs cells expressing PD-L1. In one embodiment, the miRNA is selected from the group consisting of miR-4282, miR-7853, miR-7853-5p, miR-105, miR-105-5p, miR-224, miR-224-3p, miR-4279, miR-522, miR-522-3p, miR-374c, and miR-374c-5p.

In one embodiment of any aspect, the population of modified HSCs described herein are produced by any of the methods described herein.

Another aspect of the invention described herein provides a composition of modified HSCs comprising of any of the HSCs described herein.

Another aspect of the invention described herein provides a method of treating Type 1 Diabetes or an immune disease or disorder or cancer treatment in a host in need thereof comprising administering or ex vivo contacting an effective amount of an agent that modulates the expression of miRNAs controlling the expression of PD-L1 in the HSCs in a cell to a host.

In one embodiment of any aspect, the cell is a progenitor cell. In one embodiment of any aspect, the progenitor cell is a hematopoietic progenitor cell.

In one embodiment of any aspect, the agent is a vector comprising a nucleic acid sequence that miRNAs that controls the expression of programmed cell death-1 receptor ligand (PD-L1) or an agent that inhibits the expression of the miRNA such as an antagomir of the miRNA, an anti-miRNA oligonucleotide to the miRNA, an antisense oligonucleotide to the miRNA or a locked nucleic acid that anneals to miRNA, wherein the miRNA is selected from the group consisting of miR-4282, miR-7853, miR-7853-5p, miR-105, miR-105-5p, miR-224, miR-224-3p, miR-4279, miR-522, miR-522-3p, miR-374c, and miR-374c-5p.

In one embodiment of any aspect, the vector is a virus.

Another aspect of the invention described herein provides a method of treating an autoimmune disorder or for cancer immune therapy (aka cancer therapy) in a subject in need thereof comprising administering to a subject a composition comprising any of the hematopoietic stem cells described herein. In one embodiment of any aspect, the autoimmune disorder is Type 1 diabetes (T1D).

In one embodiment of any aspect, the HSCs are autologous to the recipient subject.

In one embodiment of any aspect, the HSCs are non-autologous and allogenic to the recipient subject.

In one embodiment of any aspect, the HSCs are non-autologous and xenogeneic to the recipient subject.

Another aspect of the invention described herein provides a method of modulating an immune response (e.g., for autoimmune disease, or for cancer immune therapy) in a subject comprising: administering or transplanting any of the modified HSC's described herein, of a composition thereof, to a subject.

Another aspect of the invention described herein provides a method of modulating an immune response in a subject comprising: (a) providing a population of hematopoietic stem cells (HSCs); (b) contacting sample of HSCs with a vector carrying an exogenous copy of a nucleic acid encoding miRNAs that controls the expression of programmed cell death-1 receptor ligand (PD-L1) or an agent that inhibits the expression of the miRNA such as an antagomir of the miRNA, an anti-miRNA oligonucleotide to the miRNA, an antisense oligonucleotide to the miRNA or a locked nucleic acid that anneals to miRNA; (c) ex vivo culturing the resultant modified cells from the contacting; (d) establishing the expression of PD-L1 on the modified HSCs, thereby producing a population of modified HSCs cells expressing PD-L1; and (e) transplanting said population of PD-L1+ expressing HSCs into a recipient subject, thereby modulating the immune response in the recipient subject.

In one embodiment of any aspect, the population of HSCs is obtained from the bone marrow, umbilical cord, amniotic fluid, chorionic villi, cord blood, placental blood or peripheral blood. In one embodiment of any aspect, wherein the population of HSCs is obtained from mobilized peripheral blood.

In one embodiment of any aspect, the population of HSCs autologous to the recipient subject. In one embodiment of any aspect, the population of HSCs allogeneic to the recipient subject. In one embodiment of any aspect, the population of HSCs is xenogeneic to the recipient subject.

In one embodiment of any aspect, the miRNA is selected from the group consisting of miR-4282, miR-7853, miR-7853-5p, miR-105, miR-105-5p, miR-224, miR-224-3p, miR-4279, miR-522, miR-522-3p, miR-374c, and miR-374c-5p.

Another aspect of the invention described herein provides a composition comprising any of the PD-L1 expressing hematopoietic stem cells described herein in the prevention or treatment of an autoimmune disease or disorder, for use in suppressing an immune response in a subject, for use in the delay of the onset of T1D in a subject at risk of developing T1D, for use in the prevention and delay of an allogenic tissue or organ transplant rejection, and for the treatment of T1D in adult and pediatric subjects.

Another aspect of the invention described herein provides a composition comprising any of the PD-L1 expressing hematopoietic stem cells described herein for the manufacture of medicament for use in the prevention or treatment of an autoimmune disease or disorder, in the suppression of an immune response in a subject, in the delay of the onset of T1D in a subject at risk of developing T1D, in the prevention and delay of an allogenic tissue or organ transplant rejection, and for the treatment of T1D in adult and pediatric subjects.

Another aspect of the invention described herein provides a population of any of the PD-L1 expressing hematopoietic stem cells described herein for use in the prevention or treatment of an autoimmune disease or disorder, for use in suppressing an immune response in a subject, for use in the delay of the onset of T1D in a subject at risk of developing T1D, for use in the prevention and delay of an allogenic tissue or organ transplant rejection, and for the treatment of T1D in adult and pediatric subjects.

Another aspect of the invention described herein provides a population of any of the PD-L1 expressing hematopoietic stem cells described herein for the manufacture of medicament for use in the prevention or treatment of an autoimmune disease or disorder, in the suppression of an immune response in a subject, in the delay of the onset of T1D in a subject at risk of developing T1D, in the prevention and delay of an allogenic tissue or organ transplant rejection, and for the treatment of T1D in adult and pediatric subjects.

Definitions

As used herein, the term "comprising" means that other elements can also be present in addition to the defined elements presented. The use of "comprising" indicates inclusion rather than limitation.

The term "consisting of" refers to methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the disclosure.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically, such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques. Suitable pharmaceutical carriers are described in Remington's Pharmaceutical Sciences, A. Osol, a standard reference text in this field of art. For example, a parenteral composition suitable for administration by injection is prepared by dissolving 1.5% by weight of active ingredient in 0.9% sodium chloride solution.

In one embodiment, the "pharmaceutically acceptable" carrier does not include in vitro cell culture media.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration.

A "subject," as used herein, includes any animal that exhibits a symptom of a monogenic disease, disorder, or condition that can be treated with the gene therapy vectors, cell-based therapeutics, and methods disclosed elsewhere herein. In preferred embodiments, a subject includes any animal that exhibits symptoms of a disease, disorder, or condition of the hematopoietic system, e.g., a hemoglobinopathy, that can be treated with the gene therapy vectors, cell-based therapeutics, and methods contemplated herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. Typical subjects include animals that exhibit aberrant amounts (lower or higher amounts than a "normal" or "healthy" subject) of one or more physiological activities that can be modulated by gene therapy.

A subject can be an adult subject, e.g., >18 years of age, or a pediatric subject, e.g., <18 years of age. A subject can have been diagnosed with having a disease or disorder (e.g., an autoimmune disease or disorder), can be at risk of having (e.g., exhibit at least one risk factor), or does not have, or is not at risk of having a disease or disorder. A subject can have been previously treated for a disease or disorder, or is currently being treated for a disease or disorder.

In one embodiment, as used herein "treatment" or "treating," includes any beneficial or desirable effect on the symptoms or pathology of a disease or pathological condition, e.g., autoimmune disease (e.g., type I diabetes), and may include even minimal reductions in one or more measurable markers of the disease or condition being treated. In another embodiment, treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

In one embodiment, as used herein, "prevent," and similar words such as "prevented," "preventing" etc., indicate an approach for preventing, inhibiting, or reducing the likelihood of the occurrence or recurrence of, a disease or condition. In another embodiment, the term refers to delaying the onset or recurrence of a disease or condition or delaying the occurrence or recurrence of the symptoms of a disease or condition. In another embodiment, as used herein, "prevention" and similar words includes reducing the intensity, effect, symptoms and/or burden of a disease or condition prior to onset or recurrence of the disease or condition.

As used herein, the term "amount" refers to "an amount effective" or "an effective amount" of a virus or transduced therapeutic cell to achieve a beneficial or desired prophylactic or therapeutic result, including clinical results.

A "therapeutically effective amount" of a virus or transduced therapeutic cell may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject (e.g., a patient).

As used herein, the terms "administering," refers to the placement of a nucleic acid or agent that controls expression of PD-L1 into a subject by a method or route which results in at least partial localization of the agent at a desired site, the HSC described herein. The nucleic acid or agent can be administered by any appropriate route which results in an effective treatment in the subject.

As used herein, "cultured," or "culturing" refers to maintaining a cell population in conditions (e.g., type of culture medium, nutrient composition of culture medium, temperature, pH, $O_2$ and/or $CO_2$ percentage, humidity level) suitable for growth.

The term "decrease", "reduce", or "inhibit" are all used herein to mean a decrease by a reproducible statistically significant amount. In some embodiments, "decrease", "reduce" or "inhibit" typically means a decrease by at least 10% as compared to a reference level (e.g. the absence of a given treatment) and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, as well as a 100% decrease.

The terms "increase", "enhance", or "activate" are all used herein to mean an increase by a reproducible statistically significant amount. In some embodiments, the terms "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, a 20 fold increase, a 30 fold increase, a 40 fold increase, a 50 fold increase, a 6 fold increase, a 75 fold increase, a 100 fold increase, etc. or any increase between 2-fold and 10-fold or greater as compared to a reference level. In the context of a marker, an "increase" is a reproducible statistically significant increase in such level.

As used herein, "programmed death ligand-1 (PD-L1)" refers to a type I transmembrane protein that functions to suppress the immune system during particular events in a subject, such as pregnancy, tissue allografts, disease states (e.g., hepatitis), and presence of an autoimmune disease. PD-L1 sequences are known for a number of species, e.g., human PD-L1, also known as cluster of differentiation 274 (CD274) and B7 homolog 1 (B7-H1), (NCBI Gene ID: 29126) polypeptide (e.g., NCBI Ref Seq NP_001254635.1) and mRNA (e.g., NCBI Ref Seq NM_001267706.1). PD-L1 can refer to human PD-L1, including naturally occurring variants, molecules, and alleles thereof. PD-L1 refers to the mammalian PD-L1 of, e.g., mouse, rat, rabbit, dog, cat, cow, horse, pig, and the like.

As used herein, the term "DNA" is defined as deoxyribonucleic acid. The term "polynucleotide" is used herein interchangeably with "nucleic acid" to indicate a polymer of nucleosides. Typically, a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However, the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are envisioned. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA.

As used herein, the terms "protein" and "polypeptide" are used interchangeably herein to refer to a polymer of amino acids. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a non-polypeptide moiety covalently or noncovalently associated therewith is still considered a "polypeptide." Exemplary modifications include glycosylation and palmitoylation. Polypeptides can be purified from natural sources, produced using recombinant DNA technology or synthesized through chemical means such as conventional solid phase peptide synthesis, etc.

As used herein, "modulating" refers to altering (e.g., increasing or reducing) of the function of a miRNA, e.g., that controls PD-L1. This can be accomplished by directly altering the production of the miRNA itself in the cell, or alternatively by altering the miRNA function/activity. The function/activity for a given miRNA can be reduced, for example by directly inhibiting the miRNA itself or otherwise targeting that miRNA for degradation. miRNA function/activity can be increased, for example by directly upregulating the miRNA itself or otherwise targeting that miRNA for upregulation, or activation. As such, an agent useful in the present invention for modulation is one that alters miRNA expression, or alters miRNA function or activity. Modulation of a given miRNA can also be accomplished, e.g., by alteration of an upstream factor that induces, positively regulates, or inhibits miRNA expression or miRNA function/activity. As such, another useful agent for modulation is an agent that inhibits or increases such an upstream factor by methods that correspond to those described for a given miRNA.

The terms "microRNA" or "miRNA" are used interchangeably and these are endogenous RNAs, some of which are known to regulate the expression of protein-coding genes at the posttranscriptional level. Endogenous microRNA are small RNAs naturally present in the genome which are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs or the purpose of modulating the expression of endogenous genes through the miRNA pathway.

The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc.

As used herein, the term "viral vector" refers to a nucleic acid vector construct that includes at least one element of viral origin and has the capacity to be packaged into a viral vector particle. The viral vector can contain a nucleic acid encoding a polypeptide as described herein in place of non-essential viral genes. The vector and/or particle may be utilized for the purpose of transferring nucleic acids into cells either in vitro or in vivo. Numerous forms of viral vectors are known in the art.

As used herein, the term "expression vector" refers to a vector that directs expression of an RNA or polypeptide (e.g., a polypeptide encoding miRNA that controls PD-L1) from nucleic acid sequences contained therein linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing.

A vector can be integrating or non-integrating. "Integrating vectors" have their delivered RNA/DNA permanently incorporated into the host cell chromosomes. "Non-integrating vectors" remain episomal which means the nucleic acid contained therein is never integrated into the host cell chromosomes. Examples of integrating vectors include retrovirual vectors, lentiviral vectors, hybrid adenoviral vectors, and herpes simplex viral vector.

One example of a non-integrative vector is a non-integrative viral vector. Non-integrative viral vectors eliminate the risks posed by integrative retroviruses, as they do not incorporate their genome into the host DNA. One example is the Epstein Barr oriP/Nuclear Antigen-1 ("EBNA1") vector, which is capable of limited self-replication and known to function in mammalian cells. As containing two elements from Epstein-Barr virus, oriP and EBNA1, binding of the EBNA1 protein to the virus replicon region oriP maintains a relatively long-term episomal presence of plasmids in mammalian cells. This particular feature of the oriP/EBNA1 vector makes it ideal for generation of integration-free iPSCs. Another non-integrative viral vector is adenoviral vector and the adeno-associated viral (AAV) vector.

Another non-integrative viral vector is RNA Sendai viral vector, which can produce protein without entering the nucleus of an infected cell. The F-deficient Sendai virus vector remains in the cytoplasm of infected cells for a few passages, but is diluted out quickly and completely lost after several passages (e.g., 10 passages).

Another example of a non-integrative vector is a minicircle vector. Minicircle vectors are circularized vectors in which the plasmid backbone has been released leaving only the eukaryotic promoter and cDNA(s) that are to be expressed.

Unless otherwise explained, all technical and scientific terms used herein have the same meaning as commonly understood by one of ordinary skill in the art to which this disclosure belongs. It should be understood that this disclosure is not limited to the particular methodology, protocols, and reagents, etc., described herein and as such can vary. The terminology used herein is for the purpose of describing particular embodiments only, and is not intended to limit the scope of the present invention, which is defined solely by the claims.

Definitions of common terms in molecular biology can be found in The Merck Manual of Diagnosis and Therapy, 19th Edition, published by Merck Sharp & Dohme Corp., 2011 (ISBN 978-O-911910-19-3), (2015 digital online edition at merckmanuals.com, Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties. Further, unless otherwise required by context, singular terms shall include pluralities and plural terms shall include the singular.

Unless otherwise stated, the present invention was performed using standard procedures known to one skilled in the art, for example, in Michael R. Green and Joseph Sambrook, Molecular Cloning: A Laboratory Manual, Cold Spring Harbor Laboratory Press, Cold Spring Harbor, N.Y., USA (2012); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, Transgenesis Techniques by Alan R. Clark editor, second edition, 2002, Humana Press, and Methods in Molecular Biology, Vo. 203, 2003, Transgenic Mouse, edited by Marten H. Hofker and Jan van Deursen, which are all herein incorporated by reference in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

BRIEF DESCRIPTION OF THE DRAWINGS

FIGS. 1A-1V presents data that show PD-L1 is downregulated in HSPCs from NOD mice. (FIGS. 1A, 1B). Transcriptomic profiling of Sca-1+Lineage-c-kit+ cells (KLS) obtained from bone marrow of NOD and C57BL/6 mice showed reduced PD-L1 expression. (FIG. 1C) Bar graph representing mRNA expression of PD-L1 as measured by qRT-PCR in Lin-c-kit+(KL) cells, collected from bone marrow of C57BL/6 and NOD mice. All samples were run in triplicate and normalized to expression of the housekeeping gene GAPDH. (FIG. 1L-1N) Representative flow cytometry and quantitative bar graphs of PD-L1 expression in KL cells obtained from the bone marrow of C57BL/6 and NOD mice at different ages. (FIG. 1O-1Q) Representative flow cytometric analysis and quantitative bar graphs of PD-L1 expression in KL cells and in other non-progenitor cells from bone marrow or spleen respectively obtained from C57BL/6 and NOD mice. (FIGS. 1R1-1R3, 1S1-1S3, and 1T) Confocal imaging and quantification of bone marrow sections of C57BL/6 and NOD mice for c-kit (shown in red) and PD-L1 (shown in green) staining; the quantification of the orange-stained bone marrow element was performed by ImageJ. Histology magnification, 63×. Scale bar, 40 μm. (FIG. 1U, 1V) Western blotting and quantitative bar graphs confirming reduced PD-L1 protein expression in KL cells obtained from bone marrow of C57BL/6 and NOD mice, with GAPDH used as an internal control. Data are expressed as mean±standard error of the mean (SEM). Data are representative of at least n=3 mice and two independent experiments. *P<0.05; P<0.01; *P<0.001.

FIGS. 2A-2L presents data that show the mechanism of PD-L1 downregulation in NOD HSPCs. (FIG. 2A) Bar graphs depicting percentage of PD-L1+ cells within Lin-c-kit+ (KL) cells isolated from bone marrow of C57BL/6 and NOD mice and cultured for 3 days in normal glucose, in 20 mM or in 35 mM high glucose. (FIG. 2B) Similar proliferation rates of CFSE-labeled KL cells obtained from C57BL/6 and NOD bone marrow were evident at baseline or after 1 and 3 days of culture. (FIG. 2C) The frequency of apoptosis of KL cells obtained from bone marrow of C57BL/6 and NOD mice was higher at baseline in NOD mice as compared to C57BL/6 mice, while the opposite was observed after 1 and 3 days of culture. (FIG. 2D) MA-plot for GWAS analysis performed in Sca-1+Lineage-c-kit+ cells (KLS) obtained from bone marrow of C57BL/6 compared to NOD mice. (FIG. 2E, 2F) List of miRNAs significantly upregulated (FIG. 2E) and downregulated (FIG. 2F) in KLS cells obtained from the bone marrow of NOD as compared to C57BL/6 mice. (FIG. 2G) miRNAs network controlling PD-L1 gene expression generated with Mouse Genome Informatics MGI. (FIG. 2H, 2I) KL cells obtained from bone marrow of NOD mice were cultured in the presence of miR1905 inhibitor and WT (untreated KL) were used as controls. qRT-PCR of miR-1905 (FIG. 2H) and qRT-PCR of PD-L1 (FIG. 2I) are shown. (FIG. 2J, 2K) Western blotting and quantitative bar graphs of PD-L1 protein expression in KL cells obtained from bone marrow of NOD mice cultured in the presence of miR-1905 inhibitor and WT (untreated KL) were used as controls, with GAPDH was used as an internal control. (FIG. 2L) Methylation status of the PD-L1 locus in KLS obtained from the bone marrow of C57BL/6 and NOD mice. Data are expressed as mean±standard error of the mean (SEM). Data are representative of at least n=3 mice and two independent experiments. *P<0.05; P<0.01; *P<0.001.

(FIG. 3A, 3B, 3C) Representative flow cytometric analysis and quantitative bar graph of Lin-c-kit+(KL) cells obtained from bone marrow of NOD mice pre- and post-transduction with PD-L1 lentivirus showed upregulation of PD-L1. (FIG. 3D, 3E) Confocal imaging of KL cells obtained from bone marrow of NOD mice pre- and post-lentiviral PD-L1 transduction confirmed PD-L1 upregulation. Magnification 63×. Scale bar, 50 μm. (FIG. 3F, 3G) MA-plot and PD-L1 fold change for gene expression level in KL cells obtained from bone marrow of NOD mice transduced with PD-L1 lentivirus as compared to mock-transduced KL cells, demonstrating PD-L1 upregulation. (FIG. 3N1-3N6) Representative immunohistochemical H&E analysis and CD3/insulin staining in serial pancreatic islet tissue sections from PD-L1.Tg KL cell-treated or untreated newly hyperglycemic NOD mice showing the protection conferred by PD-L1.Tg KL. Histology magnification 20×. Scale bar, 200 μm. (FIG. 3V) Quantification of IFN-γ-producing cells (with number of spots normalized for background) in an ex vivo assay, in which splenocytes were challenged with islet peptides (BDC2.5, IGRP, GAD-65 and insulin) after 40 days following treatment in newly hyperglycemic PD-L1.Tg KL cell-treated NOD mice or in untreated hyperglycemic NOD mice. Data are expressed as mean±standard error of the mean (SEM). Data are representative of at least n=3 mice and two independent experiments. *P<0.05; P<0.01; *P<0.001. #p<0.05 vs. all; § p<0.05 vs. all.

FIGS. 4A-4V presents data that show genetically engineered PD-L1.Tg KL cells traffic to the pancreas in hyperglycemic NOD mice. (FIG. 4A, 4B) PD-L1.Tg KL cells induced greater late apoptosis in autoreactive CD4+ and CD8+ T cells as compared to WT KL cells. (FIG. 4C, 4D) Representative flow cytometric analysis for lymphoid and myeloid markers and quantitative bar graphs of isolated KL cells before and after lentiviral transduction. (FIG. 4E, 4F, 4H, 4I) Representative flow cytometric analysis and quantitative bar graphs of ZsGreen+PD-L1.Tg KL cells in the pancreas of hyperglycemic and normoglycemic NOD mice at 1, 7 days and 14 days after treatment with PD-L1.Tg KL cells. ZsGreen+PD-L1.Tg KL cells traffic efficiently to the pancreas of hyperglycemic NOD, with no evidence of their presence in the pancreas of normoglycemic NOD. (FIG. 4G, 4J) Quantification of ZsGreen mRNA in the pancreas of hyperglycemic and normoglycemic NOD mice by qRT-PCR after treatment with PD-L1.Tg KL cells showed the presence of ZsGreen mRNA in the pancreata of hyperglycemic NOD mice, but not in those of normoglycemic NOD mice. (FIG. 4K, 4M) Bar graphs depicting flow cytometric quantification of ZsGreen+PD-L1.Tg KL cells and (FIG. 4L, 4N) quantification of ZsGreen mRNA by qRT-PCR in the bone marrow of hyperglycemic and normoglycemic NOD mice, after treatment with PD-L1.Tg KL cells, showed the presence of ZsGreen+PD-L1.Tg KL cells in the bone marrow of hyperglycemic and normoglycemic NOD mice. (FIG. 4O, 4Q) Bar graphs for flow cytometric quantification of ZsGreen+PD-L1.Tg KL cells and (FIG. 4P, 4R) quantification of ZsGreen mRNA by qRT-PCR in the spleen of hyperglycemic and normoglycemic NOD mice showed ZsGreen+PD-L1.Tg KL cells in the spleen of both groups of NOD mice. (FIG. 4S1-4S4, 4T1-4T4) Confocal imaging of pancreatic sections obtained from normoglycemic or hyperglycemic NOD mice after 1, 7 and 14 days after treatment with ZsGreen+PD-L1.Tg KL cells. ZsGreen+ cells are evident in the pancreata of hyperglycemic, but not in those of normoglycemic, NOD mice. Magnification 63× in all confocal images, Scale bar, 20 μm (FIGS. 4S1-4S4 and 4T1, 4T3, 4T4); Scale bar, 5 μm (FIG. 4T2). (FIG. 4U, 4V) Luminescent images of NOD mice adoptively transferred with Luciferase+PD-L1.Tg KL cells after 24 hours and 7 days of treatment, showing the rapid disappearance from peripheral blood of Luciferase+PD-L1.Tg KL cells. Data are expressed as mean±standard error of the mean (SEM). Data are representative of at least n=3 mice and two independent experiments. *P<0.05; P<0.01; *P<0.001.

FIGS. 5A-5U presents data that show pharmacologically modulated KL cells (pKL) abrogate the autoimmune response in vitro. (FIG. 5A-5C) Results of screening of small molecules tested for their ability to upregulate PD-L1 (MFI) on mobilized CD34+ cells obtained from healthy controls, the 3-color coding shown in (FIG. 5C) represents lowest PD-L1 MFI values (orange), median PD-L1 MFI values (yellow) and highest PD-L1 MFI values (green). (FIG. 5D, 5E) PD-L1 expression (mRNA and MFI) fold change was quantified for the indicated component, alone or in combination. (FIG. 5I, 5J) Confocal imaging of KL cells pre- and post-modulation with small molecules, showing DAPI (in blue) and PD-L1 (in red) staining. Magnification 63×. Scale bar, 50 μm. (FIG. 5K, 5L) MA-plot and fold change for gene expression in KL cells obtained from bone marrow of NOD mice and pKL as compared to unmodulated KL cells (Vehicle-KL cells, WT). (FIG. 5M, 5N) Representative flow cytometric analysis and quantitative bar graph for IFN-γ+CD4+ T cells isolated from NOD-BDC2.5 TCR Tg mice and stimulated with BDC2.5 peptide in the presence of DCs (Controls) or upon co-culture with unmodulated KL (WT), pKL cells (at different ratios) or with pKL cells pre-treated with anti-PD-L1 blocking mAb. (FIG. 5O) Bar graph for flow cytometric quantification of IFN-γ+CD4+ T cells after co-culture of CD4+ T cells isolated from NOD-BDC2.5 TCR Tg mice stimulated with BDC2.5 peptide in the presence of DCs (Control) or upon co-culture with unmodulated KL cells (WT), with pKL cells, or with PD-L1.Tg KL cells, or with CD4+CD25+T regulatory cells. (FIG. 5U) Bar graph depicting flow cytometric quantification of IFN-γ+CD4+ T cells within CD4+CD25− T cells isolated from NOD mice and stimulated with soluble anti-CD3/anti-CD28 (Control) or upon co-culture with WT, with pKL, or with PD-L1.Tg KL cells, or with CD4+CD25+T regulatory cells. PD-L1.Tg KL cells—and pKL to a lesser extent—appear as potent as regulatory T cells in inhibiting the CD4/CD8-restricted autoimmune response and anti-CD3/anti-CD28-dependent T cell stimulation. Data are expressed as mean±standard error of the mean (SEM). Data are representative of at least two independent experiments. *P<0.05; P<0.01; *P<0.001. #p<0.05 vs. all; § p<0.05 vs. all.

FIGS. 6A-6k present data that show pharmacologically modulated KL cells (pKL) revert hyperglycemia in NOD mice in vivo. (FIG. 6A) In newly hyperglycemic NOD mice, treatment with pKL reverted diabetes. (FIG. 6B) Kaplan-Meier curve showing reversal of diabetes in newly hyperglycemic NOD mice with different treatments. (FIG. 6C) Quantification of IFN-γ-producing cells in an in vitro assay, in which splenocytes were challenged with islet peptides after treatment with pKL, normalized for background. (FIG. 6D) Immunophenotype of lymphocytes isolated from spleen of pKL-treated newly hyperglycemic NOD mice showed an increase in the percentage of FoxP3+ regulatory T cells. (FIG. 6E-6G) Bar graph showing the levels of pro- (IL-2/IL-6) and anti-inflammatory (IL-4) cytokines as measured by Luminex in the serum of untreated or pKL-treated newly hyperglycemic NOD mice at baseline and at 7 days after treatment. (FIG. 6H) pKL-treated NOD mice were regularly immunocompetent upon ovalbumin re-challenge. (FIG. 6I) Insulitis score is reduced in pKL-treated newly hyperglycemic NOD mice. (FIG. 6J1-6J6) Representative immunohistochemical H&E analysis and CD3/insulin staining in serial pancreatic islet tissue sections from pKL-treated or untreated NOD mice showing the protection conferred by pKL. Histology magnification 20×. Scale bar, 200 μm. (FIG. 6K) Schematic representing the defect in PD-L1 in HSPCs in T1D, as well as the effect of PD-L1 genetic/pharmacological restoration. Data are expressed as mean±standard error of the mean (SEM). Data are representative of at least n=3 mice and two independent experiments. *P<0.05; P<0.01; *P<0.001; #P<0.05 vs. all.

FIGS. 7A-7Z present data that show the PD-L1 defect is evident in HSPCs from T1D patients. (FIG. 7A, 7B, 7C) Representative flow cytometric and quantitative bar graph of PD-L1+CD34+ cells from patients with T1D as compared to healthy controls (n=10 from each group). (FIG. 7D, 7E) Western blot analysis and (FIG. 7F) qRT-PCR confirmed the PD-L1 defect in CD34+ cells from T1D patients (n=3 in each group). (FIGS. 7G1-7G3) and (FIGS. 7H1-7H3 and 7I) Confocal imaging and quantitative bar graph of bone marrow sections obtained from T1D patients and healthy controls showing CD34 (red) and PD-L1 (green) staining; the quantification of the orange-stained bone marrow element was performed by ImageJ. Histology magnification, 63×; scale bar 40 μm. (FIG. 7J) Bar graph depicting the percentage of PD-L1 on CD34+ cells obtained from peripheral blood of T1D patients or healthy controls at baseline or cultured for 3 days in normal glucose, in 20 mM or in 35 mM high glucose (n=5 samples from each group). (FIG. 7K) CFSE-based proliferation assay of peripheral CD34+ cells obtained from T1D and healthy control patients at baseline and after 1 and 3 days of culture. (FIG. 7L) The rate of apoptosis of CD34+ cells was higher in T1D patients at baseline as compared to healthy controls, while no differences were evident after 1 and 3 days of culture. (FIG. 7M) Table of human miRNAs, discovered by bioinformatic approach, involved in the regulation of PD-L1 expression. (FIG. 7N) qRT-PCR showed differentially expressed miRNA in human CD34+ cells obtained from T1D patients as compared to controls. (FIG. 7O) No difference in the DNA methylation status of the PD-L1 gene promoter was evident in peripheral CD34+ cells obtained from T1D patients as compared to healthy controls. (FIG. 7P, 7Q, 7R) Representative flow cytometric and quantitative bar graph of PD-L1 expression on peripheral CD34+ cells from T1D patients pre- and post-pharmacologic-modulation with a small molecule, either alone or in combination. (FIG. 7S, 7T) Confocal imaging of PD-L1 expression on CD34+ cells from T1D patients pre- and post-pharmacologic-modulation. Magnification, 63×. Scale bar, 50 μm. (FIG. 7U) PD-L1 expression fold change in pharmacologically-modulated CD34+(pCD34+) after 24 hours and in vehicle-treated CD34+ cells as assessed by RT-PCR. (FIG. 7V, 7W) Unmodulated CD34+ and pCD34+ cells abrogate the IFN-γ autoimmune response towards insulin-associated 2 (FIG. 7I-7A2) autoantigen in vitro, as measured via the quantification of IFN-γ-producing cells. (FIG. 7X, 7Y) An anti-PD-L1 blocking mAb abrogated the immunological effect of pCD34+ cells in vitro. (FIG. 7Z) Unmodulated CD34+ and pCD34+ cells did not abrogate the anti-CD3/CD28-stimulated PBMC response in vitro as measured via the quantification of IFN-γ-producing cells. Data are expressed as mean±standard error of the mean (SEM). Data are representative of at least two independent experiments. *P<0.05; P<0.01; *P<0.001. #p<0.05 vs. all.

(FIG. 8A-8F) Other molecules are scarcely present in hematopoietic stem progenitor cells isolated from the bone marrow of NOD and C57BL/6 mice. (FIG. 8G-8I) PD-L1 expression on other relevant immune cells (ILC1, ILC2, ILC3, early myeloid CD11b+ cells and NKT cells) obtained from bone marrow of NOD and C57BL/6 mice. (FIG. 8J-8M) PD-L1 expression on other relevant immune cells (CD4+CD25+, CD4 effector T cells, CD4 memory T cells, CD8+ T cells, CD8 effector T cells, CD8 memory T cells, CD4+CD25+ FoxP3+ T regulatory cells, NKT cells and early myeloid CD11b+ cells) obtained from spleen of NOD and C57BL/6 mice. Data are expressed as mean±standard error of the mean (SEM) unless otherwise specified. Data are representative of at least two independent experiments. *P<0.05; P<0.01; *P<0.001. #P<0.05 vs. all.

FIGS. 9A-9I present data that show generation and characteristics of PD-L1.Tg KL cells. (FIG. 9A) Schematic representation of the genetic approach employed to generate PD-L1.Tg KL cells by lentiviral transduction. (FIG. 9B, 9C) Quantification of ZsGreen mRNA in the pancreatic lymph nodes of hyperglycemic and normoglycemic NOD mice by qRT-PCR after treatment with PD-L1.Tg KL cells. (FIG. 9D, 9E) Representative flow cytometric analysis and quantitative bar graphs of GFP+ KL cells in the pancreas of hyperglycemic NOD mice at 1, 7 and 14 days after treatment with WT KL cells isolated from bone marrow cells of normoglycemic NOD Luciferase+ GFP+ mice. (FIG. 9F, 9G) Few CD11c+ZsGreen+ cells and CD11b+ZsGreen+ cells were observed in the pancreas and PLN (FIG. 9H, 9I) of adoptively transferred NOD mice. Data are expressed as mean±standard error of the mean (SEM) unless otherwise specified. Data are representative of at least two independent experiments.

FIGS. 10A and 10B present data that show immunotyping of pharmacologically-modulated KL cells. (FIG. 10A-10B) Representative flow cytometric analysis and quantitative bar graph of positive and negative costimulatory molecules, (CD40, CD80, CD86, ICOSL, PD-1) and of select pro-inflammatory and anti-inflammatory cytokines (IFN-γ, IL-10, IL-4) in pharmacologically-modulated KL cells (pKL) from NOD mice as compared to unmodulated KL-Veh cells isolated from the bone marrow of normoglycemic NOD mice. Data are expressed as mean±standard error of the mean (SEM) unless otherwise specified. Data are representative of at least two independent experiments. *P<0.05; P<0.01; *P<0.001.

(FIG. 11A) Representative flow cytometric analysis of IFN-γ+CD4+ T cells isolated from NOD-BDC2.5 TCR Tg mice stimulated with BDC2.5 peptide in the presence of DCs (Control) or upon co-culture with unmodulated KL cells (WT), with pharmacologically-modulated KL cells (pKL), with PD-L1.Tg KL cells or with CD4+CD25+ T regulatory cells. (FIG. 11B) Representative flow cytometric analysis of IFN-γ+CD8+ T cells isolated from NOD-8.3 TCR Tg mice stimulated with IGRP peptide in the presence of DCs (Control) or upon co-culture with unmodulated KL cells (WT), with pKL cells, with PD-L1.Tg KL cells, or with CD4+CD25+ T regulatory cells. (FIG. 11C) Representative flow cytometric analysis of IFN-γ+CD4+ T cells isolated from normoglycemic NOD mice and stimulated with soluble anti-CD3/anti-CD28 (Control) or upon co-culture with unmodulated KL cells (WT), with pKL, with PD-L1.Tg KL cells or with CD4+CD25+ T regulatory cells. (FIG. 11D, 11E) Treatment with anti-PD-1 stimulating mAb (clone PIM2) as previously described did not delay diabetes onset in pre-diabetic 10-week-old NOD mice, nor did it revert diabetes in newly hyperglycemic NOD mice. Data are expressed as mean±standard error of the mean (SEM). Data are representative of at least two independent experiments.

FIGS. 12A-12N present data that show gene expression of PD-L1+CD34+ cells. (FIG. 12A) Quantification of PD-L1+ CD34+ cells by flow cytometry in long-standing or new-onset T1D patients and in healthy controls (CTRL). (FIG. 12B, 12C, 12D) PD-L1 expression on other relevant immune cells in patients with T1D and in healthy controls. (FIG. 12E-12N) Other costimulatory molecules are scarcely present in CD34+ cells isolated from peripheral blood of healthy controls or from long-standing or new-onset T1D patients. Data are expressed as mean±standard error of the mean (SEM). Data are representative of at least two independent experiments. *P<0.05; P<0.01; *P<0.001. #P<0.05 vs. all.

(FIG. 13A-13B) Representative flow cytometric analysis and quantitative bar graph of positive and negative costimulatory molecules, (CD40, CD80, CD86, ICOSL, PD-1) and of select pro-inflammatory and anti-inflammatory cytokines (IFN-γ, IL-10, IL-4) in human pharmacologically-modulated CD34+ cells (pCD34+) as compared to unmodulated CD34+ cells isolated from peripheral blood of T1D patients (n=3). Data are expressed as mean±standard error of the mean (SEM) unless otherwise specified. Data are representative of at least two independent experiments.

FIGS. 14A-14B present data that show Scattered dot plot (FIG. 14A) and fold change (FIG. 14B) representing transcriptomic profiling of immune-related molecules in pCD34+ cells as compared to unmodulated CD34+ cells isolated from peripheral blood of T1D patients (n=3). Data are expressed as mean±standard error of the mean (SEM) unless otherwise specified. Data are representative of at least two independent experiments.

FIGS. 15A-15C present data that CD34+ cell mobilization with Plerixafor does not increase the percentage of peripheral PD-L1+CD34+ cells in T1D patients, and decreases the frequency of these cells in healthy controls. Data are expressed as mean±standard error of the mean (SEM). Data are representative of at least two independent experiments. *P<0.05; P<0.01; *P<0.001. #P<0.05 vs. all (FIG. 16A) Line graph showing 2-hour peak-stimulated C-peptide levels after a mixed meal tolerance test following AHSCT, at 12 and 24 months of follow-up. (FIG. 16B) Correlation between the number of HSPCs injected during AHSCT and 2-hour peak-stimulated C-peptide levels evaluated at 6 months of follow-up. (FIG. 16C, 16D) Correlation between the number of hematopoietic stem cells (HSPCs) injected during AHSCT and exogenous insulin requirement units (EIR) evaluated at 8 months (C) and 12 months (D) of follow-up. All data are expressed as mean±SEM. All parameters examined were statistically significantly different when comparing baseline values vs. those at 6, 8 and 12 months. *P<0.05, **P<0.001. Abbreviations: AHSCT, autologous hematopoietic stem cell transplantation; UI, units of insulin; EIR, exogenous insulin requirement units.

(FIG. 17A-17B) Results of screening of a prostaglandin small molecule library tested for the ability to upregulate PD-L1 (MFI) on CD34+ cells obtained from T1D patients. The schematic of the experimental design is shown in (A). The 3-color coding shown in (FIG. 17B) represents lowest PD-L1 MFI values (blue), median PD-L1 MFI values (pink) and highest PD-L1 MFI values (red). (FIG. 17C-17D) Representative flow cytometric analysis and quantitative bar graph of PD-L1 expression on CD34+ cells from T1D patients pre- and post-pharmacologic modulation with PGE2 as compared to CD34+ cells obtained from healthy controls. (FIG. 17E) PD-L1 and CXCR4 expression (mRNA) fold change was quantified for CD34$^+$ cells pre- and post-modulation with PGE2. (FIG. 17F) Migration assay using CD34$^+$ cells pre- and post-modulation with PGE2. (FIG. 17G) Confocal imaging of CD34$^+$ cells pre- and post-modulation with PGE2, showing DAPI (in blue) and PD-L1 (in green) staining. 63× magnification. Scale bar, 50 (FIG. 17H) IDO-1 expression (mRNA) fold change was quantified for CD34$^+$ cells pre- and post-modulation with PGE2. (FIG. 17I-17J) Representative flow cytometric analysis (FIG. 17I) and quantitative bar graph (FIG. 17J) of PD-L1 expression on CD34$^+$ cells from T1D patients pre- and post-pharmacologic modulation with 4 small molecule PGE2 agonists. All data are expressed as mean±SEM. *P<0.05, **P<0.001. Abbreviations: MFI, mean fluorescence intensity.

FIGS. 18A-18J show effects of human PGE2-modulated and cytokine-treated CD34$^+$ cells. (FIG. 18A-18B) Sustained and robust upregulation of PD-L1 upon culture for 7 days with PGE2 and a cocktail of cytokines (heparin, human SCF, human TPO, human FGF-1, IGFBP2, and Angptl3) on CD34$^+$ cells obtained from T1D patients as compared to those from healthy controls. (FIG. 18C) Effect of PGE2 pulsing on CD34$^+$ cells cultured for 0, 24 h, 72 h and 6 days on PD-L1 expression on CD34$^+$ cells. (FIG. 18D-18E) Bar graphs showing an increase in the number of PD-L1$^+$CD34$^+$ cells and fold increase in cell number after 7 days of culture with PGE$_2$ supplemented with cytokines. (FIG. 18F-18G) Upregulation of PD-L1 expression following culture with PGE2 (shown as percentage) on CD34$^+$ cells was not altered by the freeze/thawing process. (FIG. 18H) PGE2-modulated CD34$^+$ cells abrogate the IFN-γ autoimmune response to insulin-associated 2 (I-A2) autoantigen in vitro, as measured via the quantification of IFN-γ-producing cells in an Elispot assay; Diftavax refers to a vaccine including immunization against tetanus toxoid, difteria and hemophilus. (FIG. 18I) PGE2-modulated CD34$^+$ cells and PGE2-modulated CD34$^+$ cells cultured for 7 days in STFIA media abrogate the IFN-γ autoimmune response towards insulin-associated 2 (I-A2) autoantigen in vitro, as measured via the quantification of IFN-γ-producing cells in an Elispot assay, even when added at low dose. (FIG. 18J) PGE2-modulated CD34$^+$ cells abrogate the anti-CD3/CD28-stimulated PBMC response in vitro as measured via the quantification of IFN-γ-producing cells in an Elispot assay. Data are expressed as mean±standard error of the mean (SEM). Data are representative of at least two independent experiments. *P<0.05; **P<0.01. Abbreviations: SCF, stem cell factor; TPO, thrombopoietin; hFGF-1, human fibroblast growth factor 1; IGFBP2, insulin-like growth factor-binding protein 2; Angptl3, angiopoietin-like 3; PBMCs, peripheral blood mononuclear cells.

(FIG. 19A-19B) Representative flow cytometric analysis and quantitative bar graph of PD-L1 expression on Lineage$^-$c-kit$^+$ (KL) cells from NOD mice pre- and post-pharmacologic modulation with PGE2. (FIG. 19C-19D) Representative flow cytometric analysis and quantitative bar graph of CXCR4 expression on KL cells from NOD mice pre- and post-pharmacologic modulation with PGE2. (FIG. 19E) Quantitative bar graph of flow cytometric expression of positive and negative costimulatory molecules (CD40, CD80, CD86, PD-L1, PD-L2 and PD-1) and of select pro-inflammatory and anti-inflammatory cytokines (IFN-γ, IL-10, IL-4) in PGE2-modulated KL cells from NOD mice as compared to those modulated with a selected PGE2 clinical grade agonist (dmPGE2) and compared to unmodulated KL cells isolated from the bone marrow of normoglycemic NOD mice. (FIG. 19F) Flow cytometric expression of selected chemokine receptors (CXCR4, CCR2, CCR4, CCR5, CCR6, CCR7, CCR8, and CXCR3) in PGE2-modulated KL cells from NOD mice as compared to those modulated with a selected PGE2 clinical grade agonist (dmPGE2) and to unmodulated KL cells isolated from the bone marrow of normoglycemic NOD mice. (FIG. 19G) Quantitative bar graph of flow cytometric expression of chemokines receptors (CCR2, CCR4, CCR5, CCR6, CCR7, CCR8, CXCR3 and CXCR4) in PGE$_2$-modulated KL cells from NOD mice as compared to those modulated with a selected PGE$_2$ clinical grade agonist (dmPGE2) and compared to unmodulated KL cells isolated from the bone marrow of normoglycemic NOD mice. Data are expressed as mean±standard error of the mean (SEM). Data are representative of at least two independent experiments. *P<0.05; P<0.01; *P<0.001. Abbreviations: KL, Lineage$^-$c-kit$^+$ cells.

FIGS. 20A-20E show the effects of murine KL cells. (FIG. 20A-20B) Representative flow cytometric analysis (FIG. 20A) and quantitative bar graph (FIG. 20B) for IFN-γ$^+$CD4$^+$ T cells isolated from NOD-BDC2.5 TCR Tg mice and stimulated with BDC2.5 peptide in the presence of DCs (Control) or upon co-culture with unmodulated KL or with PGE2-modulated KL cells (at different ratios). (FIG. 20C) Quantitative bar graph of the percentage of CD4$^+$ T cells upon coculture with KL or PGE2-modulated KL cells. (FIG. 20D) Representative flow cytometric analysis of GFP$^+$ PGE2-modulated KL cells in the PLN of treated NOD mice following 24 hours of treatment with GFP$^+$PGE2-modulated KL cells, demonstrating that they traffic to the PLN following adoptive transfer into NOD mice. (FIG. 20E) Representative flow cytometric analysis of GFP$^+$PGE2-modulated KL cells in the pancreas of NOD mice 24 hours post-infusion with GFP$^+$PGE2-modulated KL cells, demonstrating the surface phenotype of GFP$^+$ cells. Abbreviations: KL, Lineage$^-$c-kit$^+$ cells; PGE2-KL, PGE2-modulated KL cells; HSPCs, hematopoietic stem and progenitor cells; GFP, green fluorescent protein.

FIGS. 21A-21D show PD-1 expression on murine T cells. (FIG. 21A-21B) Representative flow cytometric analysis (FIG. 21A) and quantitative bar graph (FIG. 21B) for PD-1$^+$CD4$^+$ T cells isolated from splenocytes of NOD mice as compared those from C57BL/6 mice. (FIG. 21C-21D) Representative flow cytometric analysis (FIG. 21C) and quantitative bar graph (FIG. 21D) for PD-1$^+$CD8$^+$ T cells isolated from splenocytes of NOD mice as compared those from C57BL/6 mice.

(FIG. 22A) Changes in miRNA-targeted genes levels as an effect of miRNA targeting in MDA-MB-231 cells; each targeted gene is indicated along with its targeting miRNA in parenthesis. (FIG. 22B) Bar graph depicting mRNA expression of PD-L1 in miRNA mimic- and anti-miR-treated cells by real-time PCR. Data are normalized by GAPDH mRNA levels. (FIG. 22C) Representative western blot pattern of MDA-MB-231 cells treated with the shown miRNA mimic or anti-miR. (FIG. 22D) Quantitative bar graphs of western blotting on miRNA mimic- and anti-miR-treated cells. All data in FIGS. 22A, 22B, and 22D are normalized to the corresponding RNA mimic or anti-miR negative control. Abbreviations: Mimic NC, miRNA mimic negative control; Anti-miR NC, Anti-miR negative control.

(FIGS. 23A and 23C) FACS histograms showing a lower number of cells expressing PD-L1 in miRNA mimic (FIG. 23A) or anti-miR (FIG. 23B) treated cells as compared to their negative controls). The percentage of untreated MDA-MB-231 cells expressing PD-L1 is also shown. (FIGS. 23B and 23C) Bar graph representing the percentage of cells expressing PD-L1 in the untreated sample, or in cells exposed to a miRNA mimic (FIG. 23B) or anti-miR (FIG. 23D) treatment. Abbreviations: Mimic NC, miRNA mimic negative control; Anti-miR NC, Anti-miR negative control.

DETAILED DESCRIPTION

Figure 1E:
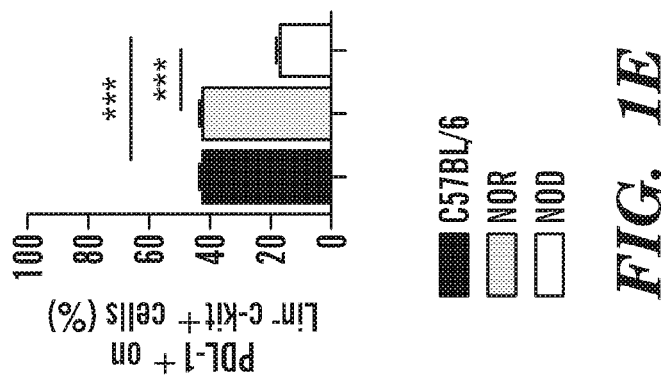
(FIG. 1D-1K) Representative flow cytometric analysis and quantitative bar graphs confirming the PD-L1 defect in 4 populations of HSPCs in C57BL/6 and NOD mice.
Figure 1D:
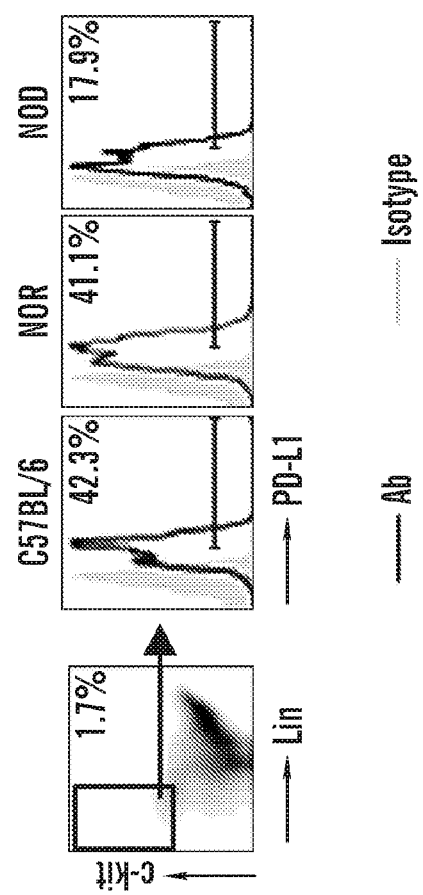
Figure 1G:
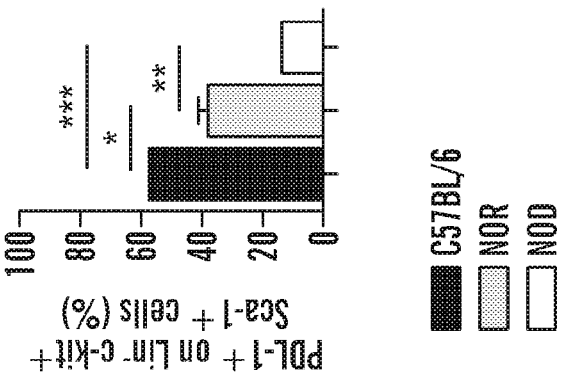
Figure 1F:
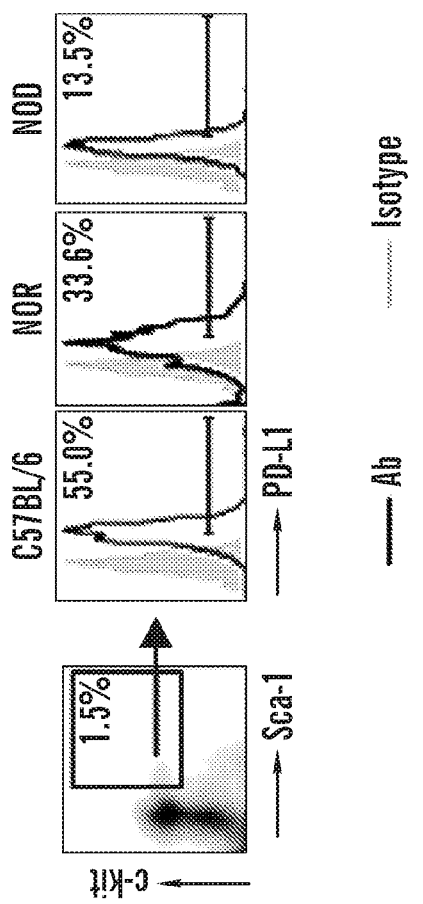
Figure 1I:
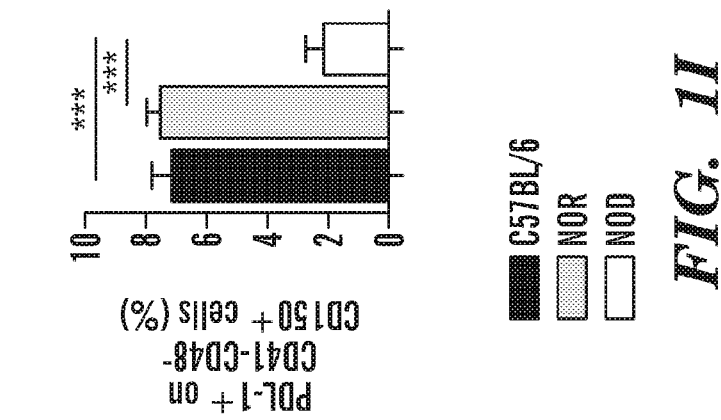
Figure 1H:
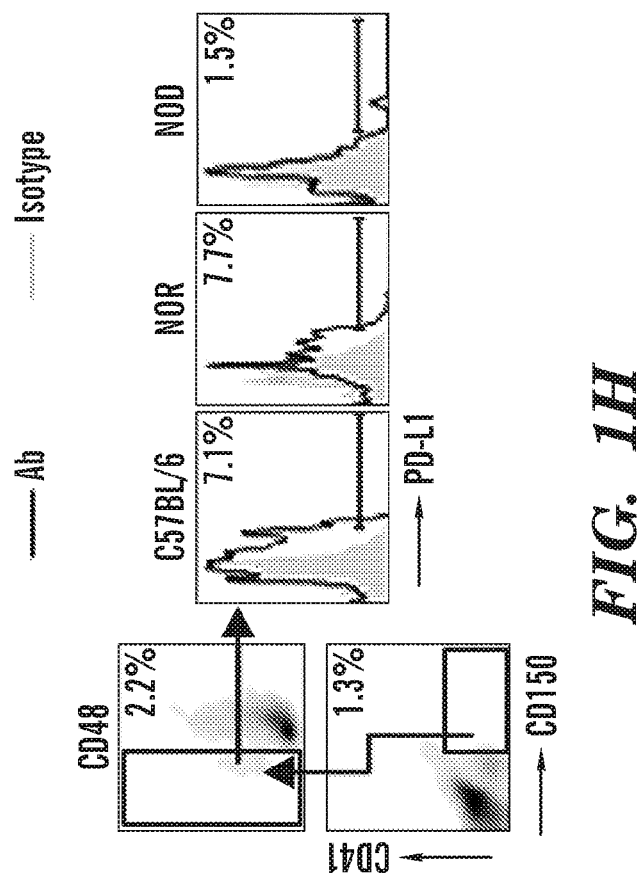
Figure 1K:
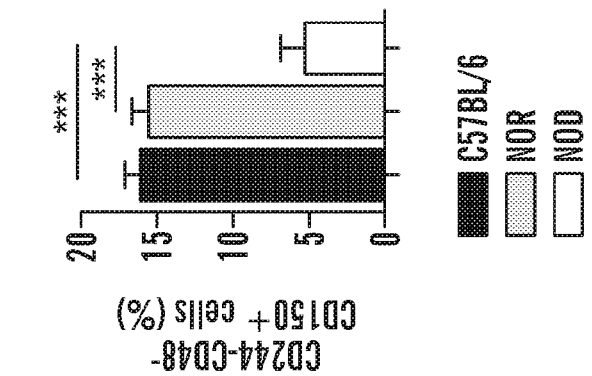
Figure 1J:
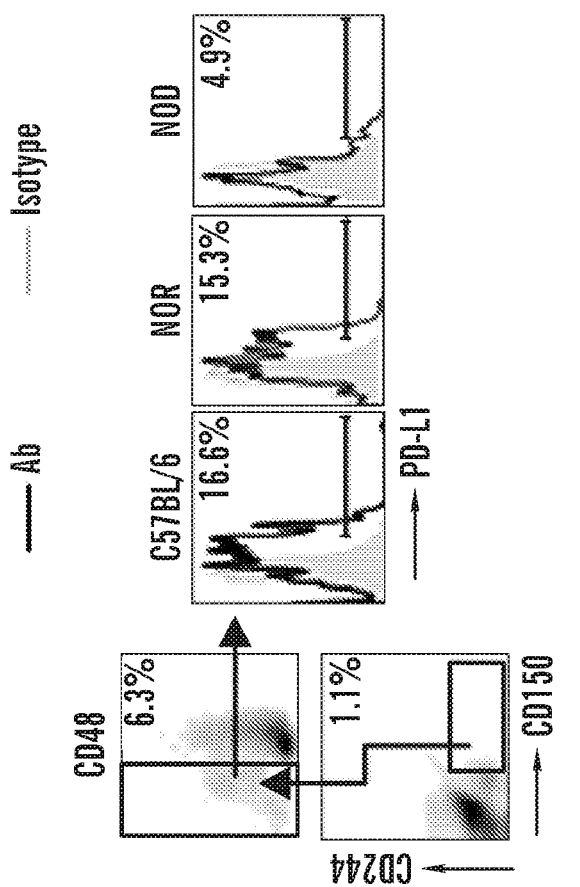

The present invention relates to methods and compositions directed at modulating a hematopoietic stem cell, or a population thereof, and uses thereof for the purpose of, e.g., treating and/or preventing a disease or disorder (e.g., an autoimmune disease or cancer), inducing an immune response, etc.

The present invention is based in part on the discovery that hematopoietic stem cells obtained from mice models of type 1 diabetes have a deficit of PD-L1 expression compared to control mice. Data presented herein show that hematopoietic stem cells overexpressing PD-L1 (PD-L1.Tg HSPCs) inhibited the autoimmune response in in vitro assays. In addition, transplantation of PD-L1.Tg HSPCs was found to be capable of reverting the onset of diabetes in newly hyperglycemic NOD mice in vivo, and PD-L1.Tg HSPCs homed to the pancreas of hyperglycemic NOD mice.

These findings were confirmed in human patient having a diagnosis of type 1 diabetes. Hematopoietic stem cells obtained from subjects having type 1 diabetes also have a deficit of PD-L1 expression compared to hematopoietic stem cells obtained from a healthy subject, or a subject who has not been diagnosed with type 1 diabetes. Modified hematopoietic stem cells that were pharmacologically modulated to have increased expression of PD-L1 were able to inhibit the autoimmune response in vitro. It is specifically contemplated herein that compositions and cell populations comprising modified, PD-L1 expressing hematopoietic stem cells can be used in the treatment, prevention, or the delay of onset of an autoimmune disease, such as type 1 diabetes.

Other embodiments of the invention described herein are directed to the use of compositions and modified hematopoietic stem cell populations described herein for reducing the immune response in a subject, and in the prevention and delay of an allogenic tissue or organ transplant rejection.

The disclosure described herein, in a preferred embodiment, does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

It is also envisioned that the methods described herein can be used as prophylaxis treatment, e.g., to prevent the onset of an autoimmune disease, such as type 1 diabetes.

Hematopoietic Stem Cells

Methods and compositions described herein comprise the use of modified hematopoietic stem cells. Hematopoietic tissues contain cells with long-term and short-term regeneration capacities, and committed multipotent, oligopotent, and unipotent progenitors. Endogenous hematopoietic stem cells can be found in a variety of tissue sources, such as the bone marrow of adults, which includes femurs, hip, ribs, sternum, and other bones, as well as umbilical cord blood and placenta, and mobilized peripheral blood. Endogenous hematopoietic stem cells can be obtained directly by removal from, for example, the hip, using a needle and syringe, or from the blood following pre-treatment with cytokines, such as G-CSF (granulocyte colony-stimulating factors), that induce cells to be released from the bone marrow compartment. However, such methods yield varying amounts of hematopoietic stem cells, which are oftentimes not enough for use in treatment options.

Accordingly, "hematopoietic stem cells," as the terms are used herein, encompass all multipotent cells capable of differentiating into all the blood or immune cell types of the hematopoietic system, including, but not limited to, myeloid cells (monocytes and macrophages, neutrophils, basophils, eosinophils, erythrocytes, megakaryocytes/platelets, dendritic cells), and lymphoid lineages (T-cells, B-cells, NKT-cells, NK-cells), and which have multi-lineage hematopoietic differentiation potential and sustained self-renewal activity.

In one embodiment, a hematopoietic stem cell is a mammalian hematopoietic stem cell. In one embodiment, a mammalian hematopoietic stem cell is a human hematopoietic stem cell.

In one embodiment, a hematopoietic stem cell is obtained from the bone marrow, umbilical cord, amniotic fluid, chorionic villi, cord blood, placental blood, peripheral blood, or mobilized peripheral blood. Methods for obtaining hematopoietic stem cells are known in the art.

In one embodiment, a hematopoietic stem cell is obtained from a healthy individual, an individual with a diagnosed disease or disorder, or an individual with a diagnosed autoimmune disease or disorder, e.g., type 1 diabetes.

In various aspects of the invention, modified hematopoietic stem cells are administered to a recipient subject in need thereof. In one embodiment, the hematopoietic stem cells are autologous to the recipient subject. As used herein, "autologous" refers to a hematopoietic stem cell obtained from the same subject, e.g., the recipient subject.

In one embodiment, the hematopoietic stem cells are non-autologous and allogenic to the recipient subject. In one embodiment, the hematopoietic stem cells are non-autologous and xenogeneic to the recipient subject. As used herein, "non-autologous and allogenic" refers to a hematopoietic stem cell obtained from a different subject, e.g., not the recipient subject, that is a genetic match for the recipient subject. As used herein, "non-autologous and xenogeneic" refers to a hematopoietic stem cell obtained from a different subject, e.g., not the recipient subject, that is a not the same species as the recipient subject.

Populations of Modified, PDL1+ Expressing Hematopoietic Stem Cells

One aspect of the invention is a cell population comprising any of the modified hematopoietic stem cells described herein. In various aspects, the hematopoietic stem cells are PD-L1 expressing hematopoietic stem cells. Programmed death-ligand 1 (PD-L1 is a transmembrane protein that functions to suppress the immune system in particular events such as pregnancy, tissue allografts, autoimmune disease, and hepatitis. Binding of PD-L1 to is receptor programmed death-1 (PD-1) transmits an inhibitory signal that reduces the proliferation of T cells and can induce apoptosis.

In one embodiment, the expression level of PD-L1 in a modified, PD-L1 expressing hematopoietic stem cell is increased by at least 2-fold, by at least 3-fold, by at least 4-fold, by at least 5-fold, by at least 6-fold, by at least 7-fold, by at least 8-fold, by at least 9-fold, by at least 10-fold or more as compared to an appropriate control, or by at least 10%, by at least 20%, by at least 30%, by at least 40%, by at least 50%, by at least 60%, by at least 70%, by at least 80%, by at least 90%, by at least 100% or more as compared to a control, non-modified hematopoietic stem cell. The expression level of PD-L1 on hematopoietic stem cells can be detected by assessing the protein or mRNA of PD-L1 on an isolated population of hematopoietic stem cells, e.g., via western blotting or PCR-based assays (e.g., qPCR), respectively.

A hematopoietic stem cell, or population thereof, can be isolated via, e.g., using flow cytometry to determine if a hematopoietic stem cell-specific marker is present or absent. Non-limiting examples of markers specific for human hematopoietic stem cell-specificity include cKit/CD117-positive, CD34-positive, CD59-positive, CD38-negative, and Thy1/CD90-positive. Hematopoietic stem cell lack expression of mature blood cell markers and are thus called Lin-negative.

One aspect of the invention is an ex vivo method of producing a population of modified, PD-L1+ expressing hematopoietic stem cells comprising modulating the expression of at least a miRNA that controls the expression of PD-L1 in the hematopoietic stem cell. In one embodiment, the modulation of the expression of miRNAs is increasing the expression of miRNA or decreasing the expression of miRNA.

Another aspect of the invention is a population of modified hematopoietic stem cells (HSCs) in which the modified cells have increased PD-L1 expression compared to control, non-modified cells, wherein the cells carry an exogenous copy of a nucleic acid encoding a miRNAs that controls the expression of programmed cell death-1 receptor ligand (PD-L1) or an agent that inhibits the expression of the miRNA such as an antagomir of the miRNA, an anti-miRNA oligonucleotide to the miRNA, an antisense oligonucleotide to the miRNA or a locked nucleic acid that anneals to miRNA.

In one embodiment, the hematopoietic stem cells are ex vivo cultured before, or after, or both before and after, the modification of the PD-L1 expression.

In one embodiment, the hematopoietic stem cells are cryopreserved prior to, or after, or both prior to and after, the modification of the PD-L1 expression. In one embodiment, the hematopoietic stem cells are cryopreserved prior to use (e.g., to be modified, or to be administered to a subject). Methods for cryopreservation are known in the art and can be performed by a skilled practitioner. Cryopreserved hematopoietic stem cells maintain their function and pluripotency.

In one embodiment, the hematopoietic stem cells comprised in the population of hematopoietic stem cells are produced by a method comprising: (a) contacting a sample of HSCs with a vector carrying an exogenous copy of a nucleic acid encoding miRNAs that controls the expression of programmed cell death-1 receptor ligand (PD-L1) or an agent that inhibits the expression of the miRNA such as an antagomir of the miRNA, an anti-miRNA oligonucleotide to the miRNA, an antisense oligonucleotide to the miRNA or a locked nucleic acid that anneals to miRNA; (b) ex vivo culturing the resultant modified cells from the contacting; and (c) establishing the expression of PD-L1 on the modified HSCs, thereby producing a population of modified hematopoietic stem cell expressing PD-L1.

Another aspect of the invention is a population of any of the PD-L1 expressing hematopoietic stem cells described herein for use in the prevention or treatment of an autoimmune disease or disorder, for use in suppressing an immune response in a subject, for use in the delay of the onset of T1D in a subject at risk of developing T1D, for use in the prevention and delay of an allogenic tissue or organ transplant rejection, and for the treatment of T1D in adult and pediatric subjects.

Yet another aspect of the invention described herein provides a population of any of the PD-L1 expressing hematopoietic stem cells described herein for the manufacture of medicament for use in the prevention or treatment of an autoimmune disease or disorder, in the suppression of an immune response in a subject, in the delay of the onset of T1D in a subject at risk of developing T1D, in the prevention and delay of an allogenic tissue or organ transplant rejection, and for the treatment of T1D in adult and pediatric subjects.

In one embodiment, a population described herein is a pure population. Used in this context, "pure" refers to a population of cells substantially similar consisting of a single cell type. The cell population, in one embodiment can be mixed, including a hematopoietic stem cells and a second, different cell type. A pure cell population can be isolated using standard techniques known in the art.

miRNA

Methods and compositions described herein comprise modulating the expression of miRNAs that control the expression of PD-L1. microRNAs are small non-coding RNAs with an average length of 22 nucleotides. These molecules act by binding to complementary sequences within mRNA molecules, usually in the 3' untranslated (3'UTR) region, thereby promoting target mRNA degradation or inhibited mRNA translation. The interaction between microRNA and mRNAs is mediated by what is known as the "seed sequence", a 6-8-nucleotide region of the microRNA that directs sequence-specific binding to the mRNA through imperfect Watson-Crick base pairing. More than 900 microRNAs are known to be expressed in mammals. Many of these can be grouped into families on the basis of their seed sequence, thereby identifying a "cluster" of similar microRNAs. A miRNA can be expressed in a cell, e.g., as naked DNA. A miRNA can be encoded by a nucleic acid that is expressed in the cell, e.g., as naked DNA or can be encoded by a nucleic acid that is contained within a vector. A miRNA can be an endogenous miRNA or an artificial miRNA.

In one embodiment, the miRNA that modulates expression of PD-L1 is miR-4282, miR-7853, miR-7853-5p, miR-105, miR-105-5p, miR-224, miR-224-3p, miR-4279, miR-522, miR-522-3p, miR-374c, or miR-374c-5p.

In on embodiment, miRNA expression is increased, e.g., by introducing an exogenous copy of a nucleic acid encoding the miRNA (e.g., a nucleic acid encoding miR-4282, miR-7853, miR-7853-5p, miR-105, miR-105-5p, miR-224, miR-224-3p, miR-4279, miR-522, miR-522-3p, miR-374c, or miR-374c-5p). In one embodiment, introducing a nucleic acid encoding the miRNA results in the expression of the miRNA in the cell.

In one embodiment, the level of the miRNA is increased by at least 2-fold, by at least 3-fold, by at least 4-fold, by at least 5-fold, by at least 6-fold, by at least 7-fold, by at least 8-fold, by at least 9-fold, by at least 10-fold or more as compared to an appropriate control, or by at least 10%, by at least 20%, by at least 30%, by at least 40%, by at least 50%, by at least 60%, by at least 70%, by at least 80%, by at least 90%, by at least 100% or more as compared to an appropriate control. As used herein, an "appropriate control" refers to a similarly or identically treated cell or population thereof that an exogenous miRNA is not introduced to. Levels of a miRNA can be measured, e.g., by measuring the miRNA in a total RNA sample via, e.g., microarray or PCR-based screening (e.g., quantitative RT-CPR (q-PCR)).

In one embodiment, a modified, PD-L1+ expressing HSCs carries an exogenous copy of a nucleic acid encoding a miRNA selected from the group consisting of miR-4282, miR-7853, miR-7853-5p, miR-105, miR-105-5p, miR-224, miR-224-3p, miR-4279, miR-522, miR-522-3p, miR-374c, and miR-374c-5p.

In one embodiment, the miRNA is decreased by an agent that inhibits expression the miRNA. An agent can be an antagomir of the miRNA, an anti-miRNA oligonucleotide that binds the miRNA, an antisense oligonucleotide to the miRNA, or a locked nucleic acid that anneals the miRNA.

As used herein, an "antagomir" refers to a small synthetic RNA having complementarity to a specific microRNA target (e.g., a miRNA that controls PD-L1 expression), with either mispairing at the cleavage site or one or more base modifications to inhibit cleavage. Antagomirs are single stranded, double stranded, partially double stranded and hairpin structured chemically modified oligonucleotides that target a microRNA. Preferably, an antagomir featured in the invention includes a nucleotide sequence sufficiently complementary to hybridize to a miRNA target sequence of about 12 to 25 nucleotides, preferably about 15 to 23 nucleotides As used herein, an "antisense oligonucleotide" refers to a synthesized nucleic acid sequence that is complementary to a DNA or mRNA sequence, such as that of a microRNA. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under cellular conditions to a given target (e.g., a miRNA to be decreased). Thus, oligonucleotides are chosen that are sufficiently complementary to the target, i.e., that hybridize sufficiently well and with sufficient specificity in the context of the cellular environment, to give the desired effect.

As used herein, a "locked nucleic acid" refers to a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to, e.g., siRNAs has been shown to increase siRNA stability in serum, and to reduce off-target effects (Elmen, J. et al., (2005) Nucleic Acids Research 33(1):439-447; Mook, O R. et al., (2007) Mol Canc Ther 6(3):833-843; Grunweller, A. et al., (2003) Nucleic Acids Research 31(12):3185-3193).

In another embodiment, an "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

Such an agent can take the form of any entity which is normally not present or not present at the levels being administered in the cell. Agents such as chemicals; small molecules; nucleic acid sequences; nucleic acid analogues; proteins; peptides; aptamers; antibodies; or fragments thereof, can be identified or generated for use to downmodulate or upmodulate SIRT1 or SIRT2.

Agents in the form of nucleic acid sequences designed to specifically inhibit miRNA expression are particularly useful. Such a nucleic acid sequence can be RNA or DNA, and can be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNA interference, short hairpin RNA, silencing RNA, etc.

The agent can be a molecule from one or more chemical classes, e.g., organic molecules, which may include organometallic molecules, inorganic molecules, genetic sequences, etc. Agents may also be fusion proteins from one or more proteins, chimeric proteins (for example domain switching or homologous recombination of functionally significant regions of related or different molecules), synthetic proteins or other protein variations including substitutions, deletions, insertion and other variants.

In one embodiment, the level of the miRNA is decreased by at least 10%, by at least 20%, by at least 30%, by at least 40%, by at least 50%, by at least 60%, by at least 70%, by at least 80%, by at least 90%, by at least 100% or more as compared to an appropriate control. As used herein, an "appropriate control" refers to a similarly or identically treated cell or population thereof that an agent is not introduced to. Levels of a miRNA can be measured as described above.

In one embodiment, a nucleic acid for use of an agent as described herein is comprised within a vector, e.g., a viral vector.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of ordinary skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. control of PD-L1 expression.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, a polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to an assay known in the art or described below herein. A functional fragment can comprise conservative substitutions of the sequences disclosed herein.

In some embodiments, a polypeptide described herein can be a variant of a polypeptide or molecule as described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity of the non-variant polypeptide. A wide variety of PCR-based site-specific mutagenesis approaches are known in the art and can be applied by the ordinarily skilled artisan.

A variant amino acid or DNA sequence can be at least 80%, at least 90%, at least 91%, at least 92%, at least 93%, at least 94%, at least 95%, at least 96%, at least 97%, at least 98%, at least 99%, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of a polypeptide also can be substituted, generally with serine, to improve the oxidative stability of the molecule and prevent aberrant crosslinking. Conversely, cysteine bond(s) can be added to a polypeptide to improve its stability or facilitate oligomerization.

Introducing a Nucleic Acid or Agent

Various aspects of the invention described herein comprise introducing a nucleic acid or agent described herein to a cell, e.g., a hematopoietic stem cell, to modulate the expression of a miRNA that controls expression of PD-L1. Agents that act on the cell internally (e.g., nucleic acid encoding miRNA, or an antagomir) may be introduced in a form readily taken up by the cell when contacted to the cell (e.g., in a formulation which facilitates cellular uptake and delivery to the appropriate subcellular location). In one embodiment, the nucleic acid or agent is in a formulation in which it is readily taken up by the cell so that it can exert it effect. In one embodiment, the nucleic acid or agent is applied to the media, where it contacts the cell and produces its modulatory effects. In one embodiment, a nucleic acid or an agent is introduced to a cell via culturing the cell in a medium comprising the nucleic acid or agent.

As used herein, "introducing" refers to an effective amount of, e.g., a nucleic acid or an agent, that enters a cell or population thereof, and properly functions, e.g., modulates the expression of a miRNA that controls expression of PD-L1. Delivery can be done using any technique known in the art. Exemplary techniques include, but are not limited to transduction, nucleofection, electroporation, direct injection, or transfection. Effective introducing of a nucleic acid or an agent (e.g., a nucleic acid encoding a miRNA, or a antagomir which targets a miRNA) can be assessed by measuring miRNA levels of the intended miRNA target as described herein above. Effective introducing of an agent can additionally be measured by assessing the biological function of the intended target (e.g., miRNA) of the nucleic acid or agent, e.g., via assessing the expression of PD-L1, e.g., by western blotting to measure its protein levels.

It is understood that the optimal method for delivery can vary based on the type of agent, and can be determined by a skilled practitioner.

Hematopoietic Stem Cell Transplant

Methods described herein are directed at transplanting modified, PD-L1 expressing hematopoietic stem cells into a subject. Transplantation of hematopoietic stems cells has become the treatment of choice for a variety of inherited or malignant diseases. The donor and the recipient can be a single individual or different individuals, for example, autologous or allogeneic transplants, respectively. When allogeneic transplantation is practiced, regimes for reducing implant rejection and/or graft vs. host disease, as well known in the art, should be undertaken. Such regimes are currently practiced in human therapy. The cell populations selected can also be depleted of T lymphocytes, which may be useful in the allogeneic and haploidentical transplants setting for reducing graft-versus-host disease.

Most advanced regimes are disclosed in publications by Slavin S. et al., e.g., J Clin Immunol 2002; 22:64, and J Hematother Stem Cell Res 2002; 11:265, Gur H. et al. Blood 2002; 99:4174, and Martelli M F et al, Semin Hematol 2002; 39:48, which are incorporated herein by reference.

Methods for administering bone marrow transplants to a subject are known in the art and are described in medical textbooks, e.g., Whedon, M. B. (1991) Whedon, M. B. "Bone Marrow Transplantation: Principles, Practice, and Nursing Insights", Boston: Jones and Bartlett Publishers. Bone marrow cells from a healthy patient can be removed, preserved, and then replicated and re-infused should the patient develop an illness which either destroys the bone marrow directly or whose treatment adversely affects the marrow. If the patient is receiving his or her own cells, this is called an autologous transplant; such a transplant has little likelihood of rejection.

Exemplary methods of administering stem cells to a subject, particularly a human subject, include injection or transplantation of the cells into target sites in the subject. The induced HSCs can be inserted into a delivery device which facilitates introduction, by injection or transplantation, of the cells into the subject. Such delivery devices include tubes, e.g., catheters, for injecting cells and fluids into the body of a recipient subject. The tubes additionally have a needle, e.g., a syringe, through which the cells of the invention can be introduced into the subject at a desired location. The stem cells can be inserted into such a delivery device, e.g., a syringe, in different forms. For example, the cells can be suspended in a solution, or alternatively embedded in a support matrix when contained in such a delivery device.

As used herein, the term "solution" includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is known in the art. The solution is preferably sterile and fluid to the extent that easy syringability exists.

Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating stem cells as described herein in a pharmaceutically acceptable carrier or diluent and, as required, other ingredients enumerated above, followed by filtered sterilization.

Autoimmune Disease or Disorder

One aspect of the invention is a method of treating Type 1 Diabetes or an immune disease or disorder or cancer treatment in a host in need thereof comprising administering or ex vivo contacting an effective amount of a nucleic acid or an agent that modulates the expression of miRNAs controlling the expression of PD-L1 in the HSCs in a cell to a host.

In one embodiment, the cell is a progenitor cell. In another embodiment, the cell is a hematopoietic progenitor cell.

In one embodiment of any aspect described herein, the autoimmune disorder is Type 1 diabetes.

As used herein, an "autoimmune disease or disorder" is characterized by the inability of one's immune system to distinguish between a foreign cell and a healthy cell. This results in one's immune system targeting one's healthy cells for programmed cell death. In various embodiments, the autoimmune disease is type 1 diabetes. Non-limiting examples of additional autoimmune disease or disorder include inflammatory arthritis, mellitus, multiples sclerosis, psoriasis, inflammatory bowel diseases, SLE, and vasculitis, allergic inflammation, such as allergic asthma, atopic dermatitis, and contact hypersensitivity, rheumatoid arthritis, multiple sclerosis (MS), systemic lupus erythematosus, Graves' disease (overactive thyroid), Hashimoto's thyroiditis (underactive thyroid), chronic graft v. host disease, hemophilia with antibodies to coagulation factors, celiac disease, Crohn's disease and ulcerative colitis, Guillain-Barre syndrome, primary biliary sclerosis/cirrhosis, sclerosing cholangitis, autoimmune hepatitis, Raynaud's phenomenon, scleroderma, Sjogren's syndrome, Goodpasture's syndrome, Wegener's granulomatosis, polymyalgia rheumatica, temporal arteritis/giant cell arteritis, chronic fatigue syndrome CFS), psoriasis, autoimmune Addison's Disease, ankylosing spondylitis, Acute disseminated encephalomyelitis, antiphospholipid antibody syndrome, aplastic anemia, idiopathic thrombocytopenic purpura, Myasthenia gravis, opsoclonus myoclonus syndrome, optic neuritis, Ord's thyroiditis, pemphigus, pernicious anaemia, polyarthritis in dogs, Reiter's syndrome, Takayasu's arteritis, warm autoimmune hemolytic anemia, Wegener's granulomatosis and fibromyalgia (FM).

In one embodiment, the hematopoietic stem cells described herein are co-administered with at least one additional autoimmune disease or disorder therapy.

Cancer Treatment

Another aspect of the invention is a method of treating an autoimmune disorder or for cancer immune therapy (e.g., cancer therapy) in a subject in need thereof comprising administering to a subject a composition comprising any of the hematopoietic stem cells described herein. In one embodiment, the cancer is a carcinoma, a melanoma, a sarcoma, a myeloma, a leukemia, or a lymphoma. As used herein, "cancer" refers to a hyperproliferation of cells that have lost normal cellular control, resulting in unregulated growth, lack of differentiation, local tissue invasion, and metastasis. Cancers are classified based on the histological type (e.g., the tissue in which they originate) and their primary site (e.g., the location of the body the cancer first develops), and can be carcinoma, a melanoma, a sarcoma, a myeloma, a leukemia, or a lymphoma. "Cancer" can also refer to a solid tumor. As used herein, the term "tumor" refers to an abnormal growth of cells or tissues, e.g., of malignant type or benign type. "Cancer" can be metastatic, meaning the cancer cells have disseminated from its primary site of origin and migrated to a secondary site.

In one embodiment, the hematopoietic stem cells described herein are co-administered with at least one other anti-cancer therapy. Exemplary anti-cancer therapies include chemotherapy, radiation therapy, chemo-radiation therapy, immunotherapy, hormone therapy, and stem cell therapy. In one embodiment of any aspect described herein, the immunotherapy is a tumor vaccine, a chimeric antigen receptor T cell (CAR T cell), an adoptive T cell therapy (e.g., adoptive $CD4^+$ or $CD8^+$ effector T cell therapy), an adoptive natural killer (NK) cell therapy, or an adoptive NK T cell therapy. In one embodiment, the anticancer treatment is an antagomir or a miRNA mimic described herein. In one embodiment, the antagomir or a miRNA mimic described herein are delivered via injection. In one embodiment, the antagomir or a miRNA mimic is selected from Table 12. In one embodiment, antagomir or a miRNA mimic has a sequence selected from Table 12. In one embodiment, antagomir or a miRNA mimic consists of or consists essentially of a sequence selected from Table 12.

Modulating an Immune Response

One aspect of the invention is a method of modulating an immune response (e.g., for autoimmune disease, or for cancer immune therapy) in a subject comprising: (a) providing a population of hematopoietic stem cells (HSCs); (b) contacting sample of HSCs with a vector carrying an exogenous copy of a nucleic acid encoding miRNAs that controls the expression of programmed cell death-1 receptor ligand (PD-L1) or an agent that inhibits the expression of the miRNA such as an antagomir of the miRNA, an anti-miRNA oligonucleotide to the miRNA, an antisense oligonucleotide to the miRNA or a locked nucleic acid that anneals to miRNA; (c) transplanting said population of PD-L1+ expressing HSCs into a recipient subject, thereby modulating the immune response in the recipient subject.

Another aspect of the invention is a method of modulating an immune response in a subject comprising: (a) providing a population of hematopoietic stem cells (HSCs); (b) contacting sample of HSCs with a vector carrying an exogenous copy of a nucleic acid encoding miRNAs that controls the expression of programmed cell death-1 receptor ligand (PD-L1) or an agent that inhibits the expression of the miRNA such as an antagomir of the miRNA, an anti-miRNA oligonucleotide to the miRNA, an antisense oligonucleotide to the miRNA or a locked nucleic acid that anneals to miRNA; (c) ex vivo culturing the resultant modified cells from the contacting; (d) establishing the expression of PD-L1 on the modified HSCs, thereby producing a population of modified HSCs cells expressing PD-L1; and (e)transplanting said population of PD-L1+ expressing HSCs into a recipient subject, thereby modulating the immune response in the recipient subject.

As used herein, "modulating an immune response" can be increasing an immune response, or decreasing an immune response. An immune response can be, for example, raising antibodies to the population of PD-L1+ expressing HSCs or provoking an allergic or inflammatory response. One of skilled in the art would know how to determine if any given population of PD-L1+ expressing HSCs provokes such a response.

Compositions

One aspect of the invention is a composition comprising any of the modified hematopoietic stem cells described herein. In another aspect is a composition comprising any of the populations of modified hematopoietic stem cells described herein.

One aspect of the invention is a composition comprising any of the PD-L1 expressing hematopoietic stem cells described herein in the prevention or treatment of an autoimmune disease or disorder, for use in suppressing an immune response in a subject, for use in the delay of the onset of T1D in a subject at risk of developing T1D, for use in the prevention and delay of an allogenic tissue or organ transplant rejection, and for the treatment of T1D in adult and pediatric subjects.

Another aspect of the invention is a composition comprising any of the PD-L1 expressing hematopoietic stem cells described herein for the manufacture of medicament for use in the prevention or treatment of an autoimmune disease or disorder, in the suppression of an immune response in a subject, in the delay of the onset of T1D in a subject at risk of developing T1D, in the prevention and delay of an allogenic tissue or organ transplant rejection, and for the treatment of T1D in adult and pediatric subjects.

Yet another aspect of the invention is a population of any of the PD-L1 expressing hematopoietic stem cells described herein for the manufacture of medicament for use in the prevention or treatment of an autoimmune disease or disorder, in the suppression of an immune response in a subject, in the delay of the onset of T1D in a subject at risk of developing T1D, in the prevention and delay of an allogenic tissue or organ transplant rejection, and for the treatment of T1D in adult and pediatric subjects.

Administration

Methods and compositions described herein at directed at the treatment or prevention of an autoimmune disease or disorder, e.g., type I diabetes. In one embodiment, the modified hematopoietic stem cells described herein are administered to a subject having a diagnosed autoimmune disease to treat the disease in the subject. In one embodiment, the modified hematopoietic stem cells described herein are administered to a subject at risk of having a diagnosed autoimmune disease to prevent the disease in the subject.

Methods and compositions described herein at directed at the treatment or prevention of cancer, e.g., as a cancer immune therapy. In one embodiment, the modified hematopoietic stem cells described herein are administered to a subject having a cancer to treat the disease in the subject. In one embodiment, the modified hematopoietic stem cells described herein are administered to a subject at risk of having cancer to prevent the disease in the subject. In one embodiment, the modified hematopoietic stem cells described herein may be administered as part of a bone marrow or cord blood transplant in an individual that has or has not undergone bone marrow ablative therapy. In one embodiment, the modified hematopoietic stem cells described herein are administered in a bone marrow transplant to an individual that has undergone chemoablative or radioablative bone marrow therapy.

In one embodiment, a dose of modified hematopoietic stem cells is delivered to a subject intravenously. In one embodiment, modified hematopoietic stem cells are intravenously administered to a subject.

In particular embodiments, subjects receive a dose of modified hematopoietic stem cells of about $1\times10^5$ cells/kg, about $5\times10^5$ cells/kg, about $1\times10^6$ cells/kg, about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $5\times10^7$ cells/kg, about $1\times10^8$ cells/kg, or more in one single intravenous dose. In certain embodiments, patients receive a dose of genetically modified cells, e.g., hematopoietic stem cells, of at least $1\times10^5$ cells/kg, at least $5\times10^5$ cells/kg, at least $1\times10^6$ cells/kg, at least $2\times10^6$ cells/kg, at least $3\times10^6$ cells/kg, at least $4\times10^6$ cells/kg, at least $5\times10^6$ cells/kg, at least $6\times10^6$ cells/kg, at least $7\times10^6$ cells/kg, at least $8\times10^6$ cells/kg, at least $9\times10^6$ cells/kg, at least $1\times10^7$ cells/kg, at least $5\times10^7$ cells/kg, at least $1\times10^8$ cells/kg, or more in one single intravenous dose.

In an additional embodiment, subjects receive a dose of modified hematopoietic stem cells of about $1\times10^5$ cells/kg to about $1\times10^8$ cells/kg, about $1\times10^6$ cells/kg to about $1\times10^8$ cells/kg, about $1\times10^6$ cells/kg to about $9\times10^6$ cells/kg, about $2\times10^6$ cells/kg to about $8\times10^6$ cells/kg, about $2\times10^6$ cells/kg to about $8\times10^6$ cells/kg, about $2\times10^6$ cells/kg to about $5\times10^6$ cells/kg, about $3\times10^6$ cells/kg to about $5\times10^6$ cells/kg, about $3\times10^6$ cells/kg to about $4\times10^8$ cells/kg, or any intervening dose of cells/kg.

In various embodiments, the methods of the invention provide more robust and safe gene therapy than existing methods and comprise administering a population or dose of modified hematopoietic stem cells comprising about 5% transduced cells, about 10% transduced cells, about 15% transduced cells, about 20% transduced cells, about 25% transduced cells, about 30% transduced cells, about 35% transduced cells, about 40% transduced cells, about 45% transduced cells, or about 50% transduced cells, to a subject.

In some embodiment, the administered hematopoietic stem cell differentiates into a blood cell following transplantation into a subject. In some embodiments of all aspects, the HSC is committed to the blood lineage following transplantation into a subject. Differentiation of HSCs to fully differentiated blood cells is believed to be an irreversible process under normal physiological conditions. Hematopoietic lineage specification takes place within the bounds of strict lineal relationships: for example, megakaryocyte progenitors give rise to megakaryocytes and ultimately platelets, but not to any other blood lineages. A HSC can differentiate into all blood cell types. Non-limiting examples of blood cells that a HSC can differentiate into include a myeloid progenitor, a lymphoid progenitor, a megakaroblast, a promegakarocyte, a megakaryocyte, a thrombocyte, a proerythroblast, a basophilic erythroblast, a polychromatic erythroblast, an orthochromatic erythroblast, a polychromatic erythrocyte, an erythrocyte, a myeloblast, a B. promyelocyte, a B. myelocyte, a B. metamyelocyte, a B. band, a Basophil, a N. promyelocyte, a N. myelocyte, a N. metamyelocyte, a N. band, a neutrophil, an E. promyelocyte, an E. myelocyte, an E. metamyelocyte, an E. band, an eosinophil, a monoblast, a promonocyte, a monocyte, a macrophage, a myeloid dendritic cell, a lymphoblast, a prolymphocyte, a small lymphocyte, a B lymphocyte, a T lymphocyte, a plasma cell, a large granular lymphocyte, and a lymphoid dendritic cell.

Various studies have reported successful mammalian dosing using complementary nucleic acid sequences. For example, Esau C., et al., (2006) Cell Metabolism, 3(2):87-98 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, non-toxic dose. Another study by Krützfeldt J., et al., (2005) Nature 438, 685-689, injected anatgomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg kg-1 LNA-antimiR, leading to a long-lasting and reversible decrease in total plasma cholesterol without any evidence for LNA-associated toxicities or histopathological changes in the study animals.

In various embodiments, the modified hematopoietic stem cells described herein are administered in combination with at least one additional therapeutic (e.g., an autoimmune therapy, or an anti-cancer therapy). Administered "in combination," as used herein, means that two (or more) different treatments are delivered to the subject during the course of the subject's affliction with the disorder, e.g., the two or more treatments are delivered after the subject has been diagnosed with the disorder (e.g., an autoimmune disease, or cancer) and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The treatment described herein (e.g., modified hematopoietic stem cells described herein, or compositions comprising modified hematopoietic stem cells described herein) and the at least one additional therapy can be administered simultaneously, in the same or in separate compositions, or sequentially. For sequential administration, the treatment described herein can be administered first, and the additional agent can be administered second, or the order of administration can be reversed. The treatment described herein and/or other therapeutic agents, procedures or modalities can be administered during periods of active disorder, or during a period of remission or less active disease. The treatment described herein can be administered before another treatment, concurrently with the treatment, post-treatment, or during remission of the disorder.

Formulation

Therapeutic compositions or pharmaceutical compositions can be formulated for passage through the blood-brain barrier or direct contact with the endothelium. In some embodiments, the compositions can be formulated for systemic delivery. In some embodiments, the compositions can be formulated for delivery to specific organs, for example but not limited to the liver, spleen, the bone marrow, and the skin. Therapeutic compositions or pharmaceutical compositions can be formulated for aerosol application by inhalation the lung. Alternatively, the therapeutic compositions or pharmaceutical compositions can also be formulated for a transdermal delivery, e. g. a skin patch. Therapeutic compositions or pharmaceutical compositions can be enteric coated and formulated for oral delivery. Therapeutic compositions or pharmaceutical compositions can be encapsulated in liposomes or nanoparticles and formulated for slow sustained delivery in vivo. Alternatively, the therapeutic compositions or pharmaceutical compositions can be formulated for targeted delivery, eg., encapsulated in liposomes or nanoparticles that are designed and feature targeting moiety to on the liposomes or nanoparticles.

The modified hematopoietic stem cells, and the compositions described herein can be administered by any known route. By way of example, the modified hematopoietic stem cells and the compositions described herein can be administered by a mucosal, pulmonary, topical, or other localized or systemic route (e.g., enteral and parenteral). The modified hematopoietic stem cells may be administered by any convenient route, for example by infusion or bolus injection, by absorption through epithelial or mucocutaneous linings (e.g., oral mucosa, rectal and intestinal mucosa, etc.) and may be administered together with other biologically active agents.

Routes of administration include, but are not limited to aerosol, direct injection, intradermal, transdermal (e.g., in slow release polymers), intravitreal, intramuscular, intraperitoneal, intravenous, subcutaneous, intranasal, epidural, topical, oral, transmucosal, buccal, rectal, vaginal, transdermal, intranasal and parenteral routes. "Parenteral" refers to a route of administration that is generally associated with injection, including but not limited to intraorbital, infusion, intraarterial, intracapsular, intracardiac, intradermal, intrahepatic, intrarogan, intramuscular, intraperitoneal, intrapulmonary, intraspinal, intrasternal, intrathecal, intrauterine, intravenous, subarachnoid, subcapsular, subcutaneous, transmucosal, or transtracheal. Any other therapeutically efficacious route of administration can be used, for example, infusion or bolus injection, absorption through epithelial or mucocutaneous linings, or by gene therapy wherein a DNA molecule encoding the therapeutic protein or peptide is administered to the patient, e.g., via a vector, which causes the protein or peptide to be expressed and secreted at therapeutic levels in vivo. In various embodiments, administration can be inhaled in to the lung via aerosol administration, e.g. with nebulization. Administration also can be systemic or local. Intratumoral delivery is also included.

For example, the modified hematopoietic stem cells can be administered as a formulation adapted for passage through the blood-brain barrier or direct contact with the endothelium. In some embodiments, the modified hematopoietic stem cells can be administered as a formulation adapted for systemic delivery. In some embodiments, the modified hematopoietic stem cells can be administered as a formulation adapted for delivery to specific organs, for example but not limited to the liver, spleen, the bone marrow, and the skin.

In addition, the modified hematopoietic stem cells described herein can be administered together with other components of biologically active agents, such as pharmaceutically acceptable surfactants (e.g., glycerides), excipients (e.g., lactose), carriers, diluents and vehicles.

The modified hematopoietic stem cells described herein can be administered therapeutically to a subject prior to, simultaneously with (in the same or different compositions) or sequentially with the administration of at least one other cancer therapy. For example, the addition cancer therapy is radiation or chemotherapy or proton therapy. The modified hematopoietic stem cells described herein can be administered as adjunctive and/or concomitant therapy to a cancer therapy.

For parenteral (e.g., intravenous, subcutaneous, intramuscular) administration, modified hematopoietic stem cells described herein can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and non-aqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by commonly used techniques.

The dosage administered to a subject will vary depending upon a variety of factors, including the pharmacodynamic characteristics of the particular antagonists, and its mode and route of administration; size, age, sex, health, body weight and diet of the recipient; nature and extent of symptoms of the disease being treated, kind of concurrent treatment, frequency of treatment, and the effect desired.

Usually a daily dosage of active ingredient can be about 0.01 to 500 milligrams per kilogram of body weight. Ordinarily 1 to 40 milligrams per kilogram per day given in divided doses 1 to 6 times a day or in sustained release form is effective to obtain desired results. The active ingredient will ordinarily be present in an amount of about 0.5-95% by weight based on the total weight of the composition. Second or subsequent administrations can be administered at a dosage which is the same, less than or greater than the initial or previous dose administered to the individual.

A second or subsequent administration is preferably during or immediately prior to relapse or a flare-up of the disease or symptoms of the disease, e.g., an autoimmune disease. For example, second and subsequent administrations can be given between about one day to 30 weeks from the previous administration. Two, three, four or more total administrations can be delivered to the individual, as needed.

The precise dose to be employed in the formulation will also depend on the route of administration, and the seriousness of the disease or disorder, e.g., an autoimmune disease, and should be decided according to the judgment of the practitioner and each patient's circumstances. Effective doses may be extrapolated from dose-response curves derived from in vitro or animal model test systems.

Efficacy testing can be performed during the course of treatment using the methods described herein. Measurements of the degree of severity of a number of symptoms associated with a particular disease or disorder, e.g., an autoimmune disease, are noted prior to the start of a treatment and then at later specific time period after the start of the treatment.

For example, when treating an autoimmune disease such as type 1 diabetes, the unintentional weight loss, frequent urination, and blurred vision are symptoms that, e.g., occur at the onset of disease. Unintentional weight loss, frequent urination, and blurred vision are noted before and after a treatment. The severity of unintentional weight loss, frequent urination, and blurred vision after the treatment are compared to those before the treatment. A decrease in the unintentional weight loss, frequent urination, and blurred vision indicate that the treatment is effective in reducing the severity of the disease, thereby decreasing unintentional weight loss, frequent urination, and blurred vision.

The skilled artisan will appreciate that certain factors may influence the dosage and timing required to effectively treat a subject, including but not limited to the severity of the disease or disorder, e.g., an autoimmune disease, previous treatments, the general health and/or age of the subject, and other diseases present. The dose levels can also depend on whether modified hematopoietic stem cells encompassed by the disclosure can be made using conventional methodologies or on the basis of in vivo testing using an appropriate animal model, as known in the art, or as described herein. Preferred dosages for a modified hematopoietic stem cells are readily determinable by those of skill in the art by a variety of means.

This invention is further illustrated by the following example which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the invention described herein. Such equivalents are intended to be encompassed by the following claims.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention can be defined in any of the following numbered paragraphs:

1. An ex vivo method of producing a population of modified, PD-L1+ expressing hematopoietic stem cells (HSCs), the method comprising modulating the expression of miRNAs controlling the expression of PD-L1 in the HSCs.
2. The method of paragraph 1, wherein the modulation of the expression of miRNAs is increasing the expression of miRNA or decreasing the expression of miRNA.
3. The method of paragraph 1 or 2, wherein the miRNA expression is increased by introducing an exogenous copy of a nucleic acid encoding the miRNA for the expression of the miRNA in the cell.
4. The method of method of paragraph 1 or 2, wherein the miRNA expression is decreased by an agent that inhibits the expression of the miRNA such as an antagomir of the miRNA, an anti-miRNA oligonucleotide to the miRNA, an antisense oligonucleotide to the miRNA or a locked nucleic acid that anneals to miRNA.
5. The method of paragraph 3, wherein the exogenous copy is introduced by way of a vector, such as a viral vector.
6. The method of paragraph 4, wherein the agent is introduced into the HSC by a vector, such as a viral vector.
7. The method of any of paragraphs 1-6, wherein the miRNA is selected from the group consisting of miR-4282, miR-7853, miR-7853-5p, miR-105, miR-105-5p, miR-224, miR-224-3p, miR-4279, miR-522, miR-522-3p, miR-374c, and miR-374c-5p.
8. The method of any of paragraphs 1-7, wherein the modified, PD-L1+ expressing HSCs carries an exogenous copy of a nucleic acid encoding a miRNA selected from the group consisting of miR-4282, miR-7853, miR-7853-5p, miR-105, miR-105-5p, miR-224, miR-224-3p, miR-4279, miR-522, miR-522-3p, miR-374c, and miR-374c-5p.
9. A population of modified hematopoietic stem cells (HSCs) in which the modified cells have increased PD-L1 expression compared to control, non-modified cells, where the cells carry an exogenous copy of a nucleic acid encoding a miRNAs that controls the expression of programmed cell death-1 receptor ligand (PD-L1) or an agent that inhibits the expression of the miRNA such as an antagomir of the miRNA, an anti-miRNA oligonucleotide to the miRNA, an antisense oligonucleotide to the miRNA or a locked nucleic acid that anneals to miRNA.
10. The population of modified HSCs of paragraph 9, wherein the HSC cells are mammalian HSC cells.
11. The population of modified HSCs of paragraph 10, wherein the mammalian HSC cells are human HSC cells.
12. The population of modified HSCs of any of paragraphs 9-11, wherein prior to the modification, the HSCs are obtained from the bone marrow, umbilical cord, amniotic fluid, chorionic villi, cord blood, placental blood or peripheral blood.
13. The population of modified HSCs of any of paragraphs 9-11, wherein the HSCs are obtained from mobilized peripheral blood.
14. The population of modified HSCs of any of paragraphs 9-13, wherein the HSCs are obtained from a healthy individual.
15. The population of modified HSCs of any of paragraphs 9-13, wherein the HSCs are obtained from an individual with a diagnosed disease or disorder.
16. The population of modified HSCs of paragraph 15, wherein the diagnosed disease or disorder is an autoimmune disease or disorder.
17. The population of modified HSCs of paragraph 16, wherein the autoimmune disease or disorder is Type 1 diabetes (TID).
18. The population of modified HSCs of any of paragraphs 9-17, wherein the HSC cells are ex vivo cultured before or after or both before and after the modification of the PD-L1 expression.
19. The population of modified HSCs of any of paragraphs 9-17, wherein the HSC cells are cryopreserved prior to or after or both prior to and after the modification of the PD-L1 expression.
20. The population of modified HSCs of any of paragraphs 9-17, wherein the modified HSC cells are cryopreserved prior to use.
21. The population of modified HSCs of any of paragraphs 9-20, wherein the HSC cells are produced by a method comprising:
a. contacting a sample of HSCs with a vector carrying an exogenous copy of a nucleic acid encoding miRNAs that controls the expression of programmed cell death-1 receptor ligand (PD-L1) or an agent that inhibits the expression of the miRNA such as an antagomir of the miRNA, an anti-miRNA oligonucleotide to the miRNA, an antisense oligonucleotide to the miRNA or a locked nucleic acid that anneals to miRNA;
b. ex vivo culturing the resultant modified cells from the contacting; and
c. establishing the expression of PD-L1 on the modified HSCs, thereby producing a population of modified HSCs cells expressing PD-L1.
22. The population of modified HSCs of any paragraphs 9-21, the miRNA is selected from the group consisting of miR-4282, miR-7853, miR-7853-5p, miR-105, miR-105-5p, miR-224, miR-224-3p, miR-4279, miR-522, miR-522-3p, miR-374c, and miR-374c-5p.
23. The population of modified HSCs of any of paragraphs 9-20 that is produced by the method paragraphs of 1-8.
24. A composition of modified HSCs comprising of HSCs of any of paragraphs 1-23.
25. A method of treating Type 1 Diabetes or an immune disease or disorder or cancer treatment in a host in need thereof, the method comprising administering or ex vivo contacting an effective amount of an agent that modulates the expression of miRNAs controlling the expression of PD-L1 in the HSCs in a cell to a host.

26. The method of paragraph 25, wherein the cell is a progenitor cell.
27. The method of paragraph 26, wherein the progenitor cell is a hematopoietic progenitor cell.
28. The method of paragraph 27, wherein the agent is a vector comprising a nucleic acid sequence that miRNAs that controls the expression of programmed cell death-1 receptor ligand (PD-L1) or an agent that inhibits the expression of the miRNA such as an antagomir of the miRNA, an anti-miRNA oligonucleotide to the miRNA, an antisense oligonucleotide to the miRNA or a locked nucleic acid that anneals to miRNA, wherein the miRNA is selected from the group consisting of miR-4282, miR-7853, miR-7853-5p, miR-105, miR-105-5p, miR-224, miR-224-3p, miR-4279, miR-522, miR-522-3p, miR-374c, and miR-374c-5p.
29. The method of paragraph 28, wherein the vector is a virus.
30. A method of treating an autoimmune disorder or for cancer immune therapy (aka cancer therapy) in a subject in need thereof, the method comprising administering to a subject a composition comprising the hematopoietic stem cells in any of the preceding paragraphs.
31. The method of paragraph 30, wherein the autoimmune disorder is Type 1 diabetes (T1D).
32. The method of paragraph 30 or 31, wherein the HSCs are autologous to the recipient subject.
33. The method of paragraph 30 or 31, wherein the HSCs are non-autologous and allogenic to the recipient subject.
34. The method of paragraph 30 or 31, wherein the HSCs are non-autologous and xenogeneic to the recipient subject.
35. A method of modulating an immune response (e.g., for autoimmune disease, or for cancer immune therapy) in a subject comprising:
a. providing a population of hematopoietic stem cells (HSCs);
b. contacting sample of HSCs with a vector carrying an exogenous copy of a nucleic acid encoding miRNAs that controls the expression of programmed cell death-1 receptor ligand (PD-L1) or an agent that inhibits the expression of the miRNA such as an antagomir of the miRNA, an anti-miRNA oligonucleotide to the miRNA, an antisense oligonucleotide to the miRNA or a locked nucleic acid that anneals to miRNA;
c. transplanting said population of PD-L1+ expressing HSCs into a recipient subject, thereby modulating the immune response in the recipient subject.
36. A method of modulating an immune response in a subject comprising:
a. providing a population of hematopoietic stem cells (HSCs);
b. contacting sample of HSCs with a vector carrying an exogenous copy of a nucleic acid encoding miRNAs that controls the expression of programmed cell death-1 receptor ligand (PD-L1) or an agent that inhibits the expression of the miRNA such as an antagomir of the miRNA, an anti-miRNA oligonucleotide to the miRNA, an antisense oligonucleotide to the miRNA or a locked nucleic acid that anneals to miRNA;
c. ex vivo culturing the resultant modified cells from the contacting;
d. establishing the expression of PD-L1 on the modified HSCs, thereby producing a population of modified HSCs cells expressing PD-L1; and
e. transplanting said population of PD-L1+ expressing HSCs into a recipient subject, thereby modulating the immune response in the recipient subject.
37. The method of paragraph 35 or 36, wherein the population of HSCs is obtained from the bone marrow, umbilical cord, amniotic fluid, chorionic villi, cord blood, placental blood or peripheral blood.
38. The method of any of paragraphs 35-37, wherein the population of HSCs is obtained from mobilized peripheral blood.
39. The method of any of paragraphs 35-37, wherein the population of HSCs autologous to the recipient subject.
40. The method of any of paragraphs 35-37, wherein the population of HSCs allogeneic to the recipient subject.
41. The method of any of paragraphs 35-37, wherein the population of HSCs is xenogeneic to the recipient subject.
42. The method of any of paragraphs 35-41, wherein the miRNA is selected from the group consisting of miR-4282, miR-7853, miR-7853-5p, miR-105, miR-105-5p, miR-224, miR-224-3p, miR-4279, miR-522, miR-522-3p, miR-374c, and miR-374c-5p.
43. The method of any of the preceding paragraph, wherein the vector is a virus.
44. A composition comprising the PD-L1 expressing hematopoietic stem cells of any one of the preceding paragraphs for use in the prevention or treatment of an autoimmune disease or disorder, for use in suppressing an immune response in a subject, for use in the delay of the onset of T1D in a subject at risk of developing T1D, for use in the prevention and delay of an allogenic tissue or organ transplant rejection, and for the treatment of T1D in adult and pediatric subjects.
45. A composition comprising the PD-L1 expressing hematopoietic stem cells of any one of the preceding paragraphs for the manufacture of medicament for use in the prevention or treatment of an autoimmune disease or disorder, in the suppression of an immune response in a subject, in the delay of the onset of T1D in a subject at risk of developing T1D, in the prevention and delay of an allogenic tissue or organ transplant rejection, and for the treatment of T1D in adult and pediatric subjects.
46. A population of PD-L1 expressing hematopoietic stem cells of any one of the preceding paragraphs for use in the prevention or treatment of an autoimmune disease or disorder, for use in suppressing an immune response in a subject, for use in the delay of the onset of T1D in a subject at risk of developing T1D, for use in the prevention and delay of an allogenic tissue or organ transplant rejection, and for the treatment of T1D in adult and pediatric subjects.
47. A population of PD-L1 expressing hematopoietic stem cells of any one of the preceding paragraphs for the manufacture of medicament for use in the prevention or treatment of an autoimmune disease or disorder, in the suppression of an immune response in a subject, in the delay of the onset of T1D in a subject at risk of developing T1D, in the prevention and delay of an allogenic tissue or organ transplant rejection, and for the treatment of T1D in adult and pediatric subjects.

The present invention can be further defined in any of the following numbered paragraphs:

1. An ex vivo method of producing a population of modified, PD-L1+ expressing hematopoietic stem cells (HSCs), the method comprising modulating the expression of miRNAs controlling the expression of PD-L1 in the HSCs.
2. The method of paragraph 1, wherein the modulation of the expression of miRNAs is increasing the expression of miRNA or decreasing the expression of miRNA.
3. The method of paragraph 1 or 2, wherein the miRNA expression is increased by introducing an exogenous copy of a nucleic acid encoding the miRNA for the expression of the miRNA in the cell.
4. The method of method of paragraph 1 or 2, wherein the miRNA expression is decreased by an agent that inhibits the expression of the miRNA such as an antagomir of the miRNA, an anti-miRNA oligonucleotide to the miRNA, an antisense oligonucleotide to the miRNA or a locked nucleic acid that anneals to miRNA.
5. The method of paragraph 3, wherein the exogenous copy is introduced by way of a vector, such as a viral vector.
6. The method of paragraph 4, wherein the agent is introduced into the HSC by a vector, such as a viral vector.
7. The method of any of paragraphs 1-6, wherein the miRNA is selected from the group consisting of miR-4282, miR-7853, miR-7853-5p, miR-105, miR-105-5p, miR-224, miR-224-3p, miR-4279, miR-522, miR-522-3p, miR-374c, and miR-374c-5p.
8. The method of any of paragraphs 1-7, wherein the modified, PD-L1+ expressing HSCs carries an exogenous copy of a nucleic acid encoding a miRNA selected from the group consisting of miR-4282, miR-7853, miR-7853-5p, miR-105, miR-105-5p, miR-224, miR-224-3p, miR-4279, miR-522, miR-522-3p, miR-374c, and miR-374c-5p.
9. The method of any of paragraphs 1-7, wherein the agent is as an antagomir of the miRNA, an anti-miRNA oligonucleotide to the miRNA, an antisense oligonucleotide to the miRNA or a locked nucleic acid that anneals to miRNA
10. A population of modified hematopoietic stem cells (HSCs) in which the modified cells have increased PD-L1 expression, where the cells carry an exogenous copy of a nucleic acid encoding a miRNAs that controls the expression of programmed cell death-1 receptor ligand (PD-L1) or an agent that inhibits the expression of the miRNA.
11. The population of modified HSCs of paragraph 10, wherein the agent is an antagomir of the miRNA, an anti-miRNA oligonucleotide to the miRNA, an antisense oligonucleotide to the miRNA or a locked nucleic acid that anneals to miRNA.
12. The population of modified HSCs of paragraph 10, wherein the HSC cells are mammalian HSC cells.
13. The population of modified HSCs of paragraph 12, wherein the mammalian HSC cells are human HSC cells.
14. The population of modified HSCs of any of paragraphs 10-13, wherein prior to the modification, the HSCs are obtained from the bone marrow, umbilical cord, amniotic fluid, chorionic villi, cord blood, placental blood or peripheral blood.
15. The population of modified HSCs of any of paragraphs 10-13, wherein the HSCs are obtained from mobilized peripheral blood.
16. The population of modified HSCs of any of paragraphs 10-15, wherein the HSCs are obtained from a healthy individual.
17. The population of modified HSCs of any of paragraphs 10-15, wherein the HSCs are obtained from an individual with a diagnosed disease or disorder.
18. The population of modified HSCs of paragraph 17, wherein the diagnosed disease or disorder is an autoimmune disease or disorder.
19. The population of modified HSCs of paragraph 18, wherein the autoimmune disease or disorder is Type 1 diabetes (TID).
20. The population of modified HSCs of any of paragraphs 10-19, wherein the HSC cells are ex vivo cultured before or after or both before and after the modification of the PD-L1 expression.
21. The population of modified HSCs of any of paragraphs 10-19, wherein the HSC cells are cryopreserved prior to or after or both prior to and after the modification of the PD-L1 expression.
22. The population of modified HSCs of any of paragraphs 10-19, wherein the modified HSC cells are cryopreserved prior to use.
23. The population of modified HSCs of any of paragraphs 10-22, wherein the HSC cells are produced by a method comprising:
24. contacting a sample of HSCs with a vector carrying an exogenous copy of a nucleic acid encoding miRNAs that controls the expression of programmed cell death-1 receptor ligand (PD-L1) or an agent that inhibits the expression of the miRNA such as an antagomir of the miRNA, an anti-miRNA oligonucleotide to the miRNA, an antisense oligonucleotide to the miRNA or a locked nucleic acid that anneals to miRNA;
25. ex vivo culturing the resultant modified cells from the contacting; and
26. establishing the expression of PD-L1 on the modified HSCs, thereby producing a population of modified HSCs cells expressing PD-L1.
27. The population of modified HSCs of any paragraphs 10-22, the miRNA is selected from the group consisting of miR-4282, miR-7853, miR-7853-5p, miR-105, miR-105-5p, miR-224, miR-224-3p, miR-4279, miR-522, miR-522-3p, miR-374c, and miR-374c-5p.
28. The population of modified HSCs of any of paragraphs 10-22 that is produced by the method paragraphs of 1-8.
29. A composition of modified HSCs comprising of HSCs of any of paragraphs 1-25.
30. A method, the method comprising administering or ex vivo contacting an effective amount of an agent that modulates the expression of miRNAs controlling the expression of PD-L1 in the HSCs in a cell to a host.
31. The method of paragraph 27, wherein the cell is a progenitor cell.
32. The method of paragraph 28, wherein the progenitor cell is a hematopoietic progenitor cell.
33. The method of paragraph 29, wherein the agent is a vector comprising a nucleic acid sequence that miRNAs that controls the expression of programmed cell death-1 receptor ligand (PD-L1) or an agent that inhibits the expression of the miRNA such as an antagomir of the miRNA, an anti-miRNA oligonucleotide to the miRNA, an antisense oligonucleotide to the miRNA or a locked nucleic acid that anneals to miRNA, wherein the miRNA is selected from the group consisting of miR-4282, miR-7853, miR-7853-5p, miR-105, miR-105-5p, miR-224, miR-224-3p, miR-4279, miR-522, miR-522-3p, miR-374c, and miR-374c-5p.
34. The method of paragraph 30, wherein the vector is a virus.
35. The method of paragraph 27, wherein the method is used to treat type 1 diabetes, an autoimmune disease, or cancer.
36. A method of treating an autoimmune disorder or cancer in a subject in need thereof, the method comprising administering to a subject a composition comprising the hematopoietic stem cells in any of the preceding paragraphs.
37. The method of paragraph 33, wherein the autoimmune disorder is Type 1 diabetes (TID).
38. The method of paragraph 33 or 34, wherein the HSCs are autologous to the recipient subject.
39. The method of paragraph 33 or 34, wherein the HSCs are non-autologous and allogenic to the recipient subject.
40. The method of paragraph 33 or 34, wherein the HSCs are non-autologous and xenogeneic to the recipient subject.
41. A method of modulating an immune response in a subject comprising, administering or transplanting the cell of paragraphs 10-22, or administering the composition of paragraph 26.
42. A method of modulating an immune response in a subject comprising:
43. providing a population of hematopoietic stem cells (HSCs);
44. contacting sample of HSCs with a vector carrying an exogenous copy of a nucleic acid encoding miRNAs that controls the expression of programmed cell death-1 receptor ligand (PD-L1) or an agent that inhibits the expression of the miRNA;
45. ex vivo culturing the resultant modified cells from the contacting;
46. establishing the expression of PD-L1 on the modified HSCs, thereby producing a population of modified HSCs cells expressing PD-L1; and
47. transplanting said population of PD-L1+ expressing HSCs into a recipient subject, thereby modulating the immune response in the recipient subject.
48. The method of paragraph 38 or 39, wherein the population of HSCs is obtained from the bone marrow, umbilical cord, amniotic fluid, chorionic villi, cord blood, placental blood or peripheral blood.
49. The method of any of paragraphs 38-40, wherein the population of HSCs is obtained from mobilized peripheral blood.
50. The method of any of paragraphs 38-40, wherein the population of HSCs autologous to the recipient subject.
51. The method of any of paragraphs 38-40, wherein the population of HSCs allogeneic to the recipient subject.
52. The method of any of paragraphs 38-40, wherein the population of HSCs is xenogeneic to the recipient subject.
53. The method of any of paragraphs 38-44, wherein the miRNA is selected from the group consisting of miR-4282, miR-7853, miR-7853-5p, miR-105, miR-105-5p, miR-224, miR-224-3p, miR-4279, miR-522, miR-522-3p, miR-374c, and miR-374c-5p.
54. The method of paragraph 39, wherein the agent is an antagomir of the miRNA, an anti-miRNA oligonucleotide to the miRNA, an antisense oligonucleotide to the miRNA or a locked nucleic acid that anneals to miRNA.
55. The method of any of the preceding paragraph, wherein the vector is a virus.
56. A composition comprising the PD-L1 expressing hematopoietic stem cells of any one of the preceding paragraphs for use in the prevention or treatment of an autoimmune disease or disorder, for use in suppressing an immune response in a subject, for use in the delay of the onset of T1D in a subject at risk of developing T1D, for use in the prevention and delay of an allogenic tissue or organ transplant rejection, and for the treatment of T1D in adult and pediatric subjects.
57. A composition comprising the PD-L1 expressing hematopoietic stem cells of any one of the preceding paragraphs for the manufacture of medicament for use in the prevention or treatment of an autoimmune disease or disorder, in the suppression of an immune response in a subject, in the delay of the onset of T1D in a subject at risk of developing T1D, in the prevention and delay of an allogenic tissue or organ transplant rejection, and for the treatment of T1D in adult and pediatric subjects.
58. A population of PD-L1 expressing hematopoietic stem cells of any one of the preceding paragraphs for use in the prevention or treatment of an autoimmune disease or disorder, for use in suppressing an immune response in a subject, for use in the delay of the onset of T1D in a subject at risk of developing T1D, for use in the prevention and delay of an allogenic tissue or organ transplant rejection, and for the treatment of T1D in adult and pediatric subjects.
59. A population of PD-L1 expressing hematopoietic stem cells of any one of the preceding paragraphs for the manufacture of medicament for use in the prevention or treatment of an autoimmune disease or disorder, in the suppression of an immune response in a subject, in the delay of the onset of T1D in a subject at risk of developing T1D, in the prevention and delay of an allogenic tissue or organ transplant rejection, and for the treatment of T1D in adult and pediatric subjects.

EXAMPLES

Example 1

Recently, Voltarelli et al. evaluated the safety and efficacy of autologous hematopoietic stem and progenitor cell (HSPC) transplantation in combination with Thymoglobulin plus cyclophosphamide as induction in newly diagnosed T1D patients (3). The latest multicenter analysis on 65 newly diagnosed T1D patients treated with autologous HSPC transplantation achieved insulin independence in nearly 60% of treated patients (4), suggesting that HSPCs may be a therapeutic option for selected T1D patients. Interestingly, HSPCs are endowed with immunoregulatory properties, which have been shown to be linked to the expression of the immune checkpoint PD-L1 (or CD274) (5). PD-L1 is the ligand for the inhibitory programmed death 1 (PD-1) receptor, expressed primarily on activated T cells (6). Crosslinking of PD-L1 and PD-1 inhibits T cell activation and favors their exhaustion/apoptosis (7); indeed, mice deficient in PD-L1/PD-1 develop accelerated diabetes (6). PD-L1$^+$ HSPCs play an important endogenous immunoregulatory role, capable of eliminating autoreactive T cells but eventually becoming defective in T1D.

Materials and Methods

Human Studies—

T1D patients and healthy patients matched for age and gender were enrolled (Table 8). The study presented herein was conducted in accordance with Institutional Review Board approval (BCH 3851).

In Vitro Human Studies—

Isolated human CD34$^+$ HSCs were stimulated for 24 h with hIFN-β, hIFN-γ and Poly[I:C]. PD-L1 expression was evaluated before and after culture by different techniques (qRT-PCR, FACS, confocal imaging). PBMCs isolated from T1D patients, were cultured for 2 days in the presence of IA-2 peptide. Cells were plated with or without CD34$^+$ or pharmacologically-modulated CD34$^+$ cells. hIFN-γ spots were counted using an Elispot Reader.

Animal Studies—

Animal studies were conducted in NOD and C57BL/6 mice; all the mice were used according to institutional guidelines and animal protocol were approved by the Boston Children's Hospital Institutional Animal Care and Use Committee.

In Vitro Murine Studies—

Murine bone marrow KL cells were transduced with PD-L1 lentivirus and 24 hours after transduction PD-L1 expression was evaluated by multiple techniques (qRT-PCR, FACS, confocal imaging). In vitro assays were performed by co-culturing KL-PD-L1.Tg KL cells, unmodulated KL cells, or pKL with CD4$^+$CD25$^-$/CD8$^+$ T cells extracted from splenocytes of NOD BDC2.5 TCR Tg mice or 8.3 TCR Tg NOD mice in the presence of islet mimotope peptides.

In Vivo Interventional Murine Studies—

Newly diabetic NOD mice were treated with PD-L1.Tg KL cells, unmodulated KL cells, or pKL, and glycemia was monitored daily. Mechanistic studies were conducted on different groups of treated NOD mice and compared to untreated NOD mice (ELISPOT, flow cytometry, Luminex).

Statistical Analysis—

Statistical analysis was performed using the unpaired Student t test. A two-sided value of $P \leq 0.05$ was considered statistically significant. Kaplan-Meier curve analysis with the Wilcoxon test was used to analyze the development of diabetes in mice. For multiple comparisons, one-way ANOVA followed by Bonferroni post-test between the group of interests and all other groups was used. All graphs were generated using GraphPad Prism software version 5.0b (GraphPad Software, Inc., La Jolla, CA). All statistical tests were performed at the 5% significance level.

Results

A Defect in PD-L1 is Evident in HSPCs from NOD Mice

Figure 1N:
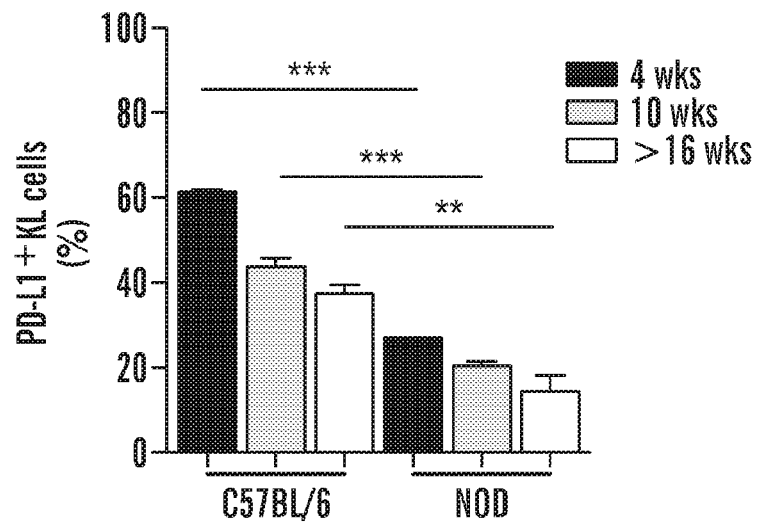
Figure 1Q:
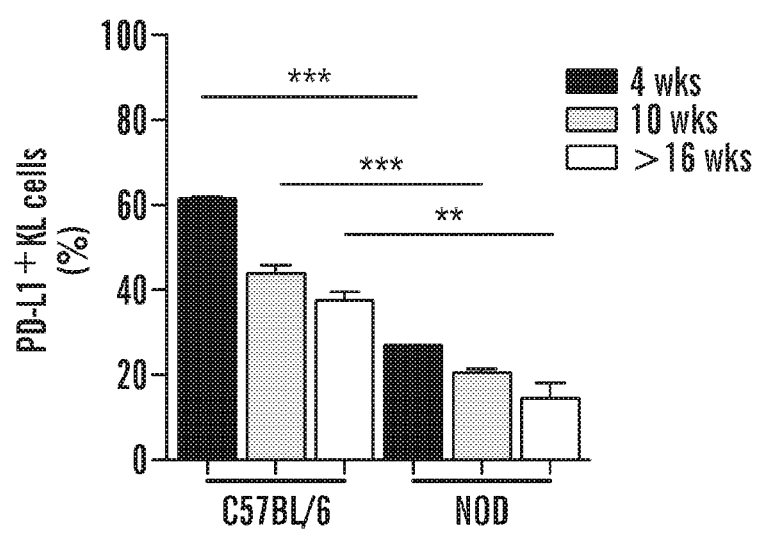
Figure 1T:
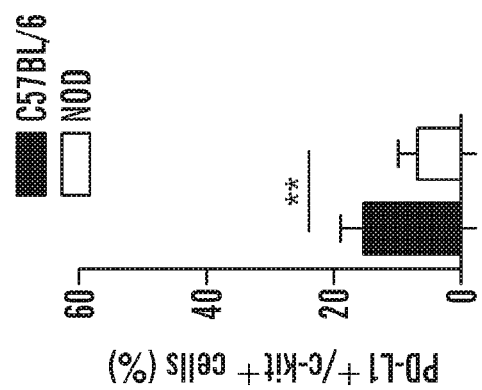
Figure 1U:
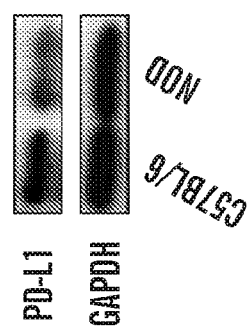
Figure 1V:
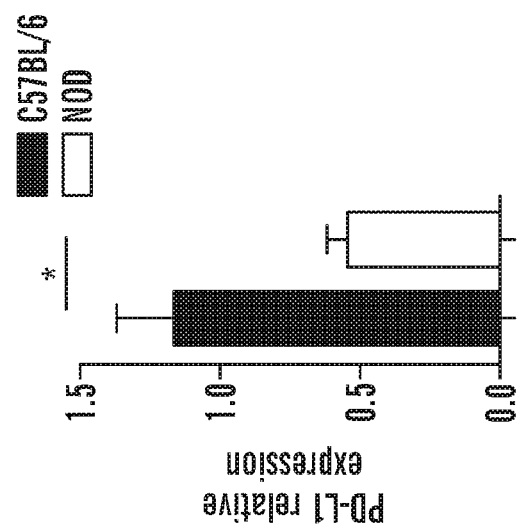

In order to identify any defects in immunoregulatory molecules in HSPCs derived from NOD mice, broad transcriptomic profiling of immune-related molecules in murine HSPCs was performed. Sca-1+Lineage-c-kit+ cells, (KLS, or murine HSPCs) obtained from normoglycemic NOD mice had decreased PD-L1 transcripts as compared to HSPCs obtained from C57BL/6 mice (FIGS. 1A-1B and Table 3). Measurement of PD-L1 mRNA expression by RT-PCR confirmed reduction in NOD HSPC as well (FIG. 1C). A range of techniques was next used to demonstrate the defect in PD-L1 expression in a variety of bone marrow HSPCs, including KLS cells, Lineage-c-kit+(KL) cells and long-term repopulating HSPCs (CD41-CD48-CD150+ cells and CD244-CD48-CD150+) and compared it to the expression observed in NOR and C57BL/6 mice (FIG. 1D-1K). The overall PD-L1 defect is primarily confined to NOD mice (FIG. 1D-1K). It was then sought to explore any association of the PD-L1 defect in HSPCs with age or disease status. A slight decline in the number of KL-PD-L1+ cells was identified in both strains with progressive age, but again with a clear defect in NOD mice (FIG. 1L-1N). Other costimulatory molecules were evaluated as well, and no major significant differences were observed in HSPCs (FIG. 8A-8F), indicating the uniqueness of the PD-L1 defect. The PD-L1 defect was primarily confined to HSPCs in NOD mice, although other bone marrow-derived myeloid immune cells were slightly deficient in PD-L1 expression (i.e. F4/80+ cells, CD11b+ cells) (FIG. 1O-1Q, FIG. 8G-8M). In order to understand the extent of the PD-L1 defect within the HSPC niche, bone marrow tissues were analyzed using confocal imaging. Fewer c-kit+PD-L1+ cells were observed in samples obtained from NOD as compared to C57BL/6 control mice (FIG. $1R_1$-$1R_3$, $1S_1$-$1S_3$, and 1T). Western blotting confirmed reduced PD-L1 protein expression on KL cells obtained from NOD bone marrow compared to C57BL/6 bone marrow (FIG. 1U-1V). Data presented herein confirmed the existence of a defect in PD-L1 expression in HSPCs in NOD mice.

The PD-L1 Defect is Associated with an Altered Network of PD-L1-Related miRNAs

Figure 2B:
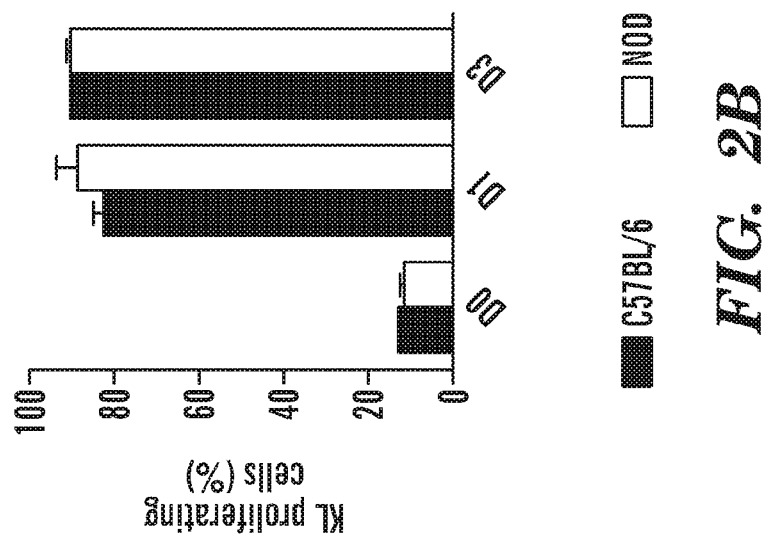
Figure 2A:
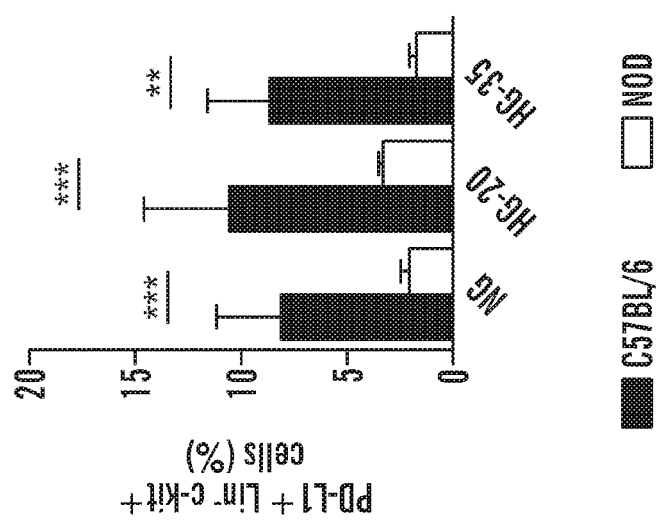
Figure 2D:
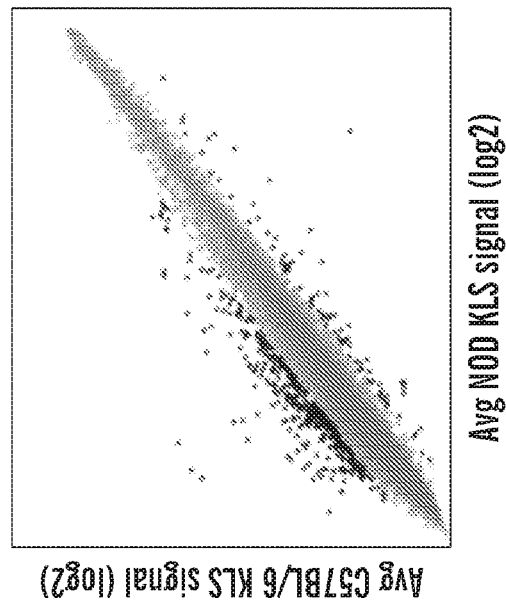
Figure 2C:
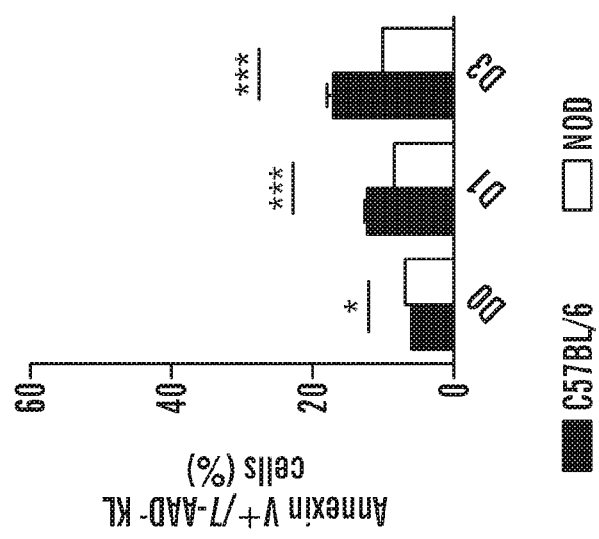
Figure 2G:
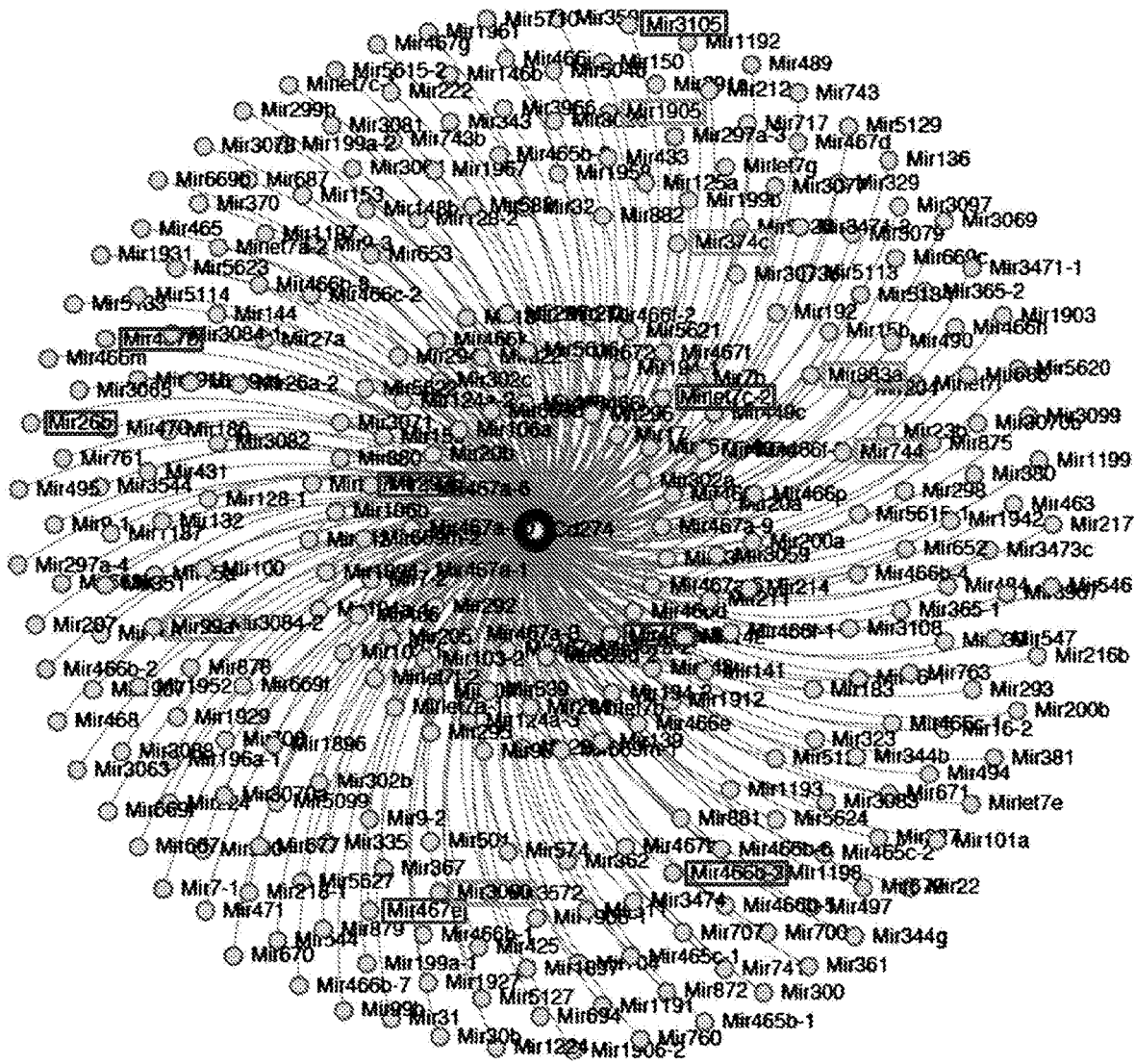

In order to better understand the mechanism behind the PD-L1 defect in HSPCs of NOD mice, a series of in vitro experiments were performed. The effect of high glucose on PD-L1 expression was tested and the existence of any HSPC survival defect that could explain the deficiency in PD-L1 was then evaluated. Isolated KL cells from NOD and C57BL/6 mice were cultured for 3 days in high glucose and no particular pattern that would indicate the existence of a high glucose-associated effect on PD-L1 expression was observed, although the fact that the observed PD-L1 defect may be caused by a metabolic derivative of high glucose cannot be excluded (FIG. 2A). No differences in the proliferation rate, and a slight difference in the percentage of apoptotic cells, were detected among KL cells from NOD or C57BL/6 mice (FIGS. 2B-2C). When extending the investigation into analysis of gene expression profiles, affymetrix microarray analysis revealed 48 microRNAs (miRNAs) differentially expressed in KLS cells of NOD and C57BL/6 mice (FIGS. 2D-2F and data not shown). Data related to upregulated and downregulated miRNAs observed in the GWAS study performed on KLS cells obtained from NOD and C57BL/6 mice are shown as an MA-Plot in FIG. 2D and listed in FIGS. 2E and 2F. Multiple databases and bioinformatics tools (Mouse Genome Informatics-MGI, DIANA-microT-CDS, [http://microrna.gr/microT-CDS] and http://www.mousemine.org) enabled the identification of ~330 miRNAs predicted to target the PD-L1 gene and revealed a comprehensive miRNA network associated with PD-L1 (FIG. 2G). Interestingly, 14 miRNAs appeared both key players in controlling PD-L1 expression and altered in KLS cells obtained from NOD mice (FIGS. 2E-2G). Next, to test the proof-of-concept that an altered miRNAs network may have influenced PD-L1 expression on HSPCs, miR-1905, one of the miRNAs found altered in NOD HSPCs, was silenced in isolated KL extracted from BM of NOD mice (FIGS. 2H-2I). Although silencing one miRNA may influence other target genes, miR-1905 was chosen as a target due to the fact that it was the only mature miRNA among the six identified as relevant to PD-L1. Furthermore, miR-1905 was confirmed as having the higher miTG score or prediction score by the online software "DIANA TOOLS/microT-CDS", thus indicating a higher probability of affecting PD-L1 expression as compared to other miRNAs on the list. Indeed, miR-1905 antagomir increased the expression of PD-L1 transcripts and protein in HSPCs (FIGS. 2I-2K). An altered network of miRNAs may be responsible for PD-L1 reduced expression in HSPCs. Finally, it was demonstrated that the absence of any difference in the methylation status of the PD-L1 promoter in KLS cells from NOD mice, which could have accounted for the PD-L1 defect (FIG. 2L).

Genetically Engineered NOD HSPCs Abrogate the Autoimmune Response In Vitro

Figure 3A:
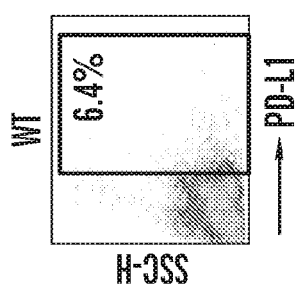
FIGS. 3A-3V presents data that show genetically engineered PD-L1.Tg KL cells abrogate the autoimmune response in vitro and revert diabetes in hyperglycemic NOD mice in vivo.
Figure 3B:
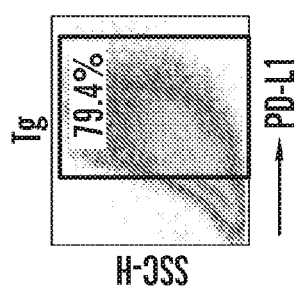
Figure 3C:
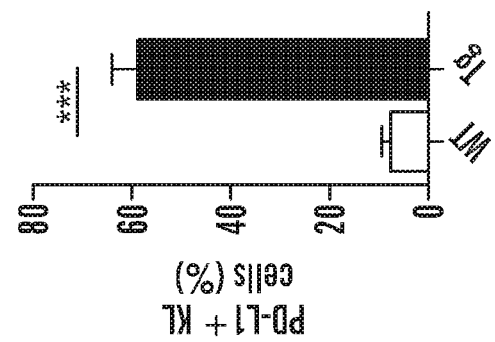
Figure 3I:
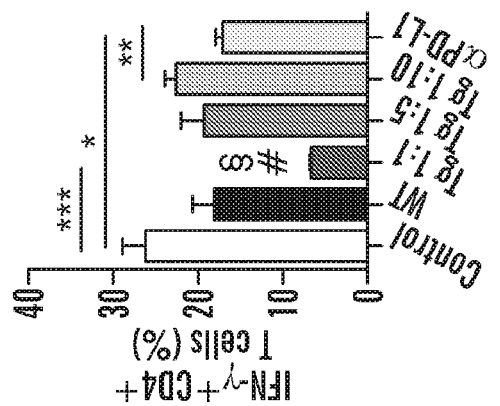
(FIG. 3H, 3I) Representative flow cytometric analysis and quantitative bar graph of IFN-γ+CD4+ T cells isolated from NOD-BDC2.5 TCR Tg mice stimulated with BDC2.5 peptide in the presence of DCs (Control) or upon co-culture with untransduced KL cells (WT), PD-L1.Tg KL cells (at different ratios) or with PD-L1.Tg KL cells pre-treated with anti-PD-L1 blocking mAb.
Figure 3H:
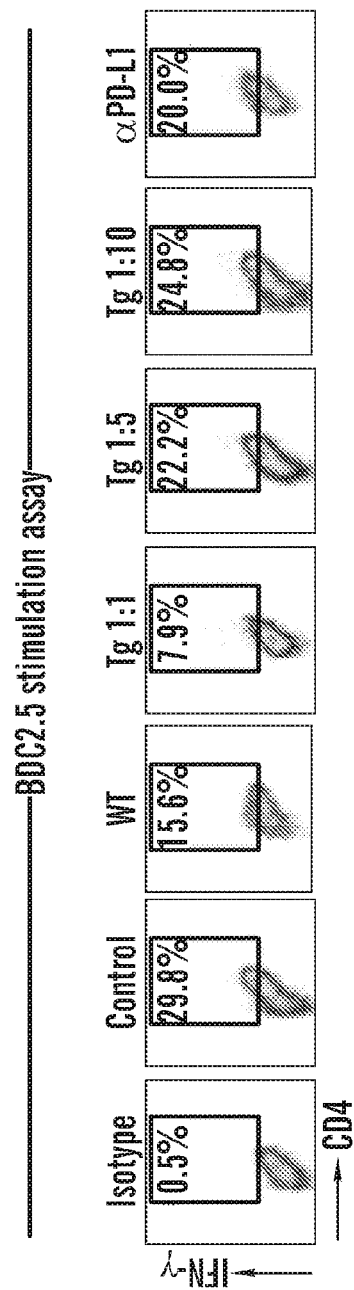
Figures 3J, 3K:
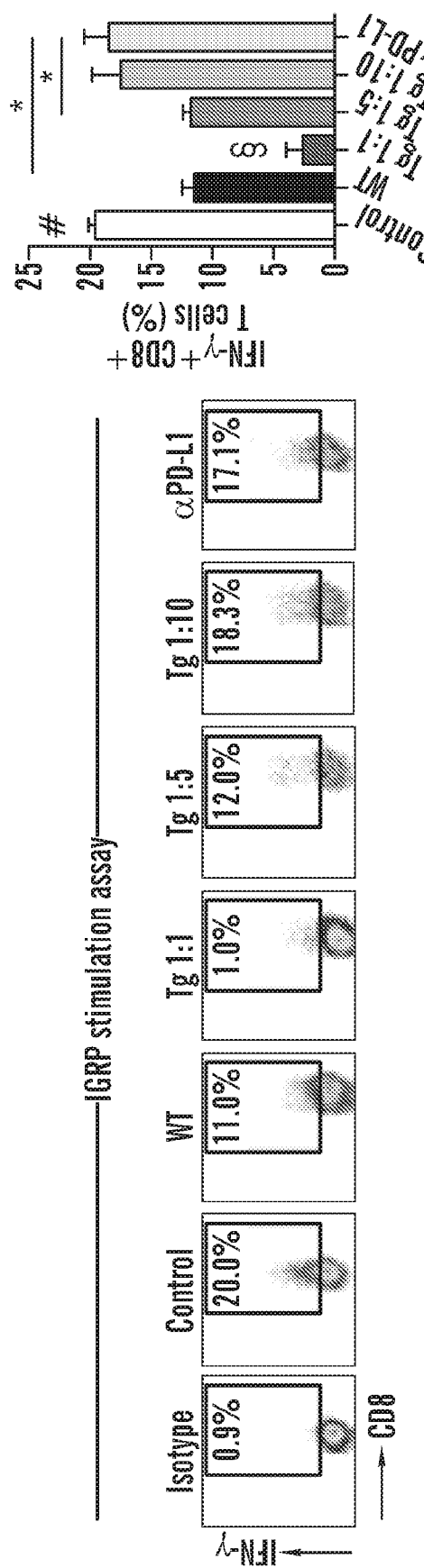
(FIG. 3J, 3K) Representative flow cytometric analysis and quantitative bar graph of IFN-γ+CD8+ T cells isolated from NOD-8.3 TCR Tg mice stimulated with IGRP peptide in the presence of DCs (Control), or upon co-culture with WT KL cells, PD-L1.Tg KL cells (at different ratios) or with PD-L1.Tg KL cells pre-treated with PD-L1 blocking mAb.
Figures 3L, 3M:
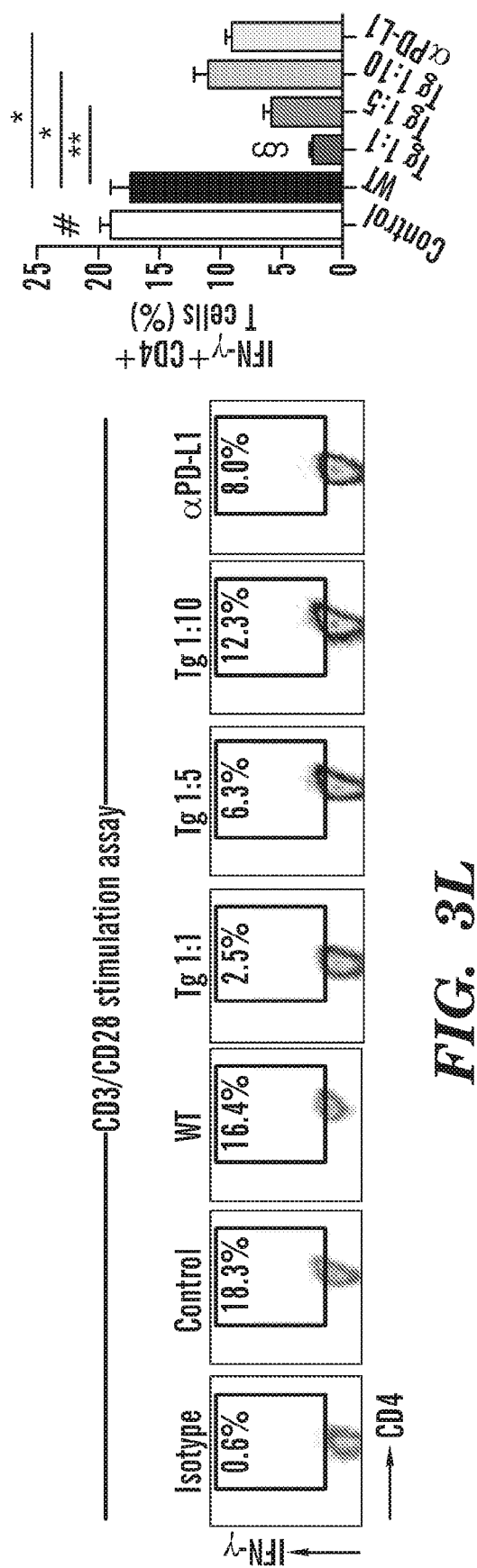
(FIG. 3L, 3M) Representative flow cytometric analysis and quantitative bar graph of IFN-γ+CD4+ T cells isolated from normoglycemic NOD mice stimulated with soluble anti-CD3/anti-CD28 (Control), or upon co-culture with WT KL cells, PD-L1.Tg KL cells (at different ratios), or with PD-L1.Tg KL cells pre-treated with PD-L1 blocking mAb. PD-L1.Tg KL cells strongly abrogate the CD4/CD8-restricted autoimmune response and anti-CD3/CD28-dependent T cell stimulation in vitro.
Figure 9A:
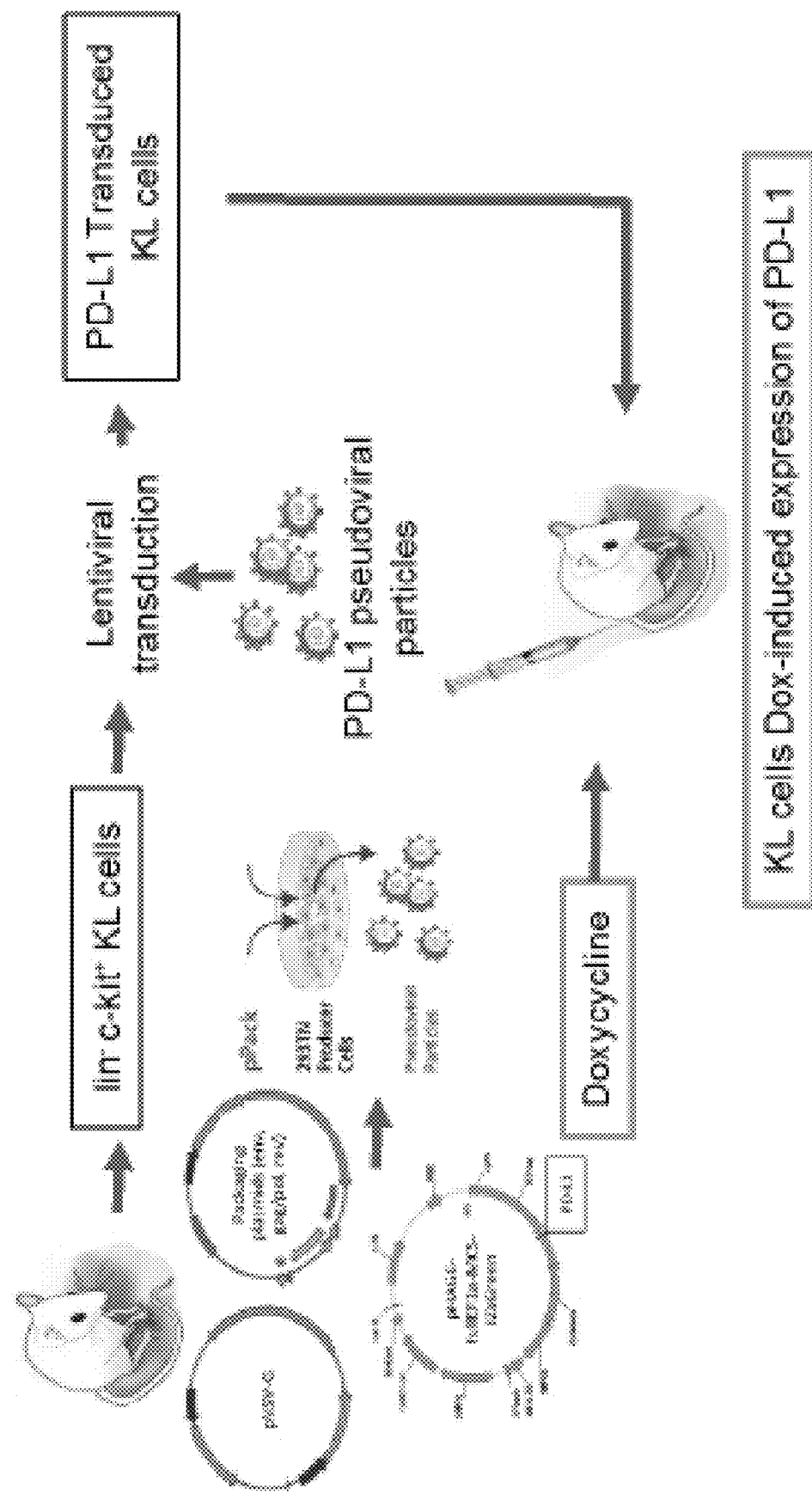
Figures 9B, 9C:
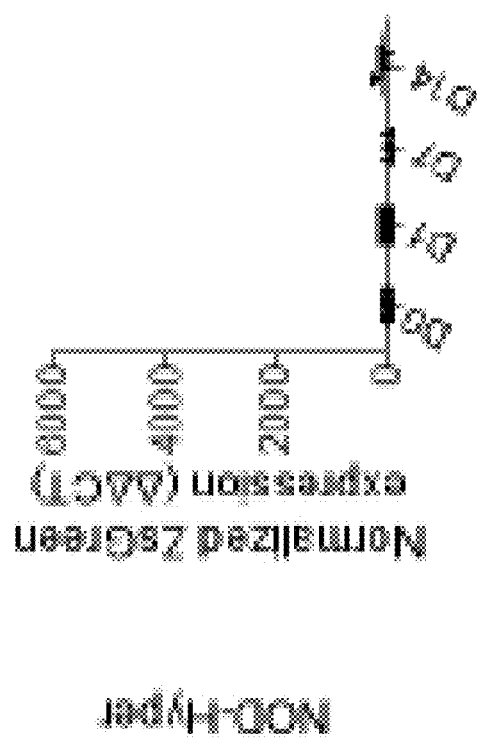

The effect of a genetic engineering approach to overcome the PD-L1 defect in NOD HSPCs was next tested. murine KL cells were genetically engineered ex vivo to generate PD-L1.Tg KL cells (FIG. 3A-3C) from normoglycemic NOD mice by using 3rd generation self-inactivating lentiviral vectors (Lv), a technique which can be use in vivo because of its high efficiency and low risk of genotoxicity (FIG. 9A) (8). Immunofluorescence and genome wide analysis of these PD-L1.Tg KL cells confirmed the increase in PD-L1 expression compared to Mock-Lv-transduced KL cells (FIGS. 3D-3G and Table 4). The immunoregulatory properties of PD-L1.Tg KL cells was then explored in an autoimmune setting in vitro. PD-L1.Tg KL cells generated from normoglycemic NOD mice were co-cultured at different ratios with T cells (1:1, 1:5 and 1:10) with CD11c+ DCs (dendritic cells) and BDC2.5 transgenic CD4+CD25− T cells in the presence of the CD4-restricted islet mimotope peptide BDC2.5. A significant decrease in the percentage of IFN-γ+CD4+ T cells, as quantified by flow cytometry, was evident when naïve T cells were co-cultured with PD-L1.Tg KL cells as compared to those cultured alone or co-cultured with untransduced KL cells (FIG. 3H-3I). The gating strategy was determined using nonreactive isotype-matched control mAbs in each culture conditions, in which 99% of non-reactive cells were excluded. When PD-L1.Tg KL cells were pre-cultured at a ratio of 1:1 to T cells with an anti-PD-L1 blocking mAb, the aforementioned immunoregulatory effect was severely hampered (FIG. 3H-3I). The robust and PD-L1-dependent immunoregulatory properties of PD-L1.Tg KL cells were confirmed using a CD8-restricted peptide-based assay (FIG. 3J-3K) as well as an assay not specific to the autoimmune setting (anti-CD3/anti-CD28 stimulation [FIG. 3L-3M]), thus confirming that PD-L1 transgenic HSPCs abrogate the autoimmune response in vitro.

Genetically Engineered NOD HSPCs Revert Hyperglycemia In Vivo

Figure 3O:
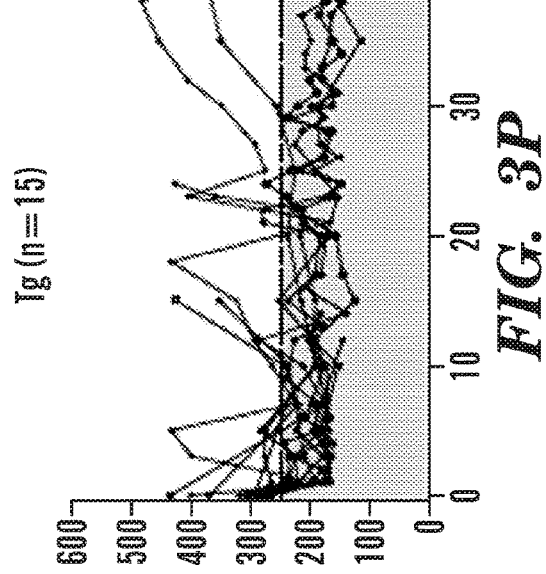
(FIG. 3O, 3P, 3Q, 3R) Newly hyperglycemic NOD mice were treated with WT KL cells, with PD-L1.Tg KL cells, with doxycycline or were left untreated. PD-L1.Tg KL cells reverted diabetes in newly hyperglycemic NOD mice.
Figure 3P:
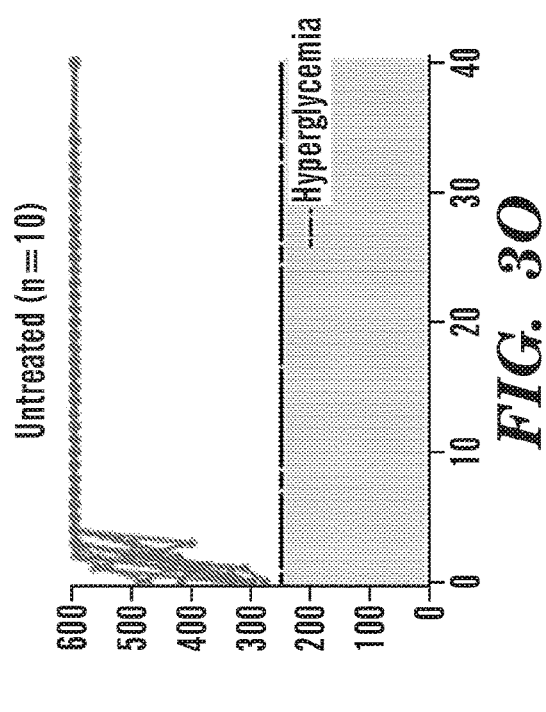
Figure 3Q:
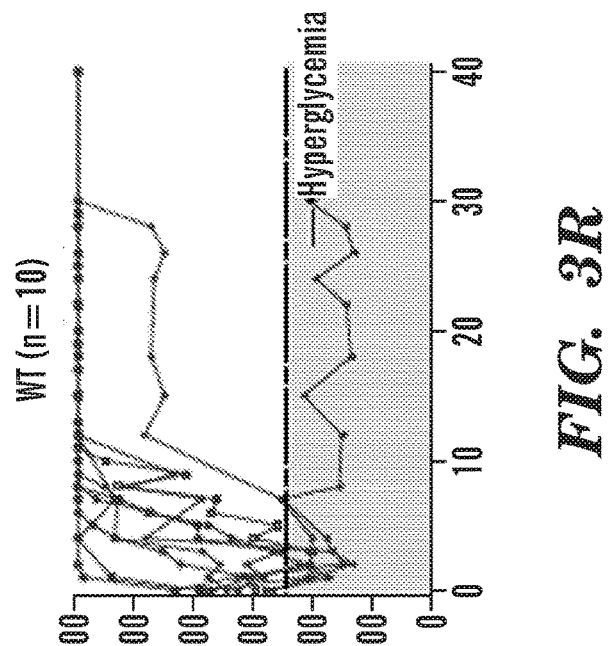
Figure 3R:
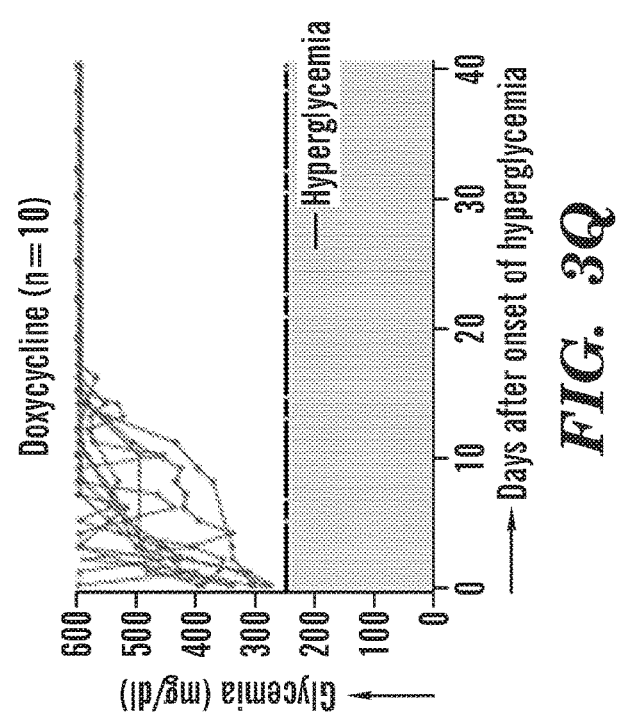
Figure 3S:
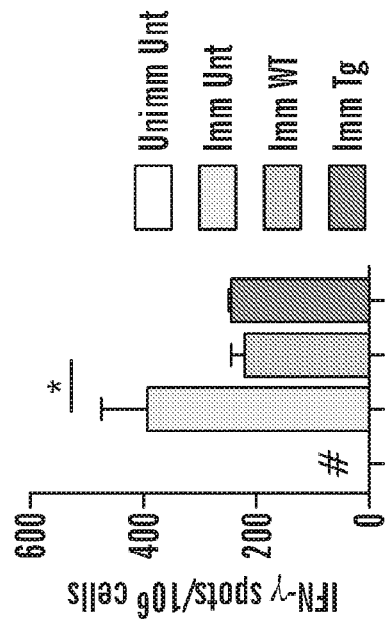
(FIG. 3S) Insulitis score confirmed the protection offered by PD-L1.Tg KL cell treatment, which resulted in fewer infiltrated islets in PD-L1.Tg KL cell-treated NOD mice.
Figure 3U:
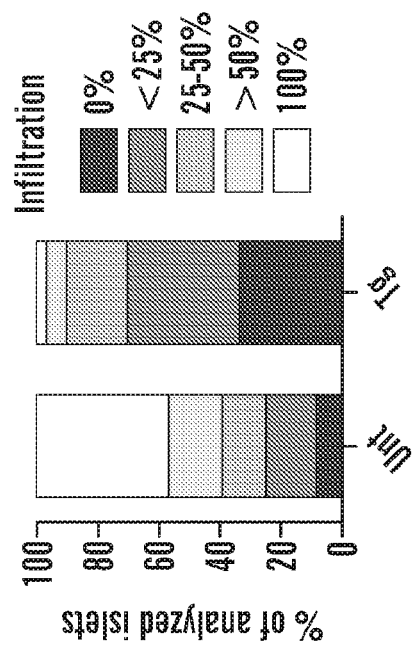
(FIG. 3U) Immunophenotypic analysis of lymphocytes isolated from spleens by flow cytometry showed an increased percentage of FoxP3+ regulatory T cells in PD-L1.Tg KL cell-treated NOD mice as compared to untreated NOD mice.
Figure 3T:
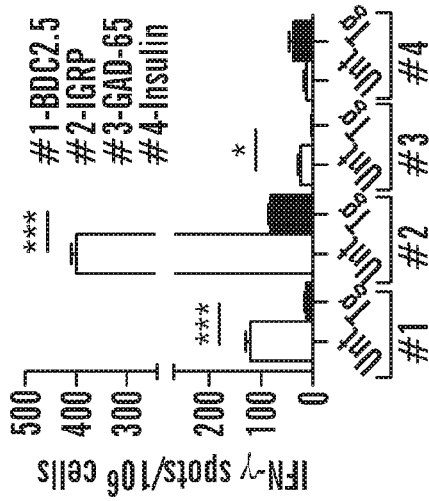
(FIG. 3T) PD-L1.Tg KL cell-treated NOD mice were regularly immunocompetent in an ovalbumin re-challenge test.
Figure 3V:
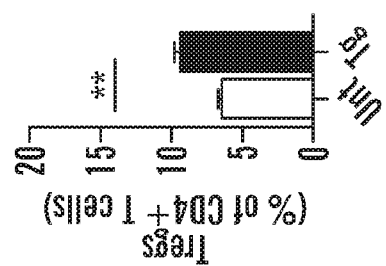

In order to evaluate the immunoregulatory properties of PD-L1.Tg KL cells in vivo, newly hyperglycemic NOD mice were adoptively transferred intravenously with 3×10⁶ PD-L1.Tg KL cells (FIG. 3P), and received doxycycline in water (2 mg/ml) till the completion of the study, or with 3×10⁶ untransduced KL cells (FIG. 3R), respectively. PD-L1.Tg KL cells successfully reverted hyperglycemia in 100% of treated hyperglycemic NOD mice with nearly 30% of treated mice remaining normoglycemic in the long-term, while none of the untreated hyperglycemic NOD mice (FIG. 3O) or those treated with doxycycline (FIG. 3Q) reverted to normoglycemia. When untransduced KL cells were used, 1 hyperglycemic NOD mouse reverted to normoglycemia and 1 showed a mild transient improvement of glycemic levels (FIG. 3R). Pathology of the pancreas of PD-L1.Tg KL cell-treated hyperglycemic NOD mice revealed reduced islet infiltration, with fewer CD3+ cells, preserved insulin staining and improved insulitis score as compared to hyperglycemic untreated NOD (FIGS. 3N1-3N6 and 3S). It was then evaluated whether immunocompetence was preserved in NOD mice during treatment with PD-L1.Tg KL cells. PD-L1.Tg KL cell-treated NOD mice, untransduced KL cell-treated NOD mice and untreated NOD mice were immunized at day 14 after the onset of hyperglycemia with ovalbumin, and after 3 days splenocytes were harvested and re-challenged in vitro with ovalbumin. Treated NOD mice were capable of mounting a regular immune response to ovalbumin similar to other groups tested and were thus immunocompetent (FIG. 3T). Immunophenotyping of PD-L1.Tg KL cell-treated hyperglycemic NOD mice showed at day 14 after treatment a 2-fold increase in the percentage of FoxP3+ regulatory CD4+ T cells as compared to untreated mice (FIG. 3U), while no changes were observed in the percentage of IFN-γ+ and IL-17+CD4+/CD8+ T cells (data not shown). Furthermore, a reduction in IFN-γ-producing cells was evident in PD-L1.Tg KL cell-treated as compared to untreated hyperglycemic NOD mice in an ex vivo assay, when splenocytes were challenged with islet peptides at day 40 following treatment (FIG. 3V). BDC2.5 transgenic CD4+CD25− T cells appear to be more susceptible to the effect of PD-L1 upregulation as compared to IGRP transgenic CD8+ T cells. To understand the mechanism by which PD-L1.Tg KL cells exert their immunosuppressive effects on autoreactive T cells, an apoptosis assay was performed in vitro during a diabetogenic autoimmune response by coculturing IGRP Tg CD8+ T cells from NOD 8.3 (stimulated with the islet peptide IGRP) or CD4+CD25− T cells from NOD BDC2.5 (stimulated with the islet peptide BDC2.5) in the presence of PD-L1-Tg KL or WT KL cells. PD-L1.Tg KL cells induced cell death of autoreactive CD4+ and CD8+ T cells, while only a minor effect was observed, primarily on autoreactive CD8+ T cells, when WT KL cells were added (FIG. 4A-4B). If a possible conversion into myeloid suppressive cells may partially explain the immunoregulatory effects of PD-L1.Tg KL cells was then explored. Interestingly, while after transduction the presence of T/B cell markers was very scant, myeloid markers were strongly expressed (FIG. 4C-4D).

Genetically Engineered HSPCs Traffic to the Pancreas in Hyperglycemic NOD Mice

Figure 9D:
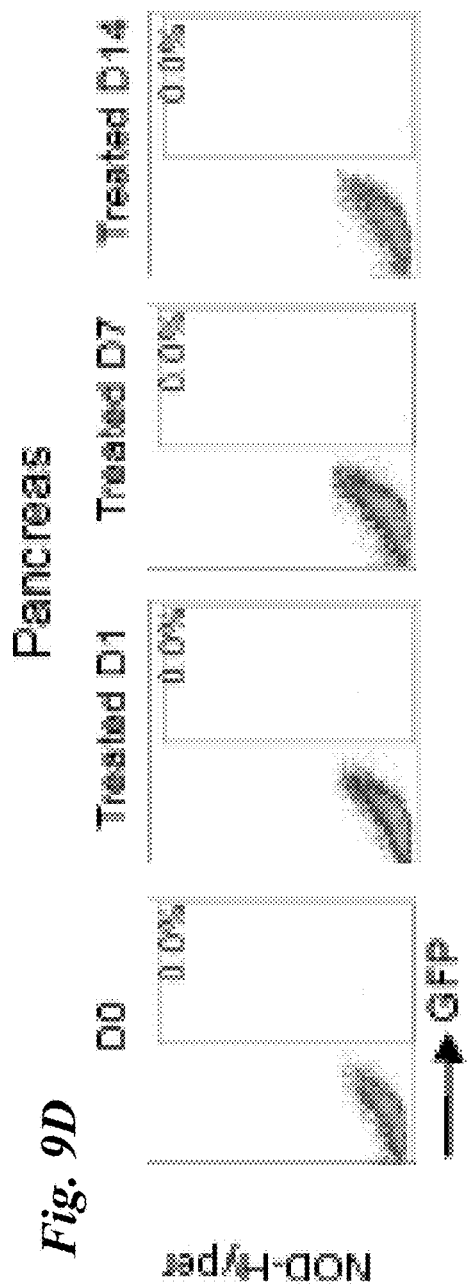
Figure 9E:
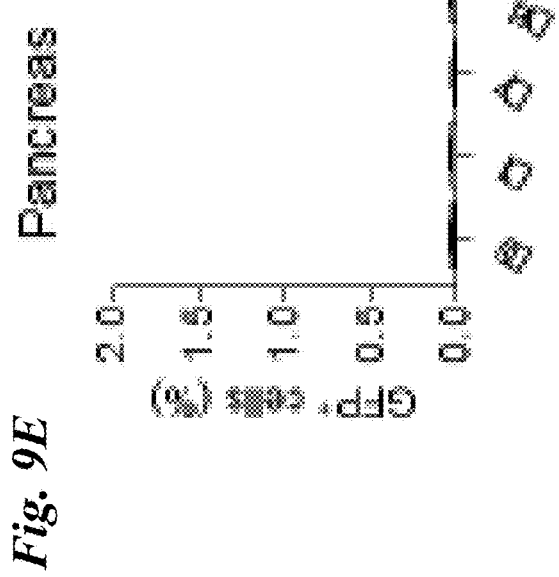

To explore the fate of infused PD-L1.Tg KL cells in NOD mice, a set of tracking experiments were performed in the pancreas, spleen, pancreatic draining lymph nodes (PLN) and bone marrow using the tracer ZsGreen, present on the vector used to transduce PD-L1.Tg KL cells. PD-L1.Tg KL cells were adoptively transferred into normoglycemic and hyperglycemic NOD mice, and tissues were harvested at days 1, 7 and 14 post-infusion. ZsGreen+ cells and ZsGreen mRNA expression were quantified in all tissues by flow cytometry and qRT-PCR, respectively. PD-L1.Tg KL cells preferentially trafficked to the pancreas once infused into hyperglycemic NOD (FIGS. 4E-4G), while they homed to a lesser extent to the PLN, bone marrow and spleen (FIGS. 4K-4L, 4O-4P, and 9B). Conversely, in normoglycemic NOD mice, PD-L1.Tg KL cells scarcely trafficked to the pancreas, to the spleen or to the PLN (FIGS. 4H-4J, 4Q-4R and 8C), but instead preferentially homed to the bone marrow (FIGS. 4M-4N). Confocal imaging confirmed that ZsGreen+ cells were absent in the pancreata of normoglycemic NOD mice (FIGS. 4S₁-4S₄), while they were detectable in the pancreata of hyperglycemic NOD mice, particularly at day 1 after PD-L1.Tg KL cell infusion (FIGS. 4T₁-4T₄). Although preferential homing of PD-L1.Tg KL cells was observed to the bone marrow (and perhaps spleen) in hyperglycemic NOD mice based on ZsGreen transcript quantification by qRT-PCR, flow cytometry and confocal imaging consistently showed trafficking of PD-L1.Tg KL cells to the pancreas. A tracking experiment was also performed using GFP+KL cells (WT, untransduced KL cells) infused into treated hyperglycemic NOD mice and examined these mice by flow cytometry at days 1, 7 and 14; results showed no migration into the pancreas of the treated hyperglycemic NOD mice (FIGS. 9D-9E). Moreover, the chemokine receptor profile of PD-L1.Tg KL cells were explored in order to determine which chemokine receptors are more likely involved in the homing of transgenic HSPCs. Interestingly, results showed that CXCR4 is the most expressed and possibly the most relevant chemokine receptor for PD-L1.Tg KL cell trafficking (Table 7). Bioluminescence imaging of NOD mice adoptively transferred with Luciferase+PD-L1.Tg KL cells showed a rapid disappearance of Luciferase+PD-L1.Tg KL cells from the peripheral blood (FIGS. 4U-4V). It was also determined whether PD-L1.Tg KL cells differentiated after their infusion into NOD mice. Tracking studies revealed a predominant transformation into myeloid cells (e.g., CD11b) into the PNL of treated mice (FIGS. 9F-9I). These PDL-1 expressing myeloid cells may interact with autoreactives CD4 and CD8 T cells contributing to their death.

Pharmacologically Modulated HSPCs Abrogate the Autoimmune Response In Vitro

Figures 5A, 5B:
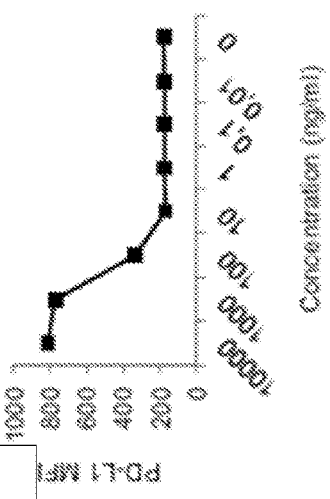
Figure 5G:
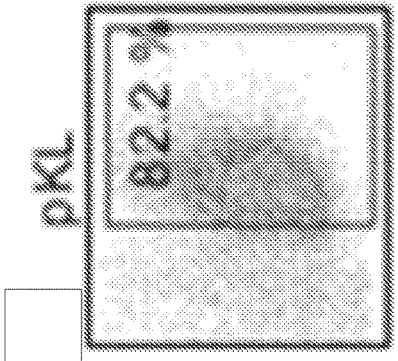
(FIG. 5F-5H) Representative flow cytometric analysis and quantitative bar graph of PD-L1 expression on Lin-c-kit+(KL) cells from NOD mice pre- and post-pharmacologic modulation with the indicated small molecules, alone or in combination.
Figure 5F:
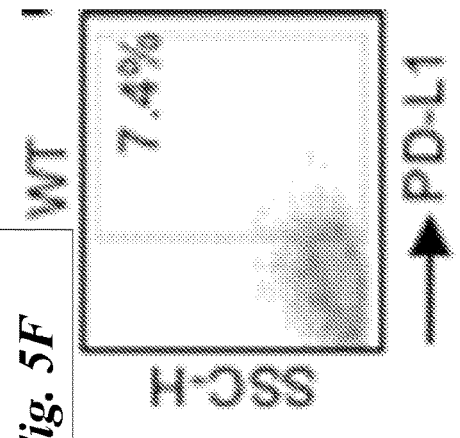
Figure 5J:
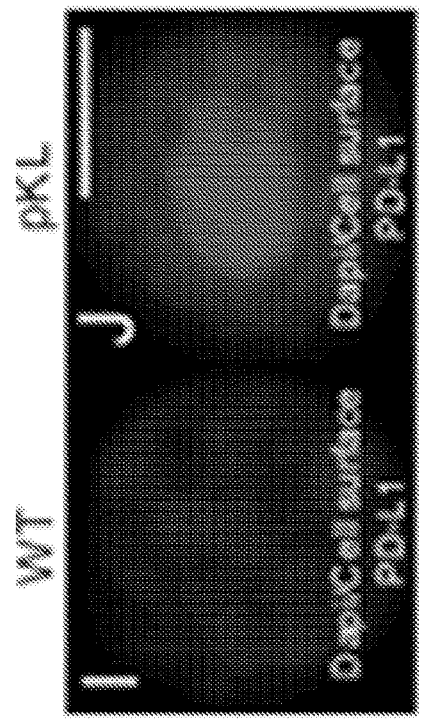
Figure 5H:
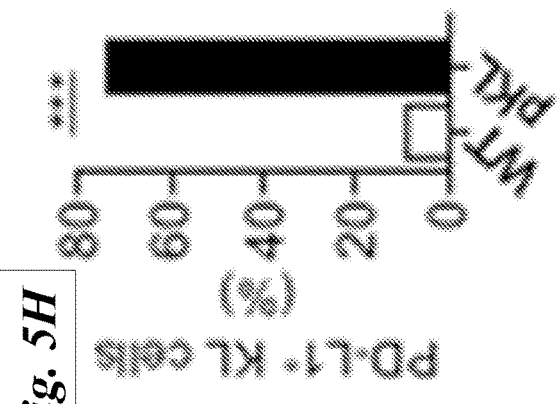
Figure 5P:
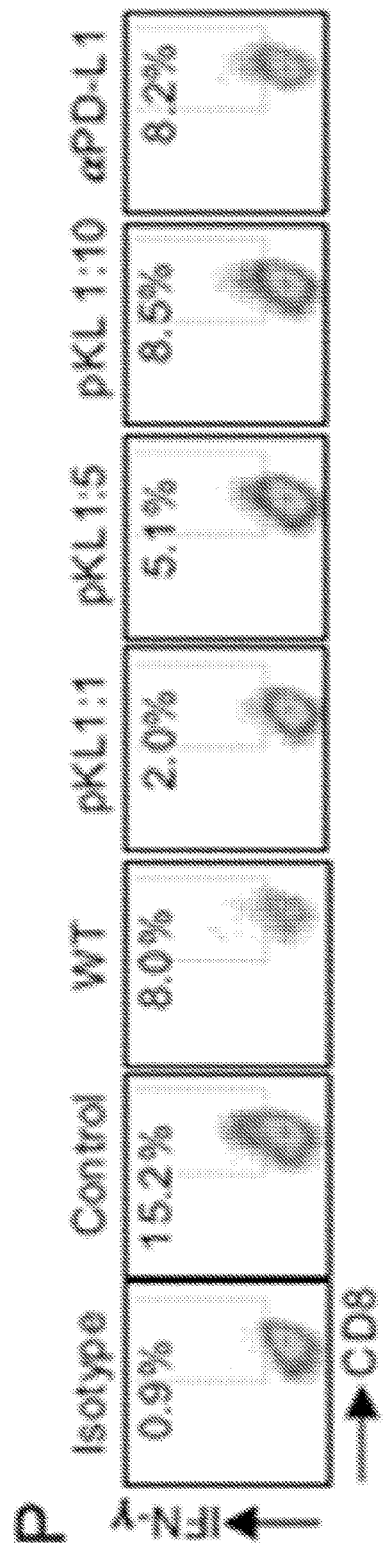
(FIG. 5P, 5Q) Representative flow cytometric analysis and quantitative bar graph for IFN-γ+CD8+ T cells isolated from NOD-8.3 TCR Tg mice and stimulated with IGRP peptide in the presence of DCs (Control) or upon co-culture with unmodulated KL cells (WT), pKL cells, (at different ratios) or pKL cells pre-treated with anti-PD-L1 blocking mAb.
Figure 5Q:
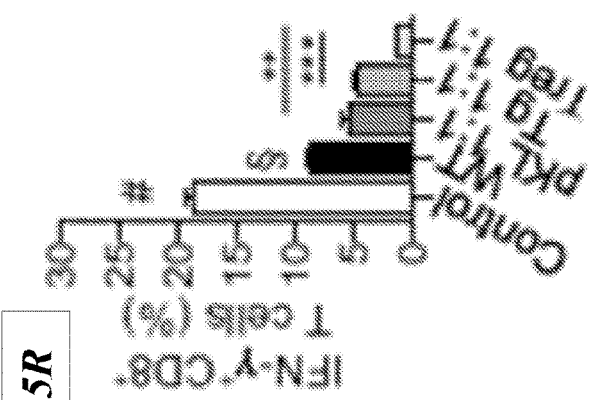
Figure 5R:
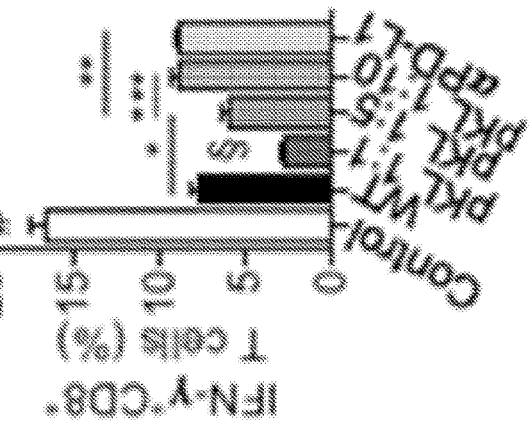
(FIG. 5R) Bar graph for flow cytometric quantification of IFN-γ+CD8+ T cells after co-culture of CD8+ T cells isolated from NOD-8.35 TCR Tg mice stimulated by IGRP peptide in the presence of DCs (Control) or upon co-culture with unmodulated KL cells (WT), with pKL cells, or with PD-L1.Tg KL cells, or with CD4+CD25+T regulatory cells.
Figure 5S:
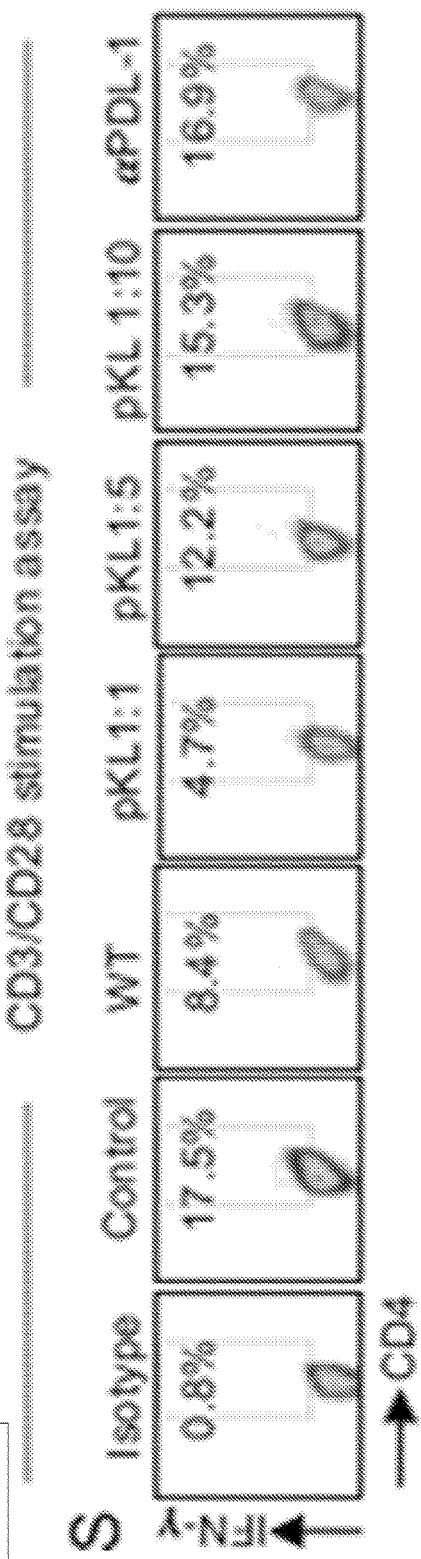
(FIG. 5S, 5T) Representative flow cytometric analysis and quantitative bar graph for IFN-γ+CD4+ T cells isolated from NOD mice and stimulated with soluble anti-CD3/anti-CD28 (Control) or upon co-culture with unmodulated KL cells (WT), with pKL cells (at different ratios), or with pKL cells pre-treated with PD-L1 blocking/neutralizing mAb. pKL strongly abrogate the CD4/CD8-restricted autoimmune response and anti-CD3/anti-CD28-dependent T cell stimulation in vitro.
Figure 5U:
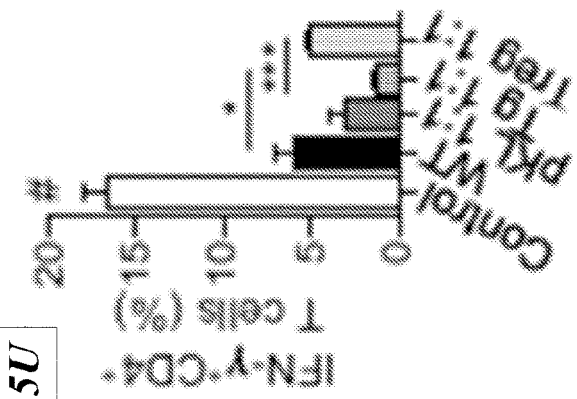
Figure 5T:
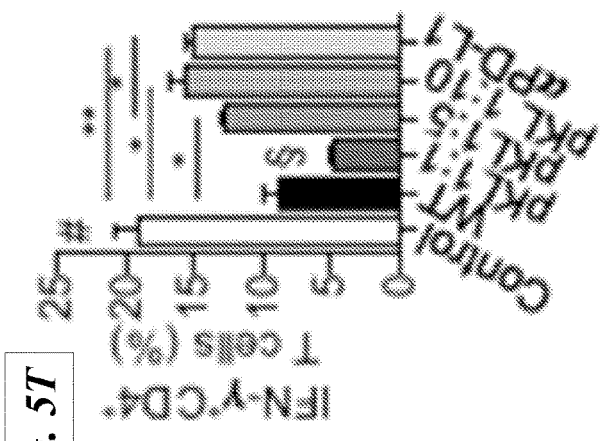

In order to offer an alternative approach to gene therapy, the feasibility of pharmacological modulation of PD-L1 was explored. Agents, either alone or in combination, that are capable of upregulating PD-L1 in human CD34+ cells were tested (FIGS. 5A-5C) and identified as being able to robustly upregulate PD-L1 (FIGS. 5D-5E). The use of these agents in combination are further described in, e.g., Nasr, M. B., et al. Sci. Transl. 9, eaam7543 (2017), which is incorporated herein by reference in its entirety. The ability of the agent, alone or in combination, to upregulate PD-L1 in murine KL cells isolated from normoglycemic NOD mice was then confirmed, thus generating pharmacologically modulated KL cells (pKL cells) (FIGS. 5F-5L, and Tables 5 and 6). The expression of costimulatory molecules, e.g., pro-inflammatory and anti-inflammatory cytokines, were then analyzed by flow cytometry, which demonstrated upregulation of IL-4, PD-1, CD80, CD86 and ICOSL in pKL cells as compared to unmodulated-KL (KL-Veh) cells, with CD40 comparatively downregulated in pKL cells (FIGS. 10A-10B). The immunoregulatory properties of pKL cells were explored in an autoimmune setting in vitro. pKL cells generated from normoglycemic NOD mice were co-cultured at ratios of 1:1, 1:5 and 1:10 to T cells with CD11c+ DCs and BDC2.5 transgenic CD4+CD25− T cells in the presence of BDC2.5 peptide. Quantification by flow cytometry revealed a pronounced and significant decrease in the percentage of IFN-γ+CD4+ T cells when pKL cells were added to the assay as compared to when unmodulated KL cells were used (FIGS. 5M-5N). Immunoregulation was determined to be PD-L1-dependent by pre-culturing pKL cells at a ratio of 1:1 to T cells with an anti-PD-L1 blocking mAb, which resulted in a dramatic reduction in the immunoregulatory effect (FIGS. 5M-5N). These effects and PD-L1 dependency were confirmed in CD8-dependent (FIGS. 5P-5Q) and in non-autoimmune-specific anti-CD3/anti-CD28 (FIGS. 5S-5T) assays. Finally, the immunosuppressive effects of PD-L1.Tg KL cells, pKL cells and unmodulated KL cells (WT) were compared with that of CD4+CD25+ regulatory T cells similarly obtained from normoglycemic NOD mice. In the 3 aforementioned CD4- and CD8-restricted autoimmune and anti-CD3/anti-CD28 assays, PD-L1.Tg KL cells and pKL cells exerted robust immunoregulatory properties almost comparable or higher to those obtained with CD4+CD25+ regulatory T cells; indeed, this was particularly evident for PD-L1.Tg KL cells (FIGS. 5O, 5R, 5U, and 11A-11C). A less pronounced effect was observed when unmodulated KL (WT) were added to the assays. Pharmacologically modulated HSPCs are thus endowed with immunoregulatory properties and abrogate the autoimmune response in vitro.

Pharmacologically Modulated HSPCs Revert Hyperglycemia In Vivo

Figures 6J, 6K:
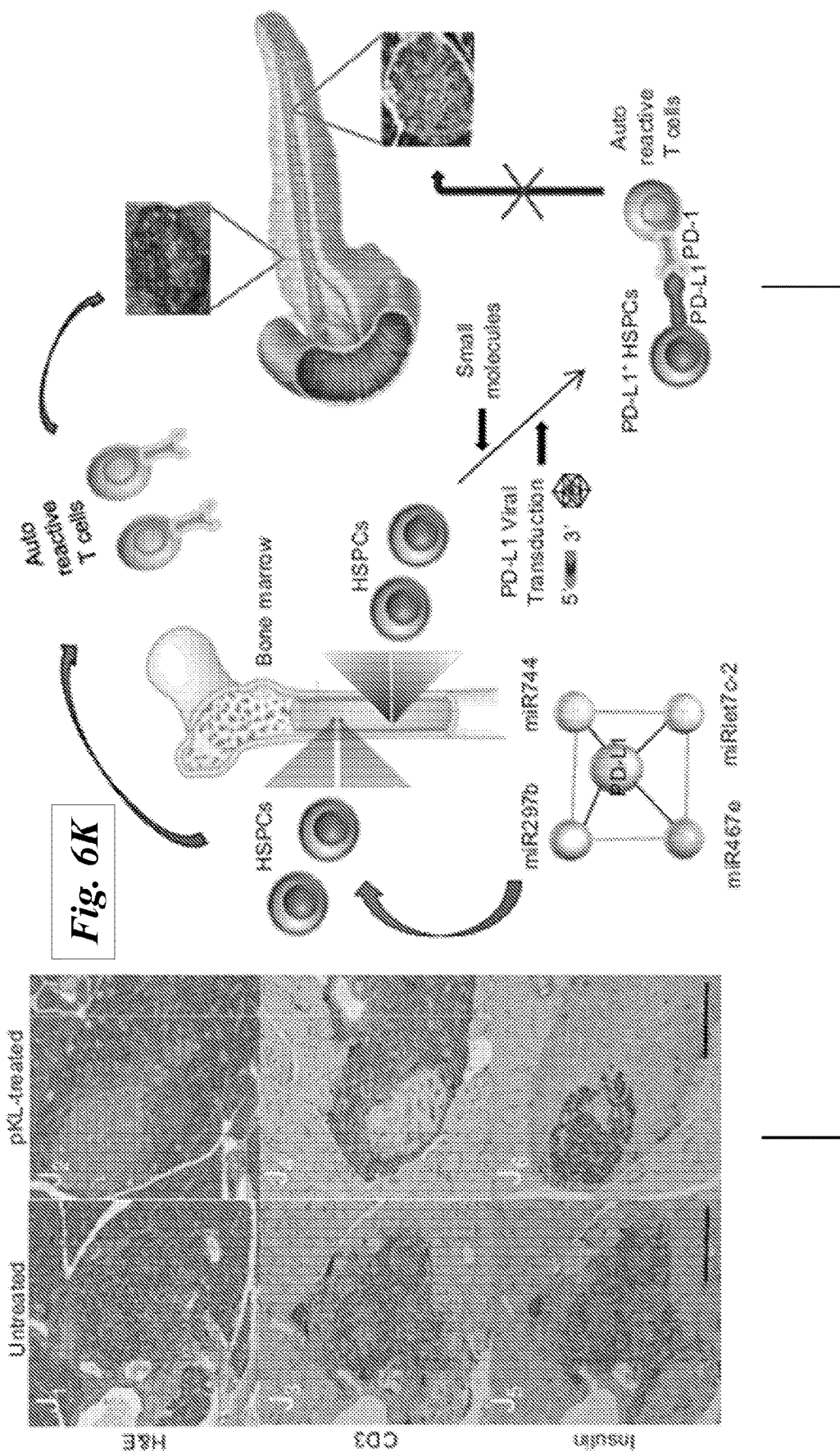
Figure 8C:
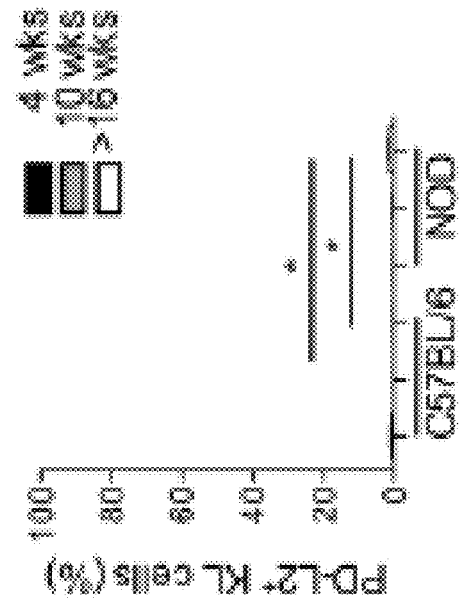
FIGS. 8A-8M present data that show costimulatory molecules other than PD-L1 (i.e. PD-L2 and PD-1).
Figure 8A:
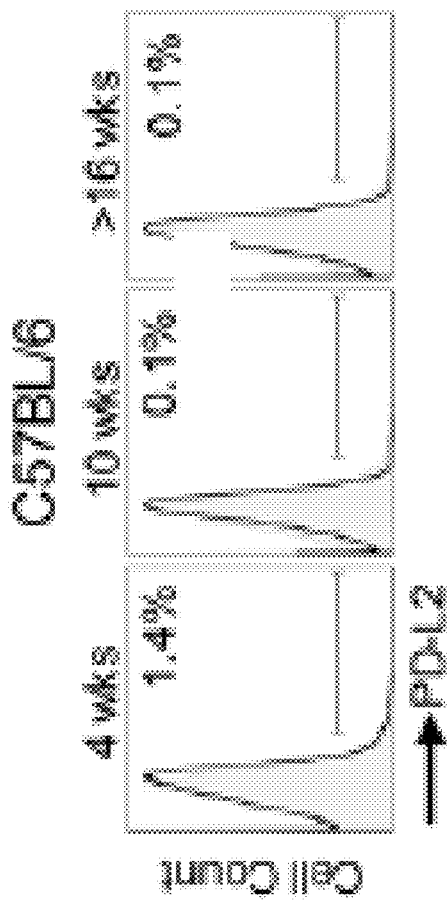
Figure 8B:
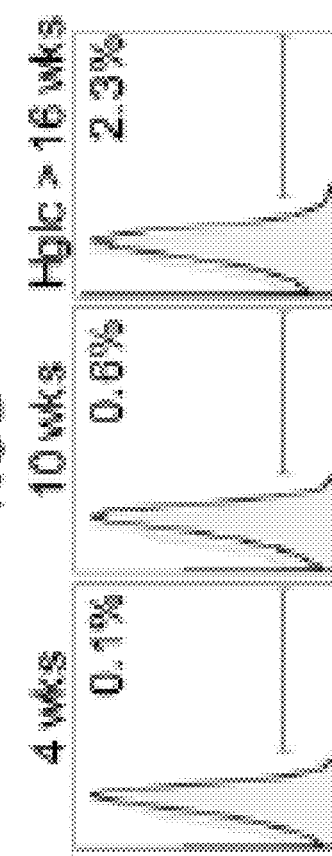
Figure 8F:
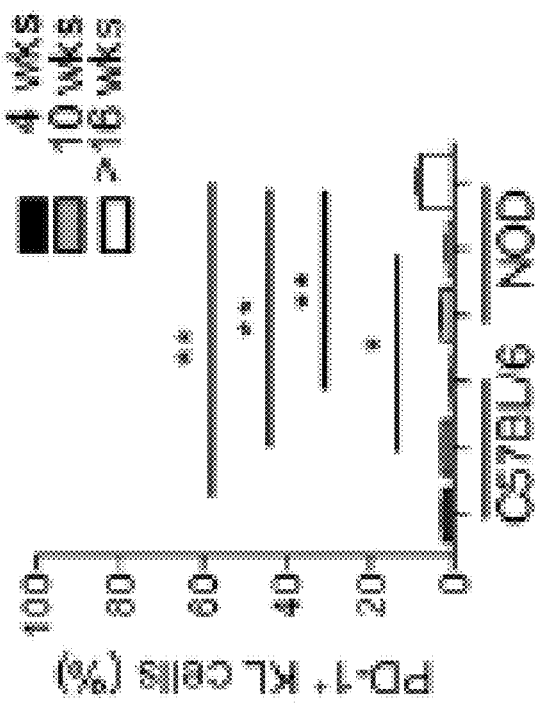
Figure 8D:
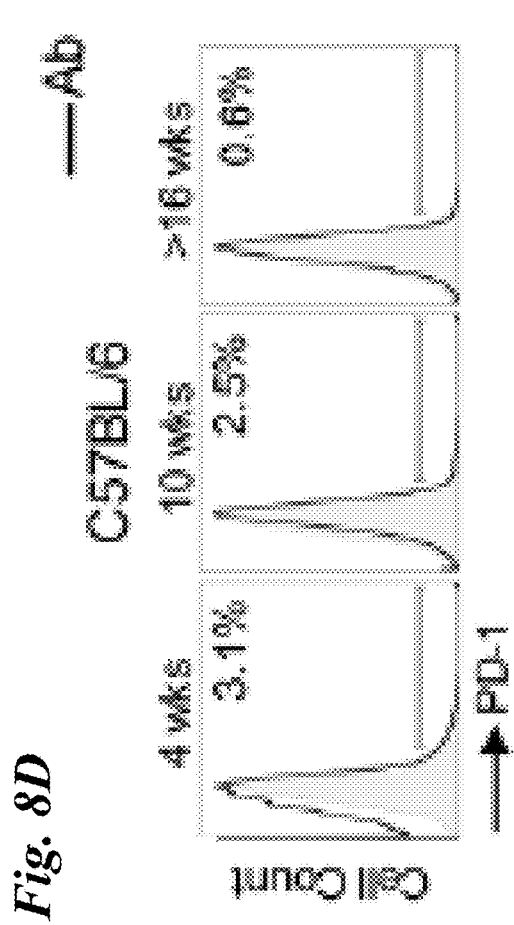
Figure 8E:
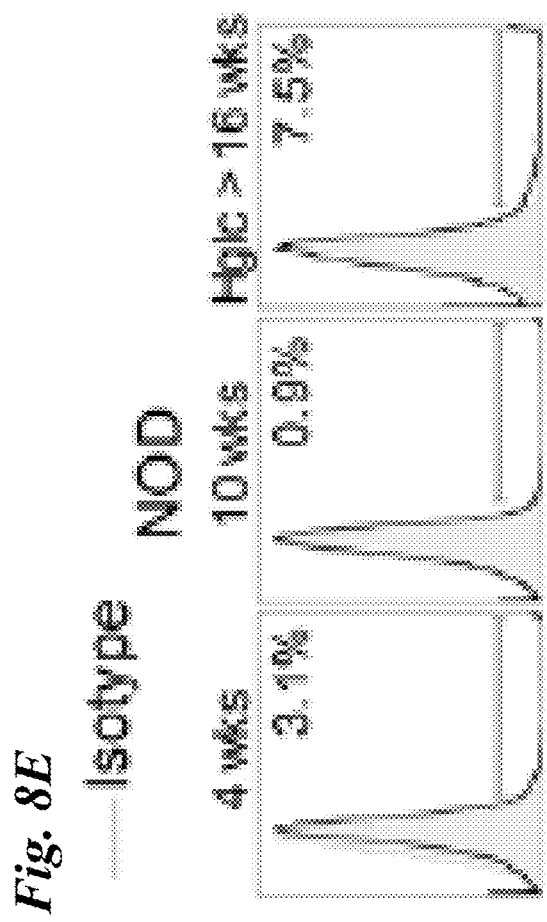
Figure 8G:
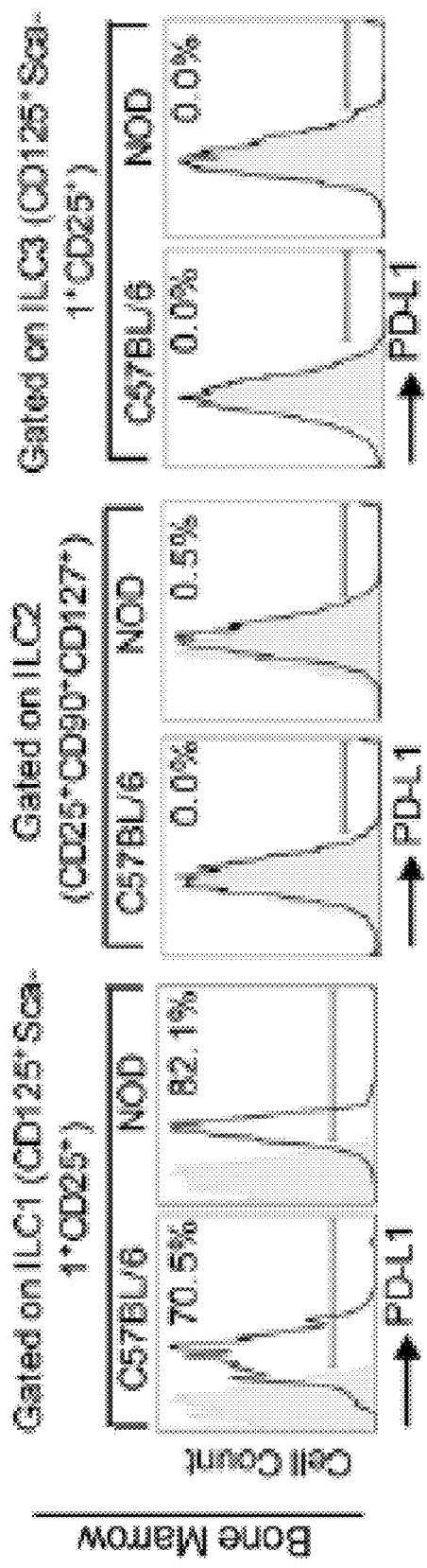
Figure 8H:
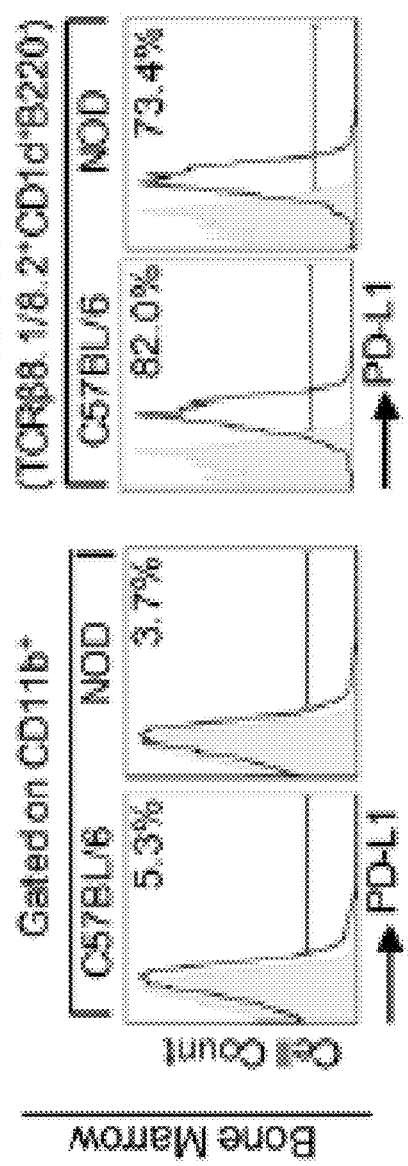
Figure 8I:
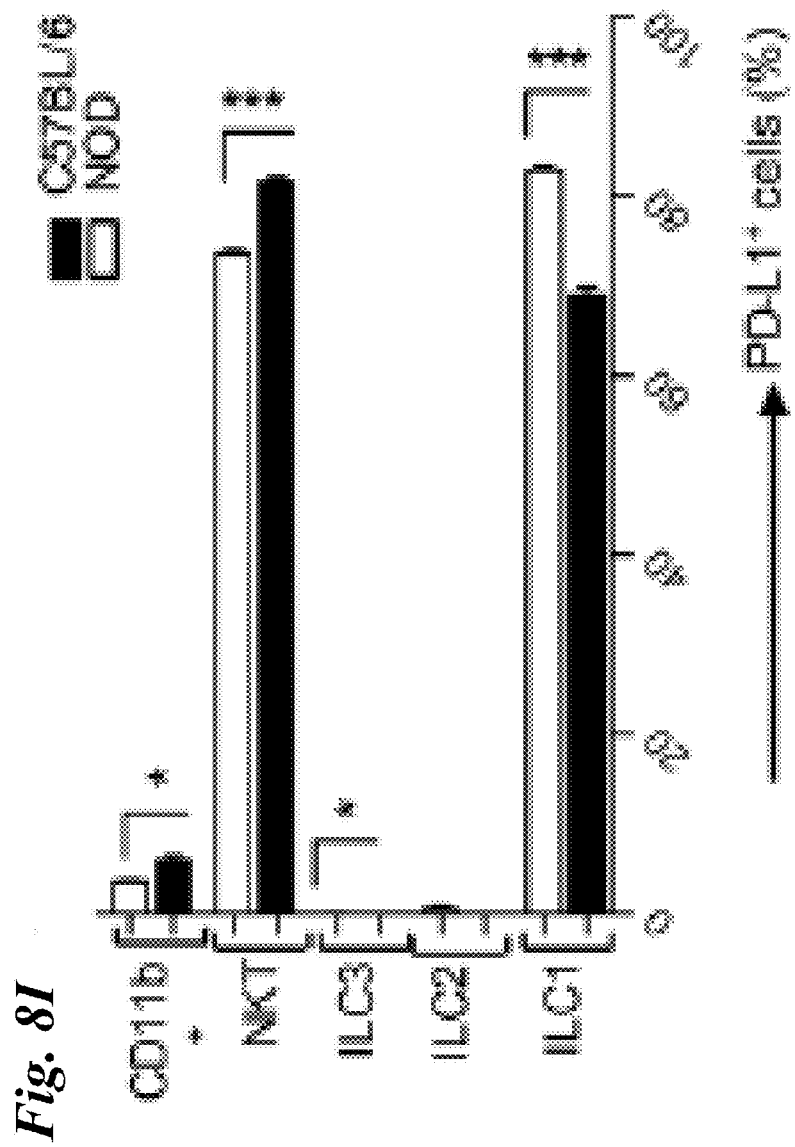
Figure 8J:
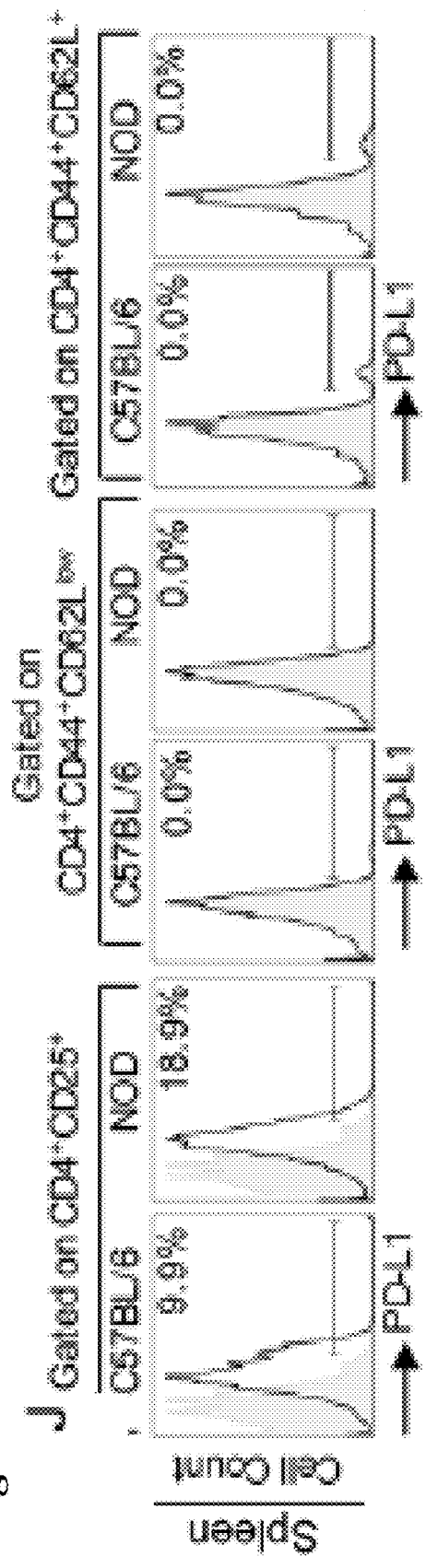
Figure 8K:
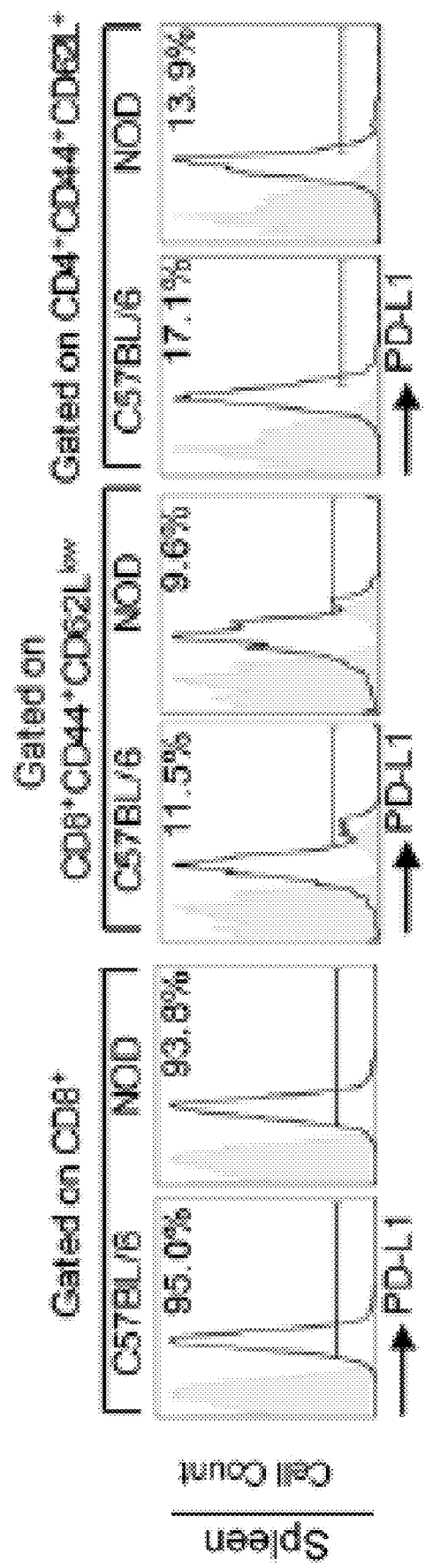
Figure 8L:
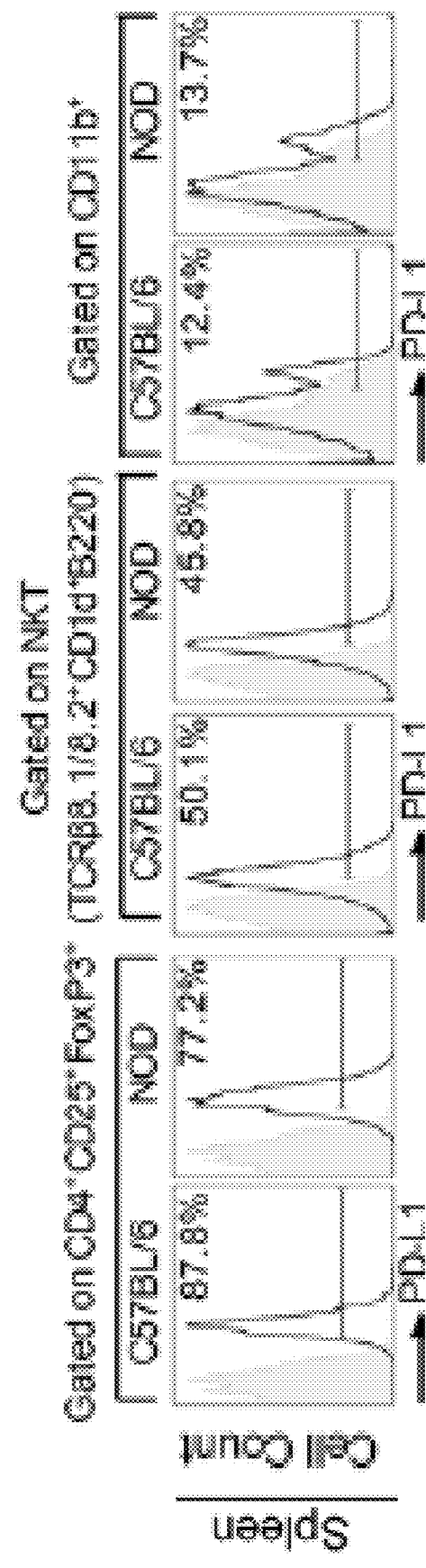
Figure 8M:
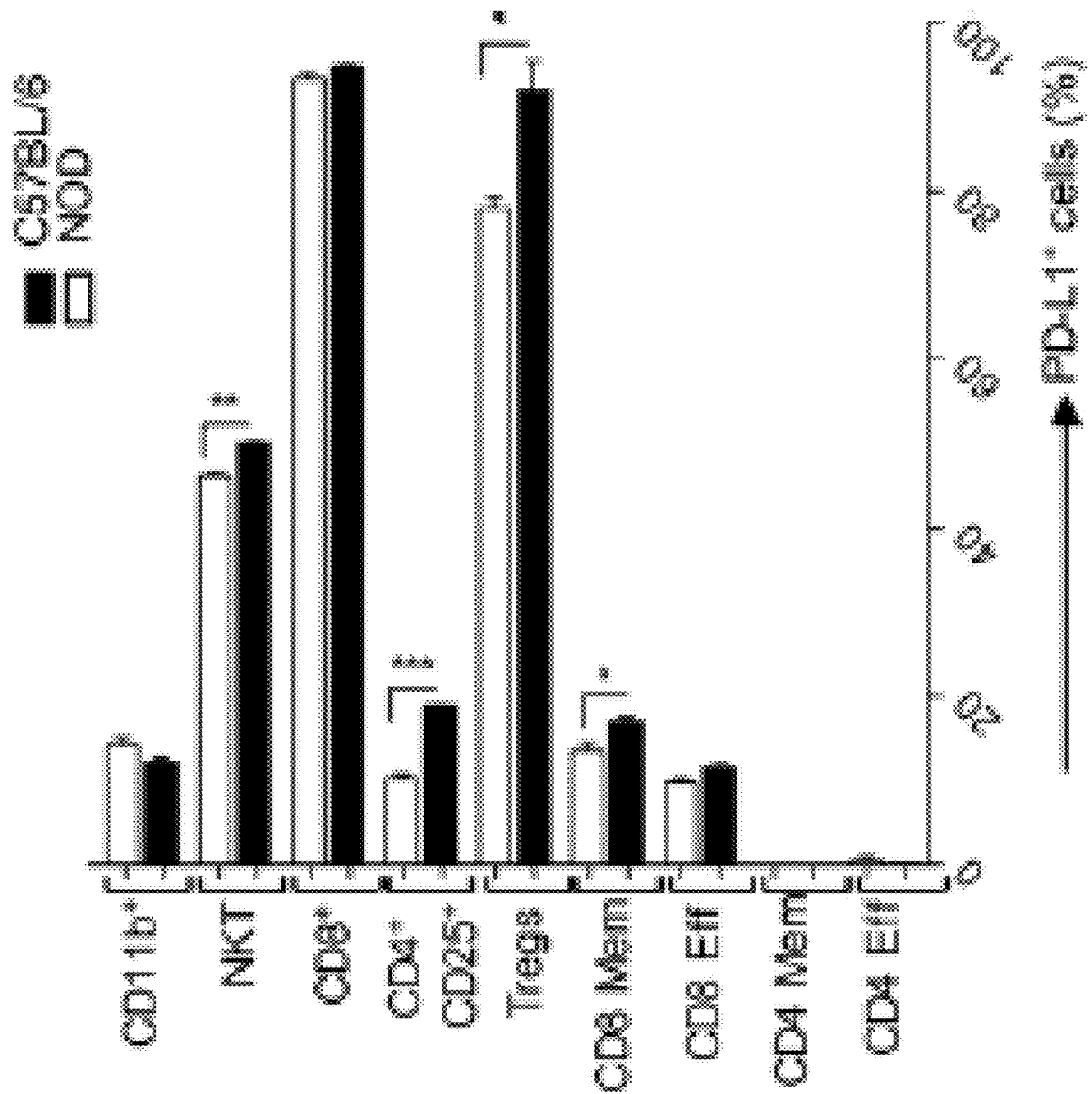
Figure 11A:
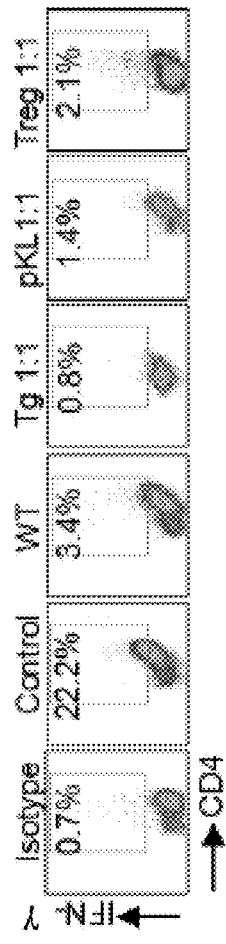
FIGS. 11A-11E present data that show analysis of IFN-γ+CD4+ T cells.
Figure 11B:
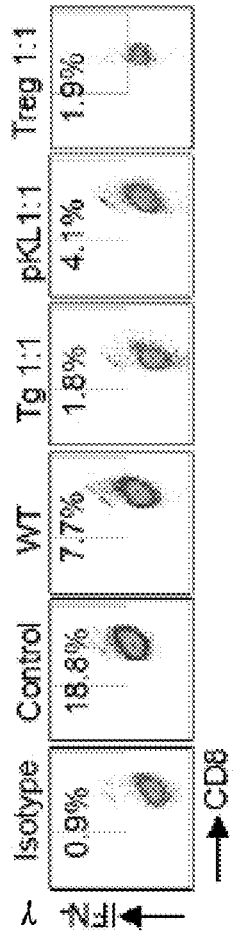
Figure 11C:
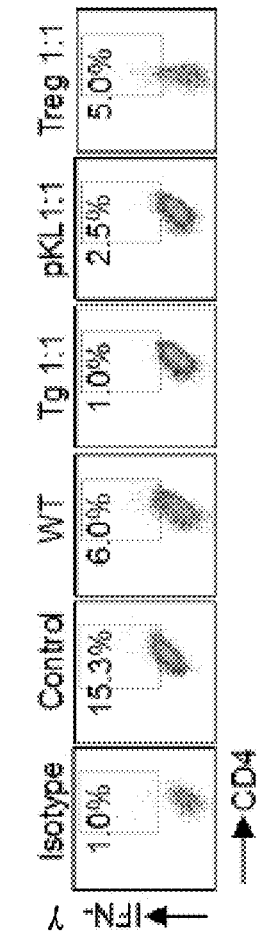
Figure 11D:
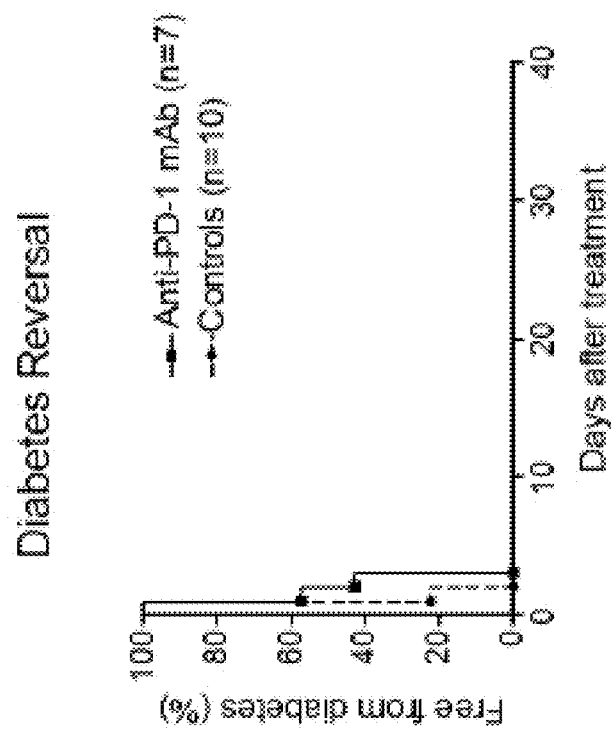
Figure 11E:
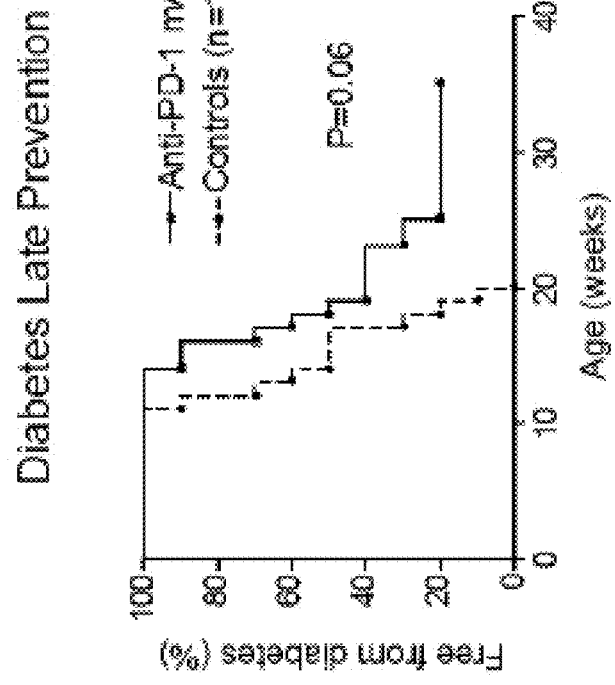
Figure 13A:
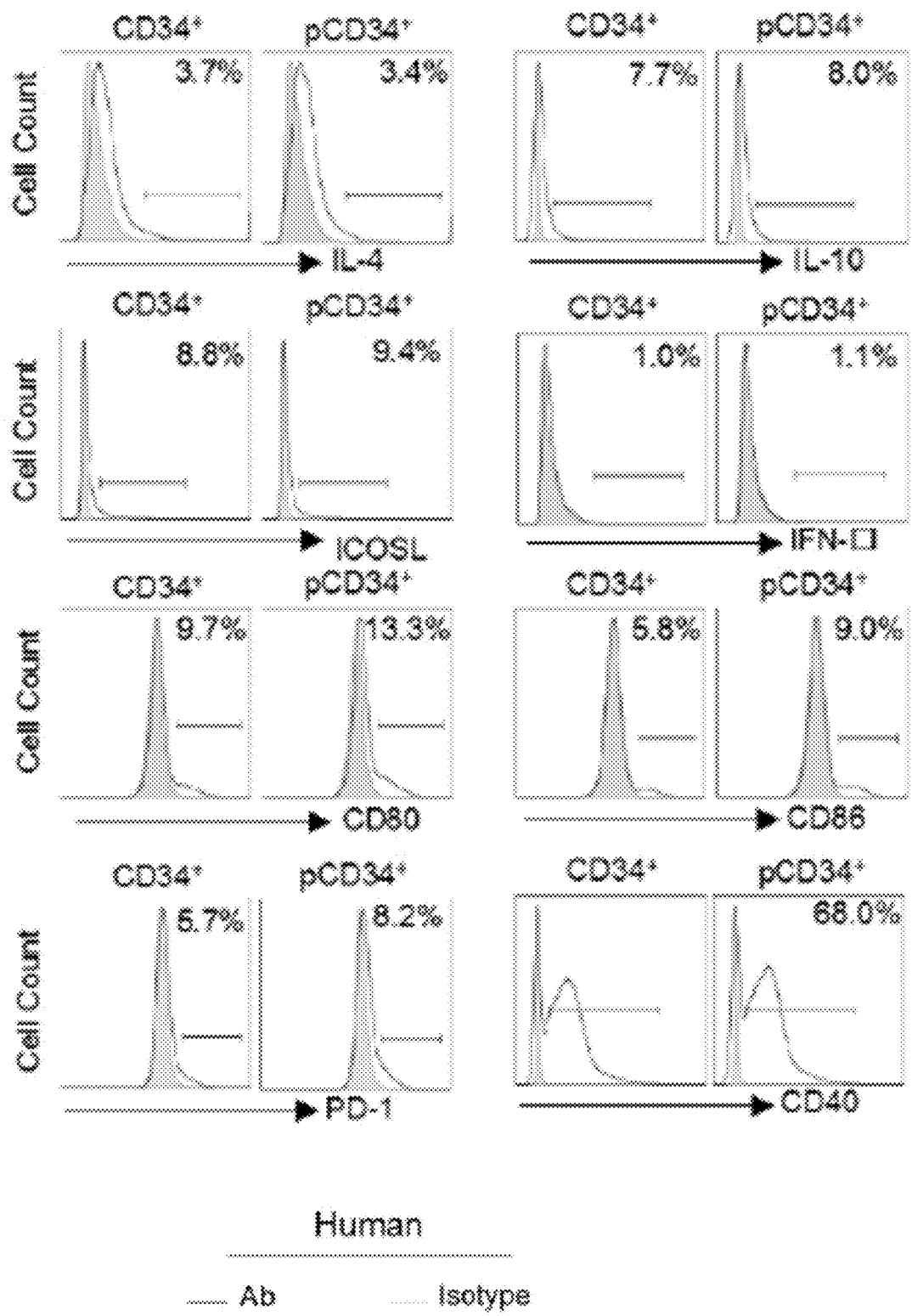
FIGS. 13A-13B present data that show analysis of pharmacologically-modulated CD34+ cells.
Figure 13B:
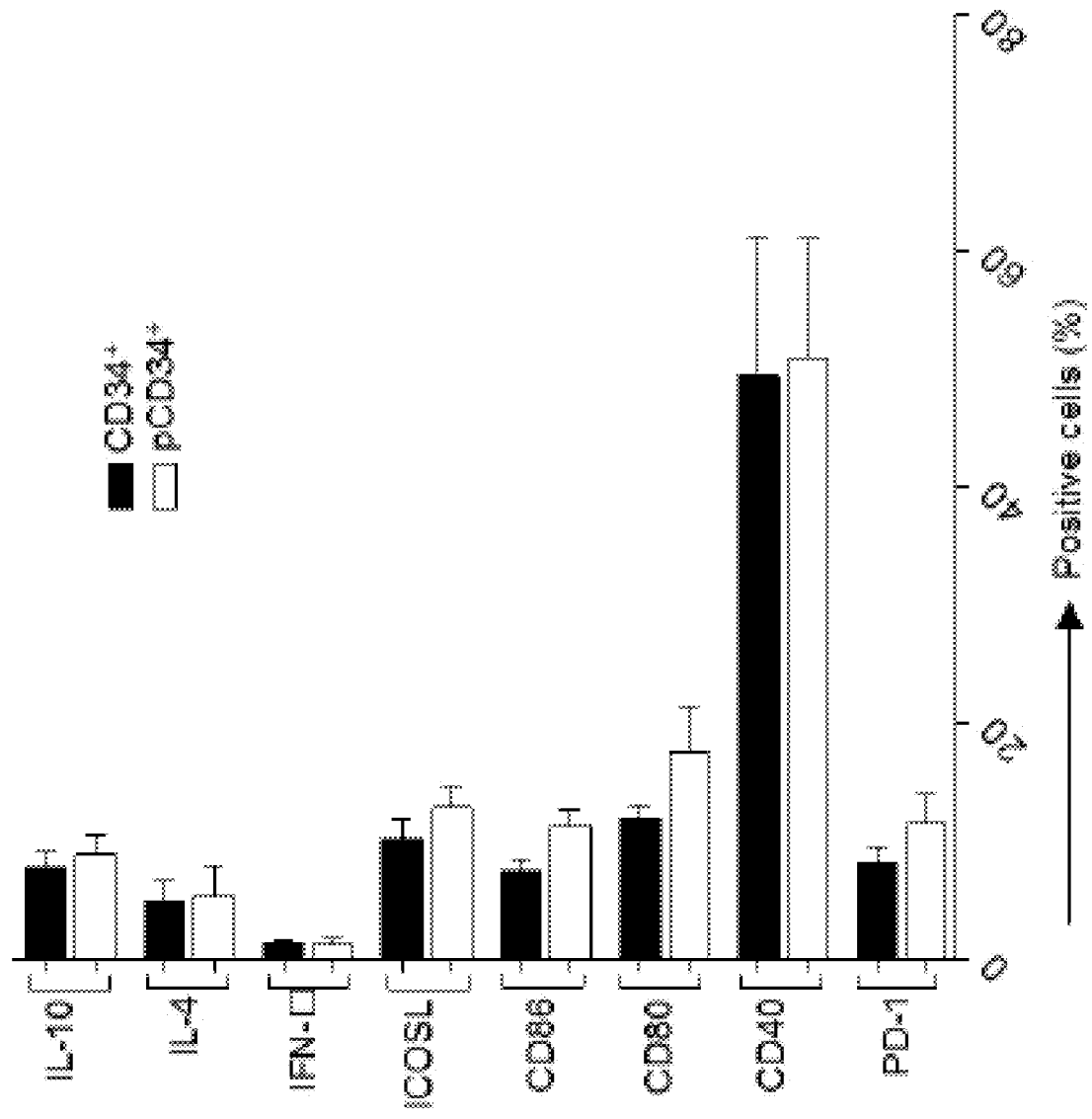

In order to evaluate the effect of pKL cells in vivo, newly hyperglycemic NOD mice were adoptively transferred with 3×10$^6$ pKL cells (FIG. 6A). pKL cells successfully reverted diabetes in 40% of treated newly hyperglycemic NOD mice, with 30% remaining normoglycemic until the completion of the study at day 40. Kaplan-Meier analysis showed a greater effect of PD-L1.Tg KL cells in reverting hyperglycemia in NOD mice, as compared to pKL cells (FIG. 6B). Quantification of IFN-γ-producing cells in an ex vivo assay where splenocytes were challenged with islet peptides at day 40 (BDC2.5, IGRP, GAD-65 and insulin) revealed a reduction in IFN-γ-producing cells in pKL cell-treated hyperglycemic NOD mice (FIG. 6C). Immunophenotyping of treated NOD mice showed at day 40 post-treatment a marked increase in FoxP3+ regulatory CD4+ T cells (FIG. 6D) and a reduction in the percentage of IFN-γ+CD4+ and IFN-γ+/IL-17+CD8+ T cells (data not shown). A reduction in the peripheral levels of pro-inflammatory (IL-2/IL-6) (FIGS. 6E-6F) and an increase in anti-inflammatory (IL-4) (FIG. 6G) cytokines were evident in pKL cell-treated NOD mice. whether immunocompetence was maintained during treatment of NOD mice with pKL cells was evaluated, in the same manner as using PD-L1.Tg KL cells. pKL cell-treated NOD mice were capable of mounting a regular immune response to ovalbumin once immunized and re-challenged in vitro with ovalbumin similar to untreated NOD mice and were thus immunocompetent (FIG. 6H). Pathology of the pancreas of pKL cell-treated NOD mice revealed mild infiltration of the islets, with preserved insulin staining and reduced insulitis score as compared to untreated hyperglycemic NOD mice (FIGS. 6I and $6J_1$-$6J_6$). Finally, the effects of a PD-1 signaling mAb capable of mimicking PD-L1/PD-1 cross-linking was tested. PD-1 mAb treatment did not delay diabetes onset in prediabetic NOD mice nor did it revert diabetes in newly hyperglycemic NOD mice (FIG. 11D, 11E). It is possible that the mAb used was unable to reach the inflamed islets within the pancreas, which conversely could be accessed by modified HSPCs because of their CXCR4 expression, which allows the trafficking of HSPCs into inflamed areas that release high levels of SDF-1. Without wishing to be bound by a particular theory, a working hypothesis, in which an altered network of miRNAs is responsible for the PD-L1 defect in HSPCs in T1D, is proposed. The genetic and pharmacological restoration of this PD-L1 defect in HSPCs in T1D generates a new pool of PD-L1+ HSPCs, which once adoptively transferred traffic to the pancreas and are able to delete autoreactive T cells via a PD-L1/PD-1-dependent mechanism, thus reverting hyperglycemia (FIG. 6K).

The PD-L1 Defect is Evident in Human HSPCs from T1D Patients

To assess whether patients with T1D displayed defects in HSPCs similar to those observed in the preclinical models presented herein, PD-L1 expression was analyzed on CD34+ cells isolated from peripheral blood (Table 8). In line with the findings in NOD mice presented herein, fewer PD-L1+CD34+ cells were detectable in T1D patients as compared to healthy controls (FIG. 7A-7C). Interestingly, the defect was evident in newly diagnosed T1D patients as well, when it is unlikely there is any effect of high glucose (FIG. 12A). Western blot and PCR analysis confirmed reduced PD-L1 protein and mRNA expression in CD34+ cells obtained from T1D patients as compared to those obtained from healthy controls (FIG. 7D-7F). Other relevant immune cells were not deficient in PD-L1 (FIG. 12B-12D), thus confirming that the PD-L1 defect is mainly restrained to HSPCs in T1D patients. Interestingly, PD-L2 was expressed on CD34+ cells from T1D patients at higher levels as compared to controls; however, PD-L2 has been described to be less relevant for T1D onset as shown by the lack of effect when knocking down PD-L2 in NOD mice (FIG. 12E-12I). PD-1 expression was slightly reduced by MFI in T1D patients compared to healthy controls (FIG. 12J-12N). Finally, a reduced number of PD-L1+CD34+ cells in the bone marrow of T1D patients was confirmed by confocal imaging as compared to healthy controls (FIG. $7G_1$-$7G_3$; $7H_1$-$7H_3$ and 7I). Data presented herein confirmed the existence of a defect in PD-L1 expression in HSPCs of T1D patients.

The Altered miRNA Network is Also Evident in Human HSPCs

In order to understand the immunological basis of the PD-L1 defect in human HSPCs, in vitro experiments similar to those performed in mice were performed. Any potential high glucose-associated effect on PD-L1 expression on CD34+ cells, or small differences, if any, in the proliferation and apoptosis rate in CD34+ cells obtained from T1D patients and controls were not found (FIG. 7J-7L). Bioinformatic analysis of miRNAs showed a number of miRNA species involved in controlling PD-L1 expression (FIG. 7M). qRT-PCR analysis of several relevant miRNAs confirmed that a number of miRNA species were differentially expressed in human CD34+ cells obtained from T1D patients as compared to controls (FIG. 7N), with no differences observed in the methylation status of the promoter of the PD-L1 gene (FIG. 7O). In line with preclinical findings, an altered miRNA network is evident in HSPCs of T1D patients.

Pharmacologically Modulated Human HSPCs Abrogate the Autoimmune Response Ex Vivo The effect of overcoming PD-L1 deficiency in human HSPCs was tested by using the same agents described herein above (e.g., tested in NOD mice). As shown by flow cytometric analysis, confocal imaging and qRT-PCR, modulation of CD34+ cells with an agent, alone or in combination, upregulated PD-L1 expression in human CD34+ cells obtained from T1D patients (pCD34+) as compared to unmodulated CD34+ cells (FIG. 7P-7U). Immunophenotyping and transcriptome profiling of pharmacologically modulated CD34+ cells (pCD34+) (FIGS. 13A,13B, FIGS. 14A-14B, and Table 9) confirmed specific PD-L1 upregulation in pCD34+ cells as compared to unmodulated CD34+ cells. To study the ex vivo immunoregulatory functions of pCD34+, CD34-depleted PBMCs were co-cultured with unmodulated CD34+ or pCD34+ in the presence of insulin-associated autoantigen-2 (I-A2), and the number of IFN-γ-producing cells was quantified in an ELISPOT assay. Interestingly, the addition of unmodulated CD34+ or pCD34+ resulted in a significant decrease in the number of IFN-γ-producing cells as compared to those obtained when PBMCs were cultured without unmodulated CD34+/pCD34+ in the presence of the islet peptide IA-2 (FIGS. 7V-7W). The suppression was more pronounced when pCD34+ were added, indicating that pCD34+ are endowed with greater immunoregulatory activity than unmodulated CD34+(FIG. 7V-7W). To further confirm that the immunosuppressive effect exerted by pCD34+ was primarily due to PD-L1 expression, pCD34+ were pre-cultured in the presence of an anti-PD-L1 blocking mAb and then tested in the autoimmune assay. Ab-mediated PD-L1 blockade hampered the immunoregulatory effect exerted by pCD34+(FIG. 7X-7Y). This strongly confirms that pCD34+ are endowed with PD-L1-dependent regulatory properties ex vivo. Surprisingly, the effects of pCD34+ were not confirmed in a non-autoimmune-specific anti-CD3/anti-CD28 assay (FIG. 7Z). Finally, the effect of plerixafor-mediated mobilization, used in clinic (5, 9), was analyzed on PD-L1 expression in CD34+ cells obtained from 5 T1D patients and 8 healthy controls (Table 10). While the percentage and absolute number of CD34+ cells significantly increased, the percentage of CD34+PD-L1+ cells remained stable in T1D patients but decreased after mobilization in healthy controls, highlighting that CD34+ cell mobilization may have failed in previous clinical trials due to PD-L1 downregulation (FIG. 15A-15C).

Discussion

T1D is regarded as one of the most aggressive autoimmune diseases and requires life-long exogenous insulin administration. Efforts to halt β-cell decline or stall chronic complications are ongoing (10-13); however, the immunotherapies tested thus far have failed, mostly due to their lack of specificity as well as the fact that they are usually simply adopted from other settings (e.g. kidney transplantation) (14-16). The need for more T1D-tailored therapies led the inventors to explore the existence of immune checkpoint abnormalities unique to the disease. Various pieces of evidence led to the hypothesis that an HSPC-specific PD-L1 defect may be involved in the onset of T1D and that the resolution of this defect may provide a cure for the disease. First of all, the expansion and reinfusion of autologous HSPCs was the most potent therapy in reverting hyperglycemia in T1D patients (4); secondly, there is a strong link between the PD-L1 defect and T1D (6, 17), and finally, PD-L1 is a key player in HSPC immunobiology, such that the lack of PD-L1 reduces the ability of HSPCs to abrogate the immune response (5). Indeed, while immunosuppressant treatment alone (i.e. ATG) failed to preserve β-cell function in recent onset T1D, HSPCs plus immunosuppressant were successful in the Voltarelli trial. This result indicates that either there is a synergistic effect between HSPCs and immunosuppression or that the PD-L1 defect prevents HSPCs from being fully effective in their suppression. Transcriptomic profiling, flow cytometric analysis, RT-PCR and direct analysis of bone marrow showed a reduction in PD-L1 expression in HSPCs in both NOD mice and T1D patients. While high glucose, altered HSPC survival or epigenetic abnormalities cannot account for the impaired PD-L1 expression, gene expression profiling unveiled abnormalities in the HSPC miRNA network in T1D that may be responsible for the PD-L1 defect. Therefore, a genetic approach to overcome the PD-L1 defect was developed and PD-L1.Tg HSPCs were generated to test their ability to affect the autoimmune response in vitro and in vivo. These PD-L1+ HSPCs successfully abrogated the autoimmune response in vitro. The use of an anti-PD-L1 blocking antibody impeded the observed effect of PD-L1.Tg HSPCs, thus confirming that HSPC immunoregulatory properties are PD-L1-dependent. Notably, PD-L1.Tg HSPCs described herein successfully converted all treated hyperglycemic NOD mice to normoglycemia, with suppression of the autoimmune response. Tracking studies suggested that PD-L1.Tg HSPCs preferentially homed to the inflamed pancreas, due to substantial CXCR4 expression, which is in line with the CXCL12 shown to be released by inflamed pancreatic islets (18). Once in the pancreas, PD-L1.Tg HSPCs may induce apoptosis of autoreactive T cells. The recent progress in the field of gene therapy (19) provides a basis for the potential use of the aforementioned genetic approach in T1D as well. Interestingly and clinically relevant, pharmacologically modulated HSPCs also exhibited immunoregulatory effects, as they markedly abrogated CD4/CD8-restricted autoimmune responses in vitro and partially reverted diabetes in newly hyperglycemic NOD mice. The human data parallel the preclinical findings, confirming the presence of the PD-L1 defect in human CD34+ cells. Results described herein have 2 major implications. Firstly, a novel and important path involved in the onset of T1D was identified, and the PD-L1 defect in HSPCs have a permissive role on the generation of autoreactive T cells (20). The study described herein thus provides key insight into the potential role of miRNAs in the regulation of PD-L1 expression of HSPCs and potentially of T1D pathogenesis. Secondly, expression of PD-L1 in HSPCs can be used as a novel tool for targeted immunotherapy in T1D, which appears more efficacious than mAbs and also appears to be safe (21, 22). In conclusion, data presented herein has discovered a novel mechanism involved in the onset of T1D, whose correction may provide an immunological tool to be used to cure T1D.

The references cited herein and throughout the specification are incorporated herein by reference in their entireties.

REFERENCES

1. J. A. Bluestone, K. Herold, G. Eisenbarth, Genetics, pathogenesis and clinical interventions in type 1 diabetes. Nature 464, 1293-1300 (2010).
2. M. Ben Nasr et al., The rise, fall, and resurgence of immunotherapy in type 1 diabetes. Pharmacol Res 98, 31-38 (2015).
3. C. E. Couri et al., C-peptide levels and insulin independence following autologous nonmyeloablative hematopoietic stem cell transplantation in newly diagnosed type 1 diabetes mellitus. JAMA 301, 1573-1579 (2009).
4. F. D'Addio et al., Autologous nonmyeloablative hematopoietic stem cell transplantation in new-onset type 1 diabetes: a multicenter analysis. Diabetes 63, 3041-3046 (2014).
5. P. Fiorina et al., Targeting the CXCR4-CXCL12 axis mobilizes autologous hematopoietic stem cells and prolongs islet allograft survival via programmed death ligand 1. J Immunol 186, 121-131 (2011).
6. M. J. Ansari et al., The programmed death-1 (PD-1) pathway regulates autoimmune diabetes in nonobese diabetic (NOD) mice. J Exp Med 198, 63-69 (2003).
7. T. Yokosuka et al., Programmed cell death 1 forms negative costimulatory microclusters that directly inhibit T cell receptor signaling by recruiting phosphatase SHP2. J Exp Med 209, 1201-1217 (2012).
8. K. D. Bunting, C. K. Qu, The hematopoietic stem cell landscape. Methods Mol Biol 1185, 3-6 (2014).
9. J. D. Scandling et al., Chimerism, graft survival, and withdrawal of immunosuppressive drugs in HLA matched and mismatched patients after living donor kidney and hematopoietic cell transplantation. Am J Transplant 15, 695-704 (2015).
10. M. G. von Herrath, O. Korsgren, M. A. Atkinson, Factors impeding the discovery of an intervention-based treatment for type 1 diabetes. Clin Exp Immunol 183, 1-7 (2016).
11. R. Romaniello et al., Cerebroretinal microangiopathy with calcifications and cysts associated with CTC1 and NDP mutations. J Child Neurol 28, 1702-1708 (2013).
12. Retinopathy and nephropathy in patients with type 1 diabetes four years after a trial of intensive therapy. The Diabetes Control and Complications Trial/Epidemiology of Diabetes Interventions and Complications Research Group. N Engl J Med 342, 381-389 (2000).
13. M. A. Atkinson, M. von Herrath, A. C. Powers, M. Clare-Salzler, Current concepts on the pathogenesis of type 1 diabetes—considerations for attempts to prevent and reverse the disease. Diabetes Care 38, 979-988 (2015).
14. S. E. Gitelman et al., Antithymocyte globulin treatment for patients with recent-onset type 1 diabetes: 12-month results of a randomised, placebo-controlled, phase 2 trial. Lancet Diabetes Endocrinol 1, 306-316 (2013).
15. K. C. Herold et al., Teplizumab (anti-CD3 mAb) treatment preserves C-peptide responses in patients with new-onset type 1 diabetes in a randomized controlled trial: metabolic and immunologic features at baseline identify a subgroup of responders. Diabetes 62, 3766-3774 (2013).
16. M. D. Pescovitz et al., Rituximab, B-lymphocyte depletion, and preservation of beta-cell function. N Engl J Med 361, 2143-2152 (2009).
17. I. Guleria et al., Mechanisms of PDL1-mediated regulation of autoimmune diabetes. Clin Immunol 125, 16-25 (2007).
18. M. J. Cowley et al., Human islets express a marked proinflammatory molecular signature prior to transplantation. Cell Transplant 21, 2063-2078 (2012).
19. M. Sessa et al., Lentiviral haemopoietic stem-cell gene therapy in early-onset metachromatic leukodystrophy: an ad-hoc analysis of a non-randomised, open-label, phase 1/2 trial. Lancet, (2016).
20. J. Yang et al., The novel costimulatory programmed death ligand 1/B7.1 pathway is functional in inhibiting alloimmune responses in vivo. J Immunol 187, 1113-1119 (2011).
21. M. J. Haller et al., Autologous umbilical cord blood transfusion in very young children with type 1 diabetes. Diabetes Care 32, 2041-2046 (2009).
22. P. Fiorina, J. Voltarelli, N. Zavazava, Immunological applications of stem cells in type 1 diabetes. Endocr Rev 32, 725-754 (2011)

Example 2

Encouraging results of previous pilot trials suggest that autologous hematopoietic stem and progenitor cell transplantation (AHSCT) may be a relevant alternative therapeutic option to immunosuppressive drugs in the treatment of several refractory autoimmune disorders (1, 2). Over 3,000 transplants using AHSCT have been performed worldwide with a very high safety profile (2, 3). It was recently demonstrated that AHSCT could induce long-term, drug free and symptoms-free remission in patients newly diagnosed with type 1 diabetes (T1D). Insulin independence was achieved in nearly 60% of treated subjects at 6 months, with 40% showing sustained insulin-free remission over 4 years following the procedure (4). The aim behind the use of AHSCT is to suppress autoreactive immune cells, while allowing for de novo generation of a naïve immune compartment tolerant to pancreatic 13 cells antigens (5), thus preventing T cell infiltration into targeted organs (6). AHSCT trials showed that in treated patients, an overall resetting of the immune system toward a "regulatory"-like T cell landscape was evident, with an increase in CD4+ Foxp3+ Tregs (7). Unfortunately, the use of immunosuppression during AHSCT limits the potential use of this therapy in T1D to experimental conditions, due to patients' potential exposure to adverse effects. Interestingly, the immunoregulatory properties of HSPCs seem to be linked to their expression of the immune checkpoint-signaling molecule PD-L1 (or CD274) (8, 9). They further express CXCR4, which allows HSPCs to traffic to inflamed area/sites of injuries (10). Unlike mesenchymal or embryonic stem cells, which are associated with the potential development of tumorogenesis and formation of ectopic tissue (5, 11-13), HSPCs have been safely used for years (14-16). Several studies suggested that PGE2 might have anti-inflammatory effects through inhibition of several pro-inflammatory cytokines (17). Others have demonstrated that the endogenous anti-inflammatory role of PGE2 is mainly mediated through it receptor EP4, thereby inhibiting macrophage derived-pro-inflammatory chemokines production during atherogenesis (18, 19). While others have mainly studied in depth the mechanism by which PGE2 can control inflammation and demonstrated that PGE2 plays its regulatory role by limiting T cell activation thereby impairing T cell arrest and inhibiting T cells interactions with DCs (20). Previous reports have introduced and identified PGs as potentials HSPCs enhancing candidates capable of inducing/improving their long-term maintenance and engraftment faculties (21). Without wishing to be bound by a particular theory, it was hypothesized that enhancing the immunoregulatory properties of HSPCs using pharmacological modulation with small molecules may create a novel powerful immunoregulatory tool for the treatment of T1D.

Methods and Materials

Human Studies

Study population included in the AHSCT clinical trial. Two cohorts consisting of 36 T1D patients were enrolled in the AHSCT (autologous hematopoietic stem cell transplantation) program and were also enrolled in 3 independent clinical trials as previously described (6). Auto-antibodies were analyzed on serum by RIA (for IAA) and ELISA (for IA-2A, GAD, Znt8) according to the standard of care clinical procedure. The study was performed in accordance with Institutional Review Board committee approval of each participant Institution, informed consent was provided by all individuals. All baseline demographic and clinical characteristics of the study population are reported in Table 1.

Study population included in the PG-library screening. Blood samples were obtained from long lasting T1D patients (n=24) and healthy controls (CTRL) (n=5) in accordance with Institutional Review Board committee approval of San Raffaele Hospital and of Boston children's Hospital (BCH 3851); informed consent was provided by all individuals included in the present study. Baseline characteristics of the study population are summarized in Table 2. Peripheral blood mononuclear cells (PBMCs) isolated from 20 ml blood samples using Lymphoprep (Stem Cell Technologies, Cambridge, MA) were frozen in freezing medium (RPMI 1640 20% FBS and 8% DMSO) and stored at −80° C. After thawing, PBMCs were recovered in culturing medium consisting of RPMI 1640 (Life Technologies, Carlsbad, CA) supplemented with 10% FBS, 2 mM L-glutamine (Life Technologies), 100 U/ml penicillin (Life Technologies), for 48 h, and CD34+ cells were then isolated using a CD34 Positive Isolation Kit (Miltenyi Biotec, San Diego, CA) according to the manufacturer's instructions.

Pharmacological modulation of human CD34+ cells. $1\times10^5$ of isolated human CD34+ HSPCs (purity 99%) were cultured in 200 µl of StemSpan SFEM II media (SEMCELL Technologies Inc., Cambridge, MA, USA), and each compound in the Prostaglandin Screening Library II (Cayman Chemicals, Ann Arbor, MI), was added individually at day 0 and at day 1 at a concentration of 10 µM as previously reported by the inventors and others (9, 21). In another assay, isolated CD34+ cells from freshly isolated human PBMCs or from cryopreserved PBMCs, and processed as described earlier, were cultured in the presence of a cocktail of cytokines containing: 10 µg/ml heparin (SEMCELL Technologies Inc., Cambridge, MA, USA), 10 ng/ml human SCF (Miltenyi Biotec, San Diego, CA), 20 ng/ml human TPO (Miltenyi Biotec, San Diego, CA), 10 ng/ml human FGF-1 (Miltenyi Biotec, San Diego, CA), 100 ng/ml IGFBP2 (R&D Systems, Inc., Minneapolis, MN), and 500 ng/ml Angptl3 (R&D Systems, Inc., Minneapolis, MN). PGE2 (PromoKine, PromoCell Gmbh, Germany) was added by pulsing the culture at 0, 24h, 72h and 6 days with 2 µl of diluted PGE2 (10 µM). Cells were cultured for 7 days at 37° C. in 5% CO2, and CD34+ cells were then subjected to FACS analysis and were run on a FACSCelesta™ (Becton Dickinson, Franklin Lakes, NJ). Data were analyzed using FlowJo software version 8.7.3 (Treestar, Ashland, OR). The different cytokines used here and their related concentration as well as the choice of the incubation timing was used as previously reported in the literature (22).

qRT-PCR. RNA was extracted from CD34+ cells using Direct-Zol™ RNA Kits (Zymo, Irvine, CA, USA) and Trizol Reagent (Invitrogen Carlsbad, CA), RNA quality was assessed by Multiskan™ GO Microplate spectrophotometer and the ratios of absorbance at 260 nm and 280 nm were assessed for all the samples. Only samples with RNA ratios within 1.9 were included in the present study. cDNA synthesis was made from purified total RNA by reverse transcription using High capacity cDNA Reverse Transcription RETROscript® Kit (Thermo Fisher Scientific, Waltham, MA, USA) followed by a pre-amplification using Taqman PreAmp Kit (Applied Biosystems) according to the manufacturer's instructions. qRT-PCR analysis was performed using TaqMan assays (Life Technologies, Grand Island, NY) containing PCR primers and TaqMan probes according to the manufacturer's instructions. Normalized expression values were determined using the ΔCt method. Quantitative reverse transcriptase polymerase chain reaction (qRT-PCR) data were normalized for the expression of GAPDH. qRT-PCR reactions were performed in triplicate in a 96-well format using an Applied Biosystems 7900HT fast real-time PCR instrument. Relative expression was calculated using the comparative threshold cycle method as previously described (23, 24). For two-group comparisons, a Student's t test was employed. Reported below are the main characteristics of the primers used:

TABLE 11

Main characteristics of the primers used for qPCR.

| Gene Symbol | Assay ID | Refseq Accession # | Band Size (bp) | Reference Position |
|---|---|---|---|---|
| CD274 (PD-L1) | Hs01125299_m1 | NM_001267706.1 | 89 | 441 |
| CD184 (CXCR4) | Hs00237052_m1 | NM_001008540.1 | 153 | 973 |
| IDO1 | Hs00984148_m1 | NM_0022164.5 | 66 | 651 |
| GAPDH | Hs99999905_m1 | NM_001289746.1 | 122 | 229 |

Human ELISPOT assay. An ELISPOT assay was used to measure the number of IFN-γ-producing cells according to the manufacturer's protocol (BD Biosciences, San Jose, CA) as previously shown by the inventors (2). 1×106 PBMCs isolated from T1D patients were cultured for 2 days in the presence of IA-2 peptide (Thermo Fisher Scientific Gmbh, Germany) (100 µg/ml) in RPMI medium supplemented with 10% FBS. At 24h after stimulation, 500 µl of medium was added to the culture. Cells were collected at day 2 and added to plates coated with anti-IFN-γ antibody (eBioscience, Thermo Fisher Scientific, Waltham, MA USA) with or without PGE2-modulated CD34+ cells at ratios of 1:2 or 1:10 or 1:32 in RPMI medium supplemented with 10% FBS. Spots were counted using an A.EL.VIS Elispot Reader (A.EL.VIS GmbH, Hannover, Germany) or on an Immunospot Reader (C.T.L. Cellular Technology Ltd, Cleveland, OH).

Immunofluorescence and confocal microscopy. Regulatory CD34+(PGE2-modulated) cells and unmodulated CD34+ cells isolated from peripheral blood of healthy controls were fixed in 4% PFA for 1h at 4 C, washed 3 times for 20 min in PBS, and cells were counterstained with blue fluorescent DAPI (1:10000, BioLegend, San Diego, CA) and anti-human PD-L1 (BD Biosciences). Cells were photographed under a 63× objective. Images were captured on a Leica SPSX system with an upright DM6000 microscope and AIR confocal microscope (Nikon Instruments, Melville, NY). Histology was evaluated by at least two expert pathologist (9).

Migration assay. Transwell migration assays were performed on PGE2-modulated HSPCs compared to unmodulated HSPCs in the presence of 0 to 50 ng/ml SDF-1 (R&D Systems, Minneapolis, MN). In brief, cells were suspended in 0.5% BSA Phenol Red-Free RPMI and plated in the upper chambers of an HTS-Transwell-96-well permeable support plate (Corning, Acton, MA) and incubated at 37° C. in 5% CO2 for 2 hours. After 2 hours incubation, migrated cells were counted using BD TruCount (BD Biosciences) by flow cytometry.

Murine Studies

Mice. Female NOD/ShiLtJ (NOD) or non-obese diabetic mice (NOD) which is the commonly used model for autoimmune type 1 diabetes studies, NOD.FVB-Tg (CAG-luc,-GFP)L2G85Chco/FathJ (Luciferase NOD) mice which exhibit a widespread expression of the two cell tracers eGFP and firefly luciferase directed by the CAG promoter allowing thus an easily tracking of the cells and NOD.CgTg (TcraBDC2.5,TcrbBDC2)1Doi/DoiJ (BDC2.5 NOD) mice which has the particularity to carry a rearranged TCR a and 8 genes from a diabetogenic T cell clone, BDC2.5 and is commonly used in vitro autoimmune assays; were purchased from the Jackson Laboratory (Bar Harbor, Maine). All mice were housed under specific pathogen-free conditions at an AAALAC (Association for Assessment and Accreditation of Laboratory Animal Care International)-accredited facility at Boston Children's Hospital. Institutional guidelines and protocols were approved and adhered to the Institutional Animal Care and Use Committee (IACUC).

Murine regulatory KL cell modulation. Murine bone marrow KL (c-Kit+Lineage-) cells were isolated using magnetic beads and MACS® separation columns (Miltenyi Biotec, San Diego, CA) and ~2×105 cells were plated in a U-bottomed 96-well plate with 200 µl of stem cell medium, Stemspan-SFEMII (STEMCELL Technologies, Cambridge, MA) and PGE2 (PromoKine, PromoCell Gmbh, Germany) was added at day 0 and day 1, at a concentration of 10 µM.

Flow cytometric analysis and intracellular cytokine staining. Flow cytometry was performed to analyze surface expression markers of PGE2-modulated HSPCs and dmPGE2 (16, 16-dimethyl PGE2)-modulated HSPCs. Anti-mouse PD-L1, PD-L2, PD-1, CD40, CD80, CD86, CD4, CD8, Ly-6G (Gr-1), B220, CD3, CXCR4, CCR2, CCR4, CCR5, CCR6, CCR7, CCR8, CXCR3, IL-4, IL-10 and IFN-γ were purchased from BD Biosciences, eBioscience (San Diego, CA) and BioLegend. The following antibodies corresponded to isotype controls for the murine antibodies above: PE mouse IgG1, κ isotype ctrl, Armenian hamster IgG; APC mouse IgG2b, κ isotype ctrl, Armenian hamster IgG. Cells were subjected to FACS analysis and were run on a FACSCalibur™ (Becton Dickinson). Data were analyzed using FlowJo software version 8.7.3 (Treestar).

Intracellular staining for flow cytometry. Naïve CD4+ CD25− T cells (5×105) were isolated from BDC2.5 TCR tg mice with a negative selection strategy using a CD4+CD25+ Regulatory T cell isolation kit (Miltenyi Biotec) and were stimulated with BDC2.5 peptides and CD11c+ dendritic cells (DCs) (2.5×105) previously isolated using CD11c+ mAb-coated microbeads. DCs were added at a 1:2 ratio to T cells and were co-cultured with PGE2-modulated KL cells at ratios of 1:1, 5:1 and 10:1 (ratio of T cells to PGE2-modulated KL cells) or alone (controls) or with untransduced KL cells for 24 hours in RPMI 10% FBS in a humidified incubator at 37° C., 5% CO2. After incubation, cells were collected, washed and plated in RPMI 10% FBS, then stimulated with 50 ng/ml PMA (Sigma Aldrich, St. Louis, MO), 750 ng/ml ionomycin (Sigma Aldrich) and the protein transport inhibitor BD GolgiStop (6 µl per 6 ml of RPMI as recommended by the manufacturer, BD Biosciences) for 5h in a humidified incubator at 37° C., 5% CO2. After incubation, cells were collected, washed, stained for surface marker CD4 APC markers (i.e CD4 APC), followed by washing and permeabilization using the BD Cytofix/Cytoperm Kit (BD Biosciences) and staining with anti-mouse IFN-g (eBioscience). Finally, CD4+ IFN-g+ cells were assessed by flow cytometric analysis.

Pancreas digestion and preparation for flow cytometry. Pancreata were collected in ice-cold IMDM medium, cut into small pieces, and digested with Collagenase D for 1h at 37° C., with DNase I added after 30 minutes. Digested pancreata were passed through a 70-µm cell strainer to obtain single cell suspensions and then analyzed by flow cytometry. For tracking GFP+ cells, biotinylated anti-GFP (BD Biosciences) was used at 20 ug/ml followed by staining with APC-conjugated streptavidin (BD Biosciences).

Statistical analysis. Statistical analysis was performed using an unpaired Student's t test. A two-sided value of p≤0.05 was considered statistically significant. All graphs were generated using GraphPad Prism software version 5.0b (GraphPad Software, Inc., La Jolla, CA). All statistical tests were performed at the 5% significance level.

Results

Figure 16A:
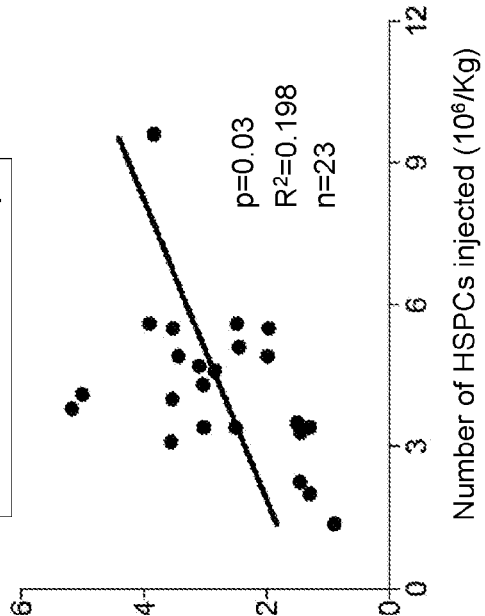
FIGS. 16A-16D show nonmyeloablative autologous hematopoietic stem cell transplantation (AHSCT) preserved pancreatic β cell function in patients newly diagnosed with T1D.
Figure 16B:
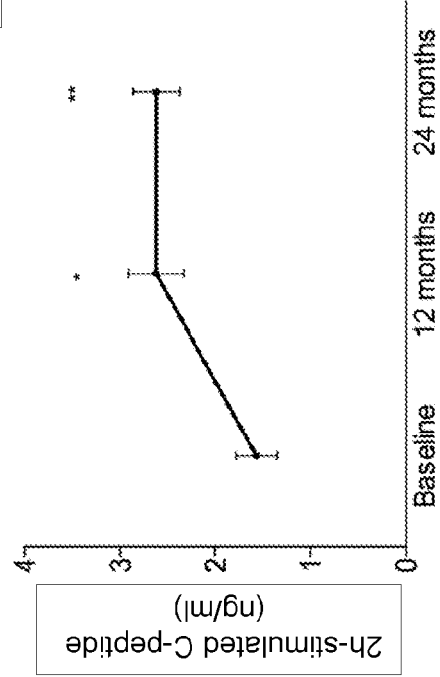
Figure 16C:
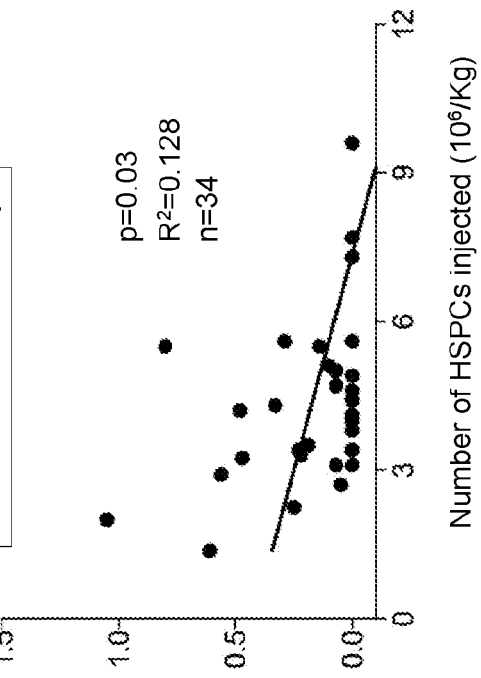
Figure 16D:
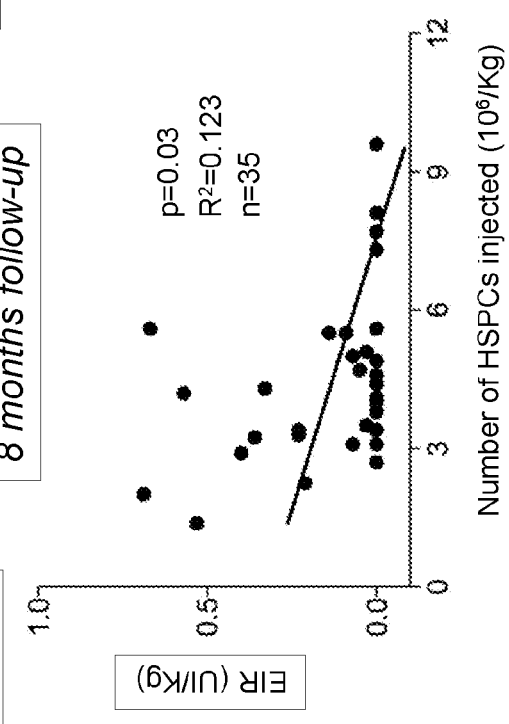

AHSCT improves β cell function in treated T1D patients. Two cohorts consisting of 36 T1D patients were enrolled in the AHSCT (autologous hematopoietic stem cell transplantation) program and were also enrolled in 3 independent clinical trials as previously described (6). All baseline demographic and clinical characteristics of the study population are reported in Table 1. The patient group was predominantly male (27 males and 9 females) with a mean age of 22.4 years and a short history of disease duration (within 6 weeks of diagnosis), confirmed by the presence of autoantibodies to islet peptides (glutamic acid decarboxylase antibodies [anti-GAD] were detected in 86% of patients, while other autoantibodies were detected in 17% of patients). Most of the patients studied (67%) had no previous history of diabetic ketoacidosis/ketosis. The mean body mass index (BMI) of patients at diagnosis was 20.7±0.5 (kg/m2±SEM), and their mean glycated haemoglobin of (HbA1c) was 86.6±6.4 (mmol/mol±SEM). All patients underwent a stem cell mobilization protocol as previously described (6) with cyclophosphamide (2 g/m2) and granulocyte colony-stimulating factor (G-CSF) (5-10 μg/kg) daily, beginning the day after cyclophosphamide administration (6). A mean dose of 5.8±0.8×106/kg cryopreserved CD34+ cells was administered as a single infusion at day 0 (6). All patients showed improvement in β cell function, as revealed by an increase in C-peptide levels over time, which reached a persistent and stable median value>2.5 ng/mL at 12 months of follow-up and lasted until 24 months after treatment (FIG. 16A). Interestingly, compared to pre-AHSCT treatment levels, 2-hour postprandial peak-stimulated C-peptide levels increased significantly at 6 months post-AHSCT treatment and reached ~2.7 ng/ml at 24 months of follow-up (FIG. 16A). Furthermore, a significant positive correlation, albeit weak, was found between the number of CD34+ cells infused and C-peptide levels at 6 months after treatment (FIG. 16B). Statistical analysis revealed a significant negative correlation between the number of CD34+ cells injected during AHSCT and exogenous insulin requirement units (EIR) evaluated at 8 months (FIG. 16C) and 12 months (FIG. 16D) of follow-up. T1D patients treated with autologous hematopoietic stem cell transplantation showed an overall improvement in glycometabolic control and maintenance of β cell function.

Figure 17A:
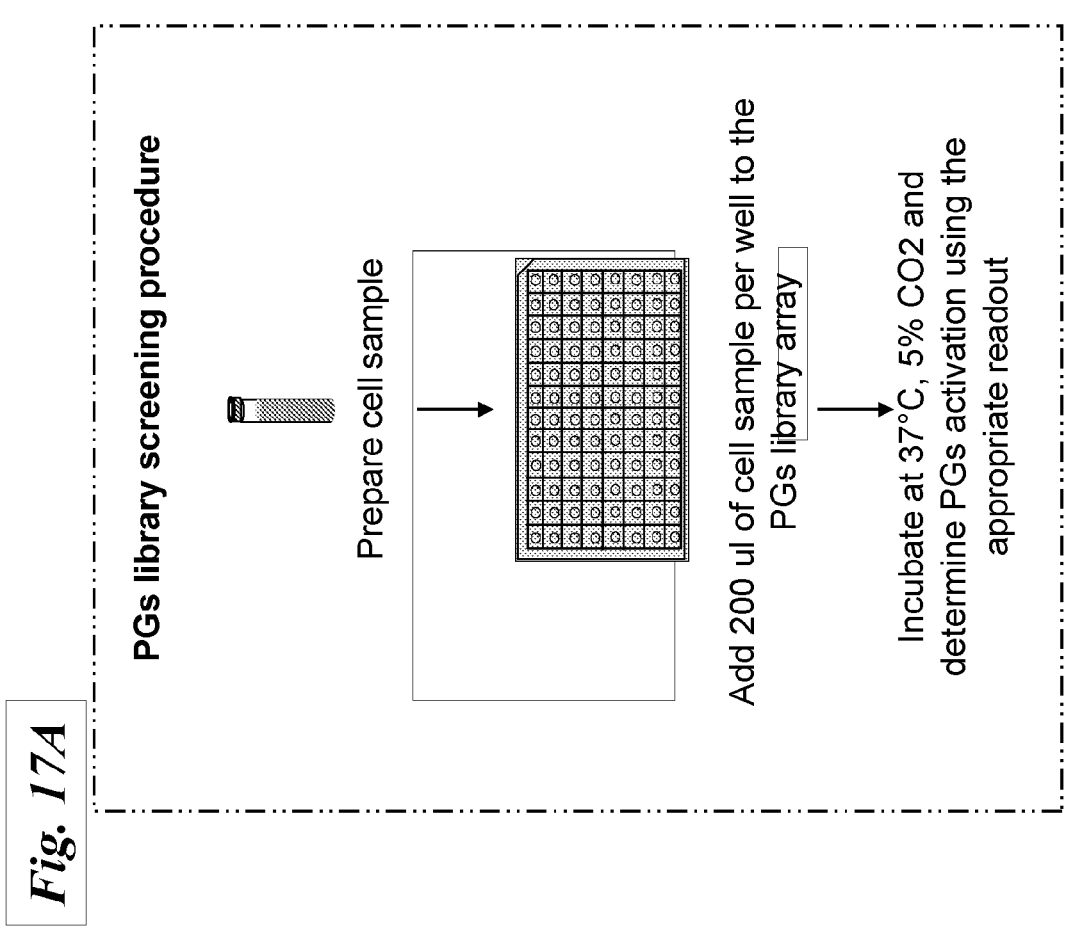
FIGS. 17A-17J show prostaglandins enhance PD-L1 expression on human CD34+ cells.
Figure 17B:
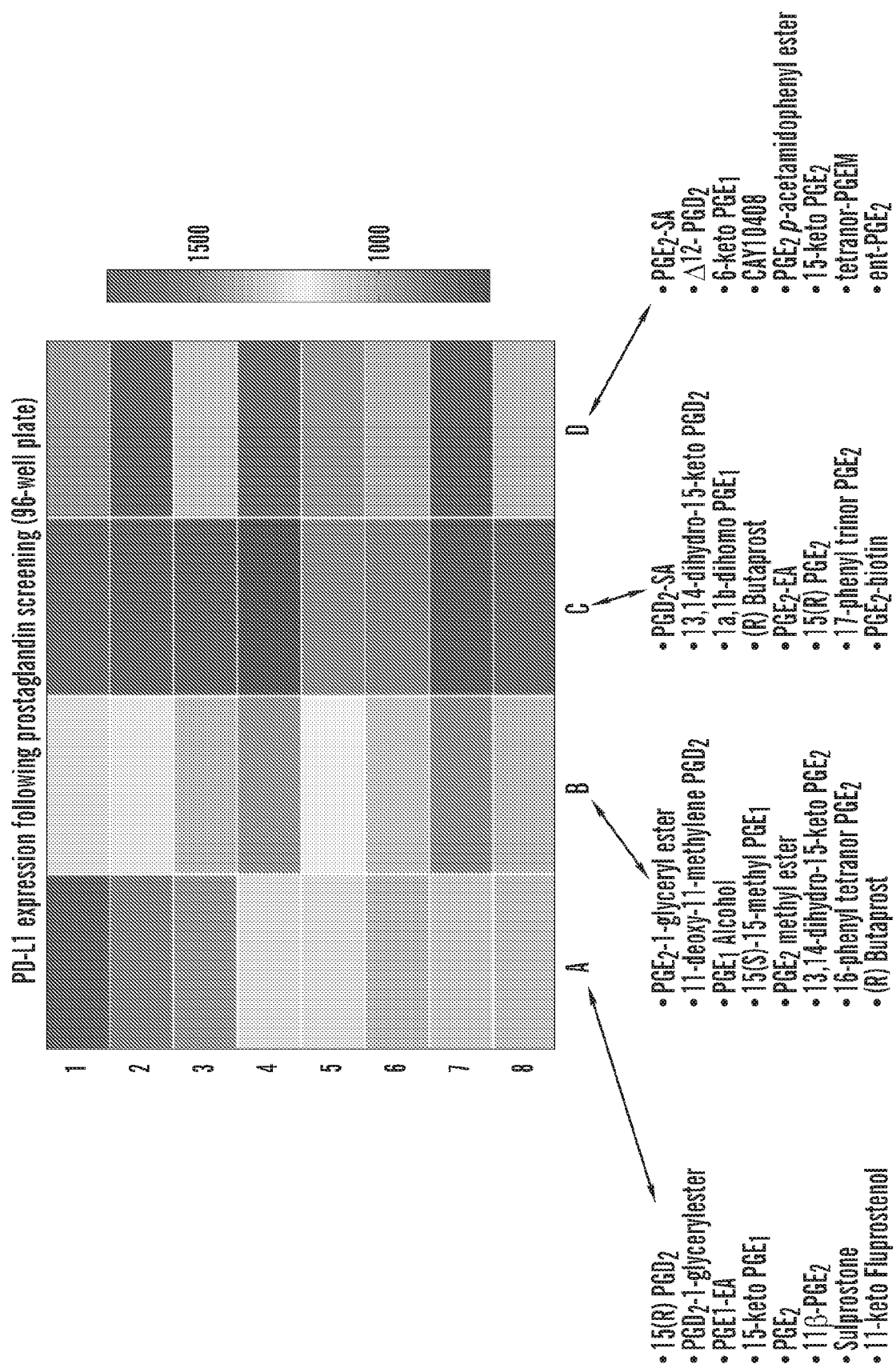
Figure 17B:
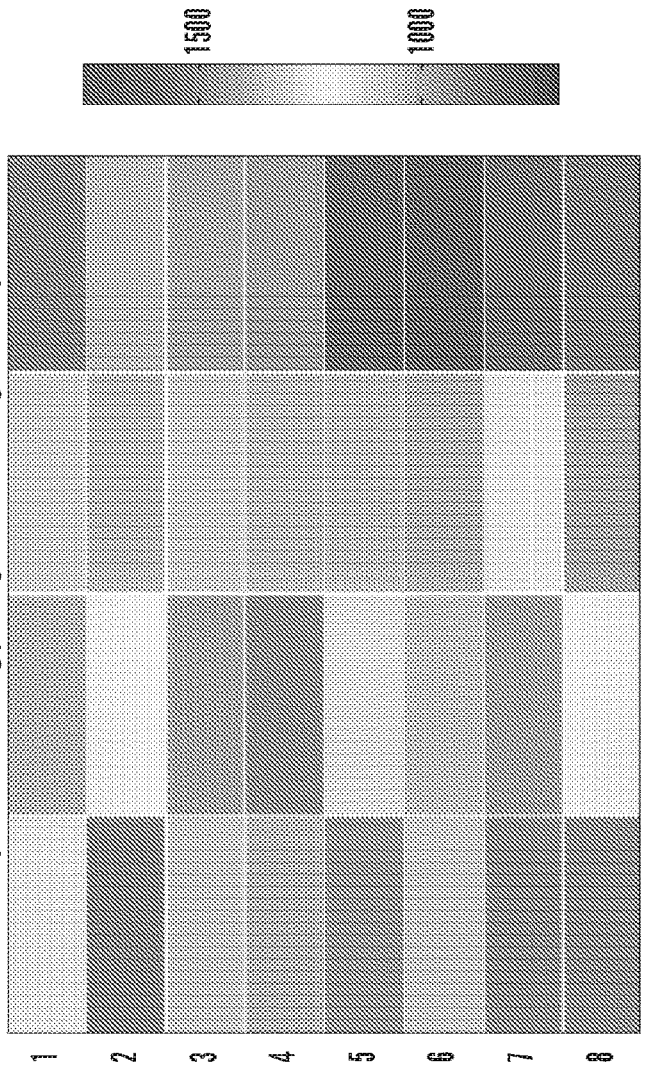
Figure 17C:
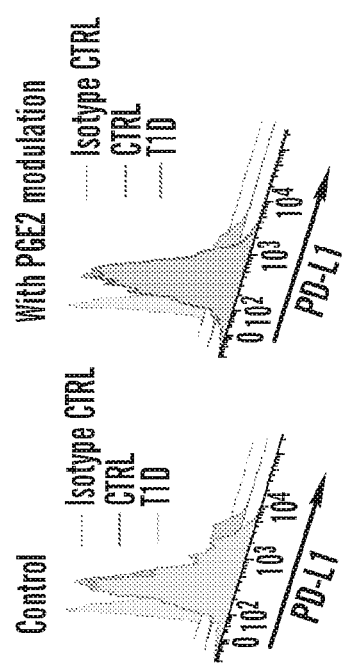
Figure 17E:
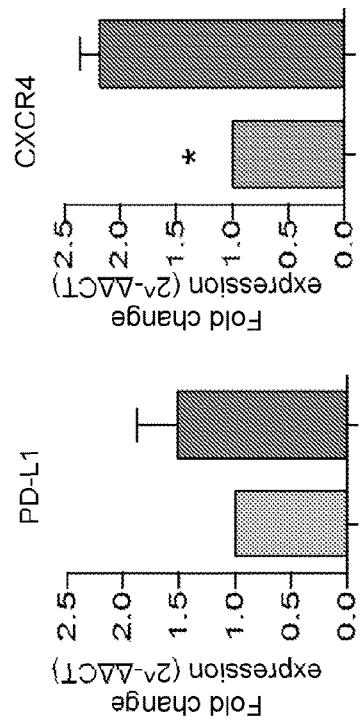
Figure 17G:
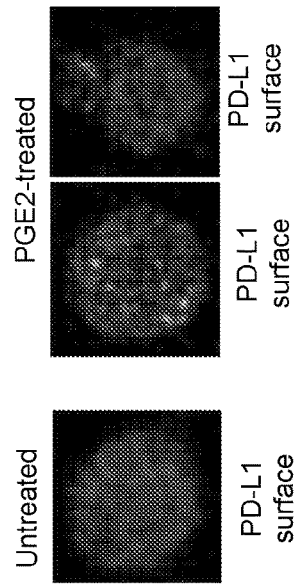
Figure 17D:
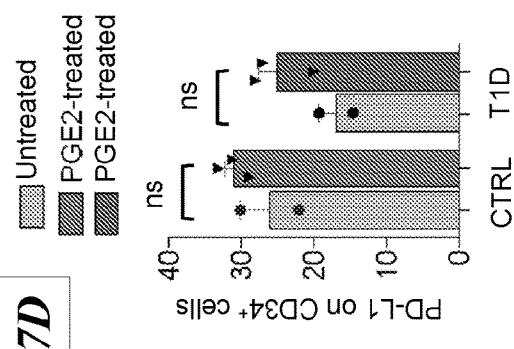
Figure 17F:
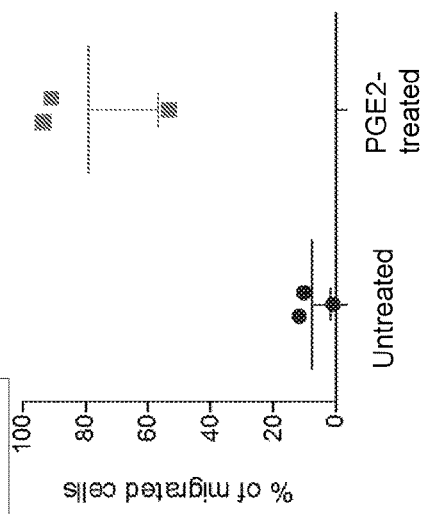
Figure 17J:
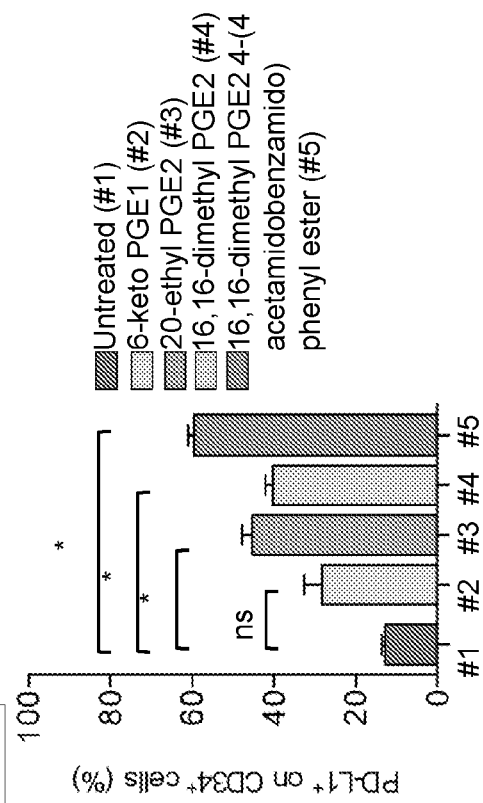
Figure 17H:
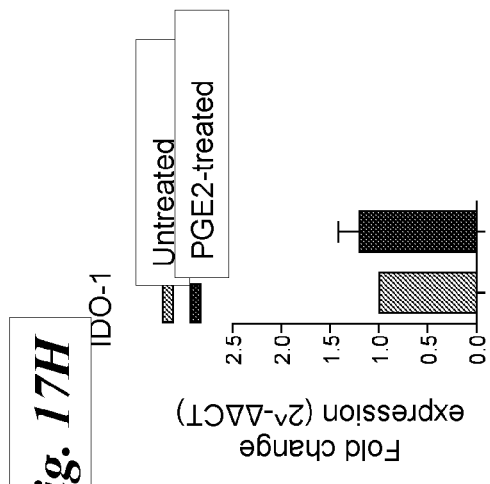
Figure 17I:
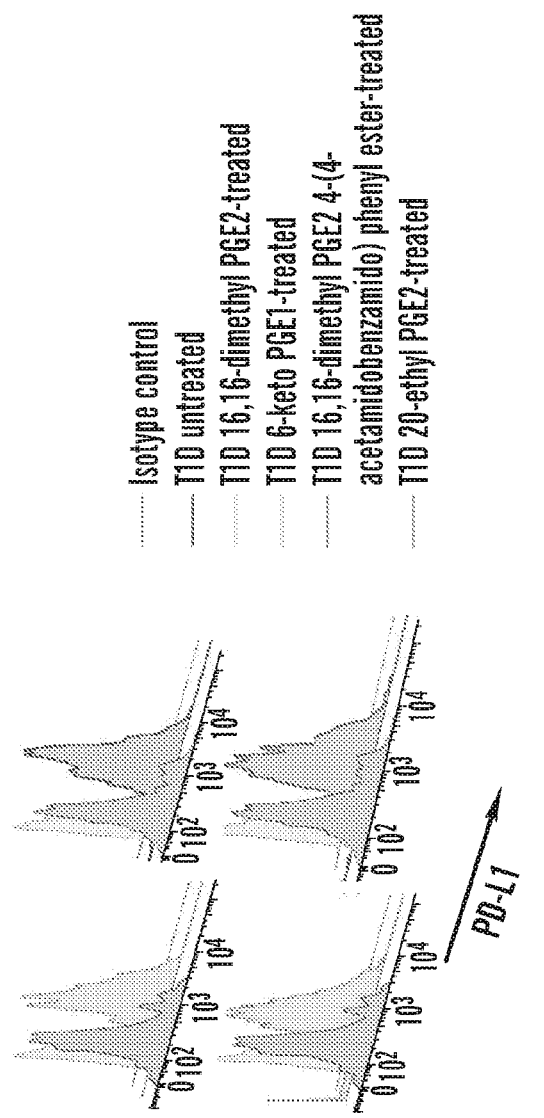

Prostaglandin library screening. PGE2 has been described as a small molecule known to enhance the homing and engraftment of HSPCs. It was therefore sought to screen all known types of prostaglandins using the Prostaglandin Screening Library II, which contains 64 small molecules. Each small molecule contained in the library was first screened for its capacity to upregulate PD-L1 in human CD34+ cells isolated from T1D patients (FIG. 17A-17B). CD34+ cells isolated from T1D patients were cultured in StemSpan SFEMII and pulsed with each PG (prostaglandin) small molecule contained in the aforementioned library at a concentration of 10 μM at 24 and 48h. Using FACS analysis, the MFI (mean fluorescence intensity) of PD-L1 expression was calculated following treatment with each small molecule used to modulate CD34+ cells as compared to untreated/unmodulated CD34+ cells (FIG. 17B). A heat map was generated depicting the degree to which each PG small molecule affected PD-L1 expression on CD34+ cells (FIG. 17B), thus allowing for the evaluation of PG candidates. Based on its ability to modulate PD-L1 expression, PGE2 was selected as a candidate for further study; in addition, PGE2 has been described in the literature and has been tested in clinical trials as a potential therapy for enhancing HSPC engraftment following cord blood transplantation (21). Isolated CD34+ cells from healthy control patients (CTRL) and from T1D patients were cultured in StemSpan SFEMII and pulsed with 10 μM of PGE2 at 24 hours and 48 hours. The effect of pharmacological modulation was first tested with PGE2 by FACS analysis, and the data revealed a slight increase in PD-L1 expression, although not significant, in cultured CD34+ cells from T1D and healthy control patients, with the latter showing a higher percentage of PD-L1 expression as compared to cells from T1D patients (FIG. 17C-17D). This pattern was further confirmed by confocal imaging, in which PD-L1 surface expression was upregulated in PGE2-treated CD34+ cells as compared to untreated (FIG. 17G). Similar results were obtained by RT-PCR, which demonstrated a slight increase (although not significant) in PD-L1 expression in CD34+ cells upon modulation with PGE2 (FIG. 17E). Notably, RT-PCR showed a 2-fold increase of CXCR4 gene expression, a protein required for the homing of HSPCs, in PGE2-treated CD34+ cells as compared to untreated (FIG. 17E). It was therefore sought to perform a migration assay in order to assess the homing properties of PGE2-treated CD34+ cells (FIG. 17F). The data confirmed a substantial increase in the homing potential of PGE2-treated CD34+ cells (FIG. 17F). The expression of another relevant immunoregulatory protein, IDO-1, remained unchanged post-pharmacologic modulation with PGE2 (FIG. 17H). The 4 PG small molecules (16,16-dimethyl PGE2, 16,16-dimethyl PGE2 4-[4-acetamidobenzamido] phenyl ester, 6-keto PGE1 and 20-ethyl PGE2) that showed the strongest capacity to upregulate PD-L1 were next selected based on the results obtained from library screening (FIG. 17I-17J). By a PGE2-analog and two competitive inhibitors of 15-hydroxy PG dehydrogenase (PGDH), which possess a prolonged half-life in vivo (16,16-dimethyl PGE2, 16,16-dimethyl PGE2 4-(4-acetamidobenzamido) phenyl ester and 20-ethyl PGE2). FACS analysis of PD-L1 protein expression following pharmacologic modulation with these 4 PGs (FIG. 17I-17J) demonstrated robust upregulation of PD-L1 expression. These results were further confirmed by RT-PCR, which showed a marked upregulation of PD-L1 mRNA following pharmacological modulation with 16,16-dimethyl PGE2, 16,16-dimethyl PGE2 4-(4-acetamidobenzamido) phenyl ester and 20-ethyl PGE2 (data not shown).

Figure 18A:
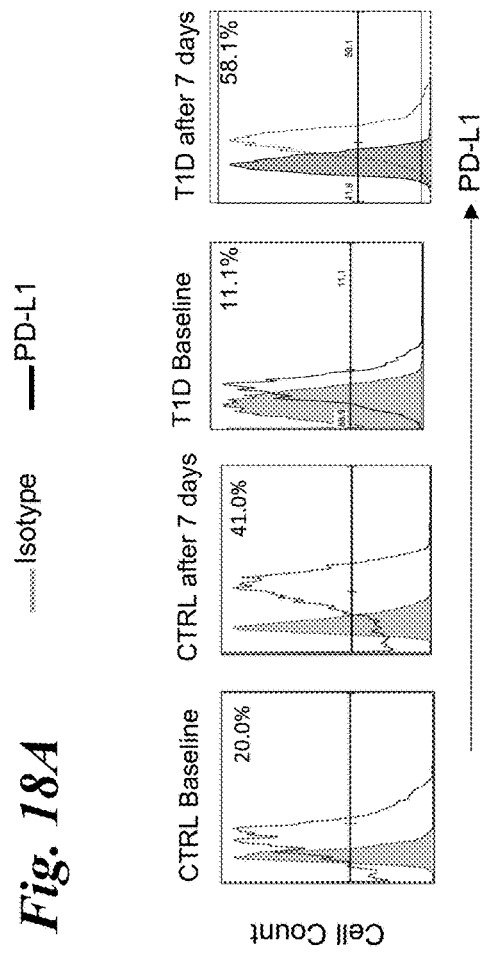
Figure 18C:
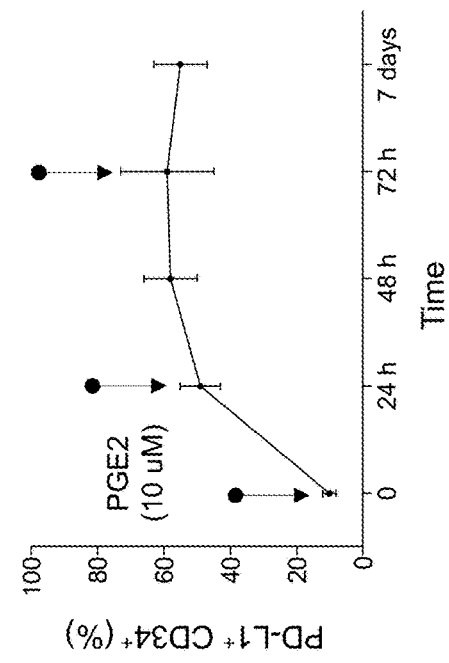
Figure 18B:
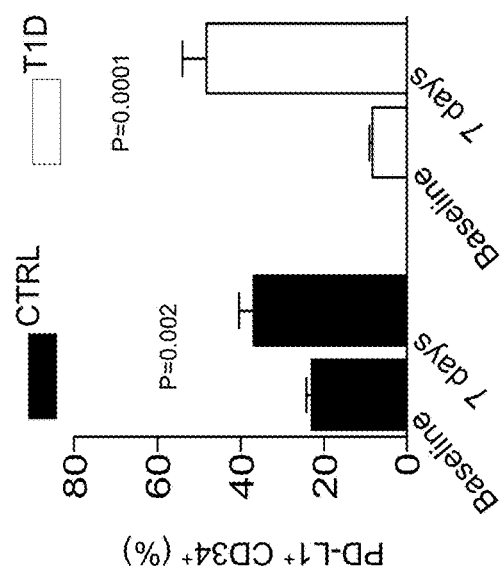

PGE2 highly augments PD-L1 expression in human HSPCs when supplemented with hematopoietic cytokine. In order to improve the strategy used for HSPC expansion and to enhance the function of PGE2-modulated HSPC, hematopoietic cytokines (SCF, TPO, FGF-1, IGFBP-2 and Angptl-3 proteins) known as a potent cocktail for HSPC maintenance, were added into the established culture conditions (22). Isolated CD34+ cells (HSPCs) obtained from T1D patients and from healthy controls were cultured using StemSpan SFEMII supplemented with the aforementioned human stem cell growth factors (STFIA medium) and pulsed with PGE2 (10 μM) at 24 hours, 96 hours and at 7 days at 37° C. 5% CO2. PD-L1+ HSPCs were then quantified by FACS analysis at different time points post-culture. After 7 days, a ~5-fold increase in the percentage of PD-L1+CD34+ cells were evident in human HSPCs obtained from T1D, with a similar albeit much less pronounced increase in the percentage of PD-L1+CD34+ cells obtained from healthy control patients (~2-fold increase) (FIG. 18A-18E). It was next determined whether freezing/cryopreservation has any effect on PD-L1 expression, by comparing freshly isolated HSPCs with frozen HSPCs, after 7 days of culture using STFIA media pulsed with PGE2 (FIG. 18F-18G). Sustained and conserved PD-L1 expression was observed pre- and post-cryopreservation, indicating that storage of HSPCs has no detrimental impact on their ex vivo expansion.

PGE2-modulated human HSPCs abrogate the autoimmune response ex vivo. To study the ex vivo immunoregulatory effects of PGE2 modulation as well as whether cytokine treatment enhances these effects, an autoimmune assay was performed using unmodulated CD34+ cells, PGE2-modulated CD34+ cells, or PGE2-modulated HSPCs cultured for 7 days in STFIA medium. CD34-depleted PBMCs were co-cultured with control CD34+ cells (unmodulated), PGE2-modulated CD34+ cells or STFIA medium-cultured PGE2-modulated human CD34+ cells in the presence of insulin-associated autoantigen-2 (I-A2) peptide at different cell ratios (1:2; 1:8 and 1:32 CD34+ cells to PBMCs), and the number of IFN-γ-producing cells was quantified using an ELISPOT assay (FIG. 18H-18I). Interestingly, addition of PGE2-modulated human CD34+ cells resulted in a significant decrease in the number of IFN-γ-producing cells (FIG. 18H), indicating that PGE2-modulated CD34+ cells are endowed with immunoregulatory activity ex vivo. Addition of PGE2-modulated CD34+ cells cultured for 7 days in STFIA medium showed a further abrogation of the autoimmune response, and this effect was observed even when cells were added at a very low ratio (1:32) to PBMCs (FIG. 18I). The effects of PGE2-modulated CD34+ cells cultured for 7 days in STFIA media were further confirmed in a nonautoimmune-specific anti-CD3/anti-CD28 assay (FIG. 18J).

Figure 19A:
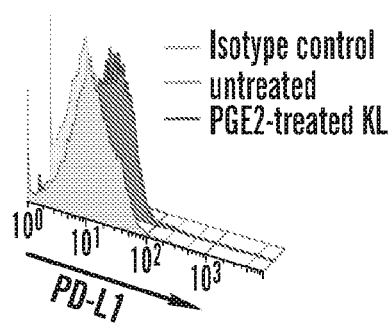
FIGS. 19A-19G show the profile of murine KL cells.
Figure 19B:
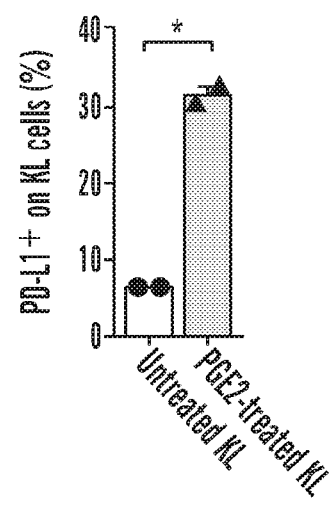
Figure 19C:
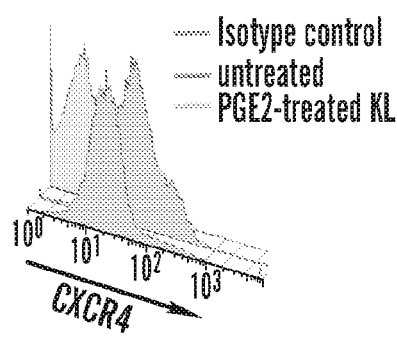
Figure 19D:
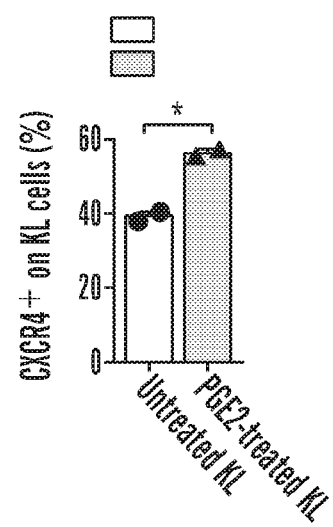
Figure 19E:
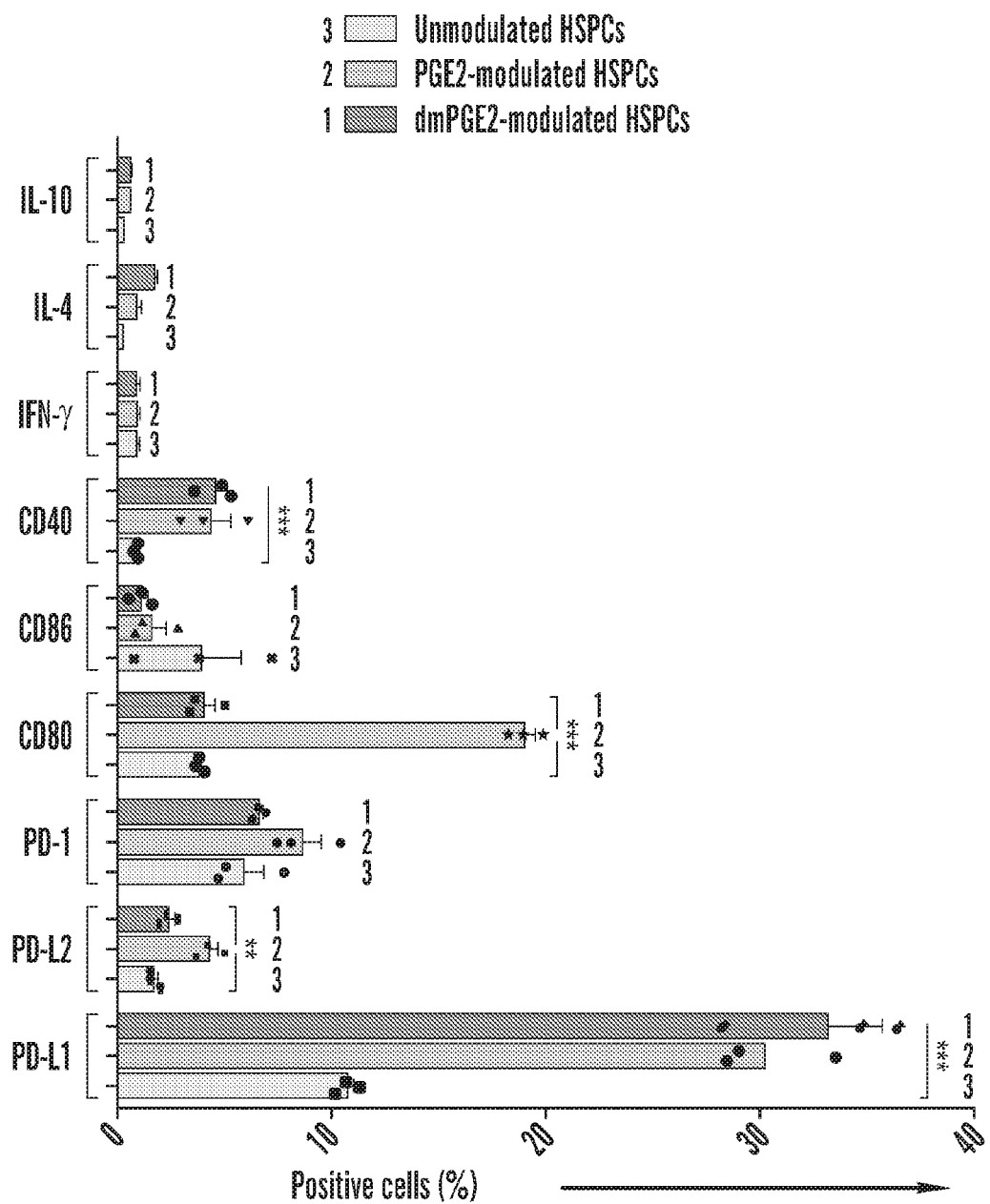
Figure 19F:
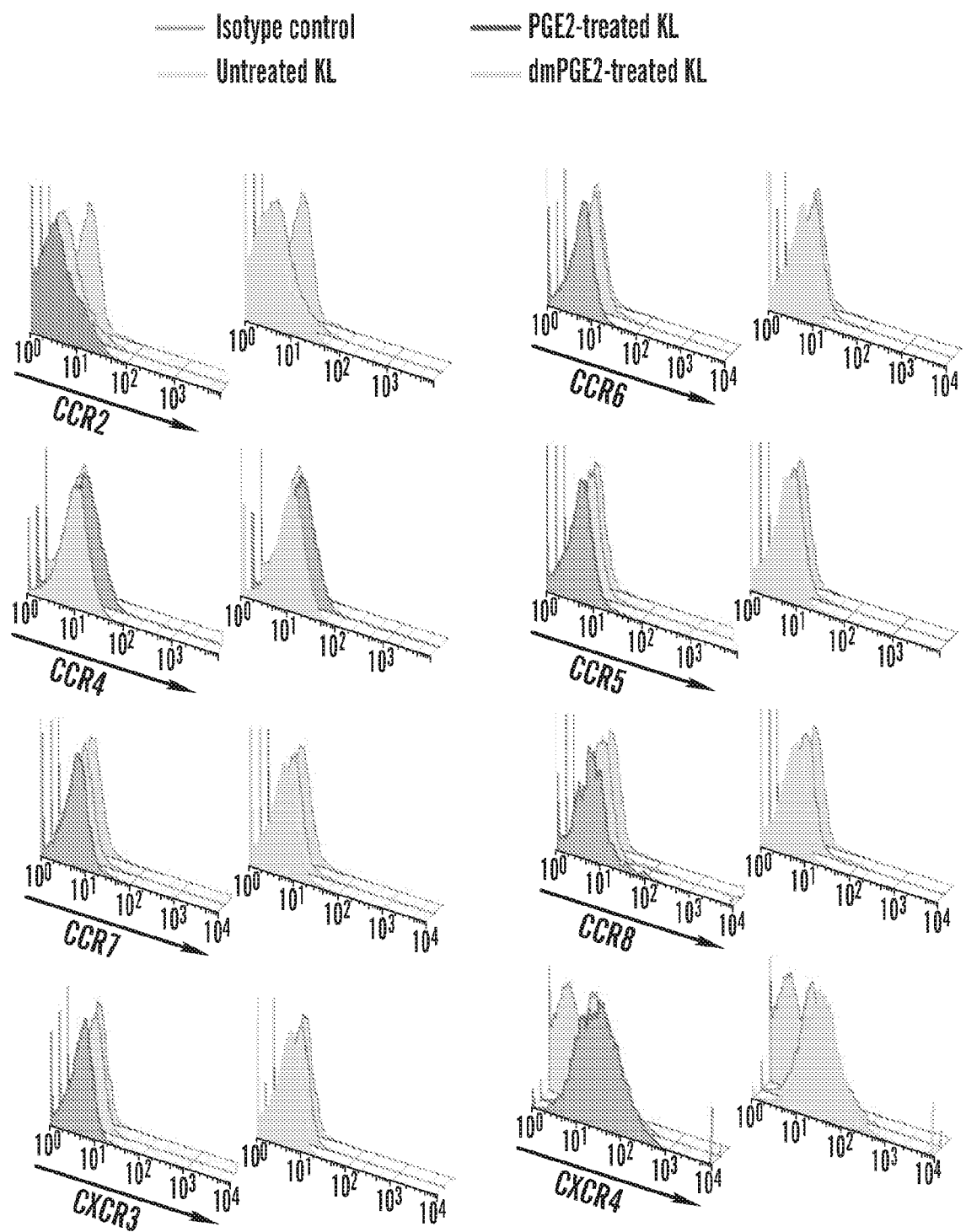
Figure 19G:
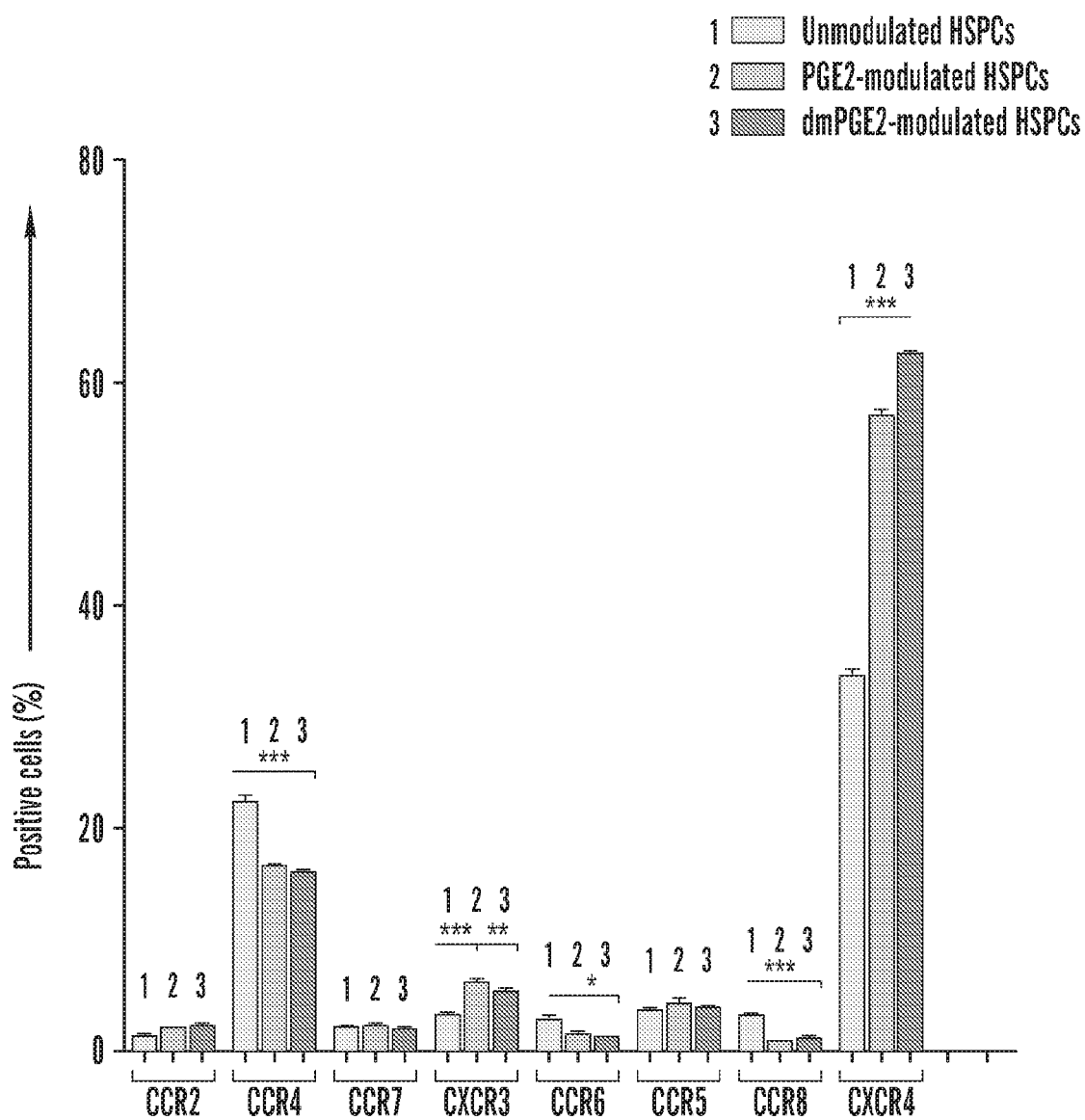

Murine PGE2-modulated HSPCs abrogate the autoimmune response in vitro. The feasibility of pharmacological modulation of PD-L1 with PGE2 was next explored in murine HSPCs. FACS analysis showed an upregulation of PD-L1 post-PGE2 modulation in KL (c-Kit+Lineage-) cells isolated from bone marrow of NOD mice (FIG. 19A-19B). Interestingly, another protein, CXCR4, primary involved in the homing of HSPCs, was markedly upregulated (FIG. 19C-19D). The expression of costimulatory molecules as well as pro-inflammatory and anti-inflammatory cytokines by flow cytometry, was then analyzed, which demonstrated upregulation of PD-L2, PD-1, CD80 and CD40 in PGE2-modulated KL cells as compared to unmodulated KL cells. The expression of these molecules in KL cells modulated with dmPGE2 (known as 16, 16-dimethyl PGE2, a molecule which exerts a prolonged effect in vivo as compared to PGE2) was similarly upregulated (FIG. 19E). Moreover, the chemokine receptor profile of PGE2-modulated KL cells as compared to dmPGE2-modulated KL cells and unmodulated KL cells was explored in order to assess which chemokines are potentially involved in the homing of PGE2-modulated and dmPGE2-modulated KL cells. Consistent with the results in FIG. 19C, CXCR4 was the most expressed chemokine in both groups of KL cells treated with PGE2 and dmPGE2 (FIG. 19F). The immunoregulatory properties of PGE2-modulated KL cells was next explored in an autoimmune setting in vitro. PGE2-modulated KL cells generated from normoglycemic NOD mice were co-cultured at ratios of 1:1, 1:5 and 1:10 (KL cells to T cells) with CD11c+ DCs and BDC2.5 transgenic CD4+CD25- T cells in the presence of BDC2.5 peptide. Quantification by flow cytometry revealed a pronounced and significant decrease in the percentage of IFN-γ+CD4+ T cells when PGE2-modulated KL cells were added to the assay as compared to when unmodulated KL cells were used (FIG. 20A-20B). Indeed, PGE2-modulated KL cells exerted a robust immunoregulatory effect even if added at low ratios (1:5 PGE2-treated KL cell to T cells). A less pronounced effect was observed when unmodulated KL were added to the assays. Interestingly, the percentage of activated CD4+CD25+ T cells declined upon coculture with KL or PGE2-modulated KL cells (FIG. 20C). PGE2-modulated HSPCs are thus endowed with immunoregulatory properties and are capable of abrogating the autoimmune response in vitro.

Adoptively transferred murine PGE2-modulated HSPCs traffic to inflamed areas. To examine the trafficking properties of GFP+PD-L1-expressing KL cells in an in vivo inflammatory setting, a set of tracking experiments was performed in NOD mice. Following infusion of GFP+KL cells extracted from the bone marrow of Luciferase NOD-GFP mice and treated with PGE2 as previously described, the pancreas and pancreatic draining lymph nodes (PLN) of NOD mice were harvested at 24 hours. GFP+ cells were quantified in the aforementioned tissues by flow cytometry and were detectable in the PLN (FIG. 20D) and in the pancreata of NOD mice (FIG. 20E). The phenotype of the GFP+ cells after adoptive transfer and after homing to the pancreata of NOD mice showed Gr-1 expression, indicative of myeloid lineage, while very few cells were CD3+(FIG. 20E). These GFP+PD-L1-expressing cells might probably interact with autoreactive CD4 and CD8 T cells.

Discussion

The prospect of successful cell therapy has recently gained greater footing in the medical landscape in the past 2 years with the arrival of many cell-based products. Recently, many AHSCT-related clinical trials have demonstrated a beneficial effect in the treatment of several autoimmune diseases, and AHSCT is now considered one of the few therapies capable of reversing T1D in humans (6, 14, 25-27). In this study described herein, preservation of β cell function following AHSCT was observed, as most patients included in the study population exhibited a sustained and adequate postprandial C-peptide response. The majority of these patients achieved and maintained peak-stimulated C-peptide levels higher than 0.6 ng/ml for at least 2 years of follow-up. Sustained C-peptide secretion is known to be associated with reduced prevalence (~30%) of hypoglycemic events and with a slower progression of diabetes complications, as reported by the DCCT Trial (28). Several patients also experienced reversal of the disease or a decrease in the exogenous insulin daily requirement. Although these are very encouraging results, many investigators have reported various complications and adverse effects associated with AHSCT in T1D patients, primarily related to the effects of immunosuppression (6). Some patients experience only temporary remission, and thus achieving prolonged remission of the disease remains the foremost goal for future clinical trials. Recently, much progress has been made with regard to the identification of small molecules and growth factors capable of both enhancing HSPC proliferation (15, 16) and further expanding the immunomodulatory subsets of HSPCs, in order to capitalize on their immunosuppressive properties. Interestingly, a screening study performed in zebrafish embryos showed that prostaglandin E2 (PGE2) enhances HSPC expansion and facilitates HSPC engraftment after bone marrow transplantation (21). Investigating and determining the effects of ex vivo modulation of HSPCs with PGE2 in an autoimmune setting may provide insight with regard to how to robustly enhance their immunoregulatory properties. The screening results performed on ~64 known prostaglandins (PGs) allowed the selection of 4 PGs, which are analogs to PGE2 and which show induce relatively high upregulation of PD-L1 expression on human CD34+ cells. It was therefore sought to test the ability of PGE2-modulated HSPCs to affect the autoimmune response in vitro. Compared to unmodulated HSPCs, HSPCs overexpressing PD-L1 successfully abrogated the human autoimmune response in vitro. Next, it was sought to explore whether refining the ex vivo culture approach by including a cocktail of potent cytokines important for HSPC maintenance and extending the length of culture to 7 days could enhance the effects observed. Importantly, this approach remarkably enhanced the immunoregulatory properties of HSPCs and induced more pronounced PD-L1 expression. This expression appeared to be stable, unaffected by the freeze/thaw process, and resulted in a potent abrogation of the autoimmune response by modulated HSPCs, even when added at a very low ratio to T cells. Paralleling the human data, these preclinical murine studies also confirmed that PGE2-modulated HSPCs similarly exhibited immunoregulatory effects, as they markedly abrogated CD4-restricted autoimmune responses in vitro. In vivo tracking studies indicated that PGE2-modulated HSPCs home to the inflamed pancreas and PLN of NOD mice, most likely due to their substantial expression of CXCR4 (9). Based on the data herein, ex vivo expansion strategies with PGE2 combined with hematopoietic cytokines could generate a novel immunoregulatory HSPC-based approach potentially useful in the treatment of autoimmune T1D, without the detrimental effect of immunosuppressive agent toxicity, which is observed with standard immunotherapy. The recent discovery that a pre-established suicide genetic system may control survival and prevent toxicity of HSPCs undergoing ex vivo expansion will implement their use in clinical settings, allowing for easier manipulation of HSPCs and for a cell therapy-based approach in immune-mediated disorders (29).

TABLE 1

Baseline demographic and clinical characteristics of patients with T1D treated with autologous non-myeloablative hematopoietic stem cell transplantation in two AHCST cohorts.
Patient characteristics

| | |
|---|---|
| Number of patients included | n = 36 |
| Age (years ± SEM) | 22.4 ± 0.9 |
| Gender (M/F) | 27/9 |
| BMI (kg/m$^2$ ± SEM) | 20.7 ± 0.5 |
| HbA1c (mmol/mol ± SEM) | 86.6 ± 6.4 |
| C-peptide (ng/mL ± SEM) | 0.73 ± 0.06 |

| Autoantibodies | (% of patients) |
|---|---|
| GAD | 86 |
| Other (IAA, IA-2A, ICA) | 17 |

| DKA or DK history | (% of patients) |
|---|---|
| No DKA/DK | 67 |
| DKA | 28 |
| DK | 5 |

Abbreviations used in Table 1. T1D, type 1 diabetes; AHSCT, autologous hematopoietic stem cell transplantation; BMI, body mass index; GAD, glutamic acid decarboxylase autoantibodies; ICA, islet cell cytoplasmic autoantibodies; IA2A, insulinoma-2-associated autoantibodies; IAA, insulin autoantibodies; DKA, diabetic ketoacidosis; DK, diabetic ketosis.

TABLE 2

Clinical characteristics of patients with T1D and of healthy controls included in the PGs library screening.

Patient characteristics

| | |
|---|---|
| Number of patients included | n = 24 |
| Age (years ± SEM) | 58.2 ± 11.6 |
| Gender (M/F) | 16/8 |
| BMI (kg/m$^2$ ± SEM) | 20.7 ± 0.5 |
| EIR (UI) | 18.3 ± 5.4 |
| Concomitant treatment | Levothyroxine (n = 8) |
| | Statin (n = 5) |

Healthy control charcateristics

| | |
|---|---|
| Number of individuals included | n = 5 |
| Age (years ± SEM) | 40.8 ± 6.4 |
| Gender (M/F) | 2/3 |

Abbreviations used in Table 2. T1D, type 1 diabetes; BMI, body mass index; EIR, exogenous insulin requirements.

Example 3

Material and Methods
In Vitro Studies
miRNA Mimic/Anti-miR Transfection.

MDA-MB-231 breast cancer cells were cultured in DMEM high glucose medium (Gibco, Thermo Fisher Scientific; Waltham, MA USA) supplemented with 10% heat-inactivated fetal calf serum (Gibco, Thermo Fisher Scientific), 100 units/ml penicillin, 100 μg/ml streptomycin, and 2 mM L-glutamine. 2×105 cells were seeded in each well of a 6-well plate and transfected with 10 pmol of the miRNA mimic or miRNA mimic negative control, or 100 pmol of the anti-miR or anti-miR negative control (all from Exiqon, Qiagen) using the Lipofectamine RNAiMAX transfection reagent (Invitrogen, Thermo Fisher Scientific) in a final culture medium volume of 2 ml, following manufacturer's instructions. Details (e.g., the targeted miRNA and nucleotide sequence) on the used miRNA mimics and anti-miRs are displayed herein in Table 12. Forty-eight hours after transfection, cells were collected from each well for RNA extraction, cell lysate preparation and FACS analysis. RNA was extracted using Direct-zol RNA miniprep plus (Zymo research, Irvine, CA, USA) and RNA quality was checked and then retro-transcribed using RETROscript® Kit (Fisher Scientific) following manufacturer's instructions. Cell lysates were obtained in RIPA buffer (50 mmol/1 Tris-HCl, pH 8.0, 1% Triton-x, 0.5% sodium deoxycholate, 0.1% SDS, 150 mmol/1 sodium chloride) with protease inhibitor cocktail (Roche).

TABLE 12

List of miRNA mimics and anti-miRs and targeted miRNAs.

| Targeting agent | Targeted miRNA | Sequence | SEQ ID NO: | Concentration |
|---|---|---|---|---|
| miRNA mimic | hsa-miR-125b-5p | UCCCUGAGACCCUAACUUGUGA | 1 | 5 nM |
| miRNA mimic | hsa-miR-511-3p | AAUGUGUAGCAAAAGACAGA | 2 | 5 nM |
| miRNA mimic | hsa-miR-99a | AACCCGUAGAUCCGAUCUUGUG | 3 | 5 nM |
| miRNA mimic | hsa-miR-744-5p | CUGUUGCCACUAACCUCAACCU | 4 | 5 nM |
| miRNA Mimic, Negative Control | — | UCACCGGGUGUAAAUCAGCUUG | 5 | 5 nM |
| Anti-miR | hsa-miR-599 | GUUUGAUAAACUGACACAAC | 6 | 50 nM |

TABLE 12-continued

List of miRNA mimics and anti-miRs and targeted miRNAs.

| Targeting agent | Targeted miRNA | Sequence | SEQ ID NO: | Concentration |
|---|---|---|---|---|
| Anti-miR | hsa-miR-206 | CACACACUUCCUUACAUUCC | 7 | 50 nM |
| Anti-miR | hsa-miR-26b-5p | CUAUCCUGAAUUACUUGA | 8 | 50 nM |
| Anti-miR, Negative Control | — | UAACACGUCUAUACGCCCA | 9 | 50 nM | qRT-PCR.

qRT-PCR for PD-L1 analysis was performed on retro-transcribed cDNA using SYBR® Green dye (Life Technologies, Thermo Fisher Scientific). Amplification was performed on a QuantStudio S6 Real Time PCR system (Thermo Fisher Scientific). To confirm a successful transfection, the mRNA level of genes known to be controlled by the targeted miRNAs were evaluated by SYBR® Green dye (Life Technologies, Thermo Fisher Scientific) according to the manufacturer's instructions. Normalized expression values were determined using the ΔΔCt method in treated as compared to negative treated samples, using GAPDH mRNA as endogenous reference. The miRNA-targeted genes tested, along with forward and reverse primer sequences used for their amplification, are listed in Table 13.

12 h with a polyclonal rabbit anti-human PD-L1 antibody (Santa Cruz Biotechnology, Dallas, TX, USA) diluted 1:200 or with a monoclonal rabbit anti-ß-tubulin antibody (Abcam, Cambridge, UK) diluted 1:10,000 in TBS-5% milk at 4° C., washed four times with TBS-0.1% Tween-20, then incubated with a peroxidase-labeled mouse anti-rabbit IgG secondary antibody diluted 1:80,000 (Sigma-Aldrich, Saint Louis, MO, USA) in TBS-5% milk for 1 h, and finally washed with TBS-0.1% Tween-20. The resulting bands were visualized using Clarity Max western ECL substrate (Bio-Rad, Hercules, CA, USA) on a Uvitec Mini HD9 (Cleaver Scientific, Rugby, Warwickshire, UK) image documentation system. Finally, for the quantification of western blot, images of PVDF membranes were analyzed by ImageJ software to quantify size and strength of protein bands.

TABLE 13

Gene IDs and qPCR primer sequences of miRNA targets used as positive controls for miRNA mimic/anti-miR transfection.

| Gene/ Targeting miRNA | Targeted gene | Primer Sequence | SEQ ID NO: |
|---|---|---|---|
| PD-L1 | — | Forward: 5'-GCAAAGTGATACACATTTGGAGGA-3' | 10 |
|  |  | Reverse: 5'-CCCCGATGAACCCCTAAACC-3' | 11 |
| hsa-miR-125b-5p | NEU1 | Forward: 5'-GCACATCCAGAGTTCCGAGT-3' | 12 |
|  |  | Reverse: 5'-CAGGGTTGCCAGGGATGAAT-3' | 13 |
| hsa-miR-99a-5p | MTOR | Forward: 5'-GGGCCATCCGGGAATTTTTG-3' | 14 |
|  |  | Reverse: 5'-TCGTGCTCTGAATTGAGGTGT-3' | 15 |
| hsa-miR-744-5p hsa-mir-599 | MYC | Forward: 5'-CGTCCTCGGATTCTCTGCTC-3' | 16 |
|  |  | Reverse: 5'-TGTTCCTCCTCAGAGTCGCT-3' | 17 |
| hsa-miR-511-3p | IGF1R | Forward: 5'-CCTGACATGCTGTTTGAACTGA-3' | 18 |
|  |  | Reverse: 5'-GCTTGTTCTCCTCGCTGTAGT-3' | 19 |
| hsa-miR-206 | VEGFA | Forward: 5'-CTTGCTGCTCTACCTCCACC-3' | 20 |
|  |  | Reverse: 5'-TGAACTTCACCACTTCGTGATG-3' | 21 |
| hsa-miR-26b-5p | RB1 | Forward: 5'-CTGAAGGAAGCAACCCTCCT-3' | 22 |
|  |  | Reverse: 5'-TCGAGTAGAAGTCATTTCTGCCA-3' | 23 |
| Endogenous reference gene | GAPDH | Forward: 5'-GTGAACCATGAGAAGTATGACAAC-3' | 24 |
|  |  | Reverse: 5'-CATGAGTCCTTCCACGATACC-3' | 25 |

Western Blot.

Protein concentration in MDA-MB-231 cell lysates was measured. Fifteen micrograms of total proteins were electrophoresed on 8-16% gradient SDS-PAGE gels and blotted onto PVDF membrane (Bio-Rad, Hercules, CA, USA). Blots were then stained with Ponceau S. Membranes were blocked fo our r 1 h in 5% non-fat dry milk in TBST (Tris [10 mmol/l], NaCl [150 mmol/l]), 0.1% Tween-20, 5% non-fat dry milk, pH 7.4 at 25° C.) and then incubated for Flow Cytometric Analysis.

Flow cytometry was performed to analyze PD-L1 surface expression on miRNA mimic-treated MDA-MB-231 cells. BV421 labelled anti-human PD-L1 (BD Biosciences) was used to stain the cells. Background staining was determined using BV421 labelled mouse IgG1, nonreactive isotype-matched control antibody with gates positioned to exclude 99% of non-reactive cells. Cells were subjected to FACS analysis and were run on a FACSCelesta™ (Becton Dickinson). Data were analyzed using FlowJo software version 8.7.3 (Treestar).

Results miRNA Targeting Decreases PD-L1 in Human Cancer Cells.

Figure 22A:
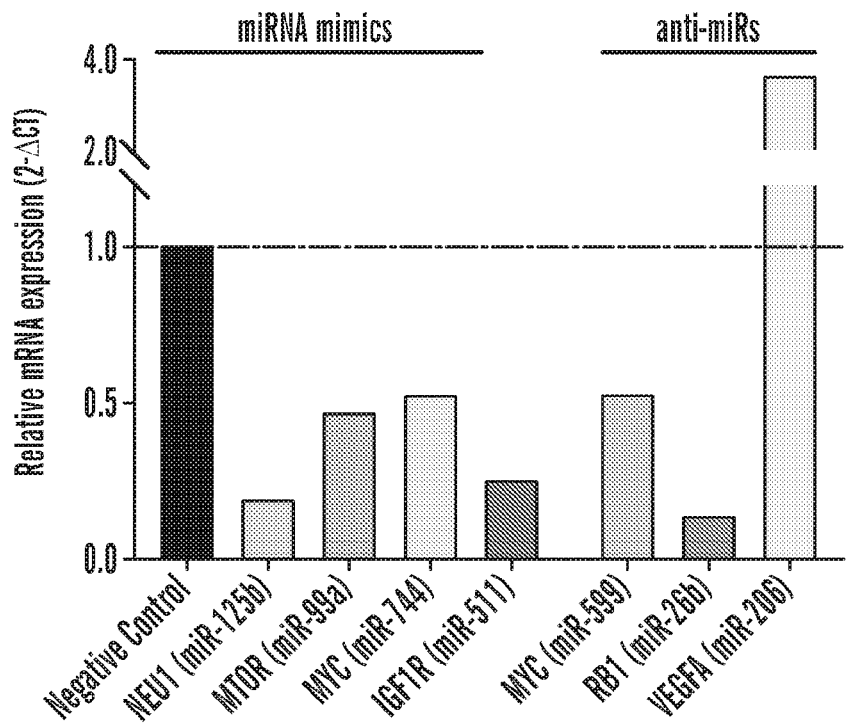
FIGS. 22A-22D show targeting miRNAs downregulates PD-L1 in human cancer MDA-MB-231 cells.
Figure 22B:
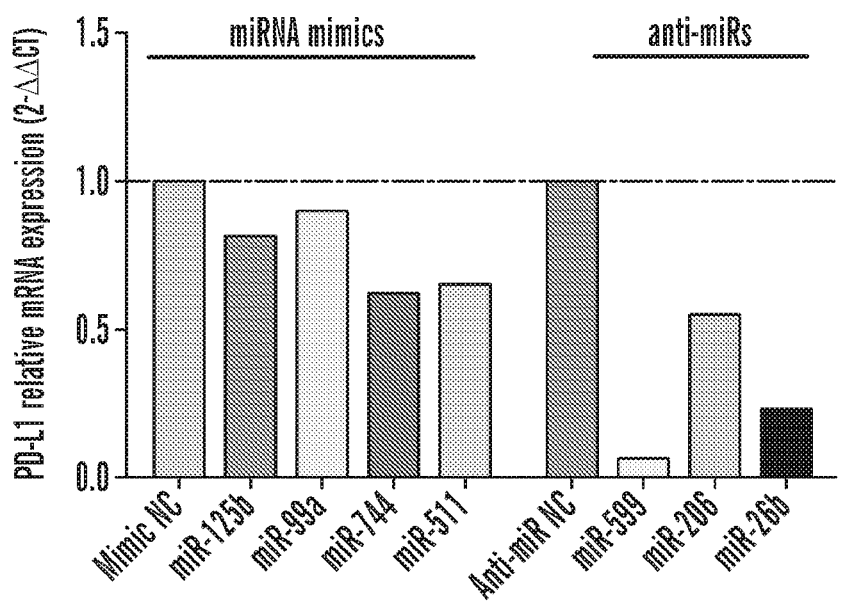
Figure 22C:
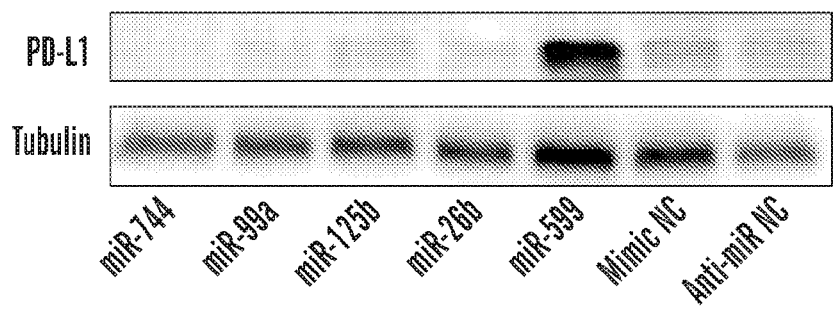
Figure 22D:
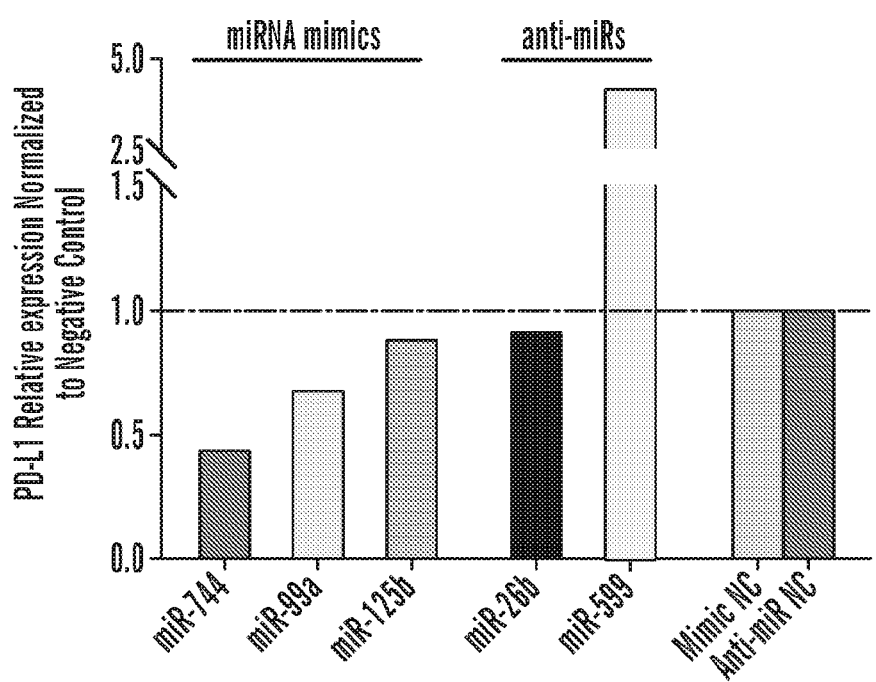
Figure 23B:
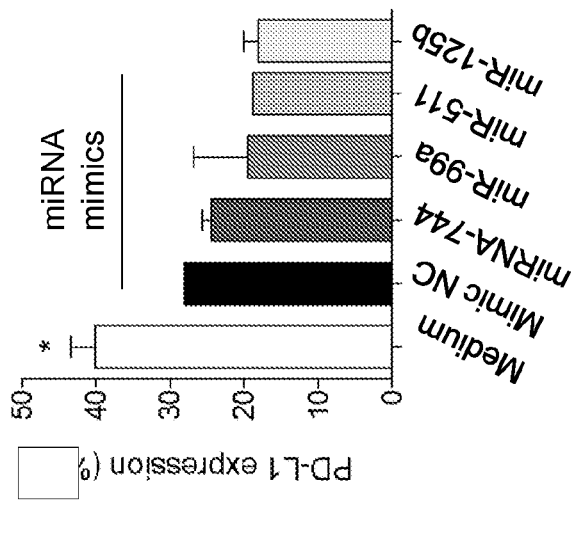
FIGS. 23A-23D show targeting miRNAs decrease the proportion of PD-L1-expressing MDA-MB-231 cells.
Figure 23A:
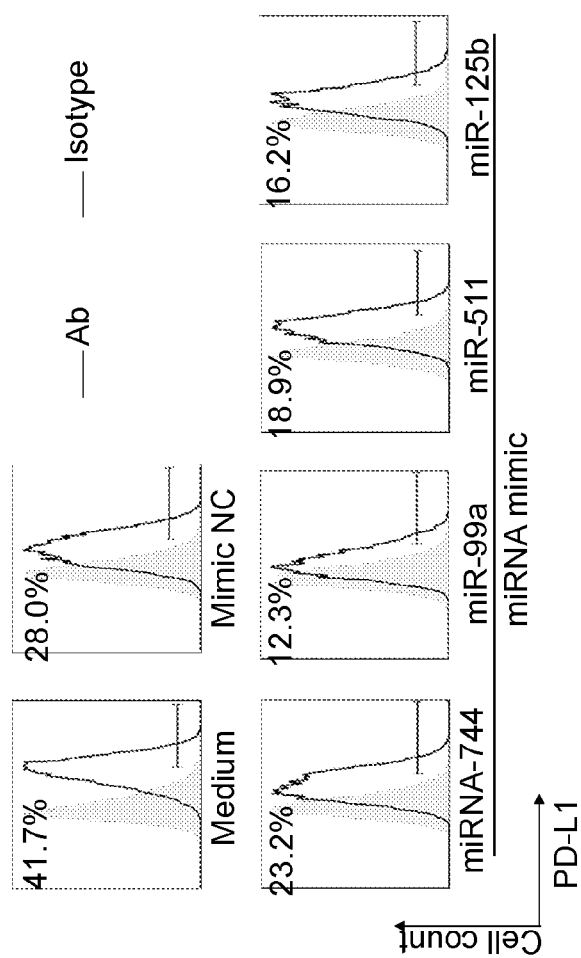
Figure 23D:
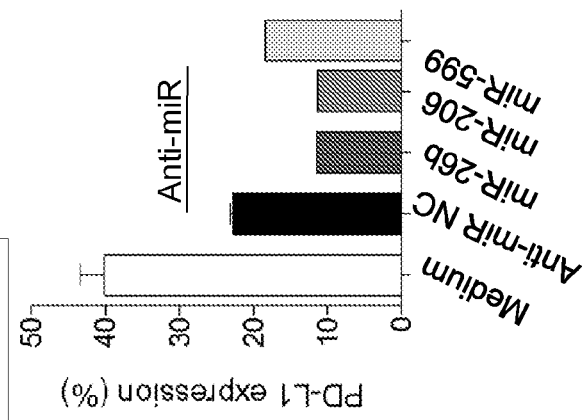
Figure 23C:
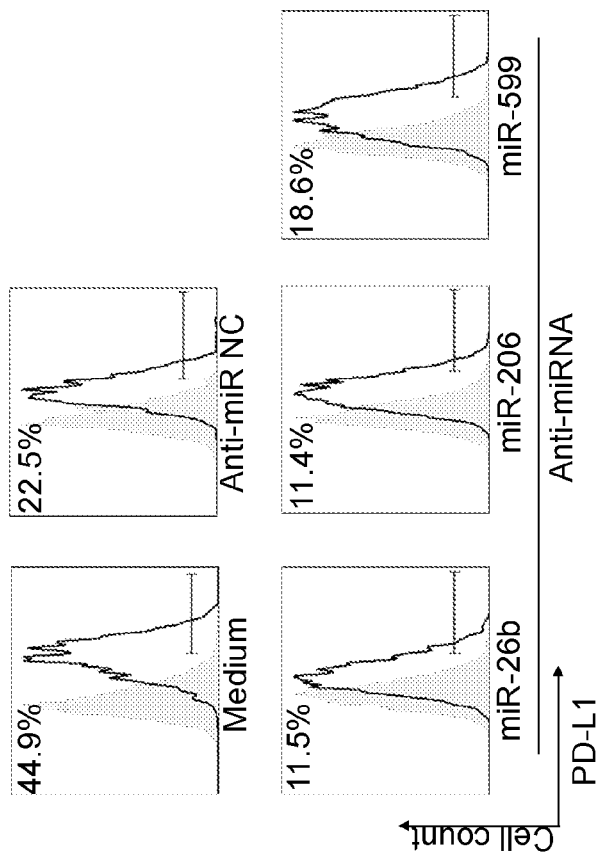

To determine if targeting the miRNA network decreases PD-L1 expression in human cancer setting, PD-L1-expressing MDA-MB-231 human breast cancer cells were transfected with a set of miRNA mimics or anti-miRs to either increase or decrease the function of a set of miRNAs not previously known to affect PD-L1 (miR-125b, miR-99a, miR-744, mir-599, miR-511, miR-206, miR-26b). The effect of treatment with miRNA mimics and anti-miRs on the percentage of PD-L1-expressing cells, as well as on PD-L1 mRNA and protein levels, was investigated. miRNA mimic/anti-miR treated-cells were compared to corresponding mimic/anti-miR negative control-treated cells by flow cytometric analysis, Real Time PCR and western blot to assess percentage of PD-L1-expressing cells, PD-L1 mRNA, and PD-L1 protein levels, respectively. A successful miRNA mimic/anti-miR transfection was confirmed by the detection of changed mRNA levels of the validated miRNA targets NEU1 (for miR-125b mimic), MTOR (for miR-99a mimic), MYC (for miR-744 mimic and miR-599 anti-miR), IGF1R (for miR-511 mimic), VEGFA (for miR-206 anti-miR) and RB1 (for miR-26b anti-miR) in treated cells (FIG. 22A). Exposure of MDA-MB-231 cells to both miRNA mimics and anti-miRs resulted in decreased levels of both PD-L1 mRNA (FIG. 22B) and protein (FIGS. 22C and 22D) as compared to the corresponding negative controls, with the only exception of miR-599 anti-miR, for which an increase of PD-L1 protein was observed. Lysates of miR-511 mimic and miR-206 anti-miR treated cells were not available for western blot analysis. Furthermore, FACS analysis showed that all the used miRNA mimics and anti-miRs induced a decreased proportion of PD-L1-expressing cells as compared to controls (FIGS. 23A-23D). Overall, these findings show that PD-L1 expression can be decreased in cancer cells by targeting miR-125b, miR-99a, miR-744, miR-511, miR-206, miR-26b, indicating that targeting the miRNA network controlling PD-L1 can be employed as a tool to regulate PD-L1 expression in cancer cells.

REFERENCES

1. F. R. Appelbaum, Haematopoietic cell transplantation as immunotherapy. Nature 411, 385-389 (2001).
2. D. Farge et al., Autologous hematopoietic stem cell transplantation for autoimmune diseases: an observational study on 12 years' experience from the European Group for Blood and Marrow Transplantation Working Party on Autoimmune Diseases. Haematologica 95, 284-292 (2010).
3. R. K. Burt et al., Clinical applications of blood-derived and marrow-derived stem cells for nonmalignant diseases. JAMA 299, 925-936 (2008).
4. F. D'Addio et al., Harnessing the immunological properties of stem cells as a therapeutic option for diabetic nephropathy. Acta Diabetol 51, 897-904 (2014).
5. P. Fiorina, J. Voltarelli, N. Zavazava, Immunological applications of stem cells in type 1 diabetes. Endocr Rev 32, 725-754 (2011).
6. F. D'Addio et al., Autologous nonmyeloablative hematopoietic stem cell transplantation in new-onset type 1 diabetes: a multicenter analysis. Diabetes 63, 3041-3046 (2014).
7. S. V. Abrahamsson et al., Non-myeloablative autologous haematopoietic stem cell transplantation expands regulatory cells and depletes IL-17 producing mucosal-associated invariant T cells in multiple sclerosis. Brain 136, 2888-2903 (2013).
8. P. Fiorina et al., Targeting the CXCR4-CXCL12 axis mobilizes autologous hematopoietic stem cells and prolongs islet allograft survival via programmed death ligand 1. J Immunol 186, 121-131 (2011).
9. M. Ben Nasr et al., PD-L1 genetic overexpression or pharmacological restoration in hematopoietic stem and progenitor cells reverses autoimmune diabetes. Sci Transl Med 9, (2017).
10. L. M. Calvi, D. C. Link, The hematopoietic stem cell niche in homeostasis and disease. Blood 126, 2443-2451 (2015).
11. R. Abdi, P. Fiorina, C. N. Adra, M. Atkinson, M. H. Sayegh, Immunomodulation by mesenchymal stem cells: a potential therapeutic strategy for type 1 diabetes. Diabetes 57, 1759-1767 (2008).
12. M. Breitbach et al., Potential risks of bone marrow cell transplantation into infarcted hearts. Blood 110, 1362-1369 (2007).
13. N. Li et al., Genetically transforming human mesenchymal stem cells to sarcomas: changes in cellular phenotype and multilineage differentiation potential. Cancer 115, 4795-4806 (2009).
14. M. Ben Nasr et al., The use of hematopoietic stem cells in autoimmune diseases. Regen Med 11, 395-405 (2016).
15. S. Wohrer et al., Distinct stromal cell factor combinations can separately control hematopoietic stem cell survival, proliferation, and self-renewal. Cell Rep 7, 1956-1967 (2014).
16. T. E. North et al., Prostaglandin E2 regulates vertebrate haematopoietic stem cell homeostasis. Nature 447, 1007-1011 (2007).
17. D. Fabricius et al., Prostaglandin E2 inhibits IFN-alpha secretion and Th1 costimulation by human plasmacytoid dendritic cells via E-prostanoid 2 and E-prostanoid 4 receptor engagement. J Immunol 184, 677-684 (2010).
18. M. Ogawa et al., The mechanism of anti-inflammatory effects of prostaglandin E2 receptor 4 activation in murine cardiac transplantation. Transplantation 87, 1645-1653 (2009).
19. K. Takayama et al., Prostaglandin E2 suppresses chemokine production in human macrophages through the EP4 receptor. J Biol Chem 277, 44147-44154 (2002).
20. A. J. Wiemer, S. Hegde, J. E. Gumperz, A. Huttenlocher, A live imaging cell motility screen identifies prostaglandin E2 as a T cell stop signal antagonist. J Immunol 187, 3663-3670 (2011).
21. C. Cutler et al., Prostaglandin-modulated umbilical cord blood hematopoietic stem cell transplantation. Blood 122, 3074-3081 (2013).
22. J. Zheng et al., Ex vivo expanded hematopoietic stem cells overcome the MHC barrier in allogeneic transplantation. Cell Stem Cell 9, 119-130 (2011).
23. F. D'Addio et al., Circulating IGF-I and IGFBP3 Levels Control Human Colonic Stem Cell Function and Are Disrupted in Diabetic Enteropathy. Cell Stem Cell 17, 486-498 (2015).
24. K. J. Livak, T. D. Schmittgen, Analysis of relative gene expression data using real-time quantitative PCR and the 2(−Delta Delta C(T)) Method. Methods 25, 402-408 (2001).

25. B. Gu et al., Clinical benefits of autologous haematopoietic stem cell transplantation in type 1 diabetes patients. Diabetes Metab, (2017).
26. L. Ye et al., Immune response after autologous hematopoietic stem cell transplantation in type 1 diabetes mellitus. Stem Cell Res Ther 8, 90 (2017).
27. K. C. Malmegrim et al., Immunological Balance Is Associated with Clinical Outcome after Autologous Hematopoietic Stem Cell Transplantation in Type 1 Diabetes. Front Immunol 8, 167 (2017).
28. M. W. Steffes, S. Sibley, M. Jackson, W. Thomas, Beta-cell function and the development of diabetes-related complications in the diabetes control and complications trial. Diabetes Care 26, 832-836 (2003).
29. N. Cieri et al., Adoptive immunotherapy with genetically modified lymphocytes in allogeneic stem cell transplantation. Immunol Rev 257, 165-180 (2014).

TABLE 3

Table 3: Transcriptomic profiling of murine KLS cells. List of differentially expressed pro-/anti-inflammatory genes identified by transcriptomic profiling in Sca-1$^+$ Lineage$^-$c-kit$^+$ (KLS) cells from NOD as compared to those obtained from C57BL/6 mice.

| Refseq | Symbol | p value |
|---|---|---|
| NM_007722 | Ackr3 | 0.112734 |
| NM_009645 | Aicda | 0.517745 |
| NM_009741 | Bcl2 | 0.453924 |
| NM_009743 | Bcl2l1 | 0.352899 |
| NM_011333 | Ccl2 | 0.032665 |
| NM_016960 | Ccl20 | 0.301623 |
| NM_009137 | Ccl22 | 0.501808 |
| NM_020279 | Ccl28 | 0.305028 |
| NM_013652 | Ccl4 | 0.00679 |
| NM_013653 | Ccl5 | 0.682931 |
| NM_009912 | Ccr1 | 0.986653 |
| NM_007721 | Ccr10 | 0.416696 |
| NM_009915 | Ccr2 | 0.052858 |
| NM_009916 | Ccr4 | 0.593762 |
| NM_009917 | Ccr5 | 0.24604 |
| NM_007719 | Ccr7 | 0.066286 |
| NM_009913 | Ccr9 | 0.005054 |
| NM_021893 | Cd274 | 0.003313 |
| NM_007778 | Csf1 | 0.142109 |
| NM_009969 | Csf2 | 0.832481 |
| NM_009971 | CsB | 0.560767 |
| NM_009843 | Ctla4 | 0.07252 |
| NM_008176 | Cxcl1 | 0.130166 |
| NM_021274 | Cxcl10 | 0.275381 |
| NM_019494 | Cxcl11 | 0.69816 |
| NM_021704 | Cxcl12 | 0.019921 |
| NM_009140 | Cxcl2 | 0.484508 |
| NM_009141 | Cxcl5 | 0.419449 |
| NM_008599 | Cxcl9 | 0.278309 |
| NM_178241 | Cxcr1 | 0.464608 |
| NM_009909 | Cxcr2 | 0.448862 |
| NM_009910 | Cxcr3 | 0.753073 |
| NM_009911 | Cxcr4 | 0.940543 |
| NM_007551 | Cxcr5 | 0.461243 |
| NM_010113 | Egf | 0.564223 |
| NM_007912 | Egfr | 0.745452 |
| NM_010177 | Fasl | 0.855735 |
| NM_054039 | Foxp3 | 0.305028 |
| NM_010259 | Gbp2b | 0.50175 |
| NM_010370 | Gzma | 0.827176 |
| NM_013542 | Gzmb | 0.208598 |
| NM_010380 | H2-D1 | 0.008824 |
| NM_001001892 | H2-K1 | 0.001135 |
| NM_010431 | Hif1a | 0.472615 |
| NM_008324 | Ido1 | 0.095082 |
| NM_008337 | Ifng | 0.347564 |
| NM_010512 | Igf1 | 0.487476 |
| NM_010548 | Il10 | 0.295336 |
| NM_008351 | Il12a | 0.011179 |

TABLE 3-continued

Table 3: Transcriptomic profiling of murine KLS cells. List of differentially expressed pro-/anti-inflammatory genes identified by transcriptomic profiling in Sca-1$^+$ Lineage$^-$c-kit$^+$ (KLS) cells from NOD as compared to those obtained from C57BL/6 mice.

| Refseq | Symbol | p value |
|---|---|---|
| NM_008352 | Il12b | 0.209679 |
| NM_008355 | Il13 | 0.152192 |
| NM_008357 | Il15 | 0.039649 |
| NM_010552 | Il17a | 0.461524 |
| NM_010554 | Il1a | 0.653187 |
| NM_008361 | Il1b | 0.479829 |
| NM_008362 | Il1rl | 0.030932 |
| NM_008366 | Il2 | 0.00208 |
| NM_016971 | Il22 | 0.247782 |
| NM_031252 | Il23a | 0.418581 |
| NM_021283 | Il4 | 0.005864 |
| NM_010558 | Il5 | 0.349687 |
| NM_031168 | Il6 | 0.187398 |
| NM_008390 | Irf1 | 0.221717 |
| NM_013598 | Kitl | 0.913051 |
| NM_010798 | Mif | 0.327861 |
| NM_010849 | Myc | 0.647938 |
| NM_010851 | Myd88 | 0.295548 |
| NM_008689 | Nfkb1 | 0.498591 |
| NM_010927 | Nos2 | 0.967604 |
| NM_008798 | Pdcd1 | 0.34361 |
| NM_011198 | Ptgs2 | 0.259837 |
| NM_009263 | Spp1 | 0.455322 |
| NM_009283 | Stat1 | 0.118395 |
| NM_011486 | Stat3 | 0.133445 |
| NM_011577 | Tgib1 | 0.910619 |
| NM_011905 | Tlr2 | 0.951419 |
| NM_126166 | Tlr3 | 0.278306 |
| NM_021297 | Tlr4 | 0.685418 |
| NM_133211 | Tlr7 | 0.016282 |
| NM_031178 | Tlr9 | 0.08124 |
| NM_013693 | Tnf | 0.056009 |
| NM_009425 | Tnfsf10 | 0.000973 |
| NM_011640 | Trp53 | 0.947607 |
| NM_009505 | Vegfa | 0.203475 |
| NM_007393 | Actb | 0.915067 |
| NM_009735 | B2m | 0.006167 |
| NM_008084 | Gapdh | 0.084597 |
| NM_010368 | Gusb | 0.315452 |
| NM_008302 | Hsp90ab1 | 0.882837 |
| SA_00106 | MGDC | 0.305028 |
| SA_00104 | RTC | 0.385845 |
| SA_00104 | RTC | 0.417732 |
| SA_00104 | RTC | 0.317356 |
| SA_00103 | PPC | 0.047277 |
| SA_00103 | PPC | 0.49981 |
| SA_00103 | PPC | 0.212719 |

TABLE 4

Genome-wide expression analysis of Tg KL cells. List of differentially expressed genes identified by genome-wide expression analysis (GWAS) performed on Tg.KL cells as compared to Mock.KL cells isolated from NOD mice (p < 0.05).

| Transcript Cluster ID | Tg | Mock | Fold Change | Gene Symbol | Description |
|---|---|---|---|---|---|
| TC1900000441.MM.1 | 14.12 | 5.77 | 327.59 | Cd274 (PD-L1) | CD274 antigen |
| TC0600000577.MM.1 | 13.41 | 5.09 | 320.41 | Gpnmb | glycoprotein (transmembrane) nmb |
| TC1200002584.MM.1 | 14.28 | 6.83 | 174.57 | LOC544905 | Ig heavy chain V region; immunoglobin heavy variable V9-3 |
| TC0900003098.MM.1 | 15.11 | 8.16 | 123.97 | Camp | cathelicidin antimicrobial peptide |
| TC0300000811.MM.1 | 17.5 | 11 | 90.29 | S100a8 | S100 calcium binding protein A8 (calgranulin A) |
| TC120000647.MM.1 | 12.62 | 6.29 | 80.58 | Ighv8-12 | Ig heavy chain V region; immunoglobin heavy variable V8-12 |
| TC0700003570.MM.1 | 10.4 | 4.54 | 57.92 | Anpep | alanyl (membrane) aminopeptidase |
| TC0900001461.MM.1 | 15.04 | 9.26 | 54.98 | Ngp | neutrophilic granule protein |
| TC1500001728.MM.1 | 13.74 | 7.97 | 54.58 | Ly6a | lymphocyte antigen 6 complex, locus A (lys6a), mRNA. |
| TC1000003214.MM.1 | 16.38 | 10.61 | 54.48 | Lilrb4 | leukocyte immunoglobulin-like receptor, subfamily B, member 4 |
| TC0400001645.MM.1 | 5.82 | 11.6 | −54.6 | Rhd | Rh blood group, D antigen |
| TSU nmapped00000051.mm.1 | 11.85 | 17.78 | −61.14 | Ahsp | alpha hemoglobin stabilizing protein |
| TC0600000664.mm.1 | 7.43 | 13.67 | −75.45 | Aqp1 | aquaporin 1 |
| TC0400003418.mm.1 | 6.47 | 13.34 | −117.38 | Ermap | erythroblast membrane-associated protein |
| TC0500003382.mm.1 | 6.2 | 13.48 | −155.47 | Cldn13 | claudin 13 |
| TC0300001667.mm.1 | 11 | 18.4 | −169.05 | Car1 | carbonic anhydrase 1 |
| TC1700000817.mm.1 | 6.47 | 14.3 | −228.24 | Rhag | Rhesus blood group-associated A glycoprotein |
| TC0300000094.MM1 | 9.67 | 17.85 | −290.12 | Gm5843 | predicted gene 5843; carbonic anhydrase 1 (car1) pseudogene |

TABLE 5

Chemokine receptors expression in different groups of KL cells. List of differentially expressed chemokine receptors in PD-L1.Tg KL cells, pharmacologically-modulated KL cells (pKL) and unmodulated-KL cells (KL-Veh) isolated from bone marrow of normoglycemic NOD mice.

| Chemokine receptors | Expression on KL-Veh (%) | Expression on pKL (%) | Expression on PD-L1 Tg.KL (%) | P value |
|---|---|---|---|---|
| CCR2 | 6.1 ± 0.1 | 5.2 ± 0.0 | 2.9 ± 0.1* | 0.02 |
| CCR4 | 1.4 ± 0.1 | 3.1 ± 0.2 | 11.6 ± 1.1* | 0.02 |
| CCR5 | 0.7 ± 0.0 | 0.0 ± 0.0 | 0.0 ± 0.0 | ns |
| CCR6 | 2.1 ± 0.3 | 8.6 ± 0.7* | 5.3 ± 0.6 | 0.02 |
| CCR7 | 2.7 ± 0.3 | 0.2 ± 0.0 | 0.7 ± 0.3 | ns |
| CCR8 | 2.0 ± 0.4 | 9.8 ± 0.4 | 2.0 ± 0.1 | ns |
| CXCR3 | 0.2 ± 0.1 | 0.0 ± 0.0 | 1.7 ± 0.8 | ns |
| CXCR4 | 41.7 ± 0.3 | 37.0 ± 2.5 | 61.6 ± 1.9* | 0.004 |
| S1PR1 | 65.4 ± 0.7 | 66.3 ± 0.8 | 64.6 ± 0.4 | ns |

Data are expressed as mean ± standard error (SEM).
*mean statistically significant vs. others.

TABLE 6

Table 6: Genome-wide expression analysis of pKL cells: up-regulated genes. List of upregulated genes identified by genome wide expression analysis (GWAS) performed on pharmacologically-modulated KL cells (pKL) as compared to vehicle-treated KL cells isolated from normoglycemic NOD mice (p < 0.05).

| Transcript Cluster ID | pKL | KL | Fold Change | ANOVA p-value | Gene Symbol |
|---|---|---|---|---|---|
| TC1800000609.mm.1 | 15.67 | 4.57 | 2202.84 | 0.033892 | F830016B08Rik |
| TC0500002755.mm.1 | 13.77 | 3.24 | 1472.96 | 0.009558 | Cxcl9 |
| TC0300003133.mm.1 | 15.32 | 5.7 | 785.65 | 0.02577 | Ifi44 |
| TC1400002869.mm.1 | 14.03 | 5.31 | 421.89 | 0.021385 | Phf11d |
| TC0500002895.mm.1 | 13.79 | 5.11 | 408.6 | 0.005609 | Gbp10 |
| TC1800000610.mm.1 | 13.45 | 4.87 | 382.79 | 0.015108 | Iigp1 |
| TC1800000607.mm.1 | 12.57 | 4.06 | 366.25 | 0.030559 | Gm5970 |
| TC1400002162.mm.1 | 14.88 | 6.45 | 344.7 | 0.007689 | Phf11b |
| TC1800000606.mm.1 | 13.01 | 4.79 | 298.3 | 0.0158 | Gm4951 |
| TC0200005290.mm.1 | 14.14 | 6 | 282.59 | 0.019226 | Zbp1 |
| TC0500003731.mm.1 | 13.87 | 5.78 | 273.4 | 0.023606 | Gbp4 |

TABLE 6-continued

Table 6: Genome-wide expression analysis of pKL cells: up-regulated genes.
List of upregulated genes identified by genome wide expression analysis (GWAS)
performed on pharmacologically-modulated KL cells (pKL) as compared to vehicle-
treated KL cells isolated from normoglycemic NOD mice (p < 0.05).

| Transcript Cluster ID | pKL | KL | Fold Change | ANOVA p-value | Gene Symbol |
|---|---|---|---|---|---|
| TC0500001240.mm.1 | 13.77 | 5.74 | 260.57 | 0.012623 | Oasl1 |
| TC0600001369.mm.1 | 16.86 | 9.07 | 221.84 | 0.026909 | Usp18 |
| TC1400001182.mm.1 | 12.78 | 5.13 | 202.12 | 0.00179 | Irg1 |
| TC1100001240.mm.1 | 12.24 | 4.76 | 178.73 | 0.011603 | |
| TC0800000659.mm.1 | 12.87 | 5.42 | 174.56 | 0.014638 | Ddx60 |
| TC1600002148.mm.1 | 12.07 | 4.68 | 167.59 | 0.028162 | Mx1 |
| TC0300001447.mm.1 | 12.98 | 5.6 | 166.73 | 0.031497 | Gbp2 |
| TC1400002161.mm.1 | 12.09 | 4.8 | 156.37 | 0.019668 | Phf11a |
| TC0500002756.mm.1 | 11.45 | 4.17 | 155.68 | 0.003655 | Cxcl10 |
| TC1800001396.mm.1 | 12.7 | 5.45 | 152.28 | 0.030824 | Gm4841 |
| TC1700002816.mm.1 | 12.05 | 4.88 | 144.54 | 0.019777 | Cfb |
| TC0500003730.mm.1 | 13.01 | 5.84 | 144.23 | 0.005339 | Gbp9 |
| TC1900001422.mm.1 | 11.51 | 4.46 | 132.76 | 0.004877 | Gm14446 |
| TC0100000744.mm.1 | 13.46 | 6.46 | 127.73 | 0.010464 | Csprs |
| TC0700004530.mm.1 | 13.15 | 6.18 | 125.77 | 0.046568 | Irf7 |
| TC1600001092.mm.1 | 12.21 | 5.35 | 115.89 | 0.020935 | Mx2 |
| TC0500003175.mm.1 | 14.31 | 7.47 | 115.12 | 0.037819 | Oas2 |
| TC0300001444.mm.1 | 12.51 | 5.69 | 113.12 | 0.007548 | Gbp2b |
| TC1100004265.mm.1 | 16.51 | 9.8 | 104.91 | 0.010256 | Igtp |
| TC0100000727.mm.1 | 15.45 | 8.76 | 103.3 | 0.013707 | Csprs |
| TC1200000225.mm.1 | 15.53 | 8.9 | 99.2 | 0.03583 | Cmpk2 |
| TC0500002896.mm.1 | 11.45 | 4.84 | 97.56 | 0.012491 | Gbp11 |
| TC0500003729.mm.1 | 11.74 | 5.27 | 88.47 | 0.025759 | Gbp8 |
| TC1100001241.mm.1 | 12.46 | 6.01 | 87.02 | 0.017125 | Slfn4 |
| TC0100003590.mm.1 | 11.67 | 5.4 | 77.1 | 0.034339 | BC094916 |
| TC1900001166.mm.1 | 10.13 | 4.01 | 69.53 | 0.04386 | |
| TC0700003946.mm.1 | 14.6 | 8.49 | 68.84 | 0.00128 | Trim30d |
| TC1000002383.mm.1 | 11.94 | 5.95 | 63.71 | 0.025344 | Gstt1 |
| TC1000001994.mm.1 | 11.77 | 5.87 | 59.87 | 0.030488 | Fam26f |
| TC0300001446.mm.1 | 12.18 | 6.29 | 59.67 | 0.012022 | Gbp3 |
| TC1700002823.mm.1 | 12.27 | 6.4 | 58.8 | 0.02762 | H2-T10 |
| TC1900001123.mm.1 | 13.1 | 7.23 | 58.21 | 0.025695 | AW112010 |
| TC1900000500.mm.1 | 13.22 | 7.36 | 58.19 | 0.047266 | Ifit2 |
| TC1100000683.mm.1 | 13.37 | 7.53 | 57.31 | 0.036366 | |
| TC1500001729.mm.1 | 12.61 | 6.81 | 55.91 | 0.043783 | Ly6c1 |
| TC0300000161.mm.1 | 11.44 | 5.74 | 51.86 | 0.042309 | Tnfsf10 |
| TC0100001574.mm.1 | 10 | 4.38 | 49.2 | 0.005685 | Fcgr4 |
| TC1900000217.mm.1 | 15.44 | 9.82 | 49.06 | 0.001199 | Ms4a4c |
| TC0100000730.mm.1 | 13.71 | 8.1 | 48.53 | 0.017127 | |
| TC0100000739.mm.1 | 13.71 | 8.1 | 48.53 | 0.017127 | |
| TC0100000748.mm.1 | 13.71 | 8.1 | 48.53 | 0.017127 | |
| TC0100000753.mm.1 | 13.71 | 8.1 | 48.53 | 0.017127 | |
| TC0100002706.mm.1 | 13.71 | 8.1 | 48.53 | 0.017127 | |
| TC0500003459.mm.1 | 13.71 | 8.1 | 48.53 | 0.017127 | |
| TC1_GL456211_random00000012.mm.1 | 13.71 | 8.1 | 48.53 | 0.017127 | |
| TC1_GL456211_random00000017.mm.1 | 13.71 | 8.1 | 48.53 | 0.017127 | |
| TC1_GL456212_random00000002.mm.1 | 13.71 | 8.1 | 48.53 | 0.017127 | |
| TC1_GL456212_random00000012.mm.1 | 13.71 | 8.1 | 48.53 | 0.017127 | |
| TC1_GL456221_random00000006.mm.1 | 13.71 | 8.1 | 48.53 | 0.017127 | |
| TC1_GL456221_random00000023.mm.1 | 13.71 | 8.1 | 48.53 | 0.017127 | |
| TC0600003503.mm.1 | 14.7 | 9.36 | 40.32 | 0.011732 | Herc6 |
| TC1100003382.mm.1 | 12.25 | 6.93 | 39.94 | 0.019584 | Slfn8 |
| TC1100003779.mm.1 | 13.06 | 7.75 | 39.72 | 0.007905 | Dhx58 |
| TC0700003947.mm.1 | 11.2 | 5.92 | 39.01 | 0.04821 | |
| TC0700003942.mm.1 | 13.05 | 7.82 | 37.6 | 0.014688 | Trim30c |
| TC0100003599.mm.1 | 13.19 | 7.97 | 37.41 | 0.035123 | Ifi202b |
| TC1100003383.mm.1 | 13.5 | 8.27 | 37.41 | 0.016144 | |
| TC0600002114.mm.1 | 14.64 | 9.5 | 35.1 | 0.03847 | Parp12 |
| TC1000001836.mm.1 | 9.09 | 3.97 | 34.81 | 0.00462 | |
| TC1100001236.mm.1 | 9.9 | 4.79 | 34.44 | 0.042429 | Slfn5 |
| TC0700003941.mm.1 | 11.07 | 5.97 | 34.32 | 0.015197 | Trim30b |
| TC1_GL456212_random00000008.mm.1 | 12.66 | 7.65 | 32.31 | 0.015784 | |
| TC0100000375.mm.1 | 14.92 | 9.92 | 31.9 | 0.00176 | Stat1 |
| TC1100003381.mm.1 | 10.8 | 5.81 | 31.89 | 0.017379 | |
| TC0100000758.mm.1 | 11.84 | 6.85 | 31.69 | 0.0269 | Gm7592 |
| TC1100002003.mm.1 | 15.08 | 10.1 | 31.45 | 0.049647 | Rnf213 |
| TC0200003630.mm.1 | 12.8 | 7.88 | 30.33 | 0.040556 | Ifih1 |
| TC1700002789.mm.1 | 13.47 | 8.56 | 30.08 | 0.028461 | H2-Q7 |
| TC0100000743.mm.1 | 11.75 | 6.85 | 29.89 | 0.019143 | Gm7609 |
| TC1200001552.mm.1 | 15.89 | 11.02 | 29.38 | 0.020888 | Rsad2 |
| TC0300001445.mm.1 | 15.83 | 11 | 28.46 | 0.012716 | Gbp7 |
| TC0500003436.mm.1 | 11.14 | 6.36 | 27.47 | 0.048814 | A630081J09Rik |

TABLE 6-continued

Table 6: Genome-wide expression analysis of pKL cells: up-regulated genes.
List of upregulated genes identified by genome wide expression analysis (GWAS)
performed on pharmacologically-modulated KL cells (pKL) as compared to vehicle-
treated KL cells isolated from normoglycemic NOD mice ($p < 0.05$).

| Transcript Cluster ID | pKL | KL | Fold Change | ANOVA p-value | Gene Symbol |
|---|---|---|---|---|---|
| TC1700002788.mm.1 | 13.31 | 8.57 | 26.72 | 0.012048 | H2-Q8 |
| TC0100002711.mm.1 | 11.32 | 6.6 | 26.48 | 0.040411 | Gm2635 |
| TC1000001596.mm.1 | 14.86 | 10.2 | 25.3 | 0.00199 | Stat2 |
| TC1700002822.mm.1 | 10.35 | 5.78 | 23.9 | 0.040511 | H2-T22 |
| TC0700004009.mm.1 | 14.63 | 10.07 | 23.5 | 0.041694 | Gm8995 |
| TC1100002641.mm.1 | 12.07 | 7.54 | 23.2 | 0.003131 | Irgm1 |
| TC0700002644.mm.1 | 9.95 | 5.46 | 22.4 | 0.041784 | Axl |
| TC0700003943.mm.1 | 13.98 | 9.51 | 22.09 | 0.02924 | Trim30a |
| TC0100003891.mm.1 | 13.67 | 9.25 | 21.46 | 0.002795 | IT1203 |
| TC1800000612.mm.1 | 9.36 | 4.94 | 21.42 | 0.021876 | BC023105 |
| TC0300002659.mm.1 | 11.72 | 7.31 | 21.28 | 0.047584 | Mov10 |
| TC0100000766.mm.1 | 14.19 | 9.79 | 21.08 | 0.017049 | Sp100 |
| TC0700004002.mm.1 | 12.92 | 8.54 | 20.72 | 0.035247 | Gvin1 |
| TC1600001556.mm.1 | 12.71 | 8.37 | 20.24 | 0.04905 | Parp14 |
| TC0100002709.mm.1 | 8.09 | 3.77 | 19.99 | 0.036287 | |
| TC0900003335.mm.1 | 13.51 | 9.19 | 19.89 | 0.007649 | Uba7 |
| TC0100003595.mm.1 | 13.21 | 8.94 | 19.25 | 0.035899 | Gm16340 |
| TC0500001349.mm.1 | 11.47 | 7.21 | 19.14 | 0.041335 | Oas1b |
| TC0200001222.mm.1 | 13.04 | 8.84 | 18.48 | 0.024467 | Ube2l6 |
| TC1100003380.mm.1 | 9 | 4.83 | 17.96 | 0.030712 | Mir7679 |
| TC0700003996.mm.1 | 12.59 | 8.43 | 17.88 | 0.016158 | Gm4070 |
| TC0400002108.mm.1 | 10.6 | 6.47 | 17.43 | 0.035926 | AW011738 |
| TC0600003231.mm.1 | 8.16 | 4.09 | 16.87 | 0.002582 | Klrk1 |
| TC0100000760.mm.1 | 8.29 | 4.31 | 15.78 | 0.017207 | |
| TC1700000621.mm.1 | 12.25 | 8.32 | 15.29 | 0.001634 | Tap1 |
| TC0800001109.mm.1 | 8.93 | 5 | 15.21 | 0.041757 | |
| TC0100003890.mm.1 | 13.91 | 10.04 | 14.62 | 0.013585 | Mnda1 |
| TC0100001634.mm.1 | 7.98 | 4.11 | 14.58 | 0.010466 | Pydc3 |
| TC0500002757.mm.1 | 7.56 | 3.78 | 13.67 | 0.049141 | Cxcl11 |
| TC0500002843.mm.1 | 11.18 | 7.46 | 13.18 | 0.047259 | Hpse |
| TC1_GL456211_random00000020.mm.1 | 9.74 | 6.02 | 13.16 | 0.007954 | |
| TC1_GL456221_random00000003.mm.1 | 9.74 | 6.02 | 13.16 | 0.007954 | |
| TC1_GL456221_random00000015.mm.1 | 9.74 | 6.02 | 13.16 | 0.007954 | |
| TC1900000441.mm.1 | 12.09 | 8.38 | 13.06 | 0.038552 | Cd274 |
| TC1400001087.mm.1 | 9.09 | 5.4 | 12.95 | 0.02631 | |
| TC1700002526.mm.1 | 11.31 | 7.63 | 12.87 | 0.017876 | Xdh |
| TC0700004003.mm.1 | 10.8 | 7.15 | 12.54 | 0.022983 | RP24-196H4.1 |
| TC0700001520.mm.1 | 10.7 | 7.05 | 12.49 | 0.008379 | Trim34b |
| TC1600002101.mm.1 | 7.75 | 4.13 | 12.27 | 0.007698 | |
| TC1100004292.mm.1 | 10.63 | 7.01 | 12.26 | 0.047885 | 9930111J21Rik1 |
| TC1100002648.mm.1 | 10.38 | 6.76 | 12.25 | 0.034066 | 9930111J21Rik2 |
| TC1100004266.mm.1 | 9.16 | 5.56 | 12.14 | 0.013088 | Irgm2 |
| TC0700003850.mm.1 | 9.8 | 6.21 | 12.07 | 0.013493 | Il18bp |
| TC0400000464.mm.1 | 10.61 | 7.05 | 11.78 | 0.012918 | Melk |
| TC1_100000496.mm.1 | 9.4 | 5.86 | 11.61 | 0.010226 | Ifi47 |
| TC1_GL456211_random00000003.mm.1 | 9.71 | 6.18 | 11.54 | 0.027189 | |
| TC0100002718.mm.1 | 13.51 | 9.98 | 11.51 | 0.03166 | Gm7281 |
| TC0_100000736.mm.1 | 9.6 | 6.08 | 11.5 | 0.047915 | Gm10553 |
| TC1000001989.mm.1 | 12.08 | 8.56 | 11.42 | 0.00509 | |
| TC1600001580.mm.1 | 10.86 | 7.38 | 11.17 | 0.015284 | Cd86 |
| TC0600001481.mm.1 | 9.7 | 6.23 | 11.14 | 0.046489 | Parp11 |
| TC1400002120.mm.1 | 12.38 | 8.91 | 11.07 | 0.006457 | Gzmb |
| TC1_GL456210_random00000003.mm.1 | 16.02 | 12.57 | 10.95 | 0.020413 | |
| TC1_100003314.mm.1 | 16.29 | 12.84 | 10.93 | 0.010389 | Lgals9 |
| TC0100000735.mm.1 | 16.35 | 12.91 | 10.89 | 0.017303 | Gm2389 |
| TC0700003998.mm.1 | 10.55 | 7.11 | 10.86 | 0.037839 | Gm8979 |
| TC0200005181.mm.1 | 12.11 | 8.67 | 10.86 | 0.018902 | Znfx1 |
| TC0200005013.mm.1 | 14.62 | 11.23 | 10.48 | 0.039543 | Samhd1 |
| TC1_GL456210_random00000011.mm.1 | 15.94 | 12.56 | 10.46 | 0.001016 | |
| TC0100003550.mm.1 | 8.93 | 5.56 | 10.36 | 0.046786 | Slamf7 |
| TC1600000500.mm.1 | 10.13 | 6.77 | 10.28 | 0.016439 | Parp9 |
| TC0700004007.mm.1 | 12.16 | 8.8 | 10.27 | 0.018557 | Gm21884 |
| TC0100000757.mm.1 | 13.48 | 10.15 | 10.11 | 0.039387 | Gm2427 |
| TC1100000209.mm.1 | 11.2 | 7.87 | 10.03 | 0.003163 | |
| TC1400002870.mm.1 | 11.33 | 8.03 | 9.87 | 0.014639 | Setdb2 |
| TC1900000246.mm.1 | 11.08 | 7.78 | 9.85 | 0.030917 | Mpeg1 |
| TC0200003528.mm.1 | 11.01 | 7.74 | 9.62 | 0.024083 | Nmi |
| TC0100000765.mm.1 | 13.56 | 10.3 | 9.6 | 0.02966 | Sp140 |
| TC0700001116.mm.1 | 11.34 | 8.11 | 9.37 | 0.040369 | Isg20 |
| TC1700001902.mm.1 | 10.92 | 7.72 | 9.2 | 0.009689 | Psmb9 |
| TC0500003083.mm.1 | 8.17 | 4.97 | 9.13 | 0.025155 | Gm13822 |
| TC0200003234.mm.1 | 12.35 | 9.21 | 8.86 | 0.023196 | Gfi1b |

TABLE 6-continued

Table 6: Genome-wide expression analysis of pKL cells: up-regulated genes. List of upregulated genes identified by genome wide expression analysis (GWAS) performed on pharmacologically-modulated KL cells (pKL) as compared to vehicle-treated KL cells isolated from normoglycemic NOD mice ($p < 0.05$).

| Transcript Cluster ID | pKL | KL | Fold Change | ANOVA p-value | Gene Symbol |
|---|---|---|---|---|---|
| TC0700003948.mm.1 | 11.54 | 8.39 | 8.85 | 0.018418 | Gm16464 |
| TC1700000684.mm.1 | 10.36 | 7.24 | 8.69 | 0.011494 | H2-Q4 |
| TC1700002778.mm.1 | 12.14 | 9.03 | 8.66 | 0.038873 | Tapbp |
| TC1100000206.mm.1 | 8.71 | 5.65 | 8.33 | 0.031788 | 2610024D14Rik |
| TC1000001347.mm.1 | 8.21 | 5.17 | 8.22 | 0.013768 | 4933412E12Rik |
| TC0700003945.mm.1 | 8.67 | 5.64 | 8.19 | 0.005147 | |
| TC0100003320.mm.1 | 11.45 | 8.43 | 8.12 | 0.036118 | Tor3a |
| TC1900000502.mm.1 | 7.26 | 4.24 | 8.09 | 0.008644 | I830012O16Rik |
| TC0100000742.mm.1 | 11.89 | 8.93 | 7.81 | 0.032576 | Gm6264 |
| TC1600000936.mm.1 | 9.75 | 6.79 | 7.75 | 0.049237 | Mir155 |
| TC0700004008.mm.1 | 8.7 | 5.76 | 7.68 | 0.005904 | Gm4759 |
| TC1000001988.mm.1 | 11.92 | 8.98 | 7.66 | 0.009241 | Zufsp |
| TC1100000205.mm.1 | 10.3 | 7.37 | 7.63 | 0.045181 | Peli1 |
| TC1300001772.mm.1 | 9.68 | 6.75 | 7.6 | 0.037364 | Gm6093 |
| TC0800000817.mm.1 | 8.31 | 5.38 | 7.57 | 0.017572 | Hsh2d |
| TC0100002707.mm.1 | 11.47 | 8.57 | 7.48 | 0.011384 | C130026I21Rik |
| TC0300001667.mm.1 | 14.49 | 11.59 | 7.44 | 0.041085 | Car1 |
| TC1900001388.mm.1 | 9.57 | 6.7 | 7.3 | 0.038598 | Asah2 |
| TC1500001727.mm.1 | 8.11 | 5.26 | 7.19 | 0.005322 | Ly6i |
| TC1700001892.mm.1 | 11.66 | 8.82 | 7.19 | 0.019862 | H2-K1 |
| TC1700002820.mm.1 | 9.99 | 7.18 | 7.02 | 0.000582 | C920025E04Rik |
| TC0900000599.mm.1 | 7.43 | 4.62 | 7 | 0.02757 | Il18 |
| TC1_GL456221_random00000019.mm.1 | 8.64 | 5.85 | 6.93 | 0.040922 | Csprs |
| TC1_100003385.mm.1 | 9.36 | 6.61 | 6.73 | 0.026339 | Slfn10-ps |
| TC0800002842.mm.1 | 12.67 | 9.95 | 6.57 | 0.025686 | Psmb10 |
| TC1100001657.mm.1 | 11.54 | 8.84 | 6.52 | 0.010344 | Ifi35 |
| TC0600002342.mm.1 | 12.82 | 10.16 | 6.31 | 0.029025 | Nt5c3 |
| TC1900000219.mm.1 | 8.23 | 5.58 | 6.25 | 0.014976 | Ms4a4b |
| TC1700001993.mm.1 | 9.52 | 6.87 | 6.25 | 0.028963 | H2-T24 |
| TC0100002726.mm.1 | 9.14 | 6.52 | 6.14 | 0.044593 | Gm10552 |
| TC1700002790.mm.1 | 14.52 | 11.91 | 6.11 | 0.011267 | H2-L |
| TC1900000141.mm.1 | 9.64 | 7.03 | 6.1 | 0.013319 | Pla2g16 |
| TC0900001431.mm.1 | 10.49 | 7.91 | 6 | 0.020383 | Shisa5 |
| TC0200004599.mm.1 | 7.92 | 5.35 | 5.92 | 0.034776 | Il1a |
| TC0300001706.mm.1 | 11.08 | 8.55 | 5.76 | 0.036011 | Mir7007 |
| TC1700001890.mm.1 | 12.29 | 9.77 | 5.76 | 0.035396 | H2-K2 |
| TC1700002558.mm.1 | 12.06 | 9.54 | 5.76 | 0.037361 | Eif2ak2 |
| TC0300002506.mm.1 | 10.05 | 7.54 | 5.69 | 0.000266 | Fcgr1 |
| TC0X00002476.mm.1 | 10.39 | 7.92 | 5.57 | 0.02738 | Mtcp1 |
| TC1_GL456211_random00000010.mm.1 | 10.53 | 8.07 | 5.51 | 0.023212 | LOC100041057 |
| TC0600001536.mm.1 | 11.94 | 9.48 | 5.5 | 0.027498 | Gabarapl1 |
| TC1700002819.mm.1 | 8.98 | 6.54 | 5.42 | 0.044742 | H2-T23 |
| TC0700003993.mm.1 | 8.14 | 5.7 | 5.42 | 0.042643 | 9130208D14Rik |
| TC1700001962.mm.1 | 11.49 | 9.07 | 5.35 | 0.000925 | |
| TC0100001600.mm.1 | 10.02 | 7.65 | 5.16 | 0.011155 | Slamf1 |
| TC0200005472.mm.1 | 9.99 | 7.63 | 5.14 | 0.017924 | Eng |
| TC1_GL456210_random00000005.mm.1 | 12.18 | 9.83 | 5.08 | 0.006966 | |
| TC1_GL456211_random00000005.mm.1 | 12.18 | 9.83 | 5.08 | 0.006966 | |
| TC1_GL456211_random00000026.mm.1 | 12.18 | 9.83 | 5.08 | 0.006966 | |
| TC1_GL456221_random00000004.mm.1 | 12.18 | 9.83 | 5.08 | 0.006966 | |
| TC0600001530.mm.1 | 12.44 | 10.1 | 5.04 | 0.004085 | Clec2d |
| TC0900002389.mm.1 | 11.87 | 9.55 | 5.03 | 0.018171 | Pml |
| TC0500003460.mm.1 | 11.43 | 9.1 | 5.02 | 0.017354 | Gm15753 |
| TC1000001757.mm.1 | 8.81 | 6.49 | 5.01 | 0.027153 | |
| TC0900001339.mm.1 | 8.73 | 6.41 | 5 | 0.025804 | Tlr9 |
| TC0300001704.mm.1 | 14.26 | 11.95 | 4.97 | 0.00845 | Cpa3 |
| TC0700004515.mm.1 | 13.87 | 11.56 | 4.97 | 0.045279 | Ifitm3 |
| TC1500001489.mm.1 | 10.89 | 8.6 | 4.89 | 0.028208 | |
| TC1900001461.mm.1 | 7.99 | 5.72 | 4.83 | 0.000898 | Myof |
| TC0600001770.mm.1 | 10.29 | 8.02 | 4.81 | 0.027721 | |
| TC0100002725.mm.1 | 10.95 | 8.7 | 4.73 | 0.027147 | Sp110 |
| TC1000001830.mm.1 | 7.35 | 5.11 | 4.72 | 0.037833 | Pde7b |
| TC0200001838.mm.1 | 18.6 | 16.37 | 4.71 | 0.028402 | B2m |
| TC0100002712.mm.1 | 9.15 | 6.92 | 4.68 | 0.031925 | |
| TC0700003995.mm.1 | 8.49 | 6.27 | 4.68 | 0.02515 | |
| TC0600000065.mm.1 | 7.42 | 5.2 | 4.67 | 0.025429 | |
| TC1600000553.mm.1 | 7.82 | 5.6 | 4.64 | 0.002505 | Cd80 |
| TC0700002414.mm.1 | 10.39 | 8.18 | 4.63 | 0.038205 | Sepw1 |
| TC1300001081.mm.1 | 10.43 | 8.27 | 4.47 | 0.024993 | F2rl2 |
| TC0300000769.mm.1 | 10.79 | 8.66 | 4.37 | 0.03856 | Adar |
| TC0200002588.mm.1 | 10.96 | 8.83 | 4.36 | 0.015075 | Rnf114 |
| TC1100000850.mm.1 | 10.03 | 7.92 | 4.33 | 0.004073 | Sco1 |

TABLE 6-continued

Table 6: Genome-wide expression analysis of pKL cells: up-regulated genes.
List of upregulated genes identified by genome wide expression analysis (GWAS)
performed on pharmacologically-modulated KL cells (pKL) as compared to vehicle-
treated KL cells isolated from normoglycemic NOD mice ($p < 0.05$).

| Transcript Cluster ID | pKL | KL | Fold Change | ANOVA p-value | Gene Symbol |
|---|---|---|---|---|---|
| TC0700004001.mm.1 | 8.23 | 6.16 | 4.22 | 0.038356 | |
| TC0200004539.mm.1 | 10.22 | 8.15 | 4.19 | 0.042964 | Hdc |
| TC1900000327.mm.1 | 6.34 | 4.3 | 4.11 | 0.027442 | Trpm6 |
| TC1700000623.mm.1 | 8.94 | 6.9 | 4.11 | 0.00929 | Tap2 |
| TC0400001834.mm.1 | 8.2 | 6.18 | 4.08 | 0.015535 | Gm13086 |
| TC1000000449.mm.1 | 8.36 | 6.33 | 4.07 | 0.023957 | |
| TC0300000949.mm.1 | 14.62 | 12.62 | 4.01 | 0.049253 | Txnip |
| TC0500002623.mm.1 | 7.26 | 5.25 | 4.01 | 0.002767 | Kdr |
| TC1700001290.mm.1 | 9.49 | 7.51 | 3.95 | 0.029325 | |
| TC0500000171.mm.1 | 9.23 | 7.26 | 3.93 | 0.036859 | Fgl2 |
| TC0100003037.mm.1 | 14 | 12.03 | 3.92 | 0.040946 | Cd55 |
| TC1100002747.mm.1 | 6.21 | 4.24 | 3.91 | 0.012157 | Gm12216 |
| TC1100001386.mm.1 | 12.18 | 10.22 | 3.9 | 0.025164 | Trim25 |
| TC0300002718.mm.1 | 8.92 | 6.97 | 3.86 | 0.035023 | Csf1 |
| TC1700001578.mm.1 | 8.4 | 6.48 | 3.79 | 0.022937 | Zfp945 |
| TC1300000009.mm.1 | 8.36 | 6.44 | 3.78 | 0.015383 | Asb13 |
| TC0X00003360.mm.1 | 9.05 | 7.15 | 3.75 | 0.016777 | Tlr7 |
| TC1900000479.mm.1 | 5.99 | 4.08 | 3.75 | 0.039146 | |
| TC1600000366.mm.1 | 6.19 | 4.29 | 3.74 | 0.03604 | |
| TC0100001016.mm.1 | 10.01 | 8.12 | 3.7 | 0.013276 | Zcchc2 |
| TC0800000899.mm.1 | 8.65 | 6.77 | 3.68 | 0.042293 | Inpp4b |
| TC1700001294.mm.1 | 8.69 | 6.83 | 3.63 | 0.004013 | |
| TC1600000861.mm.1 | 12.06 | 10.21 | 3.61 | 0.040244 | Usp25 |
| TC0800001132.mm.1 | 9.63 | 7.8 | 3.56 | 0.016797 | Usb1 |
| TC0600002655.mm.1 | 13.46 | 11.63 | 3.56 | 0.04435 | |
| TC0400004170.mm.1 | 8.11 | 6.3 | 3.53 | 0.026668 | Agrn |
| TC1700001154.mm.1 | 9.78 | 7.97 | 3.51 | 0.038357 | Ehd3 |
| TC0500001563.mm.1 | 6.17 | 4.38 | 3.47 | 0.034593 | |
| TC1700001953.mm.1 | 11.06 | 9.29 | 3.42 | 0.038875 | Lst1 |
| TC0X00003014.mm.1 | 5.43 | 3.65 | 3.42 | 0.018916 | 1700008I05Rik |
| TC0600001689.mm.1 | 11.05 | 9.28 | 3.4 | 0.012891 | Cmas |
| TC0100002721.mm.1 | 6.56 | 4.81 | 3.38 | 0.036097 | Gm2666 |
| TC1300001448.mm.1 | 9.98 | 8.23 | 3.36 | 0.038657 | Lgals8 |
| TC1300000586.mm.1 | 7.66 | 5.92 | 3.35 | 0.017667 | Fbxw17 |
| TC1300000904.mm.1 | 11.84 | 10.11 | 3.33 | 0.00674 | Erap1 |
| TC1300000607.mm.1 | 8.77 | 7.04 | 3.33 | 0.035086 | Gadd45g |
| TC1300000651.mm.1 | 13.69 | 11.95 | 3.32 | 0.034161 | |
| TC0600002204.mm.1 | 7.32 | 5.59 | 3.31 | 0.026402 | |
| TC1300000364.mm.1 | 6.42 | 4.7 | 3.29 | 0.038593 | Serpinb9 |
| TC0200000222.mm.1 | 9.05 | 7.35 | 3.26 | 0.035532 | Il15ra |
| TC0600001769.mm.1 | 12.07 | 10.38 | 3.22 | 0.022163 | 2810474O19Rik |
| TC0400001149.mm.1 | 6.68 | 5.01 | 3.18 | 0.038712 | Gm12737 |
| TC0200004525.mm.1 | 6 | 4.34 | 3.15 | 0.023572 | Fbn1 |
| TC0800002728.mm.1 | 6.46 | 4.81 | 3.13 | 0.007505 | 9330175E14Rik |
| TC1900000527.mm.1 | 12.39 | 10.75 | 3.11 | 0.021719 | 5-Mar |
| TC0100001645.mm.1 | 9.75 | 8.12 | 3.11 | 0.015455 | |
| TC1100002565.mm.1 | 6.13 | 4.52 | 3.05 | 0.025796 | Mir146 |
| TC1200002083.mm.1 | 11.85 | 10.25 | 3.02 | 0.022646 | Arel1 |
| TC1000001661.mm.1 | 9.16 | 7.57 | 3.01 | 0.049749 | Tespa1 |
| TC0200002157.mm.1 | 8.58 | 7 | 2.99 | 0.032755 | Slc24a3 |
| TC1200001972.mm.1 | 7.41 | 5.84 | 2.98 | 0.021739 | Plek2 |
| TC1500001828.mm.1 | 15.86 | 14.29 | 2.96 | 0.008521 | Csf2rb2 |
| TC0200003885.mm.1 | 6.41 | 4.86 | 2.94 | 0.042931 | P2rx3 |
| TC1300002126.mm.1 | 11.22 | 9.66 | 2.94 | 0.04887 | Zcchc6 |
| TC1100001011.mm.1 | 8.68 | 7.13 | 2.93 | 0.044604 | P2rx1 |
| TC1100000286.mm.1 | 12.44 | 10.89 | 2.93 | 0.0351 | Pnpt1 |
| TC0800000026.mm.1 | 11.38 | 9.83 | 2.93 | 0.018003 | Gm16589 |
| TC1400000574.mm.1 | 15.32 | 13.77 | 2.92 | 0.012036 | Pnp |
| TC0400001296.mm.1 | 11.94 | 10.4 | 2.92 | 0.035937 | |
| TC1800000225.mm.1 | 12.66 | 11.12 | 2.92 | 0.035417 | |
| TC0200000219.mm.1 | 6.37 | 4.83 | 2.91 | 0.02699 | Gm10851 |
| TC1600002076.mm.1 | 7.72 | 6.18 | 2.91 | 0.011258 | |
| TC1400002393.mm.1 | 10.06 | 8.53 | 2.88 | 0.049086 | Gm20290 |
| TC0500000488.mm.1 | 12.32 | 10.79 | 2.88 | 0.023557 | Lap3 |
| TC0200002544.mm.1 | 7.96 | 6.44 | 2.87 | 0.005866 | Cd40 |
| TC0100003863.mm.1 | 8.73 | 7.22 | 2.85 | 0.036155 | Gm16026 |
| TC1200001367.mm.1 | 10.18 | 8.67 | 2.84 | 0.040108 | Mfsd2b |
| TC0500002530.mm.1 | 8.85 | 7.35 | 2.83 | 0.019968 | |
| TC0900000412.mm.1 | 9.25 | 7.76 | 2.82 | 0.006484 | Vwa5a |
| TC1100002310.mm.1 | 10.99 | 9.49 | 2.82 | 0.028384 | Aftph |
| TC0200002159.mm.1 | 7.68 | 6.19 | 2.81 | 0.045268 | |
| TC0900000556.mm.1 | 6.57 | 5.08 | 2.81 | 0.021967 | |

TABLE 6-continued

Table 6: Genome-wide expression analysis of pKL cells: up-regulated genes.
List of upregulated genes identified by genome wide expression analysis (GWAS)
performed on pharmacologically-modulated KL cells (pKL) as compared to vehicle-
treated KL cells isolated from normoglycemic NOD mice (p < 0.05).

| Transcript Cluster ID | pKL | KL | Fold Change | ANOVA p-value | Gene Symbol |
|---|---|---|---|---|---|
| TC0600002959.mm.1 | 8.67 | 7.19 | 2.79 | 0.001312 | |
| TC0300000491.mm.1 | 9.37 | 7.92 | 2.73 | 0.049625 | P2ry1 |
| TC1000001834.mm.1 | 5.85 | 4.4 | 2.73 | 0.020095 | |
| TC1300001173.mm.1 | 6.78 | 5.33 | 2.72 | 0.026748 | Adamts6 |
| TC0X00000888.mm.1 | 8.42 | 6.98 | 2.72 | 0.034242 | Pcyt1b |
| TC1700002774.mm.1 | 9.71 | 8.27 | 2.71 | 0.047043 | Cmtr1 |
| TC0900002305.mm.1 | 9.88 | 8.45 | 2.71 | 0.024009 | Atm |
| TC0900003285.mm.1 | 7.21 | 5.77 | 2.7 | 0.001551 | |
| TC0900002770.mm.1 | 10.5 | 9.07 | 2.68 | 0.016343 | Fam46a |
| TC0700000253.mm.1 | 10.37 | 8.94 | 2.68 | 0.032837 | |
| TC1100001256.mm.1 | 6.32 | 4.91 | 2.66 | 0.007858 | Ccl4 |
| TC1300002140.mm.1 | 7.64 | 6.23 | 2.66 | 0.045738 | 4930486L24Rik |
| TC0100001944.mm.1 | 12.05 | 10.64 | 2.66 | 0.048457 | Vcpip1 |
| TC0500000867.mm.1 | 8.03 | 6.62 | 2.66 | 0.019599 | |
| TC0900001205.mm.1 | 7.52 | 6.11 | 2.66 | 0.044051 | |
| TC1700000496.mm.1 | 15.09 | 13.68 | 2.65 | 0.004944 | Cdkn1a |
| TC0200002495.mm.1 | 6.99 | 5.58 | 2.65 | 0.011567 | |
| TC0600002778.mm.1 | 12.05 | 10.65 | 2.65 | 0.027712 | |
| TC0300002459.mm.1 | 7.9 | 6.5 | 2.63 | 0.025766 | A730011C13Rik |
| TC1_GL456211_random00000004.mm.1 | 9.92 | 8.53 | 2.62 | 0.012504 | LOC100041034 |
| TC0200001552.mm.1 | 9.31 | 7.92 | 2.62 | 0.038212 | Cd59a |
| TC1000001266.mm.1 | 12.71 | 11.32 | 2.61 | 0.024981 | Ppp1r12a |
| TC0100002575.mm.1 | 10.67 | 9.29 | 2.61 | 0.03673 | |
| TC1700001944.mm.1 | 6.34 | 4.96 | 2.59 | 0.031813 | Ly6g6f |
| TC0600000236.mm.1 | 8.43 | 7.06 | 2.59 | 0.034276 | Irf5 |
| TC0700004274.mm.1 | 8.79 | 7.42 | 2.59 | 0.025573 | Mir7058 |
| TC1400002377.mm.1 | 5.14 | 3.77 | 2.58 | 0.048682 | |
| TC0700001794.mm.1 | 5.82 | 4.46 | 2.57 | 0.024086 | Il21r |
| TC1100000211.mm.1 | 9.75 | 8.39 | 2.56 | 0.018215 | Vps54 |
| TC0100003313.mm.1 | 9.7 | 8.35 | 2.56 | 0.043727 | Torlaip1 |
| TC1400002091.mm.1 | 12.57 | 11.22 | 2.55 | 0.008749 | Psme2 |
| TC0100002840.mm.1 | 6.48 | 5.13 | 2.55 | 0.01609 | Pdcd1 |
| TC1_GL456211_random00000025.mm.1 | 5.83 | 4.48 | 2.55 | 0.025483 | |
| TC0600002425.mm.1 | 5.77 | 4.43 | 2.54 | 0.031805 | Il23r |
| TC0800000819.mm.1 | 12.8 | 11.46 | 2.52 | 0.000685 | |
| TC1700000745.mm.1 | 8.08 | 6.76 | 2.5 | 0.018503 | Trim26 |
| TC1900000899.mm.1 | 14.68 | 13.36 | 2.5 | 0.034296 | |
| TC1700001884.mm.1 | 6.39 | 5.09 | 2.46 | 0.048092 | BC051226 |
| TC1200000807.mm.1 | 7.8 | 6.5 | 2.46 | 0.001571 | |
| TC1000002385.mm.1 | 9.69 | 8.4 | 2.45 | 0.039158 | Gstt2 |
| TC0900002907.mm.1 | 6.62 | 5.34 | 2.44 | 0.008331 | 4930579K19Rik |
| TC1300000481.mm.1 | 5.27 | 3.99 | 2.43 | 0.025689 | Edn1 |
| TC1300000913.mm.1 | 9.28 | 8.01 | 2.41 | 0.015618 | |
| TC1100001219.mm.1 | 10.59 | 9.34 | 2.38 | 0.049656 | Ccl2 |
| TC0700004532.mm.1 | 5.69 | 4.44 | 2.38 | 0.044542 | Sct |
| TC0700000638.mm.1 | 5.37 | 4.13 | 2.38 | 0.042329 | |
| TC1200000616.mm.1 | 6.2 | 4.95 | 2.38 | 0.00096 | |
| TC0700004358.mm.1 | 6.03 | 4.79 | 2.37 | 0.028665 | Cox6a2 |
| TC1500000555.mm.1 | 4.96 | 3.72 | 2.37 | 0.007562 | Ly6f |
| TC0600001839.mm.1 | 11.55 | 10.31 | 2.37 | 0.014185 | Asns |
| TC1300002265.mm.1 | 10.02 | 8.78 | 2.37 | 0.038477 | |
| TC0200000130.mm.1 | 6.64 | 5.4 | 2.36 | 0.043822 | Gm22775 |
| TC0X00001912.mm.1 | 7.95 | 6.72 | 2.35 | 0.005259 | LOC100503338 |
| TC1100003460.mm.1 | 16.53 | 15.31 | 2.32 | 0.008403 | |
| TC0600000565.mm.1 | 7.36 | 6.15 | 2.31 | 0.018207 | Gimap9 |
| TC1200002127.mm.1 | 11.37 | 10.16 | 2.31 | 0.012406 | Snw1 |
| TC1000001267.mm.1 | 7.27 | 6.06 | 2.31 | 0.0038 | |
| TC1100001197.mm.1 | 7.59 | 6.39 | 2.3 | 0.000667 | Rnf135 |
| TC1100001302.mm.1 | 5.28 | 4.08 | 2.3 | 0.030762 | Tbx2 |
| TC0600002099.mm.1 | 11.42 | 10.22 | 2.3 | 0.032149 | Zc3hav1 |
| TC0500001569.mm.1 | 7.7 | 6.5 | 2.3 | 0.040885 | Wbscr27 |
| TC1200000615.mm.1 | 6.72 | 5.52 | 2.3 | 0.036392 | |
| TC1500001452.mm.1 | 7.67 | 6.47 | 2.3 | 0.013432 | |
| TC0200000006.mm.1 | 10.1 | 8.91 | 2.29 | 0.016705 | Dclre1c |
| TC0400002945.mm.1 | 7.42 | 6.24 | 2.28 | 0.000941 | Ttc39b |
| TC0200001940.mm.1 | 6.61 | 5.44 | 2.25 | 0.040691 | Zc3h6 |
| TC1400001105.mm.1 | 15.05 | 13.88 | 2.25 | 0.007915 | Elf1 |
| TC0200004545.mm.1 | 10.93 | 9.77 | 2.24 | 0.003885 | Sppl2a |
| TC0200000112.mm.1 | 6.36 | 5.2 | 2.24 | 0.031442 | Mir669g |
| TC0100003204.mm.1 | 8.23 | 7.08 | 2.23 | 0.031135 | Rgs2 |
| TC0100001356.mm.1 | 7.77 | 6.61 | 2.23 | 0.041636 | Fam129a |
| TC0400002429.mm.1 | 5.41 | 4.25 | 2.23 | 0.002153 | |

TABLE 6-continued

Table 6: Genome-wide expression analysis of pKL cells: up-regulated genes.
List of upregulated genes identified by genome wide expression analysis (GWAS)
performed on pharmacologically-modulated KL cells (pKL) as compared to vehicle-
treated KL cells isolated from normoglycemic NOD mice ($p < 0.05$).

| Transcript Cluster ID | pKL | KL | Fold Change | ANOVA p-value | Gene Symbol |
|---|---|---|---|---|---|
| TC0600001771.mm.1 | 5.5 | 4.34 | 2.23 | 0.006018 | |
| TC0900000719.mm.1 | 11.53 | 10.38 | 2.22 | 0.009584 | Ubl7 |
| TC0500002532.mm.1 | 6.94 | 5.79 | 2.22 | 0.00558 | |
| TC0X00002710.mm.1 | 6.3 | 5.16 | 2.21 | 0.028038 | Slc7a3 |
| TC0900001206.mm.1 | 11.1 | 9.95 | 2.21 | 0.00976 | |
| TC0100002194.mm.1 | 8.29 | 7.15 | 2.2 | 0.00368 | |
| TC0900002758.mm.1 | 10.66 | 9.53 | 2.2 | 0.046655 | |
| TC1700002002.mm.1 | 5.51 | 4.38 | 2.19 | 0.040245 | Gm17782 |
| TC0700004604.mm.1 | 8.28 | 7.15 | 2.19 | 0.023801 | Cttn |
| TC1800000029.mm.1 | 8.45 | 7.32 | 2.19 | 0.010248 | Zeb1 |
| TC0100000268.mm.1 | 9.09 | 7.97 | 2.18 | 0.042451 | Mrp130 |
| TC0X00000742.mm.1 | 11.29 | 10.17 | 2.17 | 0.00221 | Brcc3 |
| TC1700000719.mm.1 | 6.03 | 4.91 | 2.17 | 0.004692 | Gm6034 |
| TC1500001815.mm.1 | 5.32 | 4.21 | 2.16 | 0.033271 | Apol10b |
| TC1200002267.mm.1 | 11.99 | 10.88 | 2.16 | 0.014938 | Ddx24 |
| TC1500000641.mm.1 | 15.59 | 14.49 | 2.15 | 0.023305 | Cs12rb |
| TC1300000735.mm.1 | 7.55 | 6.44 | 2.15 | 0.023455 | Dapk1 |
| TC1400002384.mm.1 | 4.54 | 3.43 | 2.15 | 0.010404 | Mir687 |
| TC1200000942.mm.1 | 6.99 | 5.89 | 2.15 | 0.034228 | |
| TC0200003474.mm.1 | 9.14 | 8.04 | 2.15 | 0.005798 | |
| TC0300002588.mm.1 | 7.23 | 6.12 | 2.15 | 0.008456 | |
| TC1300001391.mm.1 | 8.03 | 6.93 | 2.15 | 0.026504 | |
| TC1700001293.mm.1 | 7.12 | 6.02 | 2.15 | 0.042284 | |
| TC0400002428.mm.1 | 7.87 | 6.77 | 2.14 | 0.013225 | |
| TC0800001442.mm.1 | 7.77 | 6.67 | 2.14 | 0.021125 | |
| TC1100000411.mm.1 | 11.07 | 9.98 | 2.13 | 0.018225 | Gm12139 |
| TC0600002487.mm.1 | 13.24 | 12.15 | 2.13 | 0.000812 | Vamp5 |
| TC0500003376.mm.1 | 9.17 | 8.09 | 2.12 | 0.00039 | Lat2 |
| TC0100001172.mm.1 | 13.91 | 12.82 | 2.12 | 0.020701 | Ctse |
| TC0500001777.mm.1 | 4.85 | 3.76 | 2.12 | 0.014205 | |
| TC0500000843.mm.1 | 15.41 | 14.33 | 2.11 | 0.017981 | Pf4 |
| TC1200002359.mm.1 | 10.4 | 9.31 | 2.11 | 0.033725 | Wars |
| TC0200000164.mm.1 | 6.42 | 5.35 | 2.11 | 0.027569 | Gm26156 |
| TC1600000498.mm.1 | 5.22 | 4.14 | 2.11 | 0.030253 | |
| TC0300000003.mm.1 | 5.99 | 4.91 | 2.1 | 0.03131 | |
| TC0500000994.mm.1 | 5.23 | 4.16 | 2.1 | 0.010794 | |
| TC1300001023.mm.1 | 5.91 | 4.83 | 2.1 | 0.001388 | |
| TC1100000628.mm.1 | 6.5 | 5.44 | 2.09 | 0.014181 | Gm24198 |
| TC0200005471.mm.1 | 6.81 | 5.75 | 2.09 | 0.0015 | Ak1 |
| TC1300001020.mm.1 | 8.4 | 7.34 | 2.09 | 0.011944 | Ssbp2 |
| TC0300000468.mm.1 | 8.06 | 7 | 2.09 | 0.010343 | |
| TC1500000270.mm.1 | 6.83 | 5.77 | 2.09 | 0.017331 | |
| TC0800002023.mm.1 | 9.77 | 8.72 | 2.08 | 0.045585 | Leprotl1 |
| TC0X00002685.mm.1 | 6.04 | 4.98 | 2.08 | 0.02035 | Eda2r |
| TC0400000637.mm.1 | 4.85 | 3.79 | 2.08 | 0.030688 | |
| TC1100000015.mm.1 | 7.39 | 6.34 | 2.07 | 0.00803 | Selm |
| TC1700002347.mm.1 | 7.39 | 6.34 | 2.07 | 0.014085 | Dennd1c |
| TC0900001863.mm.1 | 8.54 | 7.49 | 2.07 | 0.036296 | Keap1 |
| TC1100003161.mm.1 | 5.27 | 4.21 | 2.07 | 0.027467 | Aspa |
| TC1400000503.mm.1 | 9.59 | 8.55 | 2.06 | 0.014882 | |
| TC1100001688.mm.1 | 10.73 | 9.69 | 2.05 | 0.020977 | Gm |
| TC0200000114.mm.1 | 6.05 | 5.02 | 2.05 | 0.016774 | Mir669j |
| TC1400002392.mm.1 | 17.11 | 16.08 | 2.05 | 0.04811 | Itm2b |
| TC0800001728.mm.1 | 6.29 | 5.25 | 2.05 | 0.006067 | Grtp1 |
| TC1300002562.mm.1 | 5.37 | 4.33 | 2.05 | 0.010288 | |
| TC1000002056.mm.1 | 8.82 | 7.79 | 2.04 | 0.038519 | Cep5711 |
| TC0100001160.mm.1 | 5.8 | 4.77 | 2.04 | 0.014266 | |
| TC0300002850.mm.1 | 5.36 | 4.33 | 2.04 | 0.010207 | |
| TC1200001729.mm.1 | 4.73 | 3.71 | 2.03 | 0.021443 | Gpr33 |
| TC1800001193.mm.1 | 5.84 | 4.82 | 2.03 | 0.049228 | Hbegf |
| TC0900001909.mm.1 | 5.52 | 4.49 | 2.03 | 0.003412 | |
| TC1000000160.mm.1 | 7.59 | 6.58 | 2.02 | 0.001282 | Ahi1 |
| TC1000000989.mm.1 | 7.25 | 6.23 | 2.02 | 0.035004 | |
| TC0500001597.mm.1 | 6.65 | 5.64 | 2.01 | 0.049027 | Rasa4 |
| TC1100002242.mm.1 | 6.85 | 5.84 | 2.01 | 0.039136 | Gm12664 |
| TC0500002588.mm.1 | 7.41 | 6.4 | 2.01 | 0.024596 | |
| TC1300002159.mm.1 | 14.3 | 13.3 | 2.01 | 0.025612 | |
| TC1400002108.mm.1 | 6.2 | 5.19 | 2 | 0.033401 | Cma1 |
| TC0200001448.mm.1 | 7.03 | 6.03 | 2 | 0.024966 | Trp53i11 |
| TC0X00003314.mm.1 | 5.9 | 4.9 | 2 | 0.014412 | Mir3473a |
| TC1300000321.mm.1 | 10.26 | 9.26 | 2 | 0.044679 | Gm23729 |

TABLE 7

Table 7: Genome-wide expression analysis of pKL cells: down-regulated genes. List of downregulated genes identified by genome wide expression analysis (GWAS) performed on pharmacologically-modulated KL cells (pKL) as compared to Vehicle treated-KL cells isolated from bone marrow of normoglycemic NOD mice (p < 0.05).

| Transcript Cluster ID | pKL | KL | Fold Change | ANOVA p-value | Gene Symbol |
|---|---|---|---|---|---|
| TC1300000691.mm.1 | 7.76 | 14.79 | −130.98 | 0.029904 | Tgfbi |
| TC0200000245.mm.1 | 7.52 | 14.18 | −101.07 | 0.007806 | Mrc1 |
| TC0300002684.mm.1 | 7.6 | 13.33 | −53.03 | 0.014861 | Chil3 |
| TC0500003399.mm.1 | 6.8 | 12.25 | −43.79 | 0.007984 | Ccl24 |
| TC1100000941.mm.1 | 7.53 | 12.55 | −32.37 | 0.039087 | Mgl2 |
| TC1100001267.mm.1 | 10.88 | 15.6 | −26.38 | 0.033053 | Wfdc21 |
| TC0800002403.mm.1 | 9.58 | 13.65 | −16.71 | 0.013546 | Ifi30 |
| TC0700000275.mm.1 | 8.14 | 12.08 | −15.34 | 0.023592 | Pglyrp1 |
| TC1500000389.mm.1 | 7.53 | 11.18 | −12.52 | 0.018949 | Nov |
| TC1200001742.mm.1 | 7.41 | 10.95 | −11.6 | 0.012045 | Egln3 |
| TC0300000807.mm.1 | 7.44 | 10.97 | −11.54 | 0.028013 | S100a4 |
| TC0500002753.mm.1 | 8.65 | 12.18 | −11.51 | 0.011324 | Naaa |
| TC1100000942.mm.1 | 6.91 | 10.24 | −10.06 | 0.03963 | Clec10a |
| TC0700001793.mm.1 | 10.86 | 14.13 | −9.7 | 0.023945 | Il4ra |
| TC0700002611.mm.1 | 5.31 | 8.58 | −9.68 | 0.033875 | Cd177 |
| TC0900000598.mm.1 | 4.36 | 7.64 | −9.67 | 0.027364 | Plet1 |
| TC1000002479.mm.1 | 7.64 | 10.85 | −9.2 | 0.002719 | Prss57 |
| TC1800000050.mm.1 | 7.59 | 10.77 | −9.07 | 0.045047 | Fabp5l2 |
| TC0200004450.mm.1 | 8.56 | 11.72 | −8.96 | 0.047326 | 6330405D24Rik |
| TC0500002320.mm.1 | 7.7 | 10.81 | −8.62 | 0.033116 | Prom1 |
| TC1900001562.mm.1 | 6.58 | 9.67 | −8.49 | 0.006597 | Scd1 |
| TC0700002128.mm.1 | 9.16 | 12.11 | −7.73 | 0.000892 | Tarm1 |
| TC0200002426.mm.1 | 7.24 | 10.1 | −7.3 | 0.047526 | Lbp |
| TC0900000702.mm.1 | 13.17 | 16.02 | −7.24 | 0.048689 | Gm6166 |
| TC1700000558.mm.1 | 13.66 | 16.49 | −7.15 | 0.015241 | |
| TC1300002716.mm.1 | 4.17 | 6.99 | −7.07 | 0.026316 | |
| TC1500001580.mm.1 | 4.98 | 7.69 | −6.53 | 0.029423 | |
| TC0200000246.mm.1 | 5.64 | 8.34 | −6.49 | 0.029152 | Mir511 |
| TC0600001397.mm.1 | 6.09 | 8.76 | −6.34 | 0.018648 | Clec4a1 |
| TC1000000352.mm.1 | 7.85 | 10.51 | −6.3 | 0.015573 | |
| TC0600003220.mm.1 | 5.47 | 8.09 | −6.17 | 0.013027 | Gm15987 |
| TC1800001048.mm.1 | 9.89 | 12.51 | −6.15 | 0.047342 | B4galt6 |
| TC1900000375.mm.1 | 7.59 | 10.2 | −6.08 | 0.047738 | |
| TC0500001487.mm.1 | 5.05 | 7.64 | −6.02 | 0.032158 | Glt1d1 |
| TC0700000005.mm.1 | 6.4 | 8.99 | −6.01 | 0.014874 | Myadm |
| TC0600002965.mm.1 | 7.74 | 10.3 | −5.9 | 0.040346 | Plxnd1 |
| TC0M00000005.mm.1 | 11.53 | 14.07 | −5.8 | 0.027548 | mt-Tm |
| TSUnmapped00000176.mm.1 | 11.47 | 13.99 | −5.73 | 0.035519 | Snora73b |
| TC0700001432.mm.1 | 7.28 | 9.78 | −5.66 | 0.008242 | Pde2a |
| TC0100002413.mm.1 | 6.75 | 9.23 | −5.56 | 0.01916 | Raph1 |
| TC1100003236.mm.1 | 4.92 | 7.39 | −5.51 | 0.040352 | Fam101b |
| TC0400003669.mm.1 | 11.54 | 13.88 | −5.07 | 0.012962 | Snora73b |
| TC0700002635.mm.1 | 6.18 | 8.47 | −4.9 | 0.00224 | Ceacam1 |
| TC1900001554.mm.1 | 6.58 | 8.86 | −4.87 | 0.034279 | Gm24336 |
| TC1300001218.mm.1 | 4.61 | 6.86 | −4.75 | 0.036265 | |
| TC0X00002266.mm.1 | 7.37 | 9.57 | −4.59 | 0.045966 | Mmgt1 |
| TC1900000819.mm.1 | 7.7 | 9.87 | −4.51 | 0.018173 | Atrnl1 |
| TC0700001953.mm.1 | 5.32 | 7.48 | −4.48 | 0.009431 | |
| TC0700002636.mm.1 | 6.74 | 8.88 | −4.41 | 0.031972 | Ceacam2 |
| TC1200001323.mm.1 | 8.65 | 10.77 | −4.37 | 0.022741 | |
| TC1300002717.mm.1 | 4.95 | 7.06 | −4.31 | 0.002954 | Itga1 |
| TC1400001972.mm.1 | 16.73 | 18.83 | −4.28 | 0.021974 | Gm3601 |
| TC0100000030.mm.1 | 7.84 | 9.92 | −4.25 | 0.004376 | Gm9826 |
| TC0200002581.mm.1 | 6.43 | 8.51 | −4.25 | 0.04173 | Gm23201 |
| TC0200001959.mm.1 | 9.04 | 11.11 | −4.19 | 0.013974 | Sirpa |
| TC1500002067.mm.1 | 4.83 | 6.89 | −4.18 | 0.014017 | Cpne8 |
| TC1100003057.mm.1 | 5.64 | 7.67 | −4.07 | 0.0291 | Gm25835 |
| TC0800002027.mm.1 | 6.98 | 9 | −4.05 | 0.047665 | Gm6100 |
| TC1900001561.mm.1 | 5.15 | 7.17 | −4.05 | 0.040968 | |
| TC1200001013.mm.1 | 4.9 | 6.91 | −4.02 | 0.027239 | |
| TC0600001634.mm.1 | 5.18 | 7.17 | −4 | 0.013773 | Ptpro |
| TC1300001215.mm.1 | 4.5 | 6.49 | −3.98 | 0.011273 | |
| TC0200001960.mm.1 | 7.28 | 9.27 | −3.96 | 0.04494 | |
| TC1800000498.mm.1 | 10.27 | 12.23 | −3.92 | 0.016258 | Eno1b |
| TC0200001120.mm.1 | 11.53 | 13.5 | −3.9 | 0.010776 | Gm13669 |
| TC0900000126.mm.1 | 8.54 | 10.49 | −3.88 | 0.024277 | Slc36a4 |
| TC1500000747.mm.1 | 4.97 | 6.91 | −3.85 | 0.008532 | 3-Sep |
| TC0200003608.mm.1 | 5.28 | 7.22 | −3.83 | 0.042554 | |
| TC1200001521.mm.1 | 6.27 | 8.21 | −3.83 | 0.033233 | |
| TC1300001451.mm.1 | 6.28 | 8.2 | −3.78 | 0.029912 | Gpr137b-ps |
| TC0700002828.mm.1 | 13.28 | 15.19 | −3.77 | 0.027086 | Gpi1 |

TABLE 7-continued

Table 7: Genome-wide expression analysis of pKL cells: down-regulated genes. List of downregulated genes identified by genome wide expression analysis (GWAS) performed on pharmacologically-modulated KL cells (pKL) as compared to Vehicle treated-KL cells isolated from bone marrow of normoglycemic NOD mice (p < 0.05).

| Transcript Cluster ID | pKL | KL | Fold Change | ANOVA p-value | Gene Symbol |
|---|---|---|---|---|---|
| TC1300002477.mm.1 | 12.37 | 14.28 | −3.76 | 0.006205 | Plp2 |
| TC0X00000989.mm.1 | 6 | 7.9 | −3.73 | 0.042717 | |
| TC1200001321.mm.1 | 3.9 | 5.79 | −3.71 | 0.000654 | |
| TC0600003383.mm.1 | 4.94 | 6.82 | −3.68 | 0.004168 | St8sia1 |
| TC0300000555.mm.1 | 10.05 | 11.92 | −3.65 | 0.027119 | Mfsd1 |
| TC0100001550.mm.1 | 8.62 | 10.48 | −3.64 | 0.048934 | Aldh9a1 |
| TC1200000166.mm.1 | 6.55 | 8.4 | −3.62 | 0.038281 | |
| TC1600000698.mm.1 | 4.17 | 6.02 | −3.58 | 0.012831 | Retnla |
| TC0400001062.mm.1 | 5.45 | 7.28 | −3.56 | 0.049629 | Tctex1d1 |
| TC0200003512.mm.1 | 5.02 | 6.85 | −3.56 | 0.0347 | Rnd3 |
| TC0100002075.mm.1 | 11.95 | 13.76 | −3.53 | 0.048288 | Gm10222 |
| TC0X00002193.mm.1 | 7.2 | 9.02 | −3.52 | 0.016505 | |
| TC1500001495.mm.1 | 4.61 | 6.41 | −3.5 | 0.010156 | |
| TC1100001251.mm.1 | 5.77 | 7.57 | −3.48 | 0.026464 | 1700020L24Rik |
| TC0900002113.mm.1 | 7.38 | 9.18 | −3.47 | 0.039865 | Sorl1 |
| TC0M00000003.mm.1 | 13.15 | 14.94 | −3.46 | 0.040803 | mt-Tv |
| TC0600001399.mm.1 | 5.17 | 6.94 | −3.4 | 0.044745 | Clec4a4 |
| TC1300001295.mm.1 | 10.9 | 12.67 | −3.4 | 0.026549 | |
| TC1300001461.mm.1 | 6.07 | 7.82 | −3.37 | 0.00105 | Gpr137b |
| TC1900001095.mm.1 | 12.48 | 14.23 | −3.36 | 0.013942 | Fads2 |
| TSUnmapped00000030.mm.1 | 7.07 | 8.81 | −3.36 | 0.013742 | H60a |
| TC0100001424.mm.1 | 11.45 | 13.19 | −3.34 | 0.021423 | Gm15428 |
| TC1600001559.mm.1 | 9.61 | 11.36 | −3.34 | 0.007514 | Fam162a |
| TC0500003395.mm.1 | 6.92 | 8.66 | −3.33 | 0.019694 | Hip1 |
| TC0200003843.mm.1 | 5.88 | 7.61 | −3.31 | 0.04474 | |
| TC0900001043.mm.1 | 6.3 | 8.02 | −3.31 | 0.01661 | |
| TC0900000204.mm.1 | 9.58 | 11.3 | −3.28 | 0.002249 | Ldlr |
| TC1600002080.mm.1 | 9.78 | 11.49 | −3.26 | 0.028475 | Tmem50b |
| TC0900001042.mm.1 | 10.33 | 12.03 | −3.25 | 0.02713 | Elovl5 |
| TC1800000626.mm.1 | 6.38 | 8.08 | −3.25 | 0.020747 | Mir6983 |
| TC0900000816.mm.1 | 6.39 | 8.08 | −3.23 | 0.036367 | Snapc5 |
| TC1000000968.mm.1 | 8.2 | 9.9 | −3.23 | 0.004532 | |
| TC0200002138.mm.1 | 4.61 | 6.29 | −3.21 | 0.045668 | |
| TC1700002776.mm.1 | 4.89 | 6.56 | −3.19 | 0.028144 | Pram1 |
| TC0500000260.mm.1 | 9.31 | 10.96 | −3.14 | 0.037644 | Insig1 |
| TC1000001406.mm.1 | 9.89 | 11.54 | −3.14 | 0.047448 | |
| TC1000001407.mm.1 | 9.89 | 11.54 | −3.14 | 0.047448 | |
| TC1000002951.mm.1 | 9.89 | 11.54 | −3.14 | 0.047448 | |
| TC1000002952.mm.1 | 9.89 | 11.54 | −3.14 | 0.047448 | |
| TC0100001325.mm.1 | 5.7 | 7.35 | −3.13 | 0.019617 | |
| TC0100001326.mm.1 | 5.7 | 7.35 | −3.13 | 0.019617 | |
| TC0100001327.mm.1 | 5.7 | 7.35 | −3.13 | 0.019617 | |
| TC0200001569.mm.1 | 5.7 | 7.35 | −3.13 | 0.019617 | |
| TC0200001615.mm.1 | 5.7 | 7.35 | −3.13 | 0.019617 | |
| TC0800000456.mm.1 | 5.7 | 7.35 | −3.13 | 0.019617 | |
| TC0X00000800.mm.1 | 5.7 | 7.35 | −3.13 | 0.019617 | |
| TC0X00001094.mm.1 | 5.7 | 7.35 | −3.13 | 0.019617 | |
| TC0X00001200.mm.1 | 5.7 | 7.35 | −3.13 | 0.019617 | |
| TC1000001319.mm.1 | 5.7 | 7.35 | −3.13 | 0.019617 | |
| TC1000002465.mm.1 | 5.7 | 7.35 | −3.13 | 0.019617 | |
| TC1200000168.mm.1 | 5.7 | 7.35 | −3.13 | 0.019617 | |
| TC1200001486.mm.1 | 5.7 | 7.35 | −3.13 | 0.019617 | |
| TC1200001838.mm.1 | 5.7 | 7.35 | −3.13 | 0.019617 | |
| TC1200002489.mm.1 | 5.7 | 7.35 | −3.13 | 0.019617 | |
| TC1600000722.mm.1 | 5.7 | 7.35 | −3.13 | 0.019617 | |
| TC1800001393.mm.1 | 5.7 | 7.35 | −3.13 | 0.019617 | |
| TC1900001143.mm.1 | 5.7 | 7.35 | −3.13 | 0.019617 | |
| TC0700003657.mm.1 | 8.3 | 9.93 | −3.11 | 0.002626 | Fah |
| TC0X00001780.mm.1 | 11.55 | 13.19 | −3.11 | 0.005311 | Plp2 |
| TC1400000186.mm.1 | 6.67 | 8.31 | −3.11 | 0.019209 | |
| TC1600001280.mm.1 | 13.9 | 15.53 | −3.1 | 0.026114 | Sdf2l1 |
| TC0800003031.mm.1 | 8.29 | 9.9 | −3.05 | 0.04969 | Cotl1 |
| TC1500000658.mm.1 | 14.68 | 16.28 | −3.04 | 0.031283 | Lgals1 |
| TC0800000394.mm.1 | 12.52 | 14.13 | −3.04 | 0.029628 | Gsr |
| TC1100003398.mm.1 | 5.21 | 6.81 | −3.03 | 0.016931 | |
| TC0X00002486.mm.1 | 7.77 | 9.36 | −3.02 | 0.029594 | Gm14708 |
| TC1800001585.mm.1 | 6.21 | 7.8 | −3.02 | 0.046751 | |
| TC0700001761.mm.1 | 3.66 | 5.25 | −3.01 | 0.010671 | |
| TC0700002718.mm.1 | 6.05 | 7.64 | −3 | 0.036272 | Kcnk6 |
| TC0900000659.mm.1 | 10.15 | 11.73 | −3 | 0.036766 | Idh3a |
| TC0400001974.mm.1 | 11.96 | 13.54 | −2.99 | 0.006804 | Eno1 |

TABLE 7-continued

Table 7: Genome-wide expression analysis of pKL cells: down-regulated genes. List of downregulated genes identified by genome wide expression analysis (GWAS) performed on pharmacologically-modulated KL cells (pKL) as compared to Vehicle treated-KL cells isolated from bone marrow of normoglycemic NOD mice (p < 0.05).

| Transcript Cluster ID | pKL | KL | Fold Change | ANOVA p-value | Gene Symbol |
|---|---|---|---|---|---|
| TC0800000172.mm.1 | 9.86 | 11.44 | −2.99 | 0.014044 | Agpat5 |
| TC1400002487.mm.1 | 7.78 | 9.35 | −2.98 | 0.039485 | Rgcc |
| TC0100002047.mm.1 | 6.57 | 8.15 | −2.98 | 0.038828 | |
| TC0700004320.mm.1 | 11.23 | 12.8 | −2.96 | 0.023586 | Dctpp1 |
| TC1200001644.mm.1 | 10.46 | 12.02 | −2.96 | 0.040646 | Bzw2 |
| TC1000003223.mm.1 | 10.89 | 12.46 | −2.96 | 0.025374 | |
| TC0500000544.mm.1 | 3.37 | 4.92 | −2.94 | 0.02258 | |
| TC0300002357.mm.1 | 6.68 | 8.23 | −2.93 | 0.029787 | Il6ra |
| TC0900002115.mm.1 | 9.7 | 11.25 | −2.93 | 0.049392 | Sc5d |
| TC0700001951.mm.1 | 6.93 | 8.48 | −2.92 | 0.049509 | Dock1 |
| TC0300002181.mm.1 | 5.59 | 7.14 | −2.92 | 0.046454 | |
| TC0500001338.mm.1 | 7.07 | 8.61 | −2.9 | 0.004893 | Slc8b1 |
| TC0100002453.mm.1 | 9.88 | 11.41 | −2.9 | 0.045259 | Gm11605 |
| TC0900001597.mm.1 | 6.39 | 7.92 | −2.89 | 0.049425 | Gm26448 |
| TC0600002518.mm.1 | 7.5 | 9.03 | −2.88 | 0.01998 | Gm9008 |
| TC1800000794.mm.1 | 9.45 | 10.97 | −2.87 | 0.01314 | Acaa2 |
| TC0X00000938.mm.1 | 7.96 | 9.47 | −2.85 | 0.038624 | Gm14814 |
| TC0800002905.mm.1 | 12.47 | 13.98 | −2.84 | 0.012589 | Hp |
| TC1500000640.mm.1 | 9.18 | 10.68 | −2.83 | 0.019595 | Ncf4 |
| TC0700000561.mm.1 | 11.38 | 12.87 | −2.83 | 0.032301 | Tyrobp |
| TC0300002040.mm.1 | 12.61 | 14.1 | −2.81 | 0.044252 | Gm5537 |
| TC1100002030.mm.1 | 7.2 | 8.69 | −2.81 | 0.003933 | Slc25a10 |
| TC1100001264.mm.1 | 5.17 | 6.67 | −2.81 | 0.020795 | Wfdc17 |
| TC1100000120.mm.1 | 6.51 | 7.99 | −2.8 | 0.008736 | Abca13 |
| TC0200003164.mm.1 | 6.66 | 8.14 | −2.8 | 0.022038 | Tmem141 |
| TC0X00001766.mm.1 | 6.27 | 7.75 | −2.8 | 0.027341 | Clcn5 |
| TC0800002618.mm.1 | 6.24 | 7.72 | −2.8 | 0.009507 | Neto2 |
| TC0600001853.mm.1 | 7.72 | 9.19 | −2.76 | 0.02348 | |
| TC0700001613.mm.1 | 6.19 | 7.65 | −2.75 | 0.026888 | Gm24888 |
| TC1000001680.mm.1 | 6.78 | 8.24 | −2.75 | 0.039079 | |
| TC1600001723.mm.1 | 3.82 | 5.28 | −2.75 | 0.048147 | |
| TC0100003655.mm.1 | 4.63 | 6.09 | −2.74 | 0.022664 | |
| TC1400002589.mm.1 | 7.53 | 8.98 | −2.74 | 0.031384 | |
| TC0500000470.mm.1 | 11.42 | 12.86 | −2.71 | 0.009054 | Gm7879 |
| TC1900000698.mm.1 | 5.22 | 6.66 | −2.71 | 0.045093 | Gm24610 |
| TC1400000573.mm.1 | 7.81 | 9.26 | −2.71 | 0.033055 | Apex1 |
| TC1000002500.mm.1 | 9.51 | 10.95 | −2.71 | 0.041088 | Uqcrl1 |
| TC0400002744.mm.1 | 7.01 | 8.45 | −2.71 | 0.034871 | Ptgr1 |
| TC0700002951.mm.1 | 5.62 | 7.05 | −2.7 | 0.014363 | Siglece |
| TC1700000436.mm.1 | 2.87 | 4.3 | −2.69 | 0.047439 | |
| TC1600000629.mm.1 | 6.25 | 7.67 | −2.68 | 0.017855 | Gm15711 |
| TC0700001629.mm.1 | 10.12 | 11.54 | −2.68 | 0.03238 | Gm10087 |
| TC1000001601.mm.1 | 9.17 | 10.58 | −2.67 | 0.022969 | Ankrd52 |
| TC0200005080.mm.1 | 11.66 | 13.08 | −2.67 | 0.037848 | Gm11451 |
| TC1800000291.mm.1 | 9.74 | 11.16 | −2.67 | 0.030243 | Kif20a |
| TC0M00000026.mm.1 | 7.8 | 9.21 | −2.67 | 0.045539 | |
| TC0100002050.mm.1 | 7.47 | 8.88 | −2.66 | 0.037695 | |
| TC0400003424.mm.1 | 10.75 | 12.15 | −2.65 | 0.031072 | Ldha-ps2 |
| TC0900001337.mm.1 | 8.19 | 9.59 | −2.64 | 0.024297 | Twf2 |
| TC0X00000218.mm.1 | 3.67 | 5.07 | −2.64 | 0.033216 | Timp1 |
| TC0300001874.mm.1 | 8.25 | 9.64 | −2.63 | 0.008446 | Gm12565 |
| TC0700001929.mm.1 | 8.74 | 10.13 | −2.63 | 0.017324 | |
| TC1600000867.mm.1 | 4.18 | 5.58 | −2.63 | 0.029319 | |
| TC0200003093.mm.1 | 10.83 | 12.23 | −2.62 | 0.026518 | Gm13339 |
| TC0M00000011.mm.1 | 11.98 | 13.37 | −2.62 | 0.016305 | ND3 |
| TC1900000693.mm.1 | 5.93 | 7.31 | −2.61 | 0.007529 | Tmem180 |
| TC0700004221.mm.1 | 8.24 | 9.62 | −2.61 | 0.037146 | Gga2 |
| TC1700002179.mm.1 | 7.42 | 8.8 | −2.6 | 0.020789 | Srf |
| TC0600002128.mm.1 | 8.6 | 9.98 | −2.6 | 0.028135 | |
| TC1800000015.mm.1 | 7.7 | 9.07 | −2.58 | 0.016668 | 9430020K01Rik |
| TC0600000954.mm.1 | 9.29 | 10.66 | −2.57 | 0.038542 | Npm3-ps1 |
| TC0200002744.mm.1 | 4.81 | 6.18 | −2.57 | 0.00691 | |
| TC1300001641.mm.1 | 6.16 | 7.52 | −2.56 | 0.029897 | Hfe |
| TC0600002137.mm.1 | 5.83 | 7.18 | −2.56 | 0.001745 | E330009J07Rik |
| TC1900000996.mm.1 | 7.87 | 9.23 | −2.56 | 0.039557 | Gm19505 |
| TC1000000937.mm.1 | 8.73 | 10.08 | −2.55 | 0.005197 | Chst11 |
| TC1100001276.mm.1 | 8.58 | 9.93 | −2.55 | 0.032203 | Acaca |
| TC0X00002393.mm.1 | 10.15 | 11.51 | −2.55 | 0.025864 | BC023829 |
| TC0900003182.mm.1 | 11.74 | 13.08 | −2.54 | 0.039627 | Stt3b |
| TC0200001741.mm.1 | 8.67 | 10.01 | −2.54 | 0.007079 | Bub1b |
| TC1900000549.mm.1 | 8.44 | 9.78 | −2.54 | 0.011511 | Slc35g1 |

TABLE 7-continued

Table 7: Genome-wide expression analysis of pKL cells: down-regulated genes. List of downregulated genes identified by genome wide expression analysis (GWAS) performed on pharmacologically-modulated KL cells (pKL) as compared to Vehicle treated-KL cells isolated from bone marrow of normoglycemic NOD mice (p < 0.05).

| Transcript Cluster ID | pKL | KL | Fold Change | ANOVA p-value | Gene Symbol |
|---|---|---|---|---|---|
| TC0100002867.mm.1 | 4.64 | 5.98 | −2.54 | 0.006226 | |
| TC1100001191.mm.1 | 6.58 | 7.91 | −2.51 | 0.029317 | Gm11203 |
| TC1300000655.mm.1 | 11.69 | 13.02 | −2.51 | 0.040755 | Prelid1 |
| TC0500003651.mm.1 | 8.87 | 10.19 | −2.51 | 0.006544 | Gm8615 |
| TC0700002168.mm.1 | 4.74 | 6.06 | −2.5 | 0.040905 | Tmem150b |
| TC1400001187.mm.1 | 5.56 | 6.88 | −2.49 | 0.025689 | |
| TC0M00000022.mm.1 | 7.52 | 8.83 | −2.48 | 0.001574 | mt-Tn |
| TC1200001262.mm.1 | 9.25 | 10.56 | −2.48 | 0.035405 | Adssl1 |
| TC0700002918.mm.1 | 11.4 | 12.71 | −2.47 | 0.046731 | Gm5593 |
| TC0200005454.mm.1 | 8.4 | 9.7 | −2.46 | 0.000598 | Rgs19 |
| TC0X00000611.mm.1 | 6.09 | 7.38 | −2.46 | 0.022132 | Gm5638 |
| TC0500003393.mm.1 | 9.17 | 10.47 | −2.46 | 0.029129 | Pom121 |
| TC0400002914.mm.1 | 7.28 | 8.57 | −2.45 | 0.036657 | Gm11247 |
| TC0X00002338.mm.1 | 6.44 | 7.74 | −2.45 | 0.038796 | Gm14672 |
| TC1700000403.mm.1 | 8.9 | 10.19 | −2.44 | 0.00035 | Mrpl28 |
| TC1700002392.mm.1 | 6.98 | 8.26 | −2.43 | 0.006052 | Gm17228 |
| TC0800000126.mm.1 | 12.88 | 14.16 | −2.43 | 0.038551 | Tfdp1 |
| TC0200005014.mm.1 | 15.46 | 16.74 | −2.43 | 0.0137 | |
| TC0400001414.mm.1 | 8.48 | 9.75 | −2.42 | 0.044399 | Gm12902 |
| TC1100000892.mm.1 | 10.19 | 11.45 | −2.41 | 0.005458 | Aurkb |
| TC0900000544.mm.1 | 6.48 | 7.75 | −2.4 | 0.041745 | Bace1 |
| TC0300001453.mm.1 | 15.63 | 16.9 | −2.4 | 0.040965 | Gm2574 |
| TC0100001283.mm.1 | 6.53 | 7.8 | −2.4 | 0.013301 | |
| TC1600001969.mm.1 | 5.16 | 6.42 | −2.4 | 0.024569 | |
| TC1000000566.mm.1 | 7.08 | 8.33 | −2.39 | 0.029289 | Lrrc20 |
| TC1000000986.mm.1 | 3.77 | 5.03 | −2.39 | 0.019359 | |
| TC1000003148.mm.1 | 10.84 | 12.09 | −2.38 | 0.00236 | Esyt1 |
| TC0X00002165.mm.1 | 8.48 | 9.72 | −2.37 | 0.033833 | Aifm1 |
| TC1800000486.mm.1 | 7.25 | 8.5 | −2.37 | 0.045632 | |
| TC1900001082.mm.1 | 6.21 | 7.45 | −2.36 | 0.015246 | |
| TC0900000854.mm.1 | 10.07 | 11.3 | −2.35 | 0.046986 | 2810417H13Rik |
| TC1500000714.mm.1 | 3.97 | 5.2 | −2.35 | 0.032305 | |
| TC1200001397.mm.1 | 7.32 | 8.55 | −2.34 | 0.035373 | Rhob |
| TC1100004220.mm.1 | 7.41 | 8.62 | −2.33 | 0.028282 | Pcyt2 |
| TC0500001940.mm.1 | 8.17 | 9.38 | −2.32 | 0.007802 | Gm7332 |
| TC1400000887.mm.1 | 7.7 | 8.92 | −2.32 | 0.027441 | Wdfy2 |
| TC1900001207.mm.1 | 9.64 | 10.86 | −2.32 | 0.027025 | Gm10819 |
| TC1700000836.mm.1 | 5.05 | 6.26 | −2.31 | 0.0418 | Cyp39a1 |
| TC0200002839.mm.1 | 6.41 | 7.62 | −2.31 | 0.017308 | |
| TC0900002102.mm.1 | 5.35 | 6.55 | −2.3 | 0.010426 | Gm16096 |
| TC0500001764.mm.1 | 10.72 | 11.92 | −2.3 | 0.004861 | Arpc1b |
| TC1200000682.mm.1 | 5.29 | 6.49 | −2.3 | 0.025133 | Plekhg3 |
| TC0900001638.mm.1 | 8.96 | 10.16 | −2.3 | 0.030878 | Abhd5 |
| TC0200002577.mm.1 | 11.58 | 12.78 | −2.3 | 0.049908 | Csel1 |
| TC0400002236.mm.1 | 10.89 | 12.08 | −2.29 | 0.046116 | Otud6b |
| TC0500001780.mm.1 | 5.56 | 6.75 | −2.29 | 0.038693 | |
| TC1000001917.mm.1 | 6.08 | 7.27 | −2.27 | 0.001674 | Gm8709 |
| TC1900000560.mm.1 | 10.03 | 11.21 | −2.27 | 0.04384 | Hells |
| TC0700001180.mm.1 | 5.02 | 6.2 | −2.27 | 0.009952 | Gm25907 |
| TC1400000306.mm.1 | 8.88 | 10.05 | −2.26 | 0.045389 | Tkt |
| TC1600001079.mm.1 | 7.95 | 9.13 | −2.26 | 0.030564 | Wrb |
| TC1500000163.mm.1 | 9.24 | 10.41 | −2.25 | 0.018882 | Gm2862 |
| TC1400001314.mm.1 | 9.6 | 10.76 | −2.25 | 0.040265 | Ipo5 |
| TC0600001974.mm.1 | 7.32 | 8.49 | −2.24 | 0.028322 | Impdh1 |
| TC1000000015.mm.1 | 9.19 | 10.36 | −2.24 | 0.047707 | Mthfd1l |
| TC0400000501.mm.1 | 10.42 | 11.58 | −2.24 | 0.015172 | Ncbp1 |
| TC1900000941.mm.1 | 9.52 | 10.68 | −2.23 | 0.013103 | Dpp3 |
| TC0400004097.mm.1 | 7.62 | 8.77 | −2.22 | 0.010273 | Kcnab2 |
| TC0200002990.mm.1 | 6.26 | 7.4 | −2.22 | 0.002564 | Ptpla |
| TC0100002077.mm.1 | 16.17 | 17.32 | −2.22 | 0.03879 | |
| TC0300002960.mm.1 | 5.79 | 6.94 | −2.22 | 0.029371 | |
| TC0300003225.mm.1 | 6.15 | 7.29 | −2.21 | 0.002687 | LOC100038947 |
| TC0700000931.mm.1 | 6.19 | 7.33 | −2.21 | 0.029119 | Siglech |
| TC1200001077.mm.1 | 12.35 | 13.49 | −2.21 | 0.040395 | Vrk1 |
| TC1100003640.mm.1 | 12.59 | 13.73 | −2.21 | 0.046699 | Kpnb1 |
| TC1400002400.mm.1 | 10.85 | 12 | −2.21 | 0.04487 | Gm6984 |
| TC1500000663.mm.1 | 4.79 | 5.92 | −2.2 | 0.013327 | Gcat |
| TC1800001024.mm.1 | 10.82 | 11.95 | −2.2 | 0.01406 | Gm7665 |
| TC0200004665.mm.1 | 6.97 | 8.11 | −2.2 | 0.017652 | Rass12 |
| TC0800002941.mm.1 | 9.01 | 10.15 | −2.2 | 0.022672 | Glg1 |
| TC0900000071.mm.1 | 3.24 | 4.38 | −2.2 | 0.010571 | |

TABLE 7-continued

Table 7: Genome-wide expression analysis of pKL cells: down-regulated genes. List of downregulated genes identified by genome wide expression analysis (GWAS) performed on pharmacologically-modulated KL cells (pKL) as compared to Vehicle treated-KL cells isolated from bone marrow of normoglycemic NOD mice (p < 0.05).

| Transcript Cluster ID | pKL | KL | Fold Change | ANOVA p-value | Gene Symbol |
|---|---|---|---|---|---|
| TC0X00001393.mm.1 | 5.23 | 6.37 | −2.19 | 0.046434 | Gm15079 |
| TC1300001140.mm.1 | 6.13 | 7.26 | −2.19 | 0.047889 | Ccdc125 |
| TC1100003407.mm.1 | 7.01 | 8.14 | −2.19 | 0.033461 | Tada2a |
| TC0700002782.mm.1 | 10.29 | 11.43 | −2.19 | 0.044209 | Usf2 |
| TC0200001703.mm.1 | 5 | 6.13 | −2.19 | 0.019328 | |
| TC1100004085.mm.1 | 7.39 | 8.5 | −2.17 | 0.01079 | Gm11702 |
| TC1300002052.mm.1 | 10.22 | 11.34 | −2.17 | 0.004026 | Rab24 |
| TC1400000354.mm.1 | 5.04 | 6.15 | −2.17 | 0.011034 | Gm7734 |
| TC1500001899.mm.1 | 4.18 | 5.3 | −2.17 | 0.044475 | Snord43 |
| TC0200004718.mm.1 | 8.28 | 9.4 | −2.17 | 0.023127 | Gm14063 |
| TC1300002594.mm.1 | 7.09 | 8.2 | −2.17 | 0.042397 | Nln |
| TC1000002988.mm.1 | 7.66 | 8.77 | −2.17 | 0.029317 | Gm9046 |
| TC0500001380.mm.1 | 11.57 | 12.69 | −2.17 | 0.023899 | Ppp1cc |
| TC0400002593.mm.1 | 8.94 | 10.06 | −2.17 | 0.035282 | Gm12444 |
| TC0500000523.mm.1 | 3.9 | 5.02 | −2.17 | 0.00857 | |
| TC0X00003430.mm.1 | 7.95 | 9.06 | −2.16 | 0.032947 | Arhgap4 |
| TC1200000675.mm.1 | 10.59 | 11.7 | −2.16 | 0.011722 | Mthfd1 |
| TC0400000870.mm.1 | 5.68 | 6.79 | −2.16 | 0.031655 | |
| TC1600000880.mm.1 | 4.84 | 5.95 | −2.16 | 0.004801 | |
| TC0600001398.mm.1 | 9.18 | 10.28 | −2.15 | 0.024866 | Clec4a3 |
| TC1100002046.mm.1 | 12.49 | 13.6 | −2.15 | 0.045829 | Hmga1-rs1 |
| TC0500003626.mm.1 | 5.41 | 6.51 | −2.15 | 0.039179 | Flt3 |
| TC1900000127.mm.1 | 13.12 | 14.22 | −2.14 | 0.017541 | Ppp1r14b |
| TC0X00001053.mm.1 | 4.96 | 6.06 | −2.14 | 0.03298 | Gm9673 |
| TC0600001203.mm.1 | 5.06 | 6.15 | −2.13 | 0.025935 | Bhlhe40 |
| TC1600001497.mm.1 | 9.66 | 10.76 | −2.13 | 0.031144 | Pak2 |
| TC0200002146.mm.1 | 9.45 | 10.55 | −2.13 | 0.001687 | Pet117 |
| TC1100002250.mm.1 | 11.01 | 12.1 | −2.13 | 0.043678 | Gm12013 |
| TC0900000280.mm.1 | 4.5 | 5.59 | −2.13 | 0.01833 | |
| TC0900000974.mm.1 | 5.04 | 6.13 | −2.13 | 0.011146 | |
| TC1800000844.mm.1 | 14.06 | 15.15 | −2.13 | 0.014757 | |
| TC1000002043.mm.1 | 11.28 | 12.36 | −2.12 | 0.04902 | Amd2 |
| TC1500002221.mm.1 | 10.97 | 12.06 | −2.12 | 0.047627 | Cers5 |
| TC1100003095.mm.1 | 8.44 | 9.52 | −2.12 | 0.010272 | Pelp1 |
| TC0100002049.mm.1 | 5.01 | 6.1 | −2.12 | 0.011683 | |
| TC0700004157.mm.1 | 6.28 | 7.36 | −2.11 | 0.036125 | Pik3c2a |
| TC0800002313.mm.1 | 9 | 10.07 | −2.11 | 0.015395 | Msmo1 |
| TC0100002053.mm.1 | 5.63 | 6.71 | −2.11 | 0.030669 | |
| TC1100000796.mm.1 | 5.05 | 6.13 | −2.11 | 0.027278 | |
| TC1100000545.mm.1 | 7.14 | 8.21 | −2.1 | 0.001149 | Gm12197 |
| TC0200004840.mm.1 | 8.74 | 9.81 | −2.1 | 0.005878 | Gm14121 |
| TC0X00003122.mm.1 | 9.52 | 10.59 | −2.1 | 0.026645 | Gm15067 |
| TC1000002188.mm.1 | 4.33 | 5.4 | −2.1 | 0.005777 | |
| TC1600001155.mm.1 | 7.48 | 8.54 | −2.09 | 0.034311 | Nagpa |
| TC0800002558.mm.1 | 8.75 | 9.82 | −2.09 | 0.003445 | Cd97 |
| TC0700001714.mm.1 | 14.47 | 15.53 | −2.09 | 0.045773 | Gm5601 |
| TC0500001462.mm.1 | 7.01 | 8.06 | −2.08 | 0.036902 | Bri3bp |
| TC0200001784.mm.1 | 6.04 | 7.1 | −2.08 | 0.040705 | |
| TC0800002840.mm.1 | 8.15 | 9.21 | −2.08 | 0.017559 | |
| TC1300001227.mm.1 | 5.42 | 6.48 | −2.08 | 0.037621 | |
| TC0400002193.mm.1 | 10.8 | 11.85 | −2.07 | 0.020666 | Gm11814 |
| TC1400000529.mm.1 | 14.76 | 15.82 | −2.07 | 0.010369 | Gm3534 |
| TC0200003141.mm.1 | 7.98 | 9.03 | −2.07 | 0.037823 | Ssna1 |
| TC0400000516.mm.1 | 7.82 | 8.87 | −2.07 | 0.033794 | Gm12424 |
| TC0900001424.mm.1 | 5.11 | 6.15 | −2.06 | 0.030186 | Celsr3 |
| TC1100000802.mm.1 | 8.12 | 9.16 | −2.06 | 0.032038 | Trpv2 |
| TC1100004270.mm.1 | 6.7 | 7.75 | −2.06 | 0.008766 | Tlcd2 |
| TC0800002413.mm.1 | 10.39 | 11.44 | −2.06 | 0.021425 | Mir7067 |
| TC0300000439.mm.1 | 4.98 | 6.02 | −2.06 | 0.007132 | |
| TC0600001731.mm.1 | 4.98 | 6.02 | −2.06 | 0.007132 | |
| TC0600002537.mm.1 | 4.98 | 6.02 | −2.06 | 0.007132 | |
| TC0600003306.mm.1 | 4.98 | 6.02 | −2.06 | 0.007132 | |
| TC0900002567.mm.1 | 4.98 | 6.02 | −2.06 | 0.007132 | |
| TC0X00000379.mm.1 | 4.98 | 6.02 | −2.06 | 0.007132 | |
| TC0X00003344.mm.1 | 4.98 | 6.02 | −2.06 | 0.007132 | |
| TC1400001128.mm.1 | 4.98 | 6.02 | −2.06 | 0.007132 | |
| TC1400002462.mm.1 | 5.19 | 6.24 | −2.06 | 0.025107 | |
| TC1400002705.mm.1 | 4.98 | 6.02 | −2.06 | 0.007132 | |
| TC1500000481.mm.1 | 4.98 | 6.02 | −2.06 | 0.007132 | |
| TC1800000768.mm.1 | 4.98 | 6.02 | −2.06 | 0.007132 | |
| TC1800001570.mm.1 | 4.98 | 6.02 | −2.06 | 0.007132 | |

TABLE 7-continued

Table 7: Genome-wide expression analysis of pKL cells: down-regulated genes. List of downregulated genes identified by genome wide expression analysis (GWAS) performed on pharmacologically-modulated KL cells (pKL) as compared to Vehicle treated-KL cells isolated from bone marrow of normoglycemic NOD mice ($p < 0.05$).

| Transcript Cluster ID | pKL | KL | Fold Change | ANOVA p-value | Gene Symbol |
|---|---|---|---|---|---|
| TC1900001634.mm.1 | 4.98 | 6.02 | −2.06 | 0.007132 | |
| TC0500000459.mm.1 | 5.86 | 6.89 | −2.05 | 0.000222 | Cpeb2 |
| TC0900002020.mm.1 | 9.57 | 10.6 | −2.05 | 0.049948 | Gm10105 |
| TC1100000093.mm.1 | 11.68 | 12.71 | −2.05 | 0.014066 | Ogdh |
| TC1300001212.mm.1 | 3.84 | 4.88 | −2.05 | 0.022614 | |
| TC0300000904.mm.1 | 15.37 | 16.39 | −2.04 | 0.04309 | Hmgb1-ps5 |
| TC1000001856.mm.1 | 13.89 | 14.92 | −2.04 | 0.028687 | Hmgb1-ps8 |
| TC1700002191.mm.1 | 10.25 | 11.28 | −2.04 | 0.02939 | Rpl7l1 |
| TC1000002985.mm.1 | 9.89 | 10.92 | −2.04 | 0.041065 | Gm9040 |
| TC1000002986.mm.1 | 9.89 | 10.92 | −2.04 | 0.041065 | Gm9044 |
| TC1700002318.mm.1 | 7.73 | 8.76 | −2.03 | 0.032179 | Dpp9 |
| TC0500002923.mm.1 | 10.84 | 11.86 | −2.03 | 0.0458 | Gm8152 |
| TC0900002638.mm.1 | 12.97 | 13.99 | −2.03 | 0.023276 | RP24-282D16.5 |
| TC0200005145.mm.1 | 6.49 | 7.51 | −2.03 | 0.023624 | Slc35c2 |
| TC1100000592.mm.1 | 8.51 | 9.53 | −2.03 | 0.008323 | Vdac1 |
| TC0700001412.mm.1 | 8.28 | 9.3 | −2.03 | 0.044622 | Cox20-ps |
| TC0100000408.mm.1 | 4.42 | 5.44 | −2.03 | 0.020475 | |
| TC0600001734.mm.1 | 10.61 | 11.63 | −2.02 | 0.020979 | Med21 |
| TC1000000056.mm.1 | 4.84 | 5.85 | −2.02 | 0.002652 | Zc3h12d |
| TC0200003240.mm.1 | 16.42 | 17.44 | −2.02 | 0.026298 | Gm13394 |
| TC0200003109.mm.1 | 6.34 | 7.36 | −2.02 | 0.021129 | Hnmt |
| TC0800000142.mm.1 | 11.36 | 12.37 | −2.02 | 0.014776 | Gm3160 |
| TC0X00000874.mm.1 | 6.39 | 7.41 | −2.02 | 0.003215 | Gm14778 |
| TC1900000188.mm.1 | 11.28 | 12.29 | −2.02 | 0.049538 | Fads1 |
| TC1700002656.mm.1 | 7.28 | 8.29 | −2.02 | 0.04045 | Lrpprc |
| TC1500000677.mm.1 | 6.98 | 8 | −2.02 | 0.014575 | Cby1 |
| TC0X00002643.mm.1 | 11.87 | 12.88 | −2.02 | 0.045167 | Eif2s3x |
| TC1200000033.mm.1 | 13.17 | 14.18 | −2.01 | 0.017567 | Gm6682 |
| TC0600000417.mm.1 | 5.4 | 6.41 | −2.01 | 0.031195 | Trbv1 |
| TC1100004215.mm.1 | 14.22 | 15.22 | −2 | 0.035288 | P4hb |
| TC1100002965.mm.1 | 15.05 | 16.05 | −2 | 0.035967 | Hmgb1-ps3 |
| TC1700002186.mm.1 | 10.25 | 11.25 | −2 | 0.010558 | Ppp2r5d |

TABLE 8

Characteristics of patients enrolled in the study. Baseline demographic characteristics of patients enrolled in the study.

| | CTRL (n = 12) | T1D (n = 12) | New-onset T1D (n = 12) |
|---|---|---|---|
| Sex (M/F) | 4/8 | 6/6 | 4/8 |
| Age (years) | 34.8 ± 2.3 | 39.6 ± 3.1 | 10.9 ± 1.1 |
| Years of T1D | N/A | 22.3 ± 3.8 | N/A |
| HbA1c % (mmol/mol) | 5.0 ± 0.05 (31 ± 0.5) | 9.2 ± 0.4 (78 ± 4.0) | 12.3 ± 0.4 (111 ± 4.9) |
| EIR (UI) | N/A | 42.0 ± 4.1 | N/A |
| Concomitant Treatments | N/A | Levothyroxine (n = 3) Statin (n = 2) | N/A |

Data are expressed as mean ± standard error (SEM).

TABLE 9

Characteristics of patients enrolled in the plerixafor mobilization study. Baseline demographic characteristics of patients enrolled in the plerixafor mobilization study.

| | CTRL (n = 8) | T1D (n = 5) | P value |
|---|---|---|---|
| Age (years) | 44.1 ± 5.1 | 39.0 ± 3.9 | 0.494 |
| Male/Female | | 4/1 | Ns |
| Weight (kg) | 76.7 ± 6.7 | 76.2 ± 6.1 | 0.961 |
| Height (cm) | 174.8 ± 1.84 | 174 4 ± 4 6 | 0.913 |
| BMI (kg/mq) | 25.0 ± 2.1 | 25.0 ± 1.5 | 0.988 |
| HbA1c (%) | 5.7 ± 0.2 | 7.9 ± 0.3 | 0.026 |
| Duration (Years) | 0.0 | 20.8 ± 4.9 | Ns |
| Hypertension (%) | 37.5 | 0 | 0.139 |
| Retinopathy (%) | 0.0 | 20.0 | 0.742 |
| Microalbuminuria (%) | 0.0 | 0.0 | Ns |
| Neuropathy (%) | 0.0 | 0.0 | Ns |
| Atherosclerosis (%) | 0.0 | 20.0 | Ns |
| White blood cells ($10^9$ per liter) | 7.1 ± 0.9 | 6.1 ± 0.6 | Ns |

Data are expressed as mean ± standard error (SEM)

TABLE 10

Table 10: Transcriptome of pCD34+ cells. List of upregulated and downregulated inflammatory and costimulation-related genes identified by transcriptome profiling in pharmacologically-modulated CD34+ cells as compared to unmodulated-CD34+ cells obtained from T1D patients. Genes with statistically significant differences ($p < 0.05$) are in italics.

| Refseq | Symbol | p value |
|---|---|---|
| NM_000022 | ADA | 0.225567 |
| NM_020661 | AICDA | 0.195329 |
| NM_000038 | APC | 0.351487 |

TABLE 10-continued

Table 10: Transcriptome of pCD34+ cells. List of upregulated and downregulated inflammatory and costimulation-related genes identified by transcriptome profiling in pharmacologically-modulated CD34+ cells as compared to unmodulated-CD34+ cells obtained from T1D patients. Genes with statistically significant differences ($p < 0.05$) are in italics.

| Refseq | Symbol | p value |
| --- | --- | --- |
| NM_000633 | BCL2 | 0.099101 |
| NM_000057 | BLM | 0.417912 |
| NM_013314 | BLNK | 0.556359 |
| NM_002983 | CCL3 | 0.188691 |
| NM_001295 | CCR1 | 0.430142 |
| NM_001123396 | CCR2 | 0.48641 |
| NM_001837 | CCR3 | 0.234087 |
| NM_005508 | CCR4 | 0.530672 |
| NM_000579 | CCR5 | 0.651288 |
| NM_001766 | CD1D | 0.669927 |
| NM_001767 | CD2 | 0.457163 |
| NM_001242 | CD27 | 0.975865 |
| NM_014143 | *CD274* | 0.028999 |
| NM_025240 | CD276 | 0.537183 |
| NM_006139 | CD28 | 0.650923 |
| NM_000732 | CD3D | 0.464723 |
| NM_000733 | CD3E | 0.79027 |
| NM_000073 | CD3G | 0.288999 |
| NM_000616 | CD4 | 0.512874 |
| NM_001250 | CD40 | 0.600445 |
| NM_000074 | CD40LG | 0.891166 |
| NM_001777 | CD47 | 0.982858 |
| NM_014207 | CD5 | 0.548741 |
| NM_006137 | CD7 | 0.410343 |
| NM_005191 | CD 80 | 0.170296 |
| NM_004356 | CD81 | 0.811353 |
| NM_006889 | CD 86 | 0.382565 |
| NM_001768 | CD8A | 0.263857 |
| NM_004931 | CD8B | 0.400975 |
| NM_000758 | CSF2 | 0.630803 |
| NM_002996 | CX3CL1 | 0.337314 |
| NM_001504 | CXCR3 | 0.351979 |
| NM_003467 | CXCR4 | 0.373218 |
| NM_001716 | CXCR5 | 0.365898 |
| NM_001935 | DPP4 | 0.764763 |
| NM_001964 | EGR1 | 0.367139 |
| NM_000043 | FAS | 0.568721 |
| NM_000639 | FASLG | 0.189251 |
| NM_014009 | FOXP3 | 0.334684 |
| NM_015259 | ICOSLG | 0.804737 |
| NM_000619 | IFNG | 0.936207 |
| NM_000572 | IL10 | 0.645899 |
| NM_000641 | IL11 | 0.391528 |
| NM_000882 | IL12A | 0.428351 |
| NM_002187 | IL12B | 0.453057 |
| NM_005535 | *IL12RB1* | 0.023026 |
| NM_001559 | IL12RB2 | 0.701111 |
| NM_002188 | IL13 | 0.291112 |
| NM_000585 | IL15 | 0.183724 |
| NM_001562 | IL18 | 0.972391 |
| NM_003855 | IL18R1 | 0.179383 |
| NM_000576 | IL1B | 0.26186 |
| NM_000586 | IL2 | 0.24441 |
| NM_000417 | IL2RA | 0.311566 |
| NM_000588 | IL3 | 0.820972 |
| NM_000589 | IL4 | 0.352994 |
| NM_000418 | IL4R | 0.223243 |
| NM_000879 | IL5 | 0.849461 |
| NM_000600 | IL6 | 0.295894 |
| NM_000880 | IL7 | 0.601403 |
| NM_000584 | CXCL8 | 0.075554 |
| NM_002460 | IRF4 | 0.32968 |
| NM_002286 | LAG3 | 0.420723 |
| NM_005356 | LCK | 0.437734 |
| NM_003188 | MAP3K7 | 0.310046 |
| NM_005931 | MICB | 0.307045 |
| NM_021950 | MS4A1 | 0.290522 |
| NM_006153 | NCK1 | 0.419349 |
| NM_000625 | NOS2 | 0.386605 |
| NM_002838 | PTPRC | 0.217912 |
| NM_000448 | RAG1 | 0.518868 |
| NM_003821 | RIPK2 | 0.395143 |
| NM_003745 | *SOCS1* | 0.032789 |
| NM_000660 | TGFB1 | 0.110908 |
| NM_003263 | TLR1 | 0.519406 |
| NM_003264 | TLR2 | 0.102702 |
| NM_138554 | TLR4 | 0.447099 |
| NM_006068 | TLR6 | 0.306693 |
| NM_017442 | TLR9 | 0.850156 |
| NM_003807 | TNFSF14 | 0.289412 |
| NM_005428 | VAV1 | 0.83807 |
| NM_001101 | ACTB | 0.169224 |
| NM_004048 | B2M | 0.812532 |
| NM_002046 | GAPDH | 0.297957 |
| NM_000194 | HPRT1 | 0.986777 |
| NM_001002 | RPLPO | 0.382779 |
| SA_00105 | HGDC | 0.374447 |
| SA_00104 | RTC | 0.488473 |
| SA_00104 | RTC | 0.829614 |
| SA_00104 | RTC | 0.290938 |
| SA_00103 | PPC | 0.565867 |
| SA_00103 | PPC | 0.386582 |
| SA_00103 | PPC | 0.394285 |

What is claimed is:

1. An ex vivo method of producing a modified hematopoietic stem cell (modified HSC) having increased expression of programmed cell death-1 receptor ligand (PD-L1), or population thereof, the method comprising contacting a hematopoietic stem cell (HSC) with an anti-miRNA oligonucleotide that inhibits miR-1905, thereby increasing expression of PD-L1 in the HSC.

2. The method of claim 1, wherein the anti-miRNA oligonucleotide is introduced to the cell via a viral or non-viral vector.

3. A modified hematopoietic stem cell (modified HSC) having increased PD-L1 expression, or population thereof, wherein the modified HSC is a hematopoietic stem cell (HSC) comprising an anti-miRNA oligonucleotide that is capable of increasing expression of PD-L1 by inhibiting miR-1905.

4. The modified HSC of claim 3, wherein the HSC is a mammalian HSC or human HSC.

5. The modified HSC of claim 3, wherein prior to the modification, the HSC is obtained from the bone marrow, umbilical cord, amniotic fluid, chorionic villi, cord blood, placental blood, mobilized peripheral blood or peripheral blood.

6. The modified HSC of claim 3, wherein the HSC is obtained from a healthy individual or an individual with a diagnosed disease or disorder.

7. The modified HSC of claim 6, wherein the diagnosed disease or disorder is an autoimmune disease or disorder.

8. The modified HSC of claim 3, wherein the modified HSC is cryopreserved.

9. The modified HSCs of claim 3, wherein the modified HSC is produced by a method comprising:
contacting the HSC with the anti-miRNA oligonucleotide ex vivo culturing the HSC following the contacting; and establishing the expression of PD-L1 on the HSC, thereby producing the modified HSC having increased PD-L1 expression, or population thereof.

10. A composition of the modified HSC made by the method of claim 1.

11. A method of treating an autoimmune disorder or cancer in a subject in need thereof, the method comprising administering to the subject the modified HSC or population thereof made by the method of claim 1.

12. The method of claim 11, wherein the autoimmune disorder is Type 1 diabetes (T1D).

13. The method of claim 11, wherein the HSCs are autologous; allogeneic; or xenogeneic to the subject.

14. The method of claim 1, further comprising at least one of the following steps:
 a) providing the HSC or population thereof prior to the contacting;
 b) obtaining the HSC or population thereof from a subject prior to the contacting;
 c) ex vivo culturing the modified HSC following the contacting; and
 d) establishing the expression of PD-L1 on the modified HSC.

15. A population of the modified HSC made by the method of claim 1.

16. A method of treating an autoimmune disorder or cancer in a subject in need thereof, the method comprising administering to the subject the modified HSC of claim 3 or population thereof.

* * * * *

SEQUENCE LISTING

<160> NUMBER OF SEQ ID NOS: 25

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
    oligonucleotide <400> SEQUENCE: 1
ucccugagac ccuaacuugu ga                                    22

<210> SEQ ID NO 2
<211> LENGTH: 20

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
aauguguagc aaaagacaga                                                     20

<210> SEQ ID NO 3
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
aacccguaga uccgaucuug ug                                                  22

<210> SEQ ID NO 4
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
cuguugccac uaaccucaac cu                                                  22

<210> SEQ ID NO 5
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ucaccgggug uaaaucagcu ug                                                  22

<210> SEQ ID NO 6
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
guuugauaaa cugacacaac                                                     20

<210> SEQ ID NO 7
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cacacacuuc cuuacauucc                                                     20

<210> SEQ ID NO 8
<211> LENGTH: 18
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 8
cuauccugaa uuacuuga                                                      18

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
uaacacgucu auacgccca                                                     19

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcaaagtgat acacatttgg agga                                               24

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccccgatgaa cccctaaacc                                                    20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcacatccag agttccgagt                                                    20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cagggttgcc agggatgaat                                                    20

<210> SEQ ID NO 14
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 14
gggccatccg ggaatttttg                                                    20

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tcgtgctctg aattgaggtg t                                                  21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgtcctcgga ttctctgctc                                                    20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgttcctcct cagagtcgct                                                    20

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cctgacatgc tgtttgaact ga                                                 22

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcttgttctc ctcgctgtag t                                                  21

<210> SEQ ID NO 20
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 20
cttgctgctc tacctccacc                                                     20

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgaacttcac cacttcgtga tg                                                  22

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctgaaggaag caaccctcct                                                     20

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tcgagtagaa gtcatttctg cca                                                 23

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtgaaccatg agaagtatga caac                                                24

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
catgagtcct tccacgatac c                                                   21
```